US012624004B2

(12) United States Patent
Fu

(10) Patent No.: US 12,624,004 B2
(45) Date of Patent: May 12, 2026

(54) OPIOID RECEPTOR AGONIST, PREPARATION METHOD THEREFOR AND PHARMACEUTICAL USE THEREOF

(71) Applicant: Fudan University, Shanghai (CN)

(72) Inventor: Wei Fu, Shanghai (CN)

(73) Assignee: Fudan University, Shanghai (CN)

( * ) Notice: Subject to any disclaimer, the term of this patent is extended or adjusted under 35 U.S.C. 154(b) by 950 days.

(21) Appl. No.: 17/755,780

(22) PCT Filed: Nov. 2, 2020

(86) PCT No.: PCT/CN2020/125799

§ 371 (c)(1),
(2) Date: May 6, 2022

(87) PCT Pub. No.: WO2021/088758

PCT Pub. Date: May 14, 2021

(65) Prior Publication Data

US 2023/0027752 A1 Jan. 26, 2023

(30) Foreign Application Priority Data

Nov. 6, 2019 (CN) ........................ 201911076305.X
Nov. 6, 2019 (CN) ........................ 201911076330.8
Nov. 6, 2019 (CN) ........................ 201911076925.3
Nov. 6, 2019 (CN) ........................ 201911076931.9
Nov. 6, 2019 (CN) ........................ 201911076965.8

(51) Int. Cl.

| | |
|---|---|
| ***C07D 211/96*** | (2006.01) |
| ***A61P 25/04*** | (2006.01) |
| ***C07C 311/20*** | (2006.01) |
| ***C07C 317/28*** | (2006.01) |
| ***C07D 401/06*** | (2006.01) |
| ***C07D 409/12*** | (2006.01) |

(52) U.S. Cl.

CPC ............ *C07D 211/96* (2013.01); *A61P 25/04* (2018.01); *C07C 311/20* (2013.01); *C07C 317/28* (2013.01); *C07D 401/06* (2013.01); *C07D 409/12* (2013.01)

(58) Field of Classification Search

CPC .. C07D 211/96; C07D 401/06; C07D 409/12; C07D 211/52; C07C 311/20; C07C 317/28; C07C 217/74; A61P 25/04; A61P 25/21; A61K 31/145; A61K 31/4418

See application file for complete search history.

(56) References Cited

FOREIGN PATENT DOCUMENTS

| | | | |
|---|---|---|---|
| CN | 1157815 | A | 8/1997 |
| CN | 1547570 | A | 11/2004 |
| CN | 105646332 | A | 6/2016 |
| WO | WO 03037863 | A2 | 5/2003 |
| WO | WO 03037870 | A1 | 5/2003 |
| WO | WO 03037873 | A1 | 5/2003 |
| WO | WO 03037879 | A1 | 5/2003 |

OTHER PUBLICATIONS

Burford, N.T., Traynor, J.R. and Alt, A. (2015), Positive allosteric modulators. Br J Pharmacol, 172: 277-286. https://doi.org/10.1111/bph.12599 (Year: 2015).*

Huang H, Wang W, Xu X, Zhu C, Wang Y, Liu J, Li W, Fu W. Discovery of 3-((dimethylamino)methyl)-4-hydroxy-4-(3-methoxyphenyl)-N-phenylpiperidine-1-carboxamide as novel potent analgesic. Eur J Med Chem. Mar. 1, 2020;189:112070. doi: 10.1016/j.ejmech.2020.112070. Epub Jan. 18, 2020. PMID: 31982651. (Year: 2020)*

International Search Report and Written Opinion issued in application No. PCT/CN2020/125799, dated Jan. 11, 2021.

* cited by examiner

*Primary Examiner* — Matthew P Coughlin
*Assistant Examiner* — Anna Grace Kuckla
(74) *Attorney, Agent, or Firm* — JCIPRNET

(57) ABSTRACT

The invention belongs to the field of pharmacy, and relates to a class of opioid receptor agonists, their preparation method and the pharmaceutical use thereof, in particular to 3-(dimethylaminomethyl) cyclohex-4-ol derivatives or salts thereof and preparation method thereof, 3-(dimethylaminomethyl) piperidin-4-ol derivatives or salts thereof and preparation method thereof, 3-(dimethylaminomethyl) piperidin-4-ol derivatives or salts thereof and preparation method thereof, 3-(dimethylaminomethyl) piperidin-4-ol derivative or salt thereof and preparation method thereof, 3-(dimethylaminomethyl) piperidin-4-ol derivative or salt thereof and preparation method thereof, and relate to the use of said compounds in the treatment of opioid receptor-mediated diseases. The use of the compound or pharmaceutically acceptable salt, solvate or hydrate thereof in the preparation of a medicament for treating indications related to opioid receptors. The opioid receptor-related indications are pain, irritable bowel syndrome, pruritus, addiction and depression.

5 Claims, No Drawings

OPIOID RECEPTOR AGONIST, PREPARATION METHOD THEREFOR AND PHARMACEUTICAL USE THEREOF

FIELD OF THE INVENTION

The invention belongs to the field of pharmacy, and relates to a class of opioid receptor agonists, their preparation method and pharmaceutical use thereof, in particular to 3-(dimethylaminomethyl) cyclohex-4-ol derivatives or salts thereof and preparation method thereof, 3-(dimethylaminomethyl) piperidin-4-ol derivatives or salts thereof and preparation method thereof, 3-(dimethylaminomethyl) piperidin-4-ol derivatives or salts thereof and preparation method thereof, 3-(dimethylaminomethyl) piperidin-4-ol derivative or salt thereof and preparation method thereof, 3-(dimethylaminomethyl) piperidin-4-ol derivative or salt thereof and preparation method thereof, and relates to the compound in the opioid receptor agonist and its preparation method and pharmaceutical use.

BACKGROUND

Pain is a common symptom in the process of many diseases, and it is one of the main problems that plague patients. It has been listed as the fifth vital sign after body temperature, pulse, respiration and blood pressure. At present, opioid analgesics have an irreplaceable role in pain treatment, such as morphine and fentanyl. But their long-term use will cause drug resistance, addiction, withdrawal, respiratory depression and other adverse reactions. Tramadol was a synthetic opioid central system analgesic developed by Grunenthal in 1977, and its trade name was tramal. It was a relatively weak p opioid receptor agonist (Ki=2400 nM at p opioid receptors, $EC_{50}$>1000 nM) and inhibited serotonin and norepinephrine reuptake. It was mainly metabolized by the liver and is almost completely excreted by the kidneys. As an atypical opioid, tramadol was different from other traditional opioids. It had its unique pharmacological characteristics. It not only had strong analgesic effect, but also had few adverse reactions. It had been widely used in pain treatment.

However, clinical application showed that the analgesic effect of tramadol was slightly weaker than that of analgesics such as morphine and fentanyl. In addition, tramadol had side effects such as respiratory depression, addiction, nausea, diarrhea, headache, dizziness, drowsiness, and constipation. Long-term use of the drug could also cause withdrawal symptoms such as sweating, anxiety, poor sleep, pain, and body shaking. In addition, studies have shown that tramadol use was associated with an increased risk of hyponatremia and hypoglycemia requiring hospitalization. Therefore, it is necessary to develop analgesics with stronger analgesic effect and less side effects.

SUMMARY OF THE INVENTION

Each of the above preferred conditions, on the basis of conforming to the common knowledge in the art, may be arbitrarily combined without going beyond the conception and protection scope of the invention.

The present invention provides a compound represented by formula (I), or a pharmaceutically acceptable salt thereof:

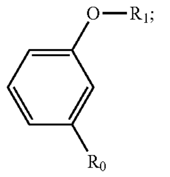

(I)

Wherein, $R_0$ is selected from formula (1), formula (2), formula (3), formula (4), formula (5), formula (6); the formula (1), formula (2), formula (3)), formula (4), formula (5), formula (6) are as follows:

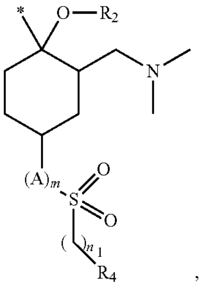

(1)

,

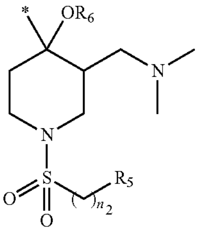

(2)

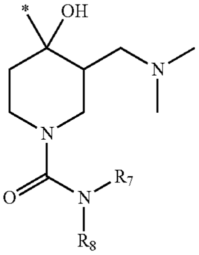

(3)

,

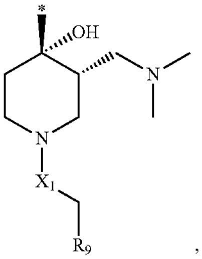

(4)

,

-continued (5)

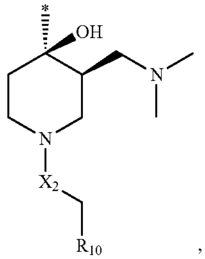

, (6)

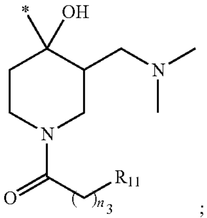

;

$R_1$ is hydrogen, C1-6 alkyl, fluoroalkyl, cycloalkyl, alkenyl, alkenyl, cycloalkenyl, substituted or unsubstituted aryl C1-6 alkyl;

$R_2$ is hydrogen, C1-6 mono- or polysubstituted alkyl, C1-6 mono- or polysubstituted alkylacyl, substituted or unsubstituted arylacyl;

$R_4$ is substituted or unsubstituted aryl, substituted or unsubstituted heteroaryl;

$R_5$ is C1-6 alkyl, cycloalkyl, substituted or unsubstituted bridged cycloalkyl, substituted or unsubstituted aryl, substituted or unsubstituted heteroaryl;

$R_6$ is hydrogen, C1-6 alkyl, fluoroalkyl, cycloalkyl, chain alkenyl, cycloalkenyl, aryl C1-6 alkyl;

$R_7$ and $R_8$ are independently selected from hydrogen, C1-6 alkyl, cycloalkyl, chain alkenyl, cycloalkenyl, bridged cycloalkyl, bridged cycloalkylalkyl, substituted or unsubstituted aryl, substituted or unsubstituted substituted arylalkyl, substituted or unsubstituted heteroaryl, or substituted or unsubstituted heteroarylalkyl;

$R_9$ and $R_{10}$ are each independently selected from substituted or unsubstituted aryl, substituted or unsubstituted heteroaryl, and their substituents can be selected from aryl, halogen, C1-6 alkyl, cyano, alkoxy, amino, nitro, alkanesulfonyl, ester, trifluoromethyl, trifluoromethoxy, difluoromethoxy, methoxy, fluorine, nitro, phenolic hydroxyl;

$R_{11}$ is substituted or unsubstituted aryl, substituted or unsubstituted arylalkyl, substituted or unsubstituted heteroaryl, substituted or unsubstituted arylcycloalkyl;

A is $CH_2$ or $NR_3$, m=0 or 1, wherein $R_3$ is hydrogen, C1-6 alkyl, substituted or unsubstituted arylalkyl;

$n_1$=0 or 1; $n_2$=0, 1, 2 or 3; $n_3$=0, 1 or 2.

$X_1$ and $X_2$ are independently selected from

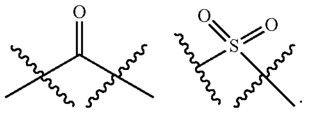

As a preferred technical solution, the compound represented by formula (I) in the present invention, or a pharmaceutically acceptable salt thereof, is selected from:

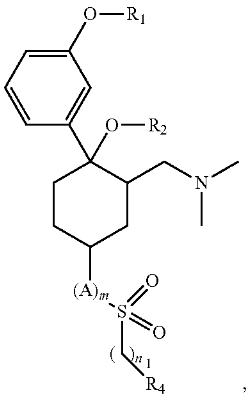

,

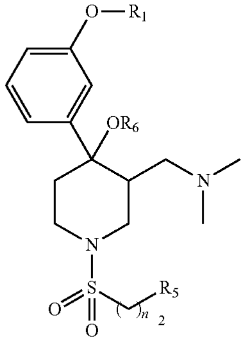

,

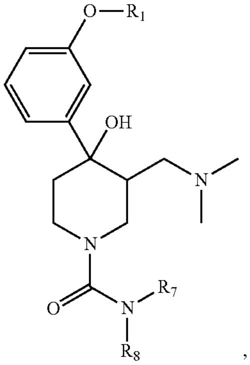

,

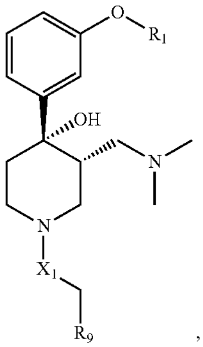

,

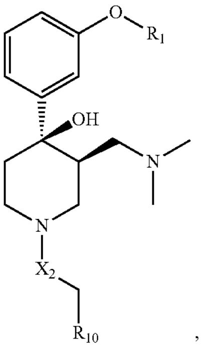

,

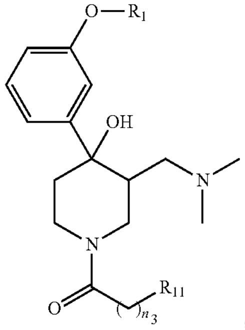

;

$R_1$ is hydrogen, C1-6 alkyl, fluoroalkyl, cycloalkyl, alkenyl, alkenyl, cycloalkenyl, substituted or unsubstituted aryl C1-6 alkyl; $R_2$ is hydrogen, C1-6 mono- or polysubstituted alkyl, C1-6 mono- or polysubstituted alkylacyl, substituted or unsubstituted arylacyl; $R_4$ is substituted or unsubstituted aryl, substituted or unsubstituted heteroaryl; $R_5$ is C1-6 alkyl, cycloalkyl, substituted or unsubstituted bridged cycloalkyl, substituted or unsubstituted aryl, substituted or unsubstituted heteroaryl; $R_6$ is hydrogen, C1-6 alkyl, fluoroalkyl, cycloalkyl, chain alkenyl, cycloalkenyl, aryl C1-6 alkyl; $R_7$ and $R_8$ are independently selected from hydrogen, C1-6 alkyl, cycloalkyl, chain alkenyl, cycloalkenyl, bridged cycloalkyl, bridged cycloalkylalkyl, substituted or unsubstituted aryl, substituted or unsubstituted substituted arylalkyl, substituted or unsubstituted heteroaryl, or substituted or unsubstituted heteroarylalkyl; $R_9$ and $R_{10}$ are each independently selected from substituted or unsubstituted aryl, substituted or unsubstituted heteroaryl, and their substituents can be selected from aryl, halogen, C1-6 alkyl, cyano, alkoxy, amino, nitro, alkanesulfonyl, ester, trifluoromethyl, trifluoromethoxy, difluoromethoxy, methoxy, fluorine, nitro, phenolic hydroxyl; Ru is substituted or unsubstituted aryl, substituted or unsubstituted arylalkyl, substituted or unsubstituted heteroaryl, substituted or unsubstituted arylcycloalkyl; A is $CH_2$ or $NR_3$, m=0 or 1, wherein $R_3$ is hydrogen, C1-6 alkyl, substituted or unsubstituted arylalkyl; $n_1$=0 or 1; $n_2$=0, 1, 2 or 3; $n_3$=0, 1 or 2. $X_1$ and $X_2$ are independently selected from

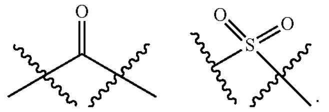

As a preferred technical scheme, in the present invention, $R_1$ is hydrogen, C1-6 alkyl, trifluoromethyl, substituted or unsubstituted aryl C1-6 alkyl; $R_2$ is hydrogen, benzoyl, substituted or unsubstituted arylacyl; A is $CH_2$ or $NR_3$, m=0 or 1, wherein $R_3$ is hydrogen, methyl, benzyl; $R_4$ is phenyl, halogen-substituted phenyl, thienyl; $R_5$ is methyl, ethyl, isopropyl, allyl, substituted or unsubstituted phenyl, substituted or unsubstituted bridged cycloalkyl; Re is hydrogen, C1-6 alkyl, fluoroalkyl; one of $R_7$ and $R_8$ is hydrogen or methyl, and the other is substituted or unsubstituted aryl, substituted or unsubstituted arylmethyl, substituted or unsubstituted arylethyl, bridged ring alkyl, bridged cycloalkylalkyl, substituted or unsubstituted heteroaryl, or substituted or unsubstituted heteroarylalkyl; $R_9$, $R_{10}$ are independently selected from substituted or unsubstituted aryl; $R_{11}$ is thienyl, indolyl, tetrazolyl, substituted or unsubstituted aryl, the substituent in the substituted aryl is halogen, trifluoromethyl, nitro, cyano or trifluoromethoxy.

As a preferred technical scheme, in the present invention, $R_1$ is hydrogen, C1-6 alkyl, trifluoromethyl; $R_2$ is hydrogen or benzoyl; $R_3$ is hydrogen, methyl, benzyl; $R_4$ is selected from phenyl, thienyl; $R_5$ is methyl, ethyl, isopropyl, allyl; $R_6$ is hydrogen, fluoroalkyl; one of $R_7$, $R_8$ is hydrogen or methyl, the other is substituted or unsubstituted aryl, substituted or unsubstituted arylmethyl, substituted or unsubstituted arylethyl, adamantyl, hydroxyadamantyl, adamantylethyl base, substituted or unsubstituted heteroaryl, or substituted or unsubstituted heteroarylalkyl; $R_9$, $R_{10}$ are independently selected from phenyl or 2,4,5-trifluorophenyl; $R_{11}$ is thienyl, indolyl, tetrazolyl, substituted or unsubstituted arylcycloalkyl, and the cycloalkyl in the arylcycloalkyl is cyclopropyl, cyclobutyl, cyclopentyl, or cyclohexyl.

As a preferred technical scheme, the compound represented by formula (I) in the present invention is selected from:

2-((dimethylamino) methyl)-1-(3-methoxyphenyl)-4-(phenylsulfonyl)cyclohexyl benzoate;
N-(3-((dimethylamino)methyl)-4-hydroxy-4-(3-methoxyphenyl)cyclohexyl) benzenesulfonamide;
4-((3-chlorophenyl)sulfonamido)-2-((dimethylamino) methyl)-1-(3-methoxyphenyl) cyclohexyl benzoate;
3-chloro-N-(3-((dimethylamino)methyl)-4-hydroxy-4-(3-methoxyphenyl)cyclohexyl) benzenesulfonamide;
2-((dimethylamino)methyl)-1-(3-methoxyphenyl)-4-(thiophene-2-sulfonamido)cyclohexyl benzoate;
N-(3-((dimethylamino)methyl)-4-hydroxy-4-(3-methoxyphenyl)cyclohexyl)thiophene-2-sulfonamide;
N-(3-((dimethylamino)methyl)-4-hydroxy-4-(3-methoxyphenyl)cyclohexyl)thiophene-2-sulfonamide;
2-((dimethylamino)methyl)-1-(3-methoxyphenyl)-4-((phenylmethyl)sulfonamido)cyclohexyl benzoate;
N-(3-((dimethylamino)methyl)-4-hydroxy-4-(3-methoxyphenyl)cyclohexyl)-1-benzenesulfonamide hydrochloride;
4-(((3-chlorophenyl)methyl)sulfonamido)-2-((dimethylamino)methyl)-1-(3-methoxyphenyl) cyclohexyl benzoate;
1-(3-chlorophenyl)-N-(3-((dimethylamino)methyl)-4-hydroxy-4-(3-methoxyphenyl) cyclohexyl)methanesulfonamide;
2-((dimethylamino)methyl)-1-(3-methoxyphenyl)-4-(N-methylbenzenesulfonamido) cyclohexyl benzoate;
N-(3-((dimethylamino)methyl)-4-hydroxy-4-(3-methoxyphenyl)cyclohexyl)-N-methylbenzenesulfonamide;
4-((3-chloro-N-methylphenyl)sulfonamido)-2-((dimethylamino)methyl)-1-(3-methoxyphenyl)cyclohexyl benzoate;
3-chloro-N-(3-((dimethylamino)methyl)-4-hydroxy-4-(methoxyphenyl)cyclohexyl)-N-methylbenzenesulfonamide;
2-((dimethylamino)methyl)-1-(3-methoxyphenyl)-4-(N-methylthiophene-2-sulfonamido)cyclohexyl benzoate;
N-(3-((dimethylamino)methyl)-4-hydroxy-4-(3-methoxyphenyl)cyclohexyl)-N-methylthiophene-2-sulfonamide;
2-((dimethylamino)methyl)-1-(3-methoxyphenyl)-4-((N-methyl-1-benzyl)sulfonamido) cyclohexyl benzoate;
N-(3-((dimethylamino)methyl)-4-hydroxy-4-(3-methoxyphenyl)cyclohexyl)-N-methyl-1-phenylmethanesulfonamide;
4-((1-(3-chlorophenyl)-N-methyl)sulfonamido)-2-((dimethylamino)methyl)-1-(3-methoxyphenyl) cyclohexyl benzoate;
N-benzyl-N-(3-((dimethylamino)methyl)-4-hydroxy-4-(3-methoxyphenyl)cyclohexyl) benzenesulfonamide;
N-benzyl-3-chloro-N-(3-((dimethylamino)methyl)-4-hydroxy-4-(3-methoxyphenyl) cyclohexyl)benzenesulfonamide;
N-benzyl-N-(3-((dimethylamino)methyl)-4-hydroxy-4-(3-methoxyphenyl)cyclohexyl) thiophene-2-sulfonamide;
4-(benzylsulfonyl)-2-((dimethylamino)methyl)-1-(3-methoxyphenyl)cyclohexan-1-ol;
2-((dimethylamino)methyl)-1-(3-methoxyphenyl)-4-((phenylsulfonyl)methyl)cyclohex-1-ol.

As a preferred technical scheme, the compound represented by formula (I) in the present invention is selected from:

1-(benzylsulfonyl)-3-((dimethylamino)methyl)-4-(3-methoxyphenyl)piperidin-4-ol;
1-((3-chlorobenzyl)sulfonyl)-3-((dimethylamino)methyl)-4-(3-methoxyphenyl)piperidin-4-ol;
3-((dimethylamino)methyl)-4-(3-methoxyphenyl)-1-((4-methylbenzyl)sulfonyl)piperidin-4-ol;
3-((dimethylamino)methyl)-4-(3-methoxyphenyl)-1-(phenylethylsulfonyl)piperidin-4-ol;
3-((dimethylamino)methyl)-4-(3-methoxyphenyl)-1-((3-(trifluoromethyl)benzyl)sulfonyl) piperidin-4-ol;
1-((4-chlorobenzyl)sulfonyl)-3-((dimethylamino)methyl)-4-(3-methoxyphenyl)piperidin-4-ol;
3-((dimethylamino)methyl)-1-((4-fluorobenzyl)sulfonyl)-4-(3-methoxyphenyl)piperidin-4-ol;
1-((3-bromobenzyl)sulfonyl)-3-((dimethylamino)methyl)-4-(3-methoxyphenyl)piperidin-4-ol;
3-((dimethylamino)methyl)-1-((2-fluorobenzyl)sulfonyl)-4-(3-methoxyphenyl)piperidin-4-ol;
1-(butylsulfonyl)-3-((dimethylamino)methyl)-4-(3-methoxyphenyl)piperidin-4-ol;
3-((dimethylamino)methyl)-4-(3-methoxyphenyl)-1-((3-nitrobenzyl)sulfonyl)piperidin-4-ol:
3-((dimethylamino)methyl)-4-(3-methoxyphenyl)-1-(phenylsulfonyl)piperidin-4-ol;

3-((dimethylamino)methyl)-4-(3-methoxyphenyl)-1-((4-(trifluoromethyl)benzyl)sulfonyl) piperidin-4-ol;

3-((dimethylamino)methyl)-1-(ethylsulfonyl)-4-(3-methoxyphenyl)piperidin-4-ol;

3-((dimethylamino)methyl)-4-(3-methoxyphenyl)-1-(propylsulfonyl)piperidin-4-ol;

3-((dimethylamino)methyl)-1-(isopropylsulfonyl)-4-(3-methoxyphenyl)piperidin-4-ol;

1-(allylsulfonyl)-3-((dimethylamino)methyl)-4-(3-methoxyphenyl)piperidin-4-ol;

(1R,4S)-1-(((3-((dimethylamino)methyl)-4-hydroxy-4-(3-methoxyphenyl)piperidin-1-yl)sulfonyl)methyl)-7,7-dimethylbicyclo[2.2.1]heptan-2-one;

3-((dimethylamino)methyl)-1-((((1R,4S)-2-hydroxy-7,7-dimethylbicyclo[2.2.1]hept-1-yl)methyl)sulfonyl)-4-(3-methoxyphenyl)piperidin-4-ol;

3-((dimethylamino)methyl)-4-(3-methoxyphenyl)-1-(methanesulfonyl)piperidin-4-ol;

(1S,4R)-1-(((3-((dimethylamino)methyl)-4-hydroxy-4-(3-methoxyphenyl)piperidin-1-yl)sulfonyl)methyl)-7,7-dimethylbicyclo[2.2.1]heptan-2-one;

3-((dimethylamino)methyl)-1-((((1S,4R)-2-hydroxy-7,7-dimethylbicyclo[2.2.1]hept-1-yl) methyl)sulfonyl)-4-(3-methoxyphenyl) piperidin-4-ol;

1-(benzylsulfonyl)-3-((dimethylamino)methyl)-4-(3-(Trifluoromethoxy)phenyl)piperidin-4-ol;

1-(1-(benzylsulfonyl)-4-(difluoromethoxy)-4-(3-methoxyphenyl)piperidin-3-yl)-N,N-dimethylaminomethylamine.

As a preferred technical scheme, the compound represented by formula (I) in the present invention is selected from:

3-((dimethylamino)methyl)-4-hydroxy-4-(3-methoxyphenyl)-N-phenylpiperidinyl-1-carboxamide;

N-(3-chlorophenyl)-3-((dimethylamino)methyl)-4-hydroxy-4-(3-methoxyphenyl)piperidine-1-carboxamide;

N-(3-chlorophenyl)-3-((dimethylamino)methyl)-4-hydroxy-4-(3-methoxyphenyl)-N-methylpiperidine-1-carboxamide;

N-(4-chlorophenyl)-3-((dimethylamino)methyl)-4-hydroxy-4-(3-methoxyphenyl)piperidine-1-carboxamide;

N-(3,4-dichlorophenyl)-3-((dimethylamino)methyl)-4-hydroxy-4-(3-methoxyphenyl) piperidine-1-carboxamide;

3-((dimethylamino)methyl)-4-hydroxy-4-(3-methoxyphenyl)-N-(3,4,5-trichlorophenyl) piperidine-1-carboxamide;

3-((dimethylamino)methyl)-N-(3-fluorophenyl)-4-hydroxy-4-(3-methoxyphenyl)piperidine-1-carboxamide;

N-(3,4-difluorophenyl)-3-((dimethylamino)methyl)-4-hydroxy-4-(3-methoxyphenyl) piperidine-1-carboxamide;

N-(3-chloro-4-fluorophenyl)-3-((dimethylamino) methyl)-4-hydroxy-4-(3-methoxyphenyl) piperidine-1-carboxamide;

N-(3,5-bis(trifluoromethyl)phenyl)-3-((dimethylamino) methyl)-4-hydroxy-4-(3-methoxyphenyl)piperidine-1-carboxamide;

3-((dimethylamino)methyl)-4-hydroxy-4-(3-methoxyphenyl)-N-(naphthalen-2-yl)piperidine-1-carboxamide;

N-benzyl-3-((dimethylamino)methyl)-4-hydroxy-4-(3-methoxyphenyl)piperidine-1-carboxamide;

3-((dimethylamino)methyl)-4-hydroxy-4-(3-methoxyphenyl)-N-((S)-1-phenylethyl) piperidine-1-carboxamide;

N-((3s,5s,7s)-adamantan-1-yl)-3-((dimethylamino)methyl)-4-hydroxy-4-(3-methoxyphenyl) piperidine-1-carboxamide;

N-(1-((3r,5r,7r)-adamantan-1-yl)ethyl)-3-((dimethylamino) methyl)-4-hydroxy-4-(3-methoxyphenyl)piperidine-1-carboxamide;

3-((dimethylamino)methyl)-4-hydroxy-N-((1r,3s,5R,7S)-3-hydroxyadamantan-1-yl)-4-(3-methoxyphenyl)piperidine-1-carboxamide;

Methyl 3-(3-((dimethylamino) methyl)-4-hydroxy-4-(3-methoxyphenyl) piperidine-1-carboxamide) thiophene-2-carboxylate;

Methyl 2-(3-((dimethylamino)methyl)-4-hydroxy-4-(3-methoxyphenyl)piperidine-1-carboxamide) thiophene-3-carboxylate;

3-((dimethylamino)methyl)-4-hydroxy-4-(3-methoxyphenyl)-N-(thiophen-2-yl)piperidine-1-carboxamide.

As a preferred technical scheme, the compound represented by formula (I) in the present invention is selected from:

1-((3R,4S)-3-((dimethylamino)methyl)-4-hydroxy-4-(3-methoxyphenyl)piperidin-1-yl)-2-(2,4,5-trifluorophenyl) ethyl-1-one;

1-((3R,4S)-3-((dimethylamino)methyl)-4-hydroxy-4-(3-hydroxyphenyl)piperidin-1-yl)-2-(2,4,5-trifluorophenyl) ethyl-1-one;

(3R,4S)-1-(benzylsulfonyl)-3-((dimethylamino)methyl)-4-(3-methoxyphenyl)piperidin-4-ol:

(3R,4S)-1-(benzylsulfonyl)-3-((dimethylamino)methyl)-4-(3-hydroxyphenyl)piperidin-4-ol.

As a preferred technical scheme, the compound represented by formula (I) in the present invention is selected from:

1-((3S,4R)-3-((dimethylamino)methyl)-4-hydroxy-4-(3-methoxyphenyl)piperidin-1-yl)-2-(2,4,5-trifluorophenyl) ethyl-1-one;

1-((3S,4R)-3-((dimethylamino)methyl)-4-hydroxy-4-(3-hydroxyphenyl)piperidin-1-yl)-2-(2,4,5-trifluorophenyl) ethyl-1-one;

(3S,4R)-1-(benzylsulfonyl)-3-((dimethylamino)methyl)-4-(3-methoxyphenyl)piperidin-4-ol; (3S,4R)-1-(benzylsulfonyl)-3-((dimethylamino)methyl)-4-(3-hydroxyphenyl)piperidin-4-ol.

As a preferred technical scheme, the compound represented by formula (I) in the present invention is selected from:

1-(3-((dimethylamino)methyl)-4-hydroxy-4-(3-methoxyphenyl)piperidin-1-yl)-2-(thiophen-3-yl)ethyl-1-one;

2-(3,5-bis(trifluoromethyl)phenyl)-1-(3-((dimethylamino) methyl)-4-hydroxy-4-(3-methoxyphenyl) piperidin-1-yl) ethyl-1-one;

1-(3-((dimethylamino)methyl)-4-hydroxy-4-(3-methoxyphenyl)piperidin-1-yl)-2-phenylethyl-1-one;

1-(3-((dimethylamino)methyl)-4-hydroxy-4-(3-methoxyphenyl)piperidin-1-yl)-2-(3-(trifluoromethyl)phenyl) ethyl-1-one;

(3-((dimethylamino)methyl)-4-hydroxy-4-(3-methoxyphenyl)piperidin-1-yl)(2,4,5-trifluorophenyl)methanone;

1-(3-((dimethylamino)methyl)-4-hydroxy-4-(3-methoxyphenyl)piperidin-1-yl)-2-(3-(trifluoromethoxy)phenyl) ethyl-1-one;

1-(3-((dimethylamino)methyl)-4-hydroxy-4-(3-methoxyphenyl)piperidin-1-yl)-2-(1H-tetrazol-1-yl)ethyl-1-one;

1-(3-((dimethylamino)methyl)-4-hydroxy-4-(3-methoxyphenyl)piperidin-1-yl)-2-(thiophen-2-yl)ethyl-1-one;

2-(3-chlorophenyl)-1-(3-((dimethylamino)methyl)-4-hydroxy-4-(3-methoxyphenyl) piperidin-1-yl) ethyl-1-one;

1-(3-((dimethylamino)methyl)-4-hydroxy-4-(3-methoxyphenyl)piperidin-1-yl)-3-(3-(trifluoromethyl)phenyl)propyl-1-one;

1-(3-((dimethylamino)methyl)-4-hydroxy-4-(3-methoxyphenyl)piperidin-1-yl)-2-(3-fluorophenyl)ethyl-1-one;

2-(3-bromophenyl)-1-(3-((dimethylamino)methyl)-4-hydroxy-4-(3-methoxyphenyl) piperidin-1-yl)ethyl-1-one;
1-(3-((dimethylamino)methyl)-4-hydroxy-4-(3-methoxyphenyl)piperidin-1-yl)-2-(1H-indol-1-yl)ethyl-1-one;
1-(3-((dimethylamino)methyl)-4-hydroxy-4-(3-methoxyphenyl)piperidin-1-yl)-2-(naphthalen-2-yl)ethyl-1-one;
1-(3-((dimethylamino)methyl)-4-hydroxy-4-(3-methoxyphenyl)piperidin-1-yl)-2-(naphthalen-1-yl)ethyl-1-one;
2-(3,4-dichlorophenyl)-1-(3-((dimethylamino)methyl)-4-hydroxy-4-(3-methoxyphenyl) piperidin-1-yl)ethyl-1-one;
1-(3-((dimethylamino)methyl)-4-hydroxy-4-(3-methoxyphenyl)piperidin-1-yl)-2-(2,4,5-trifluorophenyl)ethyl-1-one;
2-(4-chlorophenyl)-1-(3-((dimethylamino)methyl)-4-hydroxy-4-(3-methoxyphenyl) piperidin-1-yl)ethyl-1-one;
2-(2-chlorophenyl)-1-(3-((dimethylamino)methyl)-4-hydroxy-4-(3-methoxyphenyl) piperidin-1-yl)ethyl-1-one;
1-(3-((dimethylamino)methyl)-4-hydroxy-4-(3-methoxyphenyl)piperidin-1-yl)-2-(3-nitrophenyl)ethyl-1-one;
3-(2-(3-((dimethylamino)methyl)-4-hydroxy-4-(3-methoxyphenyl)piperidin-1-yl)-2-oxoethyl) benzonitrile;
(3-((dimethylamino)methyl)-4-hydroxy-4-(3-methoxyphenyl)piperidin-1-yl)(1-phenylcyclopropyl)methanone;
1-(3-((dimethylamino)methyl)-4-hydroxy-4-(3-methoxyphenyl)piperidin-1-yl)-2-methyl-2-phenylpropyl-1-one;
(3-((dimethylamino)methyl)-4-hydroxy-4-(3-methoxyphenyl)piperidin-1-yl)(1-phenylcyclopentyl)methanone;
(3-((dimethylamino)methyl)-4-hydroxy-4-(3-methoxyphenyl)piperidin-1-yl)(1-phenylcyclohexyl)methanone;
(3-((dimethylamino)methyl)-4-hydroxy-4-(3-methoxyphenyl)piperidin-1-yl)(1-phenylcyclobutyl)methanone.

The present invention also provides pharmaceutically acceptable salts of the compounds of formula (I), which can be formed with inorganic or organic acids such as hydrochloride, hydrobromide, hydroiodide, sulfate or hydrogen sulfate, phosphate or hydrogen phosphate, acetate, benzoate, tartrate, succinate, maleate, fumarate, lactate, citrate, gluconate, mesylate, benzenesulfonate or p-toluenesulfonate, preferably hydrochloride.

The present invention also provides pharmaceutically acceptable solvates or hydrates of the compounds of formula (I).

The present invention also provides a pharmaceutical composition comprising: a compound of formula (I) or a pharmaceutically acceptable salt, solvate or hydrate thereof; and a pharmaceutically acceptable carrier.

The medicaments prepared from the above compounds can be used to treat or improve diseases related to opioid receptors. The disorder may be selected from, but not limited to, pain, gastrointestinal disorders, and depression. For example, pain can be selected from, but is not limited to, centrally mediated pain, peripherally mediated pain, pain associated with structural or soft tissue injury, pain associated with inflammation, pain associated with progressive disease, neuropathic pain, acute pain, and chronic pain.

This method can be accomplished by administering to the subject a therapeutically effective amount of a compound of formula (I) or a pharmaceutically acceptable salt, solvate or hydrate thereof.

Comcrete Manifestation

The technical solutions of the present invention will be described in detail below with reference to the accompanying drawings and embodiments, but the present invention is not limited to the scope of the described embodiments.

As used throughout this application, including the claims, unless specifically stated otherwise, the following terms have the meanings defined below as used herein.

The term "C1-C6 alkyl" refers to a saturated branched or straight chain alkyl group containing 1 to 6 carbon atoms, such as (but not limited to) methyl, ethyl, n-propyl, isopropyl, n-butyl, sec-butyl, isobutyl, tert-butyl, n-pentyl, isopentyl, neopentyl and n-hexyl.

The term "C1-6 mono- or polysubstituted alkyl" means that one or more hydrogen atoms in the alkyl groups C1-C6, as defined above, are substituted with a substituent selected from the group consisting of: Oh, halo, alkyloxy, dialkylamino, or heterocyclyl, such as morpholinyl, piperidinyl, and the like.

The term "C1-6 mono- or polysubstituted alkylacyl" refers to a "C1-6 mono- or polysubstituted alkyl" as defined above attached to the parent molecular moiety through a carbonyl group.

The term "cycloalkyl" refers to a cyclic saturated monovalent monocyclic or bicyclic hydrocarbon group of carbon atoms, such as cyclopropyl, cyclohexyl, or the like. The cycloalkyl group may be optionally substituted with one, two or three substituents selected from halogen atoms, hydroxyl groups, aryl groups.

The term "chain alkenyl" refers to an aliphatic hydrocarbon group having at least one carbon-carbon double bond, including straight or branched chain groups having at least one carbon-carbon double bond. It has, for example, 2 to 6 carbon atoms. Representative examples include, but are not limited to, vinyl, 1-propenyl, 2-propenyl (allyl), isopropenyl, 2-methyl-1-propenyl, 1-butenyl, 2-butanyl Alkenyl etc. When a compound of the present invention contains a C2-C6 chain alkenyl group, the compound may exist in pure E (entgegen) form, pure Z (zusammen) form, or any mixture thereof.

The term "cycloalkenyl" refers to the formation of a double bond group by removing an additional hydrogen atom at the cycloalkenyl group to give the corresponding cycloalkenyl group.

The term "aryl" refers to all carbon monocyclic or fused ring polycyclic aromatic groups, such as phenyl or naphthyl, containing 6 to 10 carbon atoms with a conjugated π-electron system.

The term "substituted or unsubstituted aryl" means that 0 to 3 hydrogen atoms on an aryl group are replaced by a substituent selected from the group consisting of aryl, halogen, C1-6 alkyl, cyano, alkoxy, amino, nitro, alkanesulfonyl, ester, trifluoromethyl, trifluoromethoxy, difluoromethoxy, methoxy, fluorine, nitro, phenolic hydroxyl.

The term "halo" or "halogen" refers to a chlorine, fluorine, bromine or iodine atom.

The term "substituted or unsubstituted arylacyl" refers to a "substituted or unsubstituted aryl" as defined above attached to the parent molecular moiety through a carbonyl group.

The term "substituted or unsubstituted arylalkyl" means that one or more hydrogen atoms in the C1-C6 alkyl as defined above are substituted with "substituted or unsubstituted aryl" as defined above.

The term "heteroaryl" refers to a monocyclic or fused ring polycyclic aromatic heterocyclic radical wherein one or more heteroatomic ring members (ring forming atoms) in at least one ring are each independently selected from the group consisting of oxygen (O), sulfur (S), and nitrogen (N). Examples of heteroaryls include (but are not limited to) 6-membered ring substituents such as pyridyl, pyrazinyl, pyrimidinyl, and pyridazinyl; 5-membered heteroaryl such as triazolyl, imidazolyl, furanyl, isoxazolyl, isothiazolyl, 1,2,3-, 1,2,4-, 1,2,5- or 1,3,4-oxadiazolyl, oxazolyl, thienyl, thiazolyl, isothiazolyl and pyrazolyl; 6/5-membered fused ring substituents such as indolyl, indazolyl, benzofuranyl, benzimidazolyl, benzothienyl, benzoxadiazolyl, benzothiazolyl, isobenzothiophenyl, benzimidazolyl, benzoisoxazolyl, benzoxazolyl, benzoxazolyl, benzodioxolyl, furanopyridyl, purinyl, imidazopyridinyl, imidazopyrimidinyl, pyrrolopyridinyl, pyrazolopyridinyl, pyrazolopyrimidinyl Thienopyridinyl, triazolopyrimidinyl, triazolopyridinyl (e.g., 5,6,7,8-tetrahydro [1,2,4] triazolo [1,5-a] pyridin-2-yl), and anthranilyl; And 6/6-membered fused ring substituents such as quinolinyl, isoquinolinyl, cinnolinyl, quinazolinyl, oxoalkyl, and 1,4-benzoxazinyl.

The term "substituted or unsubstituted heteroaryl" means that 0 to 3 hydrogen atoms on the heteroaryl group are substituted with a substituent selected from the group consisting of aryl, halogen, C1-6 alkyl, cyano, alkoxy, amino, nitro, alkanesulfonyl, ester, trifluoromethyl, trifluoromethoxy, difluoromethoxy, methoxy, fluorine, nitro, phenolic hydroxyl.

Unless otherwise specified, in the present invention, all occurrences of compounds are intended to include all possible isomers, such as tautomers, enantiomers, diastereomers, and mixtures thereof.

As one preferred technical scheme, the compound shown in formula (I) of the invention, or a pharmaceutically acceptable salt thereof, is selected from:

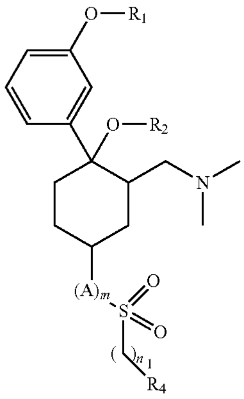

,

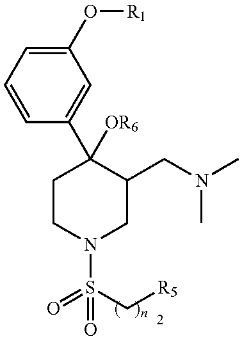

,

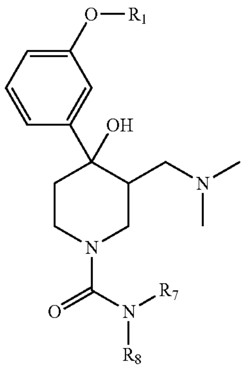

,

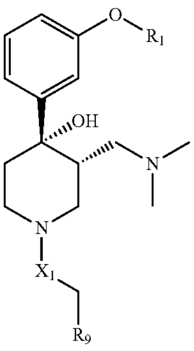

,

-continued

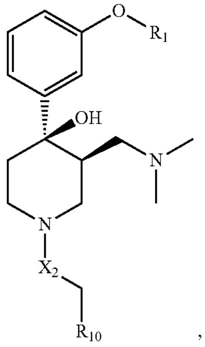

,

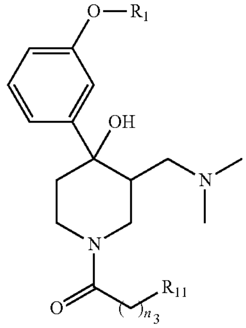

;

$R_1$ is hydrogen, C1-6 alkyl, fluoroalkyl, cycloalkyl, alkenyl, alkenyl, cycloalkenyl, substituted or unsubstituted aryl C1-6 alkyl; $R_2$ is hydrogen, C1-6 mono- or polysubstituted alkyl, C1-6 mono- or polysubstituted alkylacyl, substituted or unsubstituted arylacyl; $R_4$ is substituted or unsubstituted aryl, substituted or unsubstituted heteroaryl; $R_5$ is C1-6 alkyl, cycloalkyl, substituted or unsubstituted bridged cycloalkyl, substituted or unsubstituted aryl, substituted or unsubstituted heteroaryl; $R_6$ is hydrogen, C1-6 alkyl, fluoroalkyl, cycloalkyl, chain alkenyl, cycloalkenyl, aryl C1-6 alkyl; $R_7$ and $R_8$ are independently selected from hydrogen, C1-6 alkyl, cycloalkyl, chain alkenyl, cycloalkenyl, bridged cycloalkyl, bridged cycloalkylalkyl, substituted or unsubstituted aryl, substituted or unsubstituted substituted arylalkyl, substituted or unsubstituted heteroaryl, or substituted or unsubstituted heteroarylalkyl; $R_9$ and $R_{10}$ are each independently selected from substituted or unsubstituted aryl, substituted or unsubstituted heteroaryl, and their substituents can be selected from aryl, halogen, C1-6 alkyl, cyano, alkoxy, amino, nitro, alkanesulfonyl, ester, trifluoromethyl, trifluoromethoxy, difluoromethoxy, methoxy, fluorine, nitro, phenolic hydroxyl; $R_{11}$ is substituted or unsubstituted aryl, substituted or unsubstituted arylalkyl, substituted or unsubstituted heteroaryl, substituted or unsubstituted arylcycloalkyl; A is $CH_2$ or $NR_3$, m=0 or 1, wherein $R_3$ is hydrogen, C1-6 alkyl, substituted or unsubstituted arylalkyl; $n_1$=0 or 1; $n_2$=0, 1, 2 or 3; $n_3$=0, 1 or 2. $X_1$ and $X_2$ are independently selected from

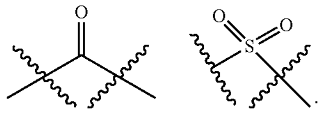

.

A "therapeutically effective amount" refers to an administered amount of a compound that alleviates to some extent one or more symptoms of the condition being treated.

The term "pharmaceutically acceptable carrier" refers to carriers that can be used in the preparation of pharmaceutical compositions, which are generally safe, non-toxic, not biologically or otherwise undesirable, and include those that are pharmaceutically acceptable to animals and humans a. "Pharmaceutically acceptable carrier" as used in the specification and claims includes one or more such carriers.

The pharmaceutical compositions described herein may be in liquid, semi-liquid or solid form, formulated in a manner suitable for the route of administration employed. The pharmaceutical compositions according to the invention may be administered in the following manner of administration: oral, parenteral, intraperitoneal, intravenous, transdermal, sublingual, intramuscular, rectal, buccal, intranasal, liposomal and the like.

Oral pharmaceutical compositions may be solid, gel or liquid. Examples of solid formulations include, but are not limited to, tablets, capsules, granules, and bulk powders. These formulations may optionally contain binders, diluents, disintegrants, lubricants, glidants, sweeteners and flavoring agents, and the like. Examples of binders include, but are not limited to, microcrystalline cellulose, glucose solutions, acacia mucilage, gelatin solutions, sucrose and starch pastes; examples of lubricants include, but are not limited to, talc, starch, magnesium stearate, calcium stearate, stearic acid; examples of diluents include, but are not limited to, lactose, sucrose, starch, mannitol, dicalcium phosphate; examples of glidants include, but are not limited to, silica; examples of disintegrants include, but are not limited to, croscarmellose sodium, sodium starch glycolate, alginic acid, corn starch, potato starch, methylcellulose, agar and carboxymethylcellulose.

The pharmaceutical compositions of the present invention can also be prepared as s sterile freeze-dried powder injection. Dissolving the compound in a sodium phosphate buffer solution containing glucose or other suitable excipients, and subsequently sterile filtering the solution under standard conditions known to those skilled in the art, followed by lyophilization, to give the desired formulation.

The term "formula (I)" or "compound of formula (I)" may be referred to as a "compound of the present invention". Such terms are also defined to include all forms of the compounds of the present invention, including hydrates, solvates, isomers, crystalline and non crystalline forms, isomorphs, polymorphs, and metabolites thereof.

The compound of formula (I) or a pharmaceutically acceptable salt thereof can be obtained by the following method.

The compounds of the present invention are generally named according to the IUPAC or CAS nomenclature system. Abbreviations known to those skilled in the art may be used (eg, "Ph" for phenyl, "Me" for methyl, "Et" for ethyl, "h" for hours, "r.t." for room temperature).

Method 1 is shown in the figure below, using tert-butyl 4-oxocyclohexylcarbamate as raw material, through Boc protection, Mannich reaction, Grignard reaction, removing a Boc, protecting a hydroxyl group, removing Boc, sulfonylation, and salification to obtain:

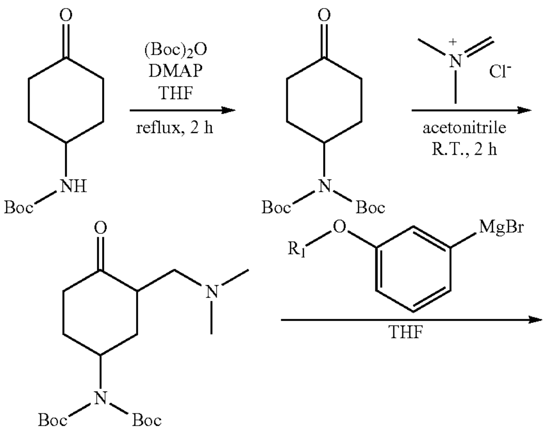

-continued

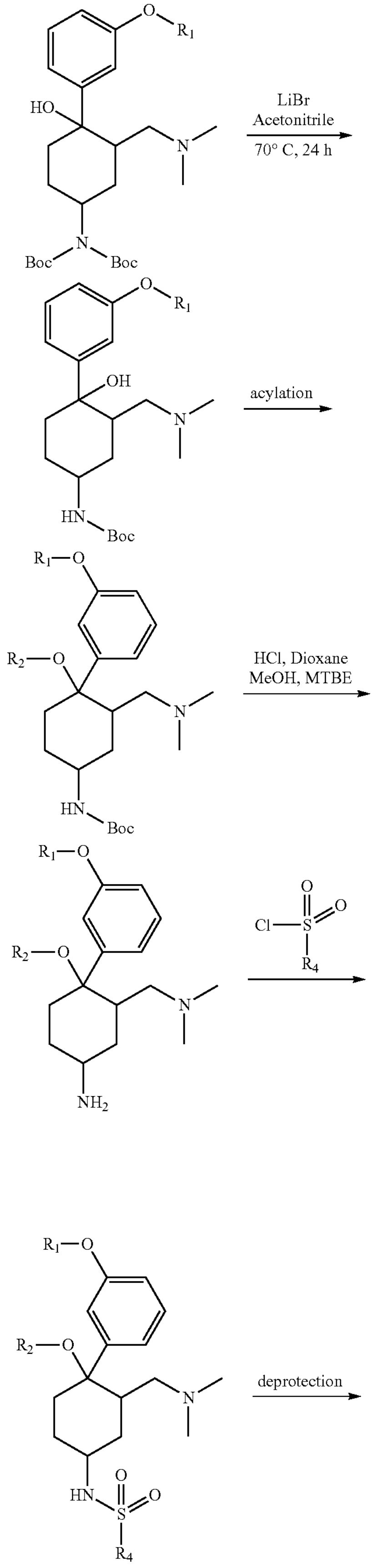

-continued

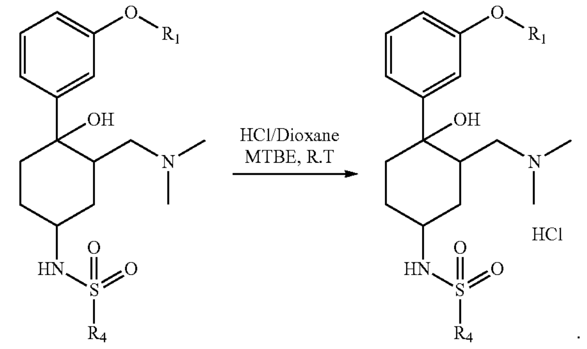

Method 2 is shown in the figure below, using 1,4-dioxospiro [4.5]decan-8-one as raw material, through reductive amination, deketalization, Boc protecting group, Mannich reaction, Grignard reaction, deBoc, N-Methylation, protection of hydroxyl groups, de-Boc, sulfoamidation, and salification to obtain; another method is to directly sulfonylate and salify after de-Boc to obtain.

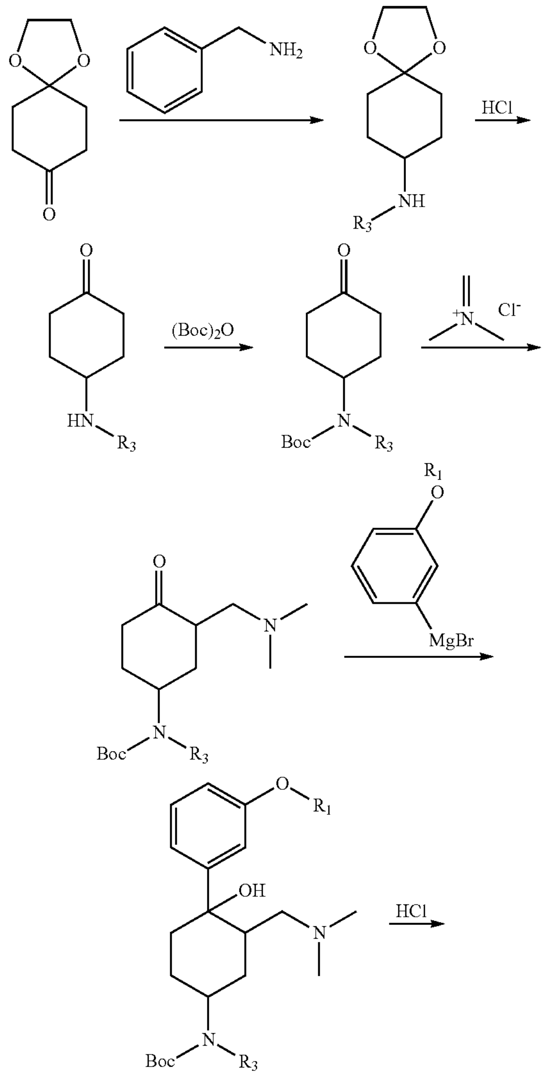

-continued

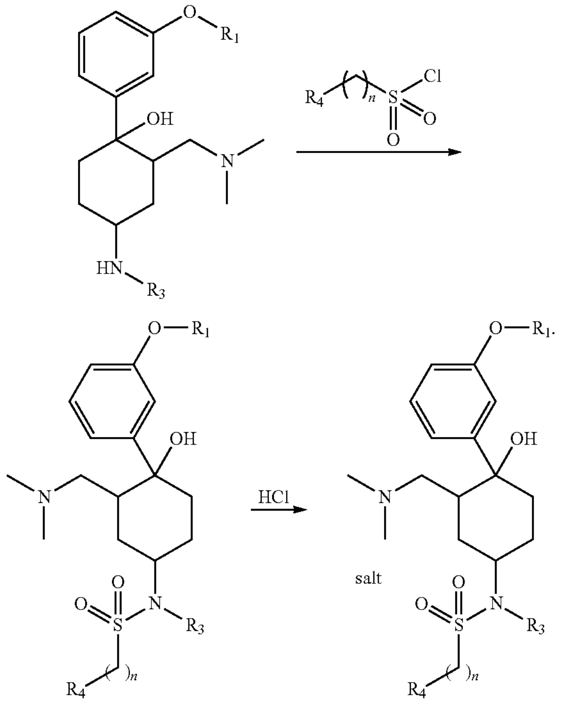

Method 3 is shown in the figure below, using 1,4-dioxospiro[4.5]dec-8-one as raw material, through reduction of carbonyl group, mesylation, nucleophilic substitution, oxidation of thioether bond, deprotection, Mannich reaction, Grignard reaction and salification to obtain.

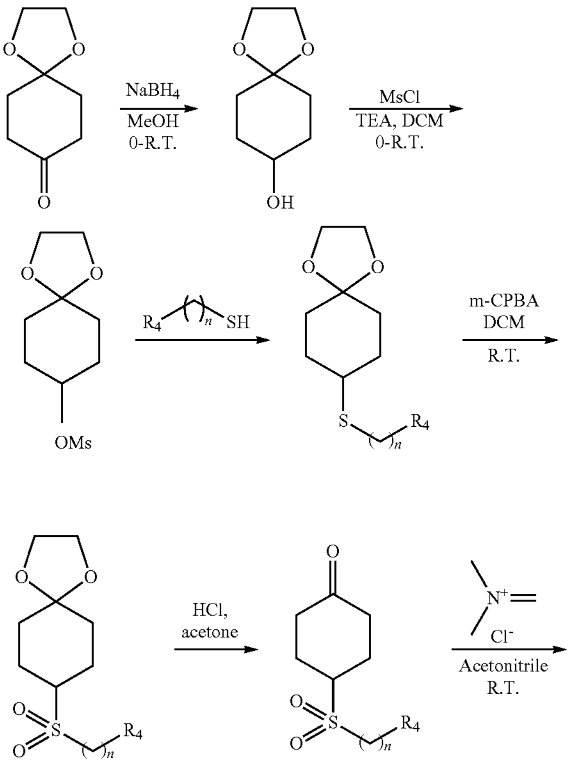

-continued

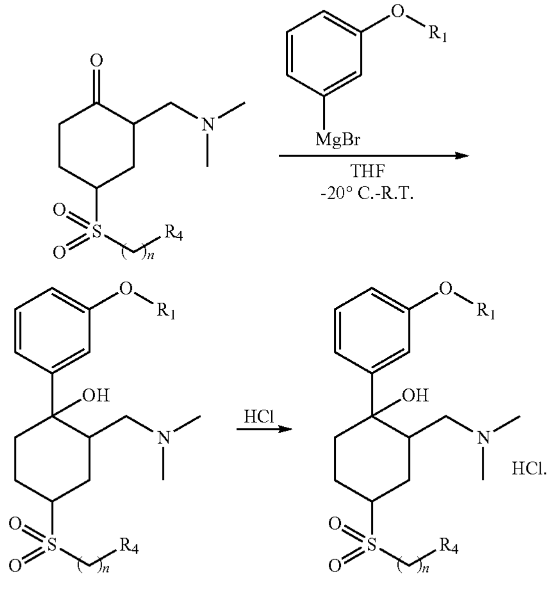

Method 4 is shown in the figure below, using 4-oxocyclohexane-1-ethyl carboxylate as raw material, protecting carbonyl group, reducing ester group, mesylation, nucleophilic substitution, oxidizing thioether to sulfone, Mannich reaction, Grignard reaction and salification to obtain.

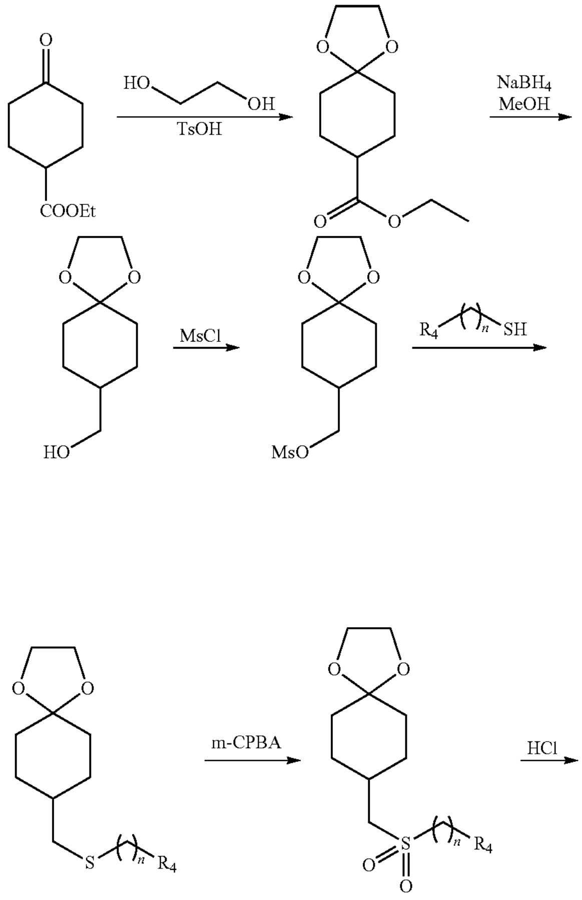

-continued

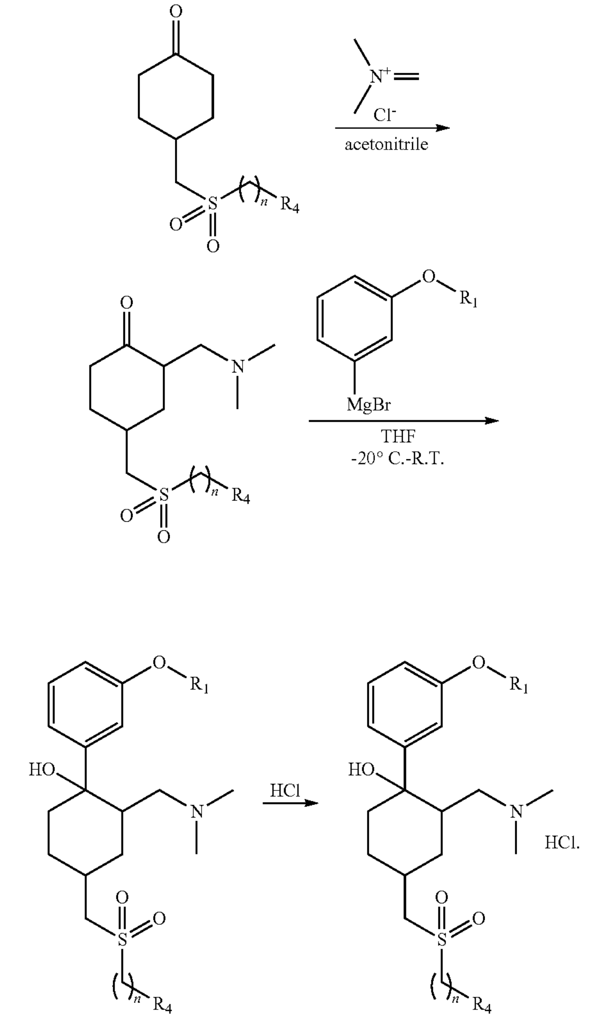

The definitions of substituents and groups in each reaction scheme are as described above.

The present invention also provides a method for synthesizing $R_0$ selected from compounds of formula (2), including Mannich reaction, Grignard nucleophilic addition, deprotection group Boc, upper protecting group TES, condensation with sulfonyl chloride, deprotection group, and salification and other procedures, as shown below.

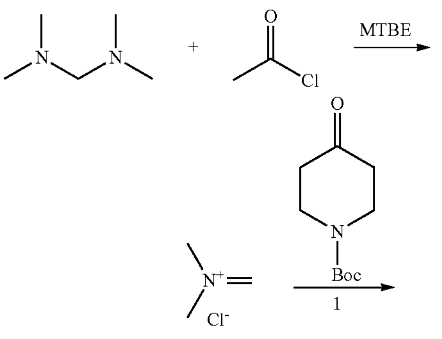

2

-continued

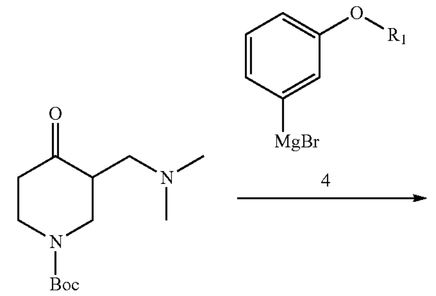

3

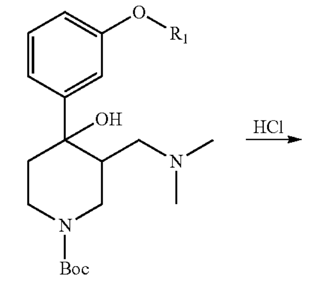

5

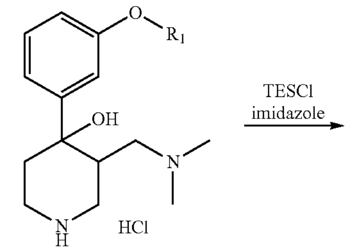

6

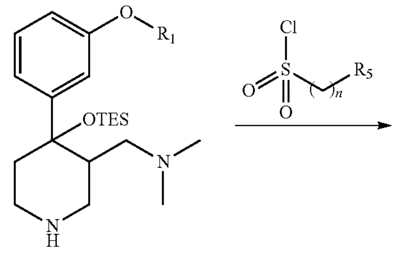

7

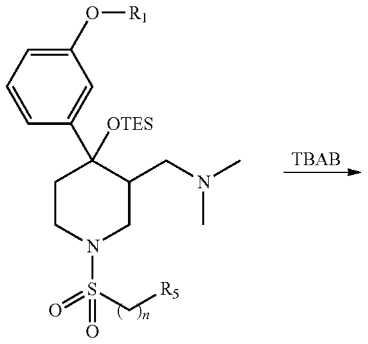

-continued

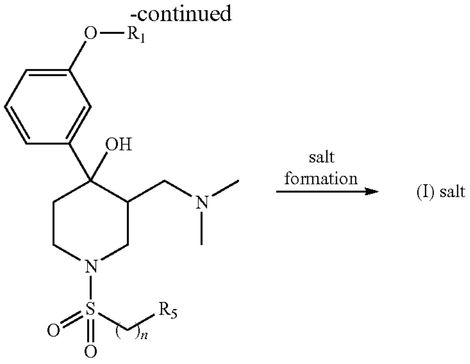

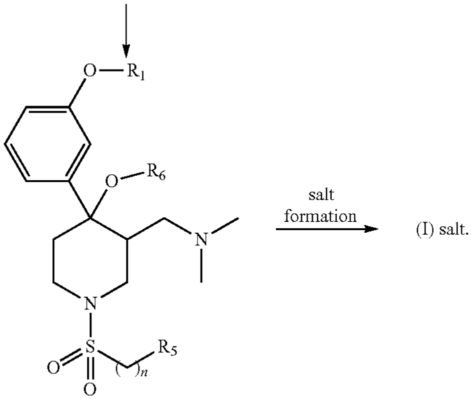

The definitions of substituents and groups in each reaction scheme are as described above.

The present invention also provides a method for synthesizing $R_0$ selected from the compound of formula (3), including the steps of Mannich reaction, Grignard nucleophilic addition, deprotection Boc, condensation, salification and other procedures.

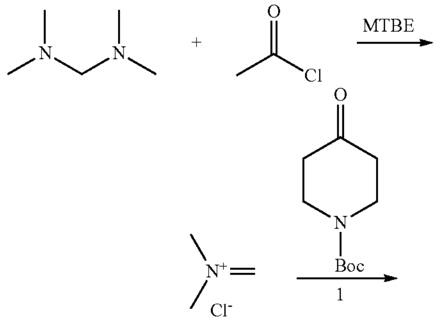

2

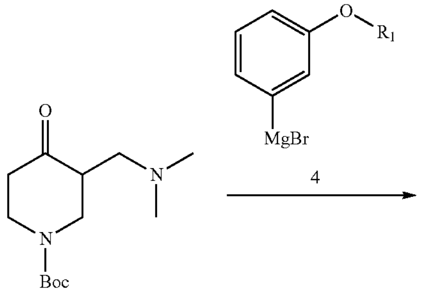

3

-continued

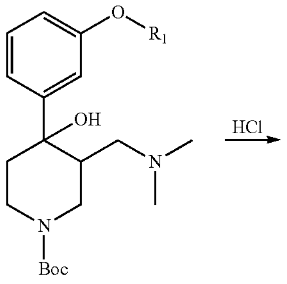

5

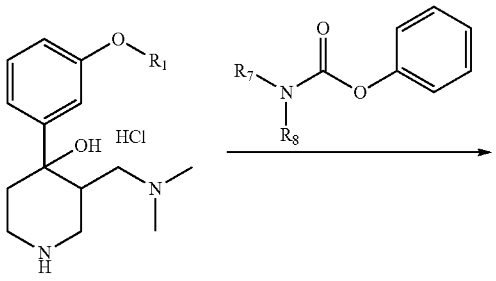

6

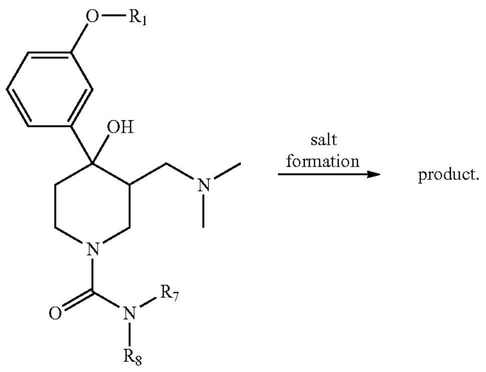

The definitions of substituents and groups in each reaction scheme are as described above.

The invention also provides a synthetic method of $R_0$ selected from the compound of formula (4) and formula (5) or its pharmaceutically acceptable salt, solvate or hydrate. When X1 and X2 are carbonyl groups, the preparation method thereof Including Mannich reaction, Grignard reagent nucleophilic addition, resolving agent resolution, deprotection Boc, condensation, salification and other steps; The enantiomer of compound 6 can be obtained by separating the mother liquor of compound 6 with a resolution agent of opposite configuration. The enantiomer of 6 can be modified by deprotecting Boc, condensation, salification and other steps to obtain the compound represented by formula (I).

The resolving agent can be selected from one of L-DBTA, D-DBTA, L-mandelic acid, D-mandelic acid, L-tartaric acid, D-tartaric acid, L-camphorsulfonic acid and D-camphorsulfonic acid. The separation solvent can be selected from one or more of methanol, ethanol, isopropanol, ethyl acetate and isopropyl acetate. The reaction temperature can be from room temperature to 120° C., preferably 60 to 90° C. The resolving agent to substrate ratio can range from 0.5 equivalents to 1.5 equivalents.

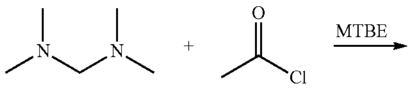

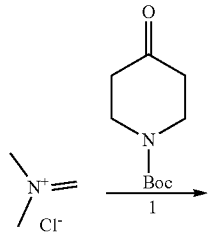

2

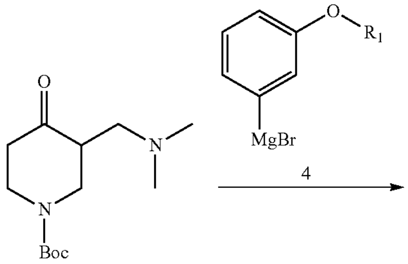

3

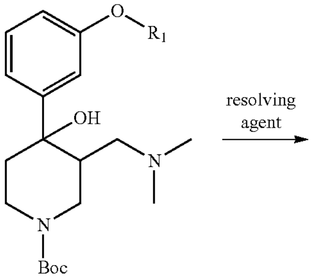

5

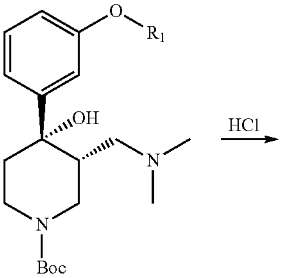

6

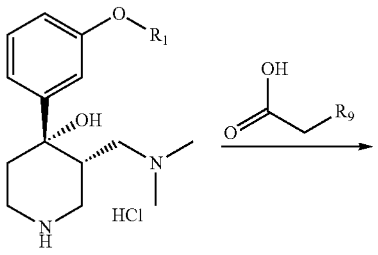

7

-continued

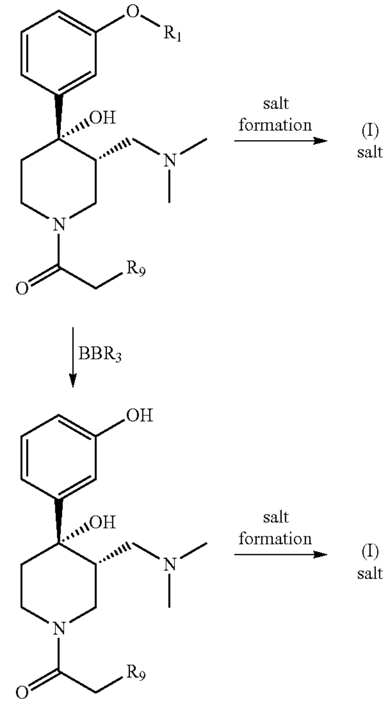

When $X_1$ and $X_2$ are sulfonyl groups, the preparation procedure includes benzoylation, deprotection Boc, condensation, hydrolysis, salification and other steps. The enantiomer of 6 is modified by benzoylation, deprotection Boc, condensation, hydrolysis, salification and other steps to obtain the compounds shown in formula (I).

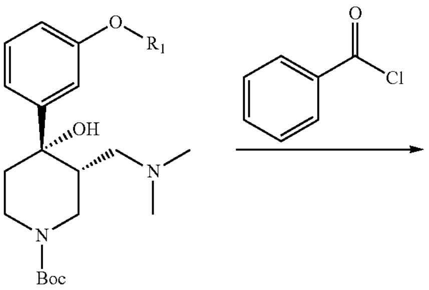

6

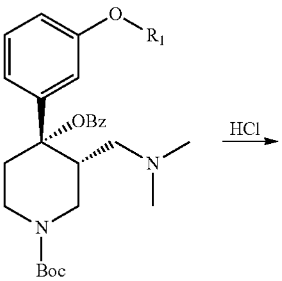

8

-continued

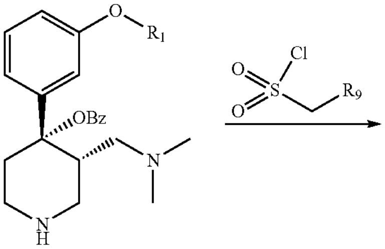

9

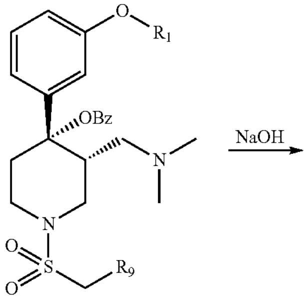

10

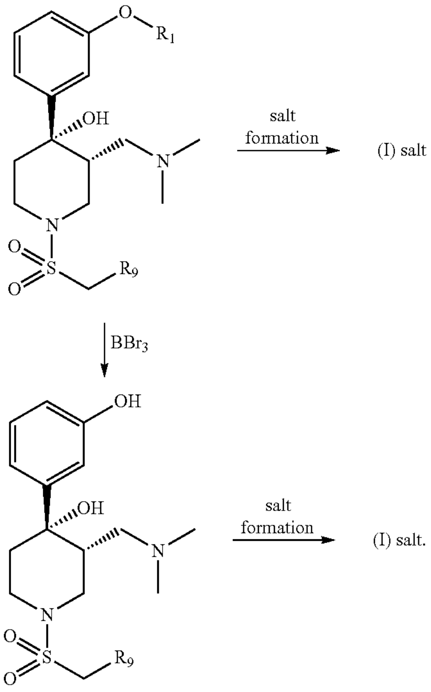

The definitions of substituents and groups in each reaction scheme are as described above.

The invention also provides a synthetic process for a compound whose $R_0$ is selected from formula (6), including the Mannich reaction, Grignard nucleophilic addition, deprotection Boc, condensation, salt formation and other steps.

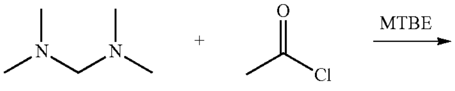

-continued

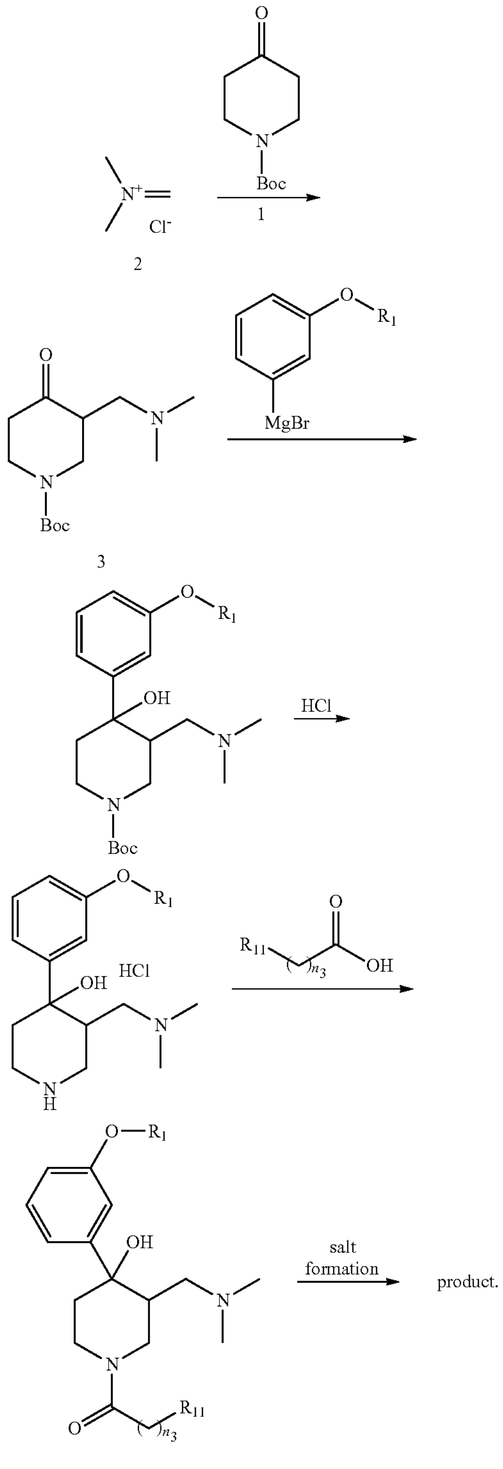

The invention is specifically described by examples below. It is necessary to point out here that the following examples, which are used only to make further illustrations of the invention, cannot be understood as being limits to the scope of protection of the invention, and some non-essential improvements and adjustment made by those skilled in the art according to the content of the present invention mentioned above, still belong to the protection scope of the present invention.

EXAMPLE 1

Example 1-1

4-[N,N-Bis(tert-butoxycarbonyl)]cyclohexyl ketone

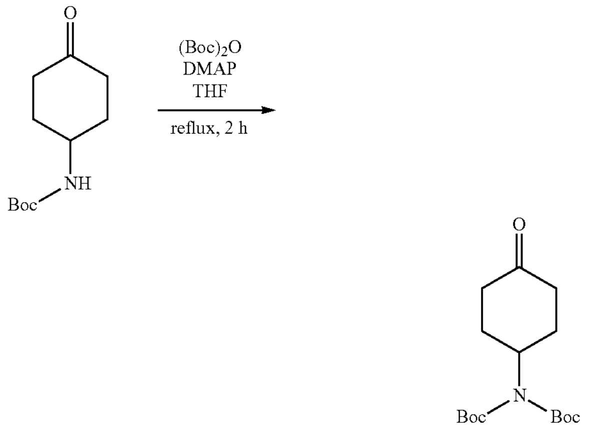

4-(Tert-butoxycarbonylamino)cyclohexanone (15 g, 70.33 mmol, 1 eq.), THF (150 mL), DMAP (8.6 g, 70.33 mmol, 1 eq.), triethylamine (14.23 g, 140.66 mmol, 2 eq.), $(Boc)_2O$ (46 g, 210.99 mmol, 3 eq.) were added to a 500 mL single-neck flask with a condenser tube and a nitrogen balloon, heated to reflux. After 2 h, TLC (DCM, developed by ninhydrin chromogenic reagent) showed that the reaction was complete. After cooling to room temperature, the THF was evaporated under reduced pressure. The mixture was stirred in a water bath for 30 min, filtered with suction, and the filter cake was rinsed with petroleum ether. The filtrates were combined and evaporated under reduced pressure to remove readily volatiles. Water (150 mL) and dichloromethane (100+100+80 mL) were added for extraction. The organic phases were combined, washed with water (120 mL), dried over anhydrous magnesium sulfate, filtered with suction, and the filtrate was evaporated under reduced pressure to obtain 37.45 g of brown liquid. Purified by silica gel column chromatography (PE~PE:DCM=6:1~1:1), 20.6 g of light yellow liquid was obtained, the yield was 93.5%. $^1H$ NMR (400 MHz, $CDCl_3$), δ 4.457~4.515 (m, 1H), 2.414~2.446 (m, 4H), 2.281~2.379 (m, 2H), 2.036~2.068 (m, 2H), 1.505 (s, 18H).

Example 1-2

2-(Dimethylaminomethyl)-4-[N,N-bis(tert-butoxycarbonyl)]cyclohexyl ketone

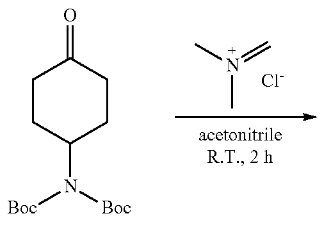

-continued

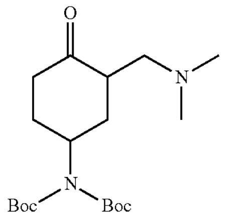

4-[N,N-bis(tert-butoxycarbonyl)]cyclohexyl ketone (16.3 g, 52.01 mmol, 1 eq.), acetonitrile (160 mL), salt (5.35 g, 57.21 mmol, 1.1 eq.) and acetyl chloride (204 mg, 2.6 mmol, 0.05 eq.) were added to a 250 mL single-neck flask, and stirred at room temperature. After 2 h, TLC (DCM:PE=4:1 and DCM:MeOH=10:1, developed by ninhydrin developer) showed that the reaction was complete. Saturated sodium bicarbonate solution (100 mL) was added, the acetonitrile was evaporated under reduced pressure, and the pH was adjusted to 8~9 with 2 mol/L NaOH solution. Extract with dichloromethane (100+100+50 mL). The organic phases were combined, washed with water (50 mL), washed with saturated sodium chloride solution (50 mL), dried over anhydrous magnesium sulfate, filtered with suction, and the filtrate was evaporated under reduced pressure to obtain 17.55 g of light yellow liquid with a yield of 91%.

Example 1-3

1-(3-Methoxyphenyl)-2-(dimethylaminomethyl)-4-[N,N-bis(tert-butoxycarbonyl)]cyclohexanol

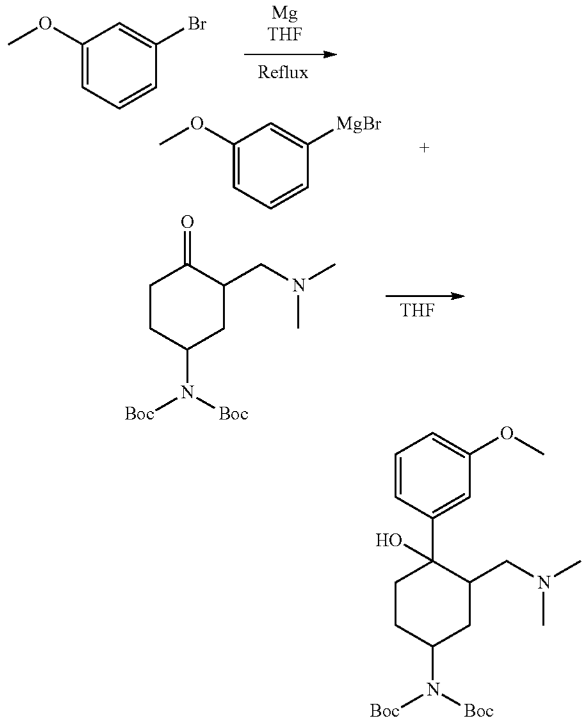

Magnesium chips (2.5 g, 104.21 mmol, 2.2 eq.), THF (75 mL), 1 grain of iodine, and a small amount of m-bromobenzene methyl ether (19.5 g, 104.21 mmol, 3 eq.) in THF (30 mL) were added to a 1 L four-necked flask with a nitrogen balloon, a constant pressure dropping funnel, a condenser tube and a thermometer and the reaction was initiated by warm reflux. When the reaction was initiated (yellow faded, lots of air bubbles), the heating was stopped. The remaining m-bromoanisole in THF was slowly added dropwise until the addition was complete. After the dropwise addition, the mixture was refluxed for 10 min, and the mixture was naturally cooled to room temperature with stirring. After cooling, 2-(dimethylaminomethyl)-4-[N,N-bis(tert-butoxycarbonyl)]cyclohexyl ketone (17.55 g, 47.37 mmol, 1 eq.) in THF (50 mL) solution was added dropwise at −20° C. After the dropwise addition was completed, the temperature was kept (−20~−10° C.) and stirred for 2 h. TLC (DCM:MeOH=25:1, 2 times, color development of ninhydrin chromogenic solution) showed the existence of raw materials. At −5° C., a saturated ammonium chloride solution (150 mL) was dropped into the reaction solution. The THF was evaporated under reduced pressure and extracted with ethyl acetate (100+100+50 mL). The organic phases were combined, washed with saturated sodium chloride (50 mL), dried over anhydrous magnesium sulfate, filtered with suction, and the filtrate was evaporated under reduced pressure to obtain 27.58 g of a pale yellow viscous substance. Purified by silica gel column chromatography (PE~EA:PE=1:6~1:1, with 0.5% CTEA), 7.06 g of colorless liquid was obtained, the yield was 31.2%. $^1$H NMR (400 MHz, $CDCl_3$), δ 7.228~7.268 (m, 1H), 7.008 (s, 1H), 7.118 (s, 1H), 6.762 (d, J=8 Hz, 1H), 4.094~4.188 (m, 1H), 3.812 (s, 3H), 2.693~2.785 (m, 1H), 2.289~2.437 (m, 2H), 2.123 (s, 6H), 1.946~1.984 (m, 1H), 1.575~1.796 (m, 4H), 1.533 (s, 18H), 1.344~1.470 (m, 2H).

Example 1-4

Tert-butyl(3-((dimethylamino)methyl)-4-hydroxy-4-(3-methoxyphenyl)cyclohexyl)carbamate

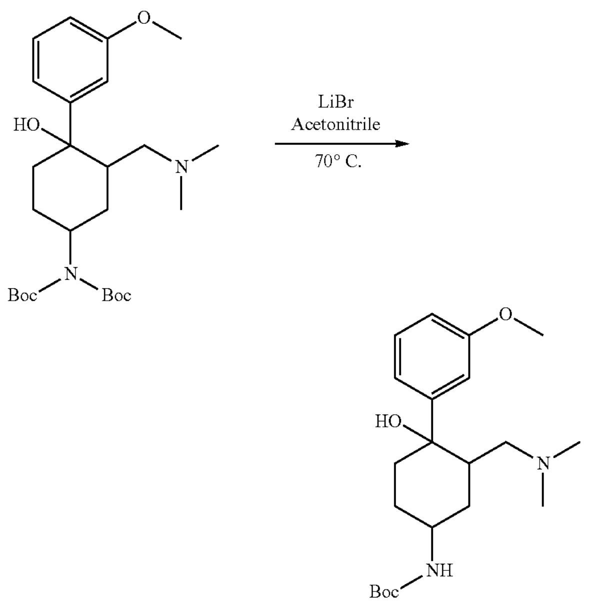

1-(3-Methoxyphenyl)-2-(dimethylaminomethyl)-4-[N,N-bis(tert-butoxycarbonyl)]cyclohexyl alcoho (5.68 g, 11.87 mmol, 1 eq.), acetonitrile (90 mL) were added to a 250 mL single-neck flask, stirred to dissolve, then lithium bromide (3.1 g, 35.61 mmol, 3 eq.) was added and the mixture was warmed up to 70° C. to react. After 24 h, TLC (DCM: MeOH=20:1) showed the existence of a small amount of raw material. The reaction was allowed to proceed for an additional 8 h, and TLC showed the reaction was mainly complete. After cooling to room temperature, acetonitrile was evaporated under reduced pressure, and water (50 mL) as well as ethyl acetate (50+50+20 mL) were added for extraction. The organic phases were combined, washed with saturated sodium chloride (20 mL), and the ethyl acetate was evaporated under reduced pressure to obtain 4.5 g of a pale yellow viscous substance with a yield of 100%. Crystallized with ethyl acetate:petroleum ether (1:1, 30 mL) to give 0.3 g of an off-white solid. The mother liquor was evaporated to dryness under reduced pressure and used directly in the next step. $^{1}$H NMR (400 MHz, $CDCl_3$), δ 7.265~7.275 (m, 1H), 7.081 (s, 1H), 6.994 (s, 1H), 6.811 (d, J=8 Hz, 1H), 3.830 (s, 3H), 3.654 (s, 1H), 3.247 (s, 1H), 2.685 (s, 3H), 2.596 (s, 3H), 2.277~2.432 (m, 4H), 1.804~2.046 (m, 4H), 1.445 (s, 9H).

Example 1-5

4-(Tert-Butoxycarbonylamino)-2-((dimethylamino) methyl)-1-(3-methoxyphenyl)cyclohexyl benzoate

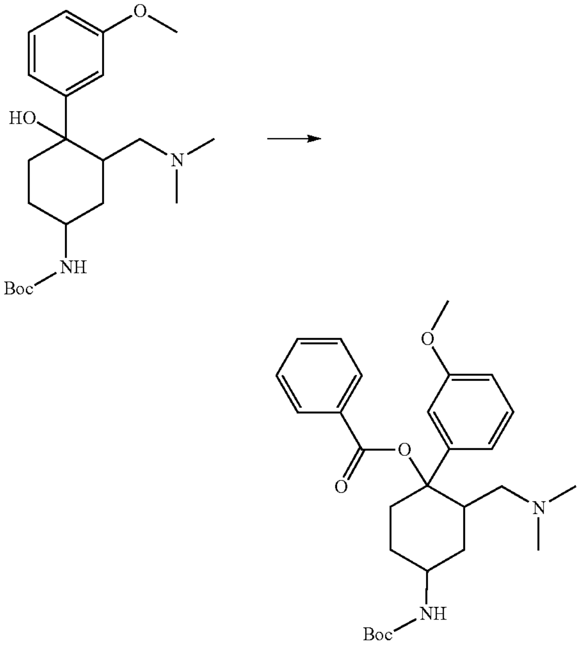

Tert-Butyl(3-((dimethylamino)methyl)-4-hydroxy-4-(3-methoxyphenyl)cyclohexyl)carbamate (4.4 g, 11.62 mmol, 1 eq.), dichloromethane (45 mL), triethylamine (3.53 g, 34.86 mmol, 3 eq.), DMAP (71 mg, 0.581 mmol, 0.05 eq.) were added to a 100 mL three-necked flask with a nitrogen balloon, thermometer and constant pressure dropping funnel, cooled down. Then benzoyl chloride (3.27 g, 23.25 mmol, 2 eq.) in dichloromethane (5 mL) was added dropwise at 10° C. After the dropwise addition, the mixture was keeped stirring for 5 min and the ice and stir were removed in a water bath. Until the reaction is complete, water (50 mL) was added, and pH was adjusted to 8~9 with 2 mol/L NaOH, then dichloromethane (50+50+30+30 mL) was added for extraction. The organic phases were combined, and the volatiles were evaporated under reduced pressure to obtain 7.8 g of a viscous yellow liquid. Purified by silica gel column chromatography (DCM:MeOH=200:1~100:1, adding 0.5‰ TEA), 3.44 g of oily substance was obtained, and the yield was 61%. $^{1}$H NMR (400 MHz, CDC13), δ 8.084 (d, J=7.6 Hz, 2H), 7.607~7.647 (m, 1H), 7.478~7.517 (t, 2H), 7.225~7.268 (m, 1H), 7.747~7.803 (m, 2H), 6.711 (s, 1H), 3.767 (s, 3H), 3.730 (s, 1H), 3.267 (d, J=14.4 Hz, 1H), 2.547~2.605 (m, 1H), 2.425 (d, J=13.2 Hz, 1H), 2.076 (s, 6H), 2.01~2.190 (m, 2H), 1.869~1.925 (m, 1H), 1.491~1.584 (m, 1H), 1.420 (s, 9H), 1.201~1.299 (m, 2H).

Example 1-6

4-Amino-2-((dimethylamino)methyl)-1-(3-methoxyphenyl)cyclohexyl benzoate dihydrochloride

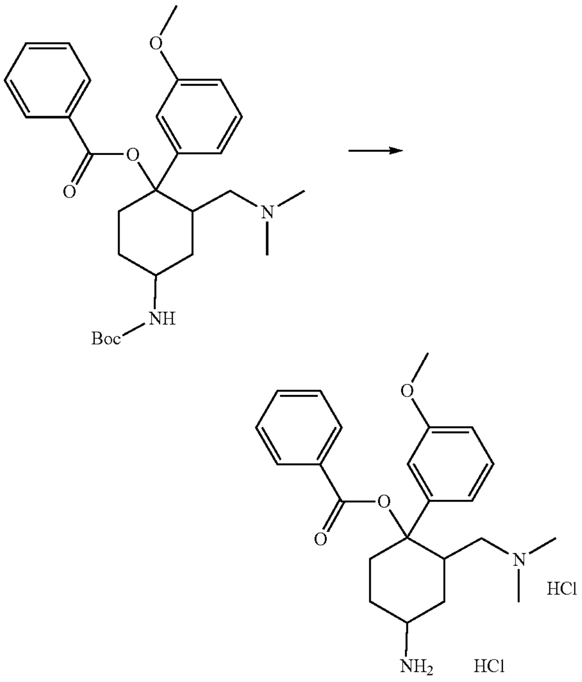

4-(Tert-butoxycarbonylamino)-2-((dimethylamino) methyl)-1-(3-methoxyphenyl)cyclohexyl benzoate (3.44 g, 7.133 mmol, 1 eq.), methanol (15 mL) were added to a 100 mL single-neck flask, stirred to dissolve, and HCl/Dioxane (4.5 mL, 17.83 mmol, 2.5 eq.) was added, stirred at room temperature. After 10 h TLC (DCM:MeOH=10:1) showed that the reaction was complete. MTBE (60 mL) was added and stirred to gradually separate out solid. After overnight, crystals were collected by suction filtration, the filter cake was rinsed with MTBE, and evaporated to dryness under reduced pressure to obtain 2.87 g of an off-white solid with a yield of 88%. $^{1}$H NMR (400 MHz, $CD_3OD$), δ 8.162 (d, J=6.8 Hz, 2H), 7.707 (t, J=7.6 Hz, 1H), 7.579 (t, J=7.6 Hz, 2H), 7.346 (t, J=8 Hz, 1H), 6.863~6.942 (m, 3H), 3.774 (s, 3H), 3.601 (t, J=11.6 Hz, 1H), 3.340~3.447 (m, 2H), 2.976 (d, J=13.2 Hz, 1H), 2.806 (s, 3H), 2.433~2.580 (m, 3H), 2.466 (s, 3H), 1.970~2.095 (m, 2H), 1.503~1.598 (m, 1H).

Example 1-7

2-((Dimethylamino)methyl)-1-(3-methoxyphenyl)-4-(benzenesulfonamide)cyclohexyl benzoate

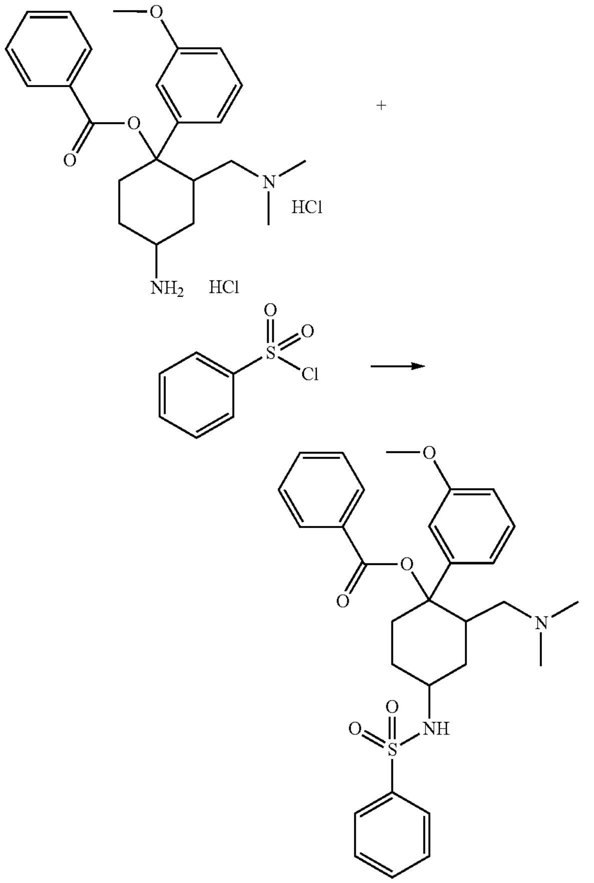

4-Amino-2-((dimethylamino)methyl)-1-(3-methoxyphenyl)cyclohexyl benzoate dihydrochloride (1 g, 2.2 mmol, 1 eq), DCM (10 mL), DMAP (27 mg, 0.22 mmol, 0.1 eq.), triethylamine (0.89 g, 8.8 mmol, 4 eq.) were added to a 50 mL single-necked bottle, and the mixture was stirred, then benzenesulfonyl chloride (0.47 g, 2.64 mmol, 1.2 eq.) was added. After the reaction was allowed to stir overnight (15 h) at room temperature, TLC (DCM:MeOH=10:1) showed complete resolution. water (30 mL) and dichloromethane (25+25 mL) were added for extraction. The organic phases were combined, washed with water (10 mL), and evaporated under reduced pressure to obtain 1.15 g of foam. Purified by silica gel column chromatography (EA:PE=1:2, with 0.5% CTEA), 0.85 g of off-white solid was obtained, and the yield was 74%. $^1$H NMR (400 MHz, $CDCl_3$), δ 8.050 (d, J=8 Hz, 2H), 7.903 (d, J=7.6 Hz, 2H), 7.603~7.641 (m, 1H), 7.473~7.565 (m, 5H), 7.195~7.233 (t, 1H), 6.774 (d, J=8.4 Hz, 1H), 6.719 (d, J=8 Hz, 1H), 6.672 (s, 1H), 3.745 (s, 3H), 3.423 (s, 1H), 3.180 (d, J=14.8 Hz, 1H), 2.479~2.536 (m, 1H), 2.277 (d, J=13.2 Hz, 1H), 2.053~2.093 (m, 2H), 1.996 (s, 6H), 1.910 (d, J=12.4 Hz, 1H), 1.828~1.860 (m, 2H), 1.568~1.659 (m, 1H).

Example 1-8

2-((Dimethylamino)methyl)-1-(3-methoxyphenyl)-4-(benzenesulfonyl)cyclohexyl benzoate hydrochloride

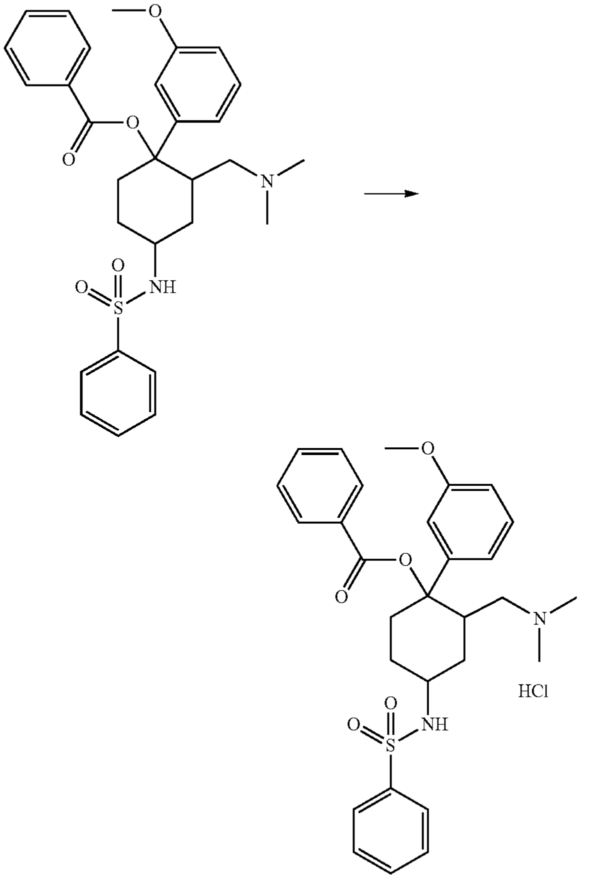

2-((Dimethylamino)methyl)-1-(3-methoxyphenyl)-4-(benzenesulfonamide)cyclohexyl benzoate (0.25 g, 0.48 mmol, 1 eq), DCM (2 mL) were added to a 50 mL single-necked bottle, then the mixture was stirred to dissolve, HCl/Dioxane (0.18 mL, 0.72 mmol, 1.5 eq.) was added with solid precipitated. MTBE (6 mL) was added and the mixture was stirred for 1 h. Crystals were collected by suction filtration, the filter cake was rinsed with MTBE, and evaporated to dryness under reduced pressure to obtain 0.253 g of an off-white solid with a yield of 94.4%. $^1$H NMR (400 MHz, $CD_3OD$), δ 8.117 (d, J=8 Hz, 2H), 7.903 (d, J=7.6 Hz, 2H), 6.673~6.711 (t, 1H), 6.542~6.639 (m, 5H), 7.272~7.313 (t, 1H), 6.883 (d, J=8.4 Hz, 1H), 6.828 (d, J=8.4 Hz, 1H), 6.785 (s, 1H), 3.741 (s, 3H), 3.542 (m, 1H), 3.305~3.348 (m, 1H), 3.104 (d, J=14.8 Hz, 1H), 2.858 (d, J=13.2 Hz, 1H), 2.599 (s, 6H), 2.365~2.393 (t, 1H), 2.234~2.267 (m, 2H), 1.864~1.957 (m, 1H), 1.577 (d, J=12.8 Hz, 1H), 1.258~1.353 (m, 1H). LC-MS-ESI$^+$: $[M+H]^+$ 523.3.

Example 1-9

N-(3-((Dimethylamino)methyl)-4-hydroxy-4-(3-methoxyphenyl)cyclohexyl)benzenesulfonamide

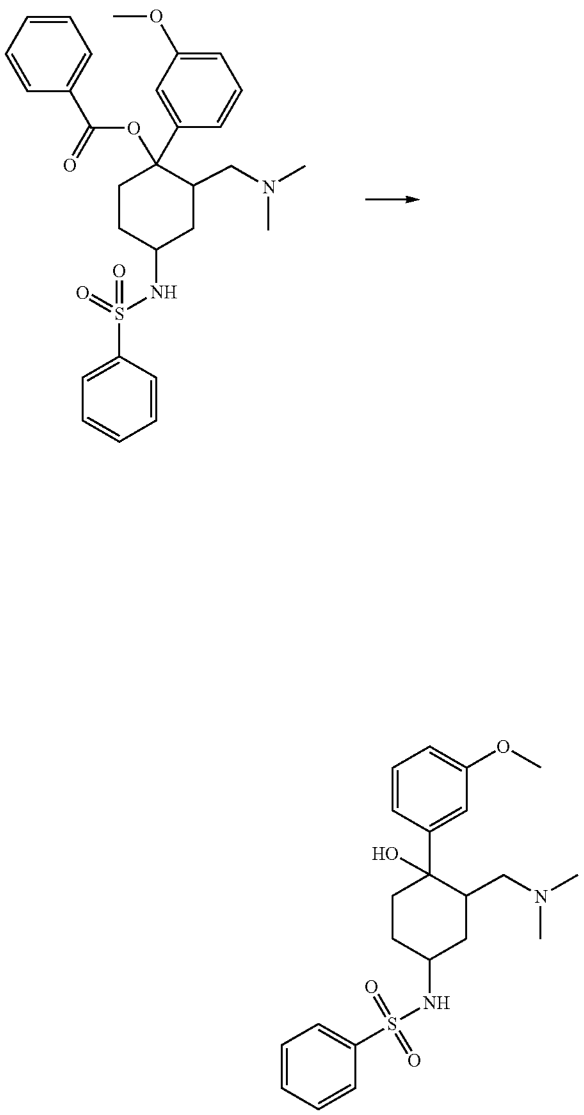

2-((Dimethylamino)methyl)-1-(3-methoxyphenyl)-4-(benzenesulfonamide)cyclohexyl benzoate (0.48 g, 0.92 mmol, 1 eq.), THF (8 mL), $LiAlH_4$ (175 mg, 4.6 mmol, 5 eq.) were added to a 100 mL single-necked bottle with condensation tube and nitrogen balloon, and the reaction was raised to 50° C. After 1 h, TLC (DCM:MeOH=10:1) showed that the reaction was complete. Under an ice-water bath, the mixture was added water (200 μl), 2 mol/L NaOH (400 μl), and water (600 μl), and stirred for 30 min, filtered with suction, and the filter cake was rinsed with dichloromethane. The filtrates were combined, and the volatile matter was evaporated under reduced pressure to obtain 0.49 g of viscous matter. Purified by silica gel column chromatography (EA:PE=1:1, with 0.5‰ TEA), 0.37 g of off-white solid was obtained, and the yield was 86%.

Example 1-10

N-(3-((Dimethylamino)methyl)-4-hydroxy-4-(3-methoxyphenyl)cyclohexyl)benzenesulfonamide hydrochloride

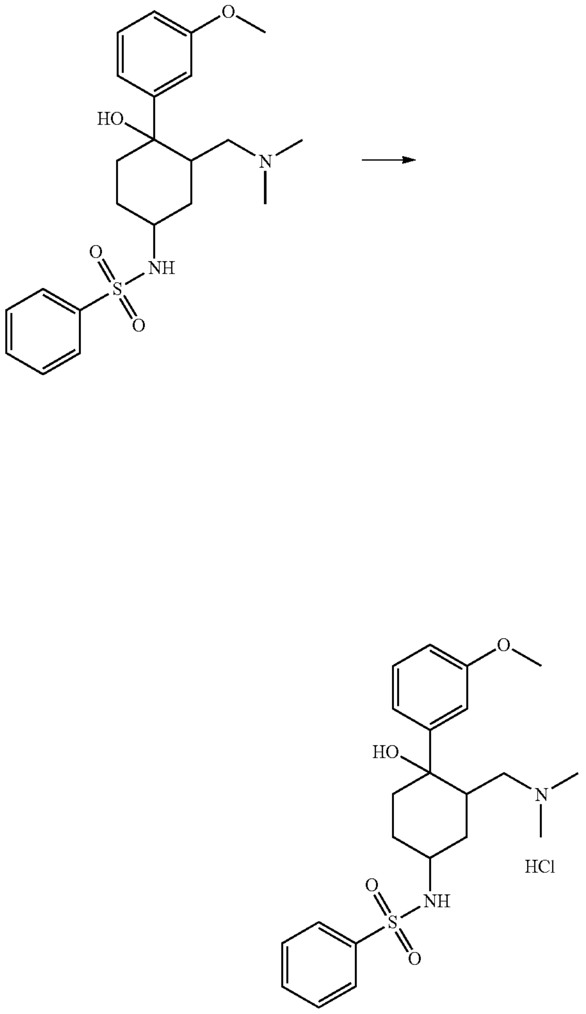

N-(3-((Dimethylamino)methyl)-4-hydroxy-4-(3-methoxyphenyl)cyclohexyl)benzenesulfonamide (0.32 g, 0.77 mmol, 1 eq.), DCM (3 mL) were added to a 50 mL single-necked bottle, dissolved by stirring, and HCl/dioxane (0.29 mL, 1.16 mmol, 1.5 eq.) was added with no solid precipitated. Then MTBE (9 mL) was added with solid precipitated, and the mixture was stirred for 1.5 h. Crystals were collected by suction filtration, and the filter cake was rinsed with MTBE, evaporated to dryness under reduced pressure to obtain 0.325 g of an off-white solid with a yield of 93%. $^1H$ NMR (400 MHz, $CD_3OD$), δ 7.977 (d, J=7.6 Hz, 2H), 7.561~7.646 (m, 3H), 7.272 (t, J=8 Hz, 1H), 7.054 (s, 1H), 7.016 (d, J=7.6 Hz, 1H), 6.812 (d, J=8.4 Hz, 1H), 3.780 (s, 3H), 3.406 (t, J=12 Hz, 1H), 2.929~2.986 (m, 1H), 2.676 (s, 3H), 2.567~2.609 (m, 1H), 2.609 (s, 3H), 2.317~2.313 (t, 1H), 1.882~1.992 (m, 2H), 1.711~1.833 (m, 2H), 1.625~1.680 (m, 1H), 1.495~1.533 (m, 1H). LC-MS-ESI$^+$: $[M+H]^+$ 419.2.

Example 1-11

4-((3-Chlorophenyl)sulfonylamino)-2-((dimethylamino)methyl)-1-(3-methoxyphenyl)cyclohexyl benzoate

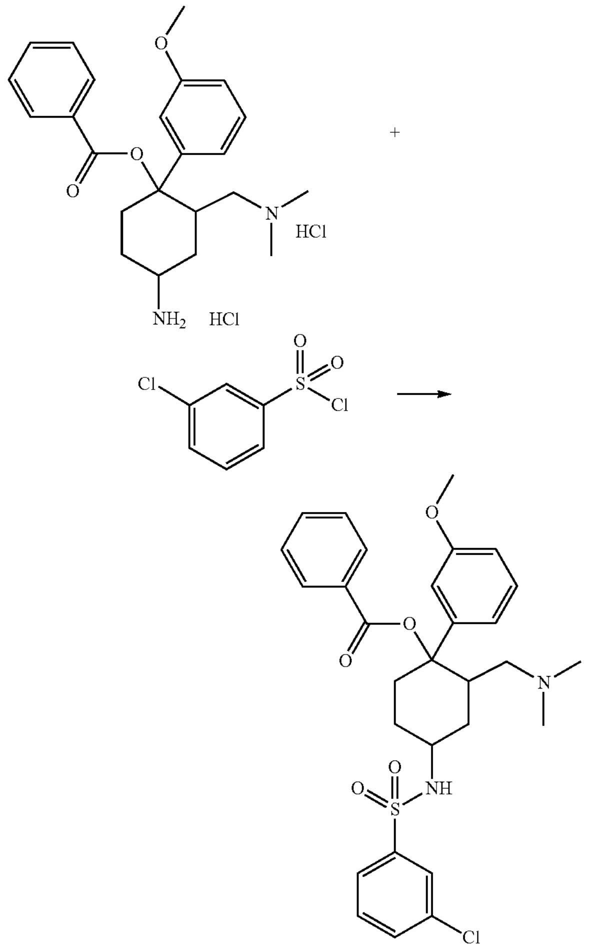

4-Amino-2-((dimethylamino)methyl)-1-(3-methoxyphenyl)cyclohexyl benzoate dihydrochloride (0.7 g, 1.54 mmol, 1 eq), DCM (8 mL), DMAP (18.8 mg, 0.154 mmol, 0.1 eq.), triethylamine (0.623 g, 6.16 mmol, 4 eq.) were added to a 50 mL single-neck flask, stirred and mixed, and m-chlorobenzenesulfonyl chloride (0.39 g, 1.844 mmol, 1.2 eq.) was added. The mixture was stirred at room temperature overnight (12 h), and TLC (DCM:MeOH=10:1) showed the reaction was complete. Water (20 mL) was added and the mixture was extracted with dichloromethane (25+25 mL). The organic phases were combined and evaporated under reduced pressure to obtain 1.05 g of a viscous substance. Purified by silica gel column chromatography (EA:PE=1:1, plus 0.5‰ TEA), 0.84 g of colorless viscous substance was obtained, and the yield was 97.7%. $^{1}H$ NMR (400 MHz, $CDCl_3$), δ 8.054 (d, J=8 Hz, 2H), 7.892 (s, 1H), 7.792 (d, J=8 Hz, 1H), 7.622~7.645 (t, 1H), 7.430~7.542 (m, 4H), 7.202~7.242 (t, 1H), 7.780 (d, J=8.4 Hz, 1H), 6.731 (d, J=8 Hz, 1H), 6.684 (s, 1H), 3.748 (s, 3H), 3.451 (m, 1H), 3.201 (d, J=14.8 Hz, 1H), 2.513~2.569 (t, 1H), 2.298 (d, J=13.2 Hz, 1H), 2.082~2.120 (m, 1H), 2.027 (s, 6H), 1.935 (d, J=12.4 Hz, 1H), 1.863 (m, 2H), 1.588~1.680 (m, 1H).

Example 1-12

4-((3-Chlorophenyl)sulfonylamino)-2-((dimethylamino)methyl)-1-(3-methoxyphenyl)cyclohexyl benzoate hydrochloride

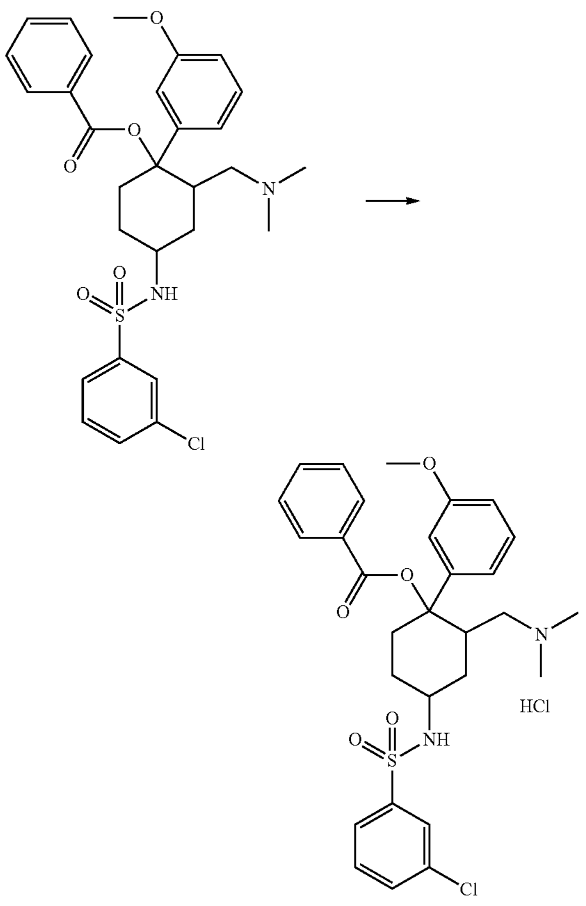

4-((3-Chlorophenyl)sulfonylamino)-2-((dimethylamino)methyl)-1-(3-methoxyphenyl)cyclohexyl benzoate (0.3 g, 0.54 mmol, 1 eq.) and DCM (2 mL) were added to a 50 mL single-neck flask, stirred to dissolve, and HCl/Dioxane (0.203 mL, 0.81 mmol, 1.5 eq.) was added, with solid slowly precipitated. Then MTBE (6 mL) was added and the mixture was stirred for 1.5 h. Crystals were collected by suction filtration, the filter cake was rinsed with MTBE, and evaporated to dryness under reduced pressure to obtain 0.308 g of an off-white solid with a yield of 96%. $^{1}H$ NMR (400 MHz, $CD_3OD$), δ 8.121 (d, J=8 Hz, 2H), 7.894 (s, 1H), 7.830 (d, J=7.6 Hz, 1H), 7.675~7.712 (t, 1H), 6.627~6.648 (d, J=8.4 Hz, 1H), 7.563 (t, J=8 Hz, 3H), 7.298 (t, J=8 Hz, 1H), 6.868 (d, J=8 Hz, 1H), 6.835 (d, J=8 Hz, 1H), 6.793 (s, 1H), 3.746 (s, 3H), 3.567 (t, J=12.4 Hz, 1H), 3.302~3.311 (m, 2H), 3.131 (d, J=14.8 Hz, 1H), 2.864 (d, J=13.2 Hz, 1H), 2.600 (s, 6H), 2.359~2.414 (t, 1H), 2.233~2.390 (m, 2H), 1.866~1.959 (m, 1H), 1.622 (d, J=13.2 Hz, 1H), 1.238~1.379 (m, 1H). LC-MS-$ESI^+$: $[M+H]^+$ 557.2.

Example 1-13

3-Chloro-N-(3-((dimethylamino)methyl)-4-hydroxy-4-(3-methoxyphenyl)cyclohexyl) benzenesulfonamide

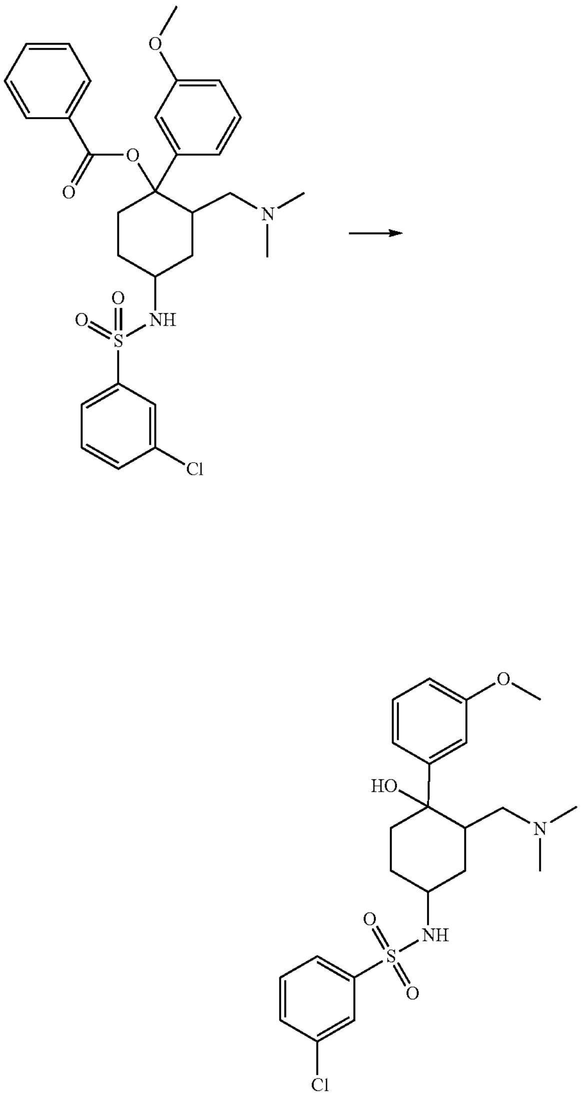

4-((3-Chlorophenyl)sulfonylamino)-2-((dimethylamino) methyl)-1-(3-methoxyphenyl)cyclohexyl benzoate (0.5 g, 0.9 mmol, 1 eq.), THF (10 mL), $LiAlH_4$ (170 mg, 4.5 mmol, 5 eq.) were added to a 100 mL single-neck flask with a condenser tube and a nitrogen balloon, and the reaction was raised to 50° C. TLC (DCM:MeOH=10:1) after 1 h showed the reaction was complete. Under an ice-water bath, water (170 μl), 2 mol/NaOH (340 μl), and water (510 μl) were added, and the mixture was stirred for 30 min, filtered with suction, and filter cake was rinsed with dichloromethane. The filtrates were combined, and the volatile matter was evaporated under reduced pressure to obtain 0.42 g of viscous matter. Purified by silica gel column chromatography (EA:PE=1:1, with 0.5‰ TEA), 0.33 g of off-white solid was obtained, and the yield was 80.5%.

Example 1-14

3-Chloro-N-(3-((dimethylamino)methyl)-4-hydroxy-4-(3-methoxyphenyl)cyclohexyl) benzenesulfonamide hydrochloride

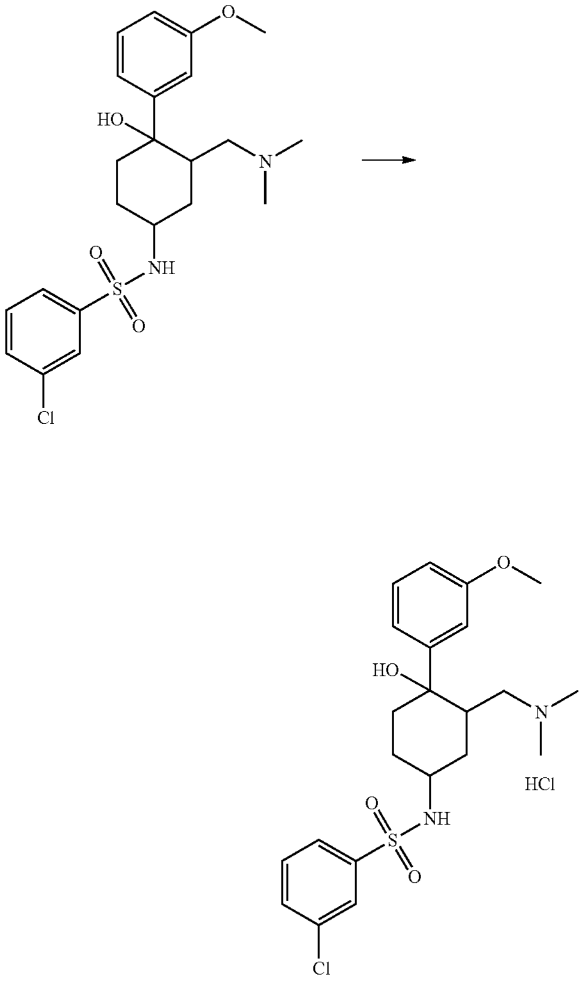

3-Chloro-N-(3-((dimethylamino)methyl)-4-hydroxy-4-(3-methoxyphenyl)cyclohexyl) benzenesulfonamide (0.3 g, 0.66 mmol, 1 eq.) and DCM (3 mL) were added to a 50 mL single-neck flask, stirred to partially dissolve, and methanol (0.25 mL) was added to dissolve the mixture completely. HCl/Dioxane (0.25 mL, 0.99 mmol, 1.5 eq.) was added with no solid precipitated. MTBE (12 mL) was added with solid precipitated, and the mixture was stirred for 1.5 h. Crystals were collected by suction filtration, and the filter cake was rinsed with MTBE, evaporated to dryness under reduced pressure to obtain 0.308 g of an off-white solid with a yield of 95.4%. $^1H$ NMR (400 MHz, $CD_3OD$), δ 7.928 (s, 1H), 7.866 (d, J=7.6 Hz, 1H), 7.559~7.651 (m, 2H), 7.256~7.294 (t, 1H), 7.013~7.060 (m, 2H), 6.814 (d, J=8.4 Hz, 1H), 3.781 (s, 3H), 3.440 (t, J=12.4 Hz, 1H), 2.935~2.990 (t, 1H), 2.680 (s, 3H), 2.577~2.615 (m, 1H), 2.577 (s, 3H), 2.243~2.398 (t, 1H), 1.918~1.994 (m, 2H), 1.646~1.839 (m, 3H), 1.537 (d, J=12.8 Hz, 1H). LC-MS-ESI$^+$: $[M+H]^+$453.2; LC-MS-ESI$^-$: $[M+H]^-$ 451.1.

Example 1-15

2-((Dimethylamino)methyl)-1-(3-methoxyphenyl)-4-(thiophene-2-sulfonylamino)cyclohexyl benzoate

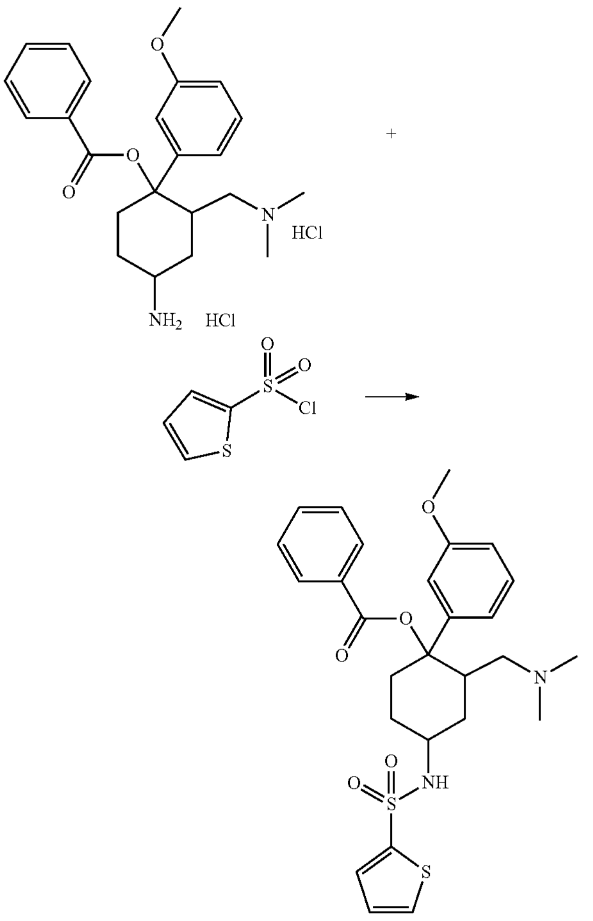

4-Amino-2-((dimethylamino)methyl)-1-(3-methoxyphenyl)cyclohexyl benzoate dihydrochloride (0.7 g, 1.54 mmol, 1 eq.), DCM (10 mL), DMAP (18.8 mg, 0.154 mmol, 0.1 eq.), triethylamine (0.623 g, 6.16 mmol, 4 eq.) were added to a 50 mL single-neck flask, stirred to mix, and thiophene-2-sulfonyl chloride (0.34 g, 1.844 mmol, 1.2 eq.). After the mixture was stirred at room temperature overnight (15 h), TLC (DCM:MeOH=10:1) showed complete reaction. Water (20 mL), dichloromethane extraction (25+25 mL) was added. The organic phases were combined, washed with water (10 mL), and evaporated under reduced pressure to obtain 0.98 g of a viscous substance. Purified by silica gel column chromatography (EA:PE=1:2, with 0.5% CTEA), 0.75 g of foamy substance was obtained, and the yield was 92%. $^1$H NMR (400 MHz, $CDCl_3$), δ 8.059 (d, J=7.6 Hz, 2H), 1.602~1.639 (m, 2H), 7.566 (d, J=5.2 Hz, 1H), 7.474~7.512 (m, 2H), 7.202~7.242 (t, 1H), 7.074~7.086 (m, 1H), 6.780 (d, J=8.8 Hz, 1H), 6.738 (d, J=8 Hz, 1H), 6.691 (s, 1H), 3.752 (s, 3H), 3.492 (m, 1H), 3.210 (d, J=14.8 Hz, 1H), 2.476~2.535 (t, 1H), 2.309 (d, J=13.2 Hz, 1H), 2.055~2.129 (m, 1H), 2.008 (s, 6H), 1.845~1.931 (m, 3H), 1.587~1.678 (m, 1H), 1.331~1.416 (m, 1H).

Example 1-16

N-(3-((Dimethylamino)methyl)-4-hydroxy-4-(3-methoxyphenyl)cyclohexyl)thiophene-2-sulfonamide

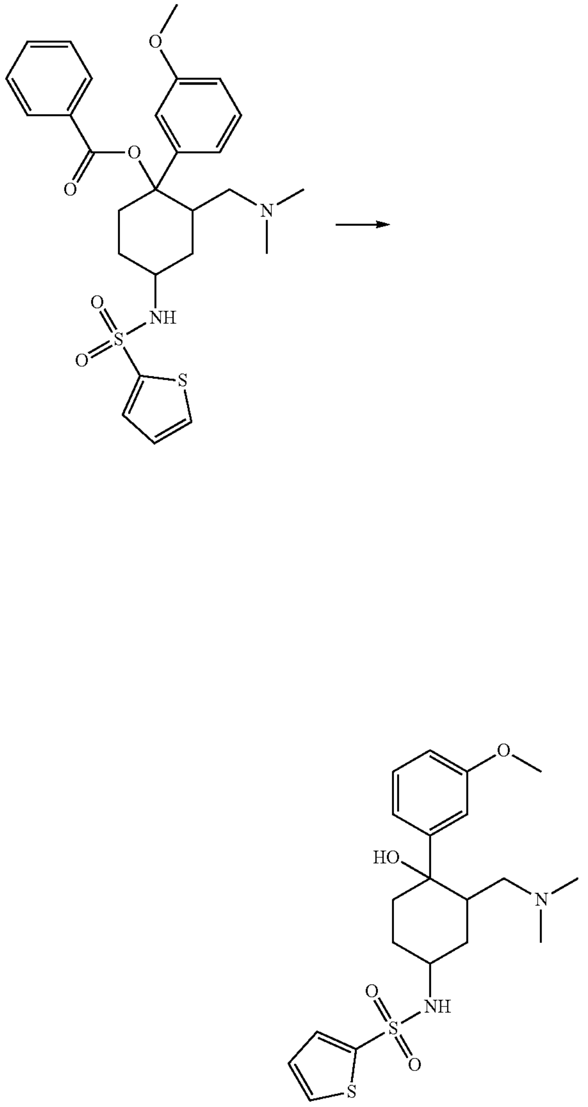

2-((Dimethylamino)methyl)-1-(3-methoxyphenyl)-4-(thiophene-2-sulfonylamino)cyclohexyl benzoate (0.5 g, 0.95 mmol, 1 eq.), THF (10 mL), $LiAlH_4$ (180 mg, 4.75 mmol, 5 eq.) were added to a 100 mL single-neck flask with a condenser tube and a nitrogen balloon, and the reaction was raised to 50° C. TLC (DCM:MeOH=10:1) after 1 h showed the reaction was complete. Under an ice-water bath, water (180 μl), 2 mol/L NaOH (360 μl), and water (540 μl) were added, and the mixture was stirred for 30 min, filtered with suction, and the filter cake was rinsed with dichloromethane. The filtrates were combined, and the volatile matter was evaporated under reduced pressure to obtain 0.38 g of viscous matter. Purified by silica gel column chromatography (EA:PE=1:1, with 0.5‰ TEA), 0.28 g of off-white solid was obtained, and the yield was 69%.

Example 1-17

N-(3-((Dimethylamino)methyl)-4-hydroxy-4-(3-methoxyphenyl)cyclohexyl)thiophene-2-sulfonamide hydrochloride

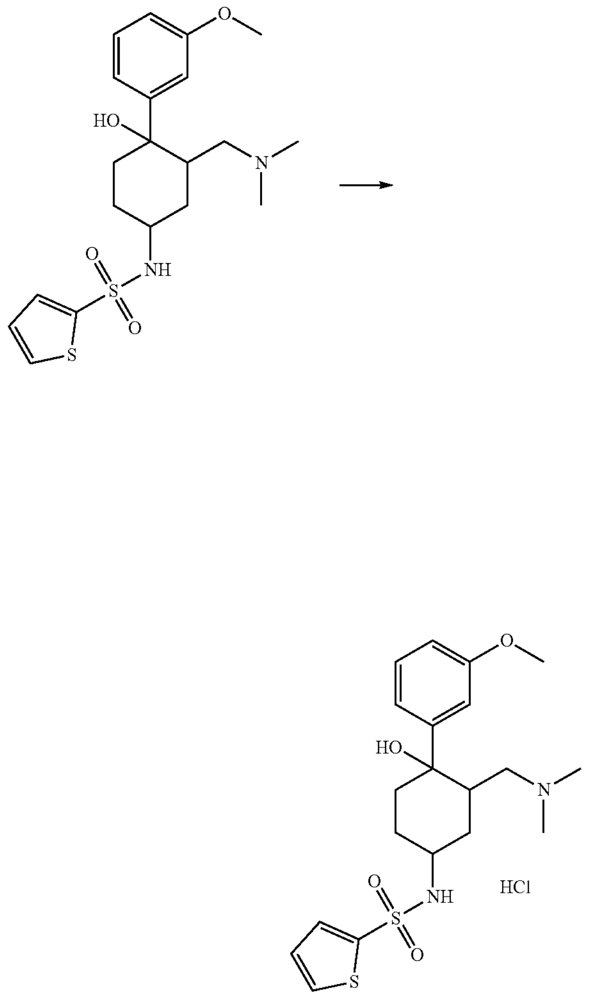 [SMILES: COc1cccc(C2(O)CCC(NS(=O)(=O)c3cccs3)CC2CN(C)C)c1 ; COc1cccc(C2(O)CCC(NS(=O)(=O)c3cccs3)CC2CN(C)C)c1 ; Cl]

N-(3-((Dimethylamino)methyl)-4-hydroxy-4-(3-methoxyphenyl)cyclohexyl)thiophene-2-sulfonamide (0.25 g, 0.59 mmol, 1 eq.), DCM (3 mL) were added to a 50 mL single-neck flask, stirred to partially dissolve, and then methanol (0.25 mL) was added to dissolve the mixture by stirring. HCl/Dioxane (0.22 mL, 0.88 mmol, 1.5 eq.) was added with solid precipitated. MTBE (12 mL) was added and the mixture was stirred for 1 h. Crystals were collected by suction filtration, and the filter cake was rinsed with MTBE, evaporated to dryness under reduced pressure to obtain 0.27 g of an off-white solid with a yield of 98.5%. $^1$H NMR (400 MHz, $CD_3OD$), δ 7.778 (d, J=5.4 Hz, 1H), 7.669 (s, 1H), 7.284 (t, J=8 Hz, 1H), 7.146~7.169 (t, 1H), 7.024~7.070 (m, 3H), 7.821 (d, J=8 Hz, 1H), 3.788 (s, 3H), 3.446~3.507 (t, 1H), 2.945~3.002 (q, 1H), 2.635 (s, 6H), 2.586~2.635 (m, 1H), 2.348~2.403 (m, 1H), 1.929~2.022 (m, 2H), 1.757~1.854 (m, 2H), 1.667~1.704 (m, 1H), 1.571~1.603 (m, 1H). LC-MS-ESI$^+$: [M+H]$^+$ 425.2.

Example 1-18

2-((Dimethylamino)methyl)-1-(3-methoxyphenyl)-4-((benzyl)sulfonamido)cyclohexyl benzoate

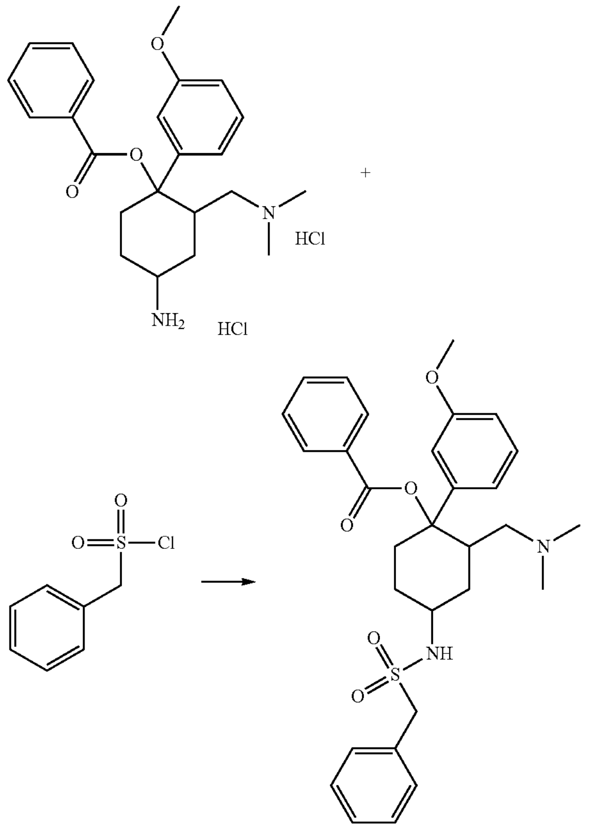

4-Amino-2-((dimethylamino)methyl)-1-(3-methoxyphenyl)cyclohexyl benzoate dihydrochloride (0.7 g, 1.54 mmol, 1 eq.), DCM (8 mL), DMAP (18.8 mg, 0.154 mmol, 0.1 eq.), triethylamine (0.623 g, 6.16 mmol, 4 eq.) were added to a 50 mL single-neck flask, stirred to mix, then benzylsulfonyl chloride (0.36 g, 1.844 mmol, 1.2 eq.) was added. After stirring at room temperature overnight (12 h), TLC (DCM:MeOH=10:1) showed about half of the raw material remaining. (25 mL), dichloromethane extraction (25+25 mL) was added. The organic phases were combined, washed with water (10 mL), and evaporated under reduced pressure to obtain 2.2 g of a brownish-yellow viscous substance. Purified by silica gel column chromatography (EA:PE=1:1, with 0.5‰ TEA), 0.45 g of yellow foam was obtained with a yield of 54.2%. $^1$H NMR (400 MHz, $CDCl_3$), δ 8.054 (d, J=7.6 Hz, 2H), 7.607~7.647 (m, 1H), 7.477~7.516 (t, 2H), 7.421 (s, 2H), 7.348 (s, 3H), 7.219~7.260 (m, 1H), 6.793 (d, J=8.4 Hz, 1H), 6.735 (d, J=8 Hz, 1H), 6.690 (s, 1H), 6.285 (s, 2H), 6.762 (s, 3H), 3.378 (s, 1H), 3.210 (d, J=14.4 Hz, 1H), 2.513~2.570 (t, 1H), 2.439 (d, J=13.2 Hz, 1H), 2.063 (s, 6H), 1.958~2.110 (m, 2H), 1.858~1.889 (m, 1H), 1.547~1.639 (m, 1H), 1.255~1.356 (m, 2H).

Example 1-19

N-(3-((Dimethylamino)methyl)-4-hydroxy-4-(3-methoxyphenyl)cyclohexyl)-1-benzenemethanesulfonamide

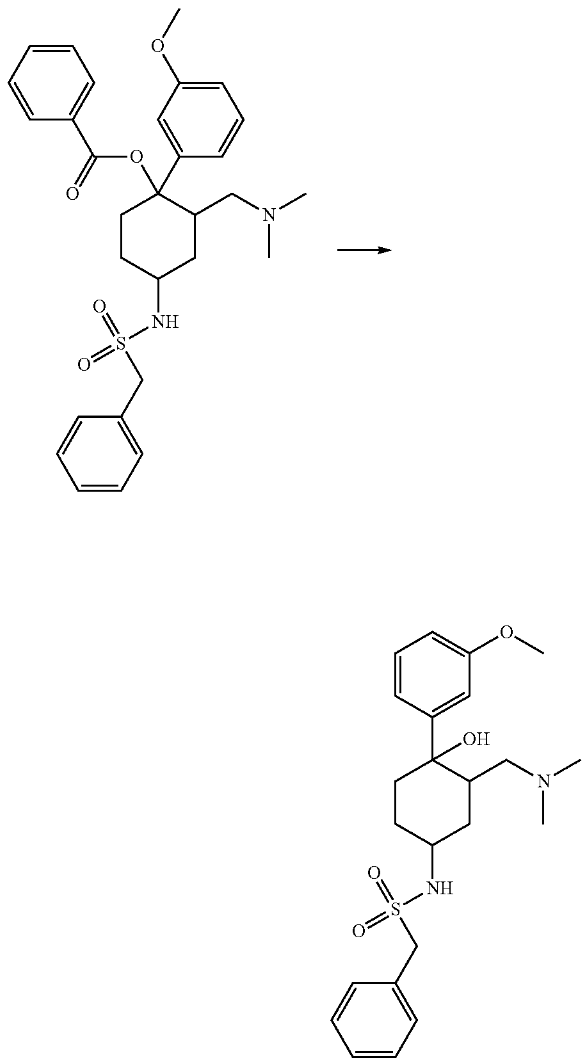

2-((Dimethylamino)methyl)-1-(3-methoxyphenyl)-4-((benzyl)sulfonamido)cyclohexyl benzoate (0.4 g, 0.75 mmol, 1 eq.), THF (10 mL), $LiAlH_4$ (140 mg, 3.75 mmol, 5 eq.) were added to a 100 mL single-neck flask with a condenser tube and a nitrogen balloon, and the reaction was raised to 50° C. After 0.5 h, TLC (DCM:MeOH=10:1) showed a small amount of starting material. After another 45 min of reaction, TLC showed that the reaction was complete. Under an ice-water bath, water (140 μl), 2 mol/L NaOH (280 μl), and water (420 μl) were added, the mixture was stirred for 30 min, filtered with suction, and the filter cake was rinsed with dichloromethane. The filtrates were combined, and the volatiles were evaporated under reduced pressure to obtain 0.37 g of a colorless viscous substance. Preparative plate purification (DCM:MeOH=15:1) yielded 0.25 g of a colorless sticky substance in 77% yield.

Example 1-20

N-(3-((Dimethylamino)methyl)-4-hydroxy-4-(3-methoxyphenyl)cyclohexyl)-1-benzenemethanesulfonamide hydrochloride

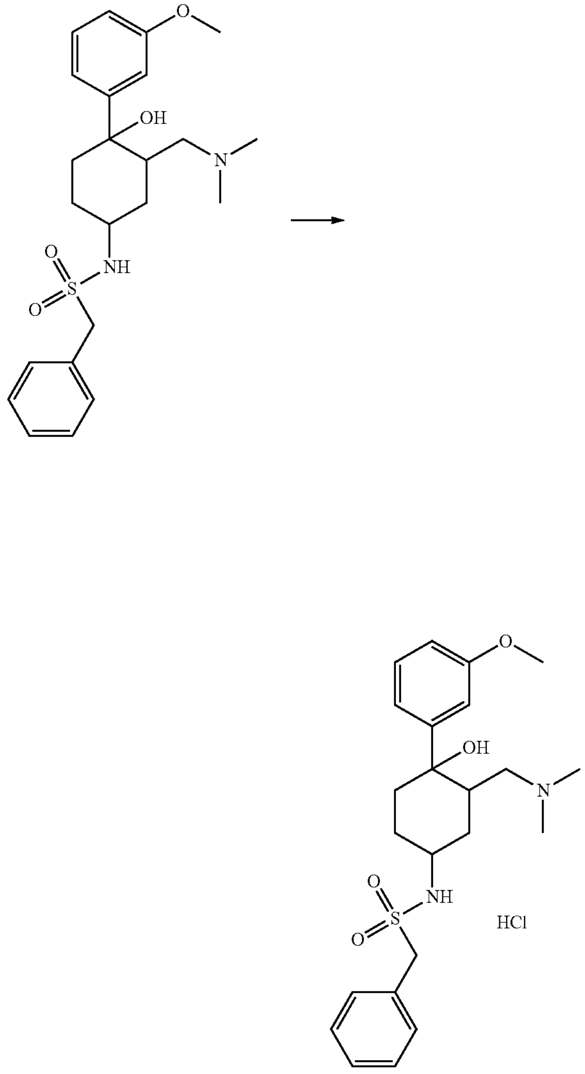 [SMILES: COc1cccc(C2(O)CCC(NS(=O)(=O)Cc3ccccc3)CC2CN(C)C)c1 ; COc1cccc(C2(O)CCC(NS(=O)(=O)Cc3ccccc3)CC2CN(C)C)c1 ; Cl]

N-(3-((Dimethylamino)methyl)-4-hydroxy-4-(3-methoxyphenyl)cyclohexyl)-1-benzenemethanesulfonamide (0.25 g, 0.58 mmol, 1 eq.) and DCM (2 mL) were added to a 50 mL single-neck flask, stirred to dissolve, and HCl/Dioxane (0.22 mL, 0.87 mmol, 1.5 eq.) was added with solid slowly precipitated. MTBE (6 mL) was added and stirred for 1 h. Crystals were collected by suction filtration, and the filter cake was rinsed with MTBE, evaporated to dryness under reduced pressure to obtain 0.24 g of an off-white solid with a yield of 91%. $^1H$ NMR (400 MHz, $CD_3OD$), δ 7.476~7.495 (m, 2H), 7.378~7.379 (m, 3H), 7.304 (t, J=8 Hz, 1H), 7.022~7.077 (m, 3H), 6.838 (d, J=8 Hz, 1H), 4.351~4.433 (q, 2H), 3.802 (s, 3H), 3.384 (m, 1H), 2.957~3.013 (m, 1H), 2.595~2.660 (m, 7H), 2.298~2.353 (t, 1H), 2.094 (d, J=12.4 Hz, 1H), 1.951~2.028 (m, 1H), 1.722~1.832 (m, 4H). LC-MS-ESI$^+$: $[M+H]^+$ 433.3.

Example 1-21

4-(((3-Chlorophenyl)methyl)sulfonamido)-2-((dimethylamino)methyl)-1-(3-methoxyphenyl) cyclohexyl benzoate

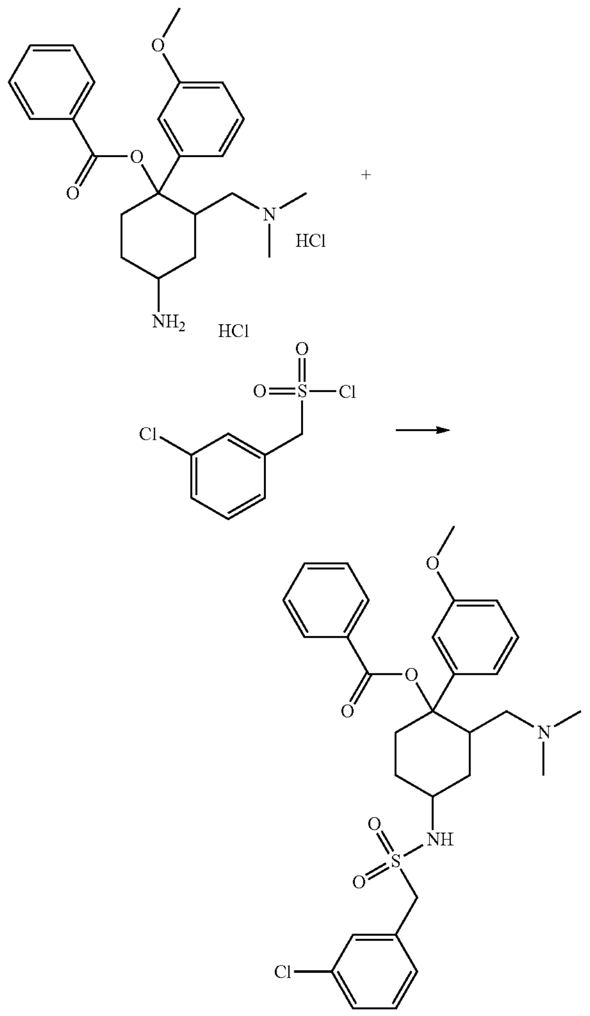

4-Amino-2-((dimethylamino)methyl)-1-(3-methoxyphenyl)cyclohexyl benzoate dihydrochloride (0.7 g, 1.54 mmol, 1 eq.), DCM (8 mL), DMAP (18.8 mg, 0.154 mmol, 0.1 eq.), triethylamine (0.623 g, 6.16 mmol, 4 eq.) were added to a 50 mL single-neck flask, stirred and mixed, and m-chlorobenzylsulfonyl chloride (0.42 g, 1.844 mmol, 1.2 eq.) was added. After stirring at room temperature overnight (12 h), TLC (DCM:MeOH=10:1) showed that no reaction occurred. The raw materials were recovered by silica gel column chromatography, and DCM (10 mL), DMAP (0.1 eq.), TEA (4 eq.), m-chlorobenzylsulfonyl chloride (1.2 eq.) were added, and there were new spots overnight, but raw materials remained. Adding DBU (4 eq.) and m-chlorobenzylsulfonyl chloride (0.6 eq.), there was no significant change, and there was no significant change when heating and refluxing. Water (25 mL) and extract with dichloromethane (25+25 mL) were added. The organic phases were combined, washed with water (20 mL), and evaporated under reduced pressure to obtain 0.87 g of a yellow viscous substance. Purified by silica gel column chromatography (EA:PE=4:5, plus 0.5‰ TEA), 0.27 g of off-white foam was obtained with a yield of 30.7%. $^1H$ NMR (400 MHz, $CDCl_3$), δ 8.056 (d, J=7.6 Hz, 1H), 7.605~7.647 (m, 1H), 7.478~7.517 (t, 2H), 7.440 (s, 1H), 7.227~7.342 (m, 5H), 6.799 (d, J=8.4 Hz, 1H), 6.752 (d, J=8 Hz, 1H), 6.704 (s, 1H), 4.265 (s, 2H), 3.765 (s, 3H), 3.458 (s, 1H), 3.243 (d, J=14.8 Hz, 1H), 2.529~2.586 (t, 1H), 2.464 (d, J=13.2 Hz, 1H), 2.075 (s, 6H), 1.908~2.155 (m, 4H), 1.571~1.662 (m, 1H), 1.333~1.427 (m, 1H).

Example 1-22

1-(3-Chlorophenyl)-N-(3-((dimethylamino)methyl)-4-hydroxy-4-(3-methoxyphenyl)cyclohexyl) methanesulfonamide

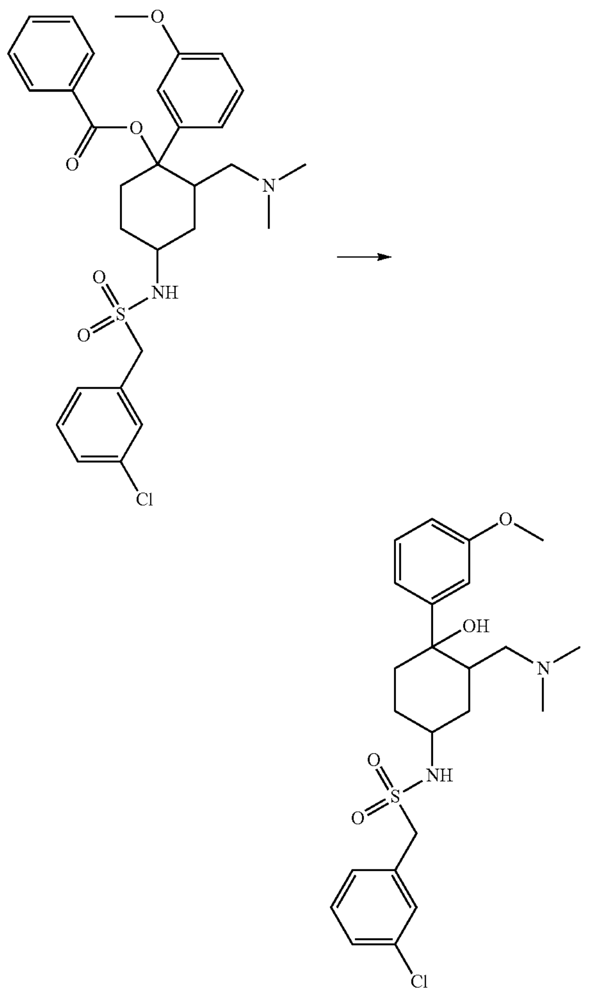

4-(((3-Chlorophenyl)methyl)sulfonamido)-2-((dimethylamino)methyl)-1-(3-methoxyphenyl) cyclohexyl benzoate (0.25 g, 0.44 mmol, 1 eq.), THF (5 mL), $LiAlH_4$ (85 mg, 2.2 mmol, 5 eq.) were added to a 100 mL single-neck flask with a condenser tube and a nitrogen balloon, and the reaction was raised to 50° C. After 1 h, TLC (DCM:MeOH=10:1) showed a small amount of raw material. There was no significant change after 2 h, $LiAlH_4$ (45 mg, about 2.5 eq.) was added complementally, and TLC showed that the reaction was complete after 1 h. Under an ice-water bath, water (130 μl), 2 mol/L NaOH (260 μl), and water (390 μl) were added, stirred for 30 min, suction filtered, and the filter cake was rinsed with dichloromethane. The filtrates were combined, and the volatiles were evaporated under reduced pressure to obtain 0.2 g of a colorless viscous substance. Preparative plate purification (DCM:MeOH=15:1) yielded 118 mg of a colorless viscous substance in 57% yield.

Example 1-23

1-(3-Chlorophenyl)-N-(3-((dimethylamino)methyl)-4-hydroxy-4-(3-methoxyphenyl)cyclohexyl) methanesulfonamide hydrochloride

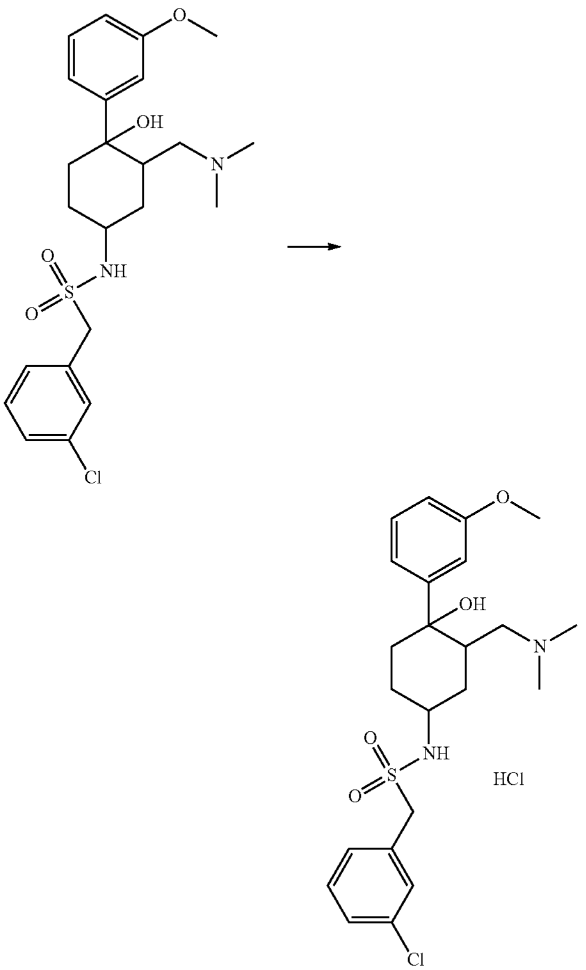

1-(3-Chlorophenyl)-N-(3-((dimethylamino)methyl)-4-hydroxy-4-(3-methoxyphenyl)cyclohexyl) methanesulfonamide (0.118 g, 0.78 mmol, 1 eq.) and DCM (1 mL) were added to a 50 mL single-neck flask, stirred to dissolve, and HCl/Dioxane (0.1 mL, 0.38 mmol, 1.5 eq.) was added with no solid precipitated. MTBE (6 mL) was added with solid precipitated, and the mixture was stirred for 1.5 h. Crystals were collected by suction filtration, and the filter cake was rinsed with MTBE, evaporated to dryness under reduced pressure to obtain 0.104 g of an off-white solid with a yield of 83%. $^1H$ NMR (400 MHz, $CD_3OD$), δ 7.358~7.381 (m, 2H), 7.277~7.294 (m, 3H), 7.186 (t, J=8 Hz, 1H), 6.980 (s, 1H), 6.924~6.946 (m, 1H), 6.713~6.738 (m, 1H), 4.314~4.405 (q, 2H), 3.677 (s, 3H), 3.248 (m, 1H), 2.924~2.981 (q, 1H), 2.595 (s, 3H), 2.551 (d, J=12.8 Hz, 1H), 2.470 (s, 3H), 2.236~2.345 (m, 2H), 1.901~2.003 (m, 4H), 1.748~1.781 (m, 1H). LC-MS-ESI$^+$: $[M+H]^+$ 418.2.

Example 1-24

N-Cenzyl-1,4-dioxaspiro [4.5]silan-8-amine

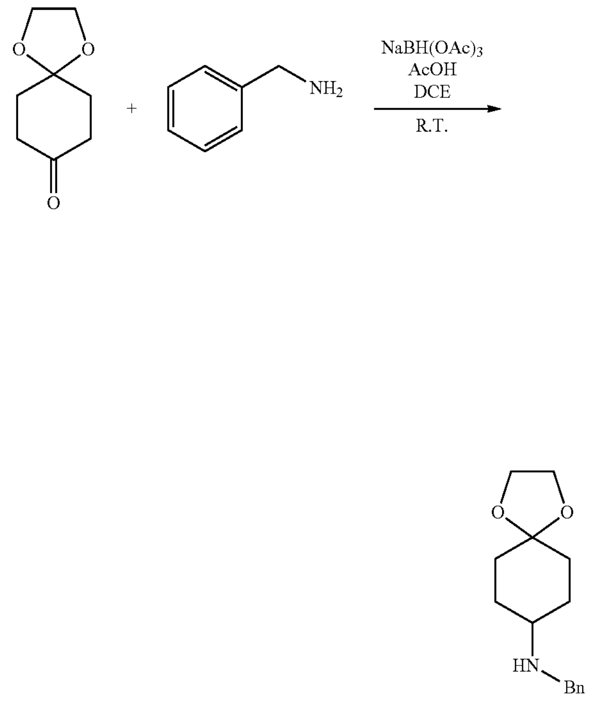 [SMILES: O=C1CCC2(CC1)OCCO2 ; NCc1ccccc1 ; c1ccc(CNC2CCC3(CC2)OCCO3)cc1]

1,4-Dioxaspiro[4.5]silan-8-one (30 g, 192.09 mmol, 1 eq.) and DCE (240 mL) were added to a 500 mL three-necked flask with a thermometer and drying tube, stirred to dissolve, then benzylamine (20.58 g, 192.09 mmol, 1 eq.) was added. After cooling in an ice-water bath, $NaBH(OAc)_3$ (44.78 g, 211.30 mmol, 1.1 eq.) was added in 4 portions at 20° C. Acetic acid (11.54 g, 192.09 mmol, 1 eq.) was added and warmed slightly. After adding, the mixture was stirred for 5 min, and the ice and water bath was removed and the mixture was stirred again. After 20 min, it could not be stirred, and DCE (60 mL) was added. After 1 h, TLC (DCM:MeOH=10:1) showed that the reaction was complete. Under an ice-water bath, the reaction solution was added to ice water (300 mL), adjusted to pH 9~10 with 2 mol/L NaOH solution (about 200 mL), mixed, stood, layered and separated. The aqueous phase was extracted with dichloromethane (300+150+50 mL). The organic phases were combined, washed with water (100 mL), washed with saturated sodium chloride (100 mL), dried over anhydrous magnesium sulfate, filtered with suction, and the filtrate was evaporated under reduced pressure to obtain 47.5 g of a brownish-yellow liquid with a yield of 99.98%. $^1H$ NMR (400 MHz, $CD_3OD$), δ 7.262~7.336 (m, 5H), 3.956 (s, 4H), 3.815 (s, 2H), 2.619 (s, 1H), 1.779~1.928 (m, 4H), 1.486~1.579 (m, 4H).

Example 1-25

4-(Benzylamino) cyclohexan-1-one

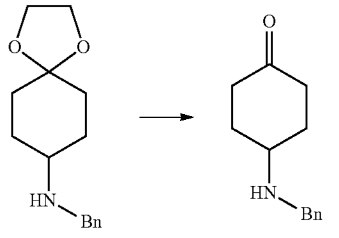 [SMILES: c1ccc(CNC2CCC3(CC2)OCCO3)cc1 ; O=C1CCC(NCc2ccccc2)CC1]

A single port bottle charged with N-benzyl-1,4-dioxaspiro [4.5] silane-8-amine (16 g, 64.69 mmol, 1 eq.) in 2 mol/L HCl (81 ml, 161.72 mmol, 2.5 eq.) was stirred at room temperature overnight (12 h), and about half of the starting material remained by TLC (DCM:MeOH=25:1, 2 times). TLC showed complete response after 10 h supplementation with 2 mol/L HCl (16 ml, 0.5 eq.). Under ice water bath, add NaOH (8 g, about 3 eq.) aqueous solution (about 24 ml), and adjust the pH to 9~10 with 2 mol/L NaOH solution. Extract with dichloromethane (150+75+30 ml). The organic phases were combined, and washed using saturated sodium chloride (30 ml). Anhydrous magnesium sulfate was dried, suction filtered, and the filtrate was evaporated under reduced pressure to obtain 12.57 g of light brown yellow liquid. Yield: 95.6%.

Example 1-26

N-Benzyl(4-oxocyclohexyl) carbamic acid tert-butyl ester

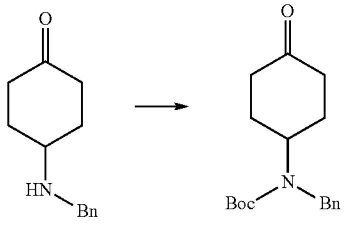 [SMILES: O=C1CCC(NCc2ccccc2)CC1 ; CC(C)(C)OC(=O)N(Cc1ccccc1)C1CCC(=O)CC1]

A 500 ml three-necked flask with a thermometer and a constant pressure dropping funnel was charged with 4-(benzylamino) cyclohexan-1-one (35.7 g, 175.61 mmol, 1 eq.), DCM (300 ml), TEA (21.32 g, 210.73 mmol, 1.2 eq.), DMAP (215 mg, 1.76 mmol, 0.01 eq.) DCM (50 ml) solution of $(Boc)_2O$ (40.24 g, 184.39 mmol, 1.05 eq.) was added dropwise at 10° C. The solution was stirred in an ice-water bath. After addition, the ice water bath was withdrawn and stirred. Overnight (13 h), TLC (DCM:MeOH=100:1 and DCM:MeOH=10:1) showed complete reaction. Water (200 ml) was added, mixed, left to stand, stratified, partitioned and the aqueous phase was extracted with dichloromethane (100+100 ml). The organic phases were combined, washed with water (100 ml), citric acid solution (100 ml), saturated sodium chloride (100 ml), dried with anhydrous magnesium sulfate, filtered, and the filtrate was removed by evaporation under reduced pressure to yield 51.68 g of yellow liquid. Purified by silica gel column chromatography (DCM:PE-DCM), 33.3 g of off-white solid was obtained. Yield: 62.5%. $^1H$ NMR (400 MHz, $CD_3OD$), δ 7.204~7.325 (m, 5H), 4.399~4.500 (m, 3H), 2.337~2.372 (m, 4H), 1.816~1.3991 (m, 4H), 1.436 (s, 9H).

Example 1-27

N-Benzyl(3-((dimethylamino)methyl)-4-oxocyclohexyl) carbamic acid tert-butyl ester

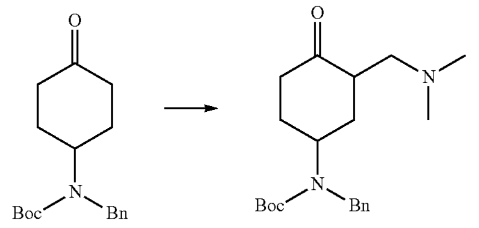 [SMILES: CC(C)(C)OC(=O)N(Cc1ccccc1)C1CCC(=O)CC1 ; CN(C)CC1CC(N(Cc2ccccc2)C(=O)OC(C)(C)C)CCC1=O]

A 500 ml single port flask was charged with tert butyl N-benzyl (4-oxocyclohexyl) carbamate (20 g, 65.97 mmol, 1 eq.), acetonitrile (200 ml) and dissolved by stirring, the salt added (6.79 g, 72.56 mmol, 1.1 eq.), acetyl chloride (0.26 mg, 3.3 mmol, 0.05 eq.) and stirred at room temperature. TLC (DCM and DCM:MeOH=25:1) after 12 h showed complete response. Acetonitrile was evaporated under reduced pressure (35° C.), saturated sodium bicarbonate solution (150 ml) was added, and pH 8~9 was adjusted with 2 mol/L NaOH. Dichloromethane extraction (100+100+50 ml). The organic phases were combined, water washed (50+50 ml), saturated sodium chloride washed (50 ml), anhydrous magnesium sulfate dried, suction filtered, and the filtrate evaporated under reduced pressure to afford 23.06 g of a pale yellow viscous substance. Yield: 0.97%. It was used directly in the next step.

Example 1-28

N-Benzyl(3-((dimethylamino)methyl)-4-hydroxy-4-(3-methoxyphenyl)cyclohexyl) carbamic acid tert-butyl ester

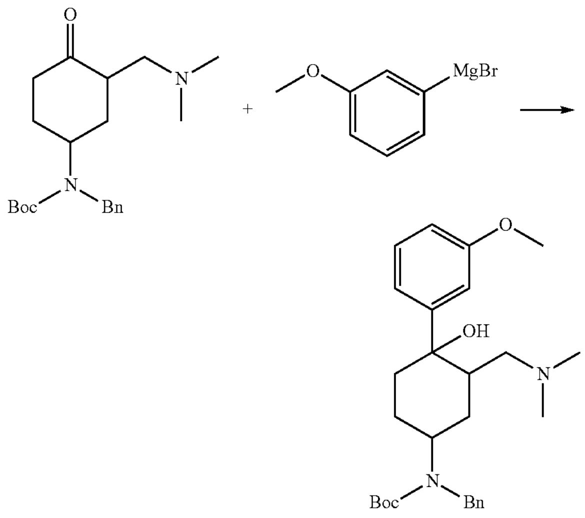

A 1 L four-necked flask with a nitrogen bulb, constant pressure dropping funnel, condenser tube and thermometer was charged with magnesium flakes (3.1 g, 127 mmol, 3 eq.), THF (90 ml), 2 grains of iodine, and a small amount of THF (25 ml) solution of m-bromomethyl ether (23.75 g, 127 mmol, 3 eq.), and the reaction was initiated by heating to reflux. When the reaction was initiated (yellow color fades, lots of bubbles), stop heating. Slowly add the remaining THF solution of m-bromoanisole dropwise until the dropwise addition is complete. After dropwise addition, reflux for 10 min and stir to bring down to room temperature naturally. Cool in an ice-salt bath and add dropwise at −20° C. a solution of tert-butyl N-benzyl(3-((dimethylamino) methyl)-4-oxocyclohexyl) carbamate (15.25 g, 42.23 mmol, 1 eq.) in THF (45 ml). The dropwise addition was completed, kept warm and stirred, and LC-MS showed the presence of raw material after 2 h. The reagent (1 mol/L, 25 ml, 0.5 eq.) was added and the feedstock was still remained after 2 h. The reagent (1 mol/L, 25 ml, 0.5 eq.) was added. Overnight, LC-MS showed that the feedstock was still present. The reaction solution was poured into an ice-water mixture of saturated ammonium chloride solution (150 ml) under an ice-water bath, and the internal temperature was raised to about 30° C. THF was evaporated under reduced pressure and extracted with ethyl acetate (100+60+30 ml). The organic phases were combined, washed with water (50 ml), saturated sodium chloride (50 ml), dried with anhydrous magnesium sulfate, and filtered, and the filtrate was evaporated under reduced pressure to yield 30.37 g of brownish-yellow viscous material. Purified by silica gel column chromatography (DCM-DCM:MeOH=200: ~100:1, with 0.5‰ TEA), 13.3 g of yellow target product was obtained. Yield: 67%. $^1$H NMR (400 MHz, $CD_3OD$), δ 7.284~7.295 (m, 4H), 7.185~7.223 (m, 2H), 6.996~7.077 (m, 2H), 6.747 (d, J=8.4 Hz, 1H), 4.392~4.592 (q, 2H), 3.797 (s, 3H), 2.334~2.369 (m, 1H), 1.976 (s, 9H), 1.712 (m, 3H), 1.406~1.547 (m, 11H).

Example 1-29

4-(Benzylamino)-2-((dimethylamino)methyl)-1-(3-methoxyphenyl)cyclohexane-1-ol dihydrochloride

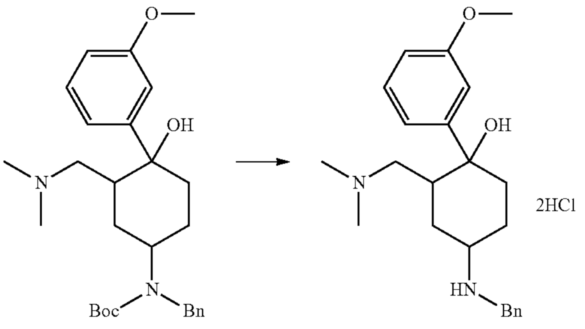

A 250 ml single-neck flask was added with tert-butyl N-benzyl(3-((dimethylamino)methyl)-4-hydroxy-4-(3-methoxyphenyl)cyclohexyl) carbamate (18.15 g, 38.73 mmol, 1 eq.), methanol (70 ml), HCl/Dioxane (4 mol/L, 24.2 ml, 96.82 mmol, 2.5 eq.), stirred at room temperature. TLC (DCM:MeOH=10:1) after 19 h showed the reaction was complete. MTBE (350 ml) was added, stirred for 20 h, suction filtered, the filter cake was rinsed with MTBE, evaporated to dryness under reduced pressure, and 14.13 g of off-white solid was obtained. Yield: 82.6%. $^1$H NMR (400 MHz, $CD_3OD$), δ 7.584~7.608 (m, 2H), 7.459~7.513 (m, 3H), 7.329 (t, J=8 Hz, 1H), 7.124 (s, 1H), 7.087 (d, J=8 Hz, 1H), 6.865 (dd, J1=8 Hz, J2=2 Hz, 1H), 4.348 (q, J=12.8 Hz, 2H), 3.814 (s, 3H), 3.518~3.576 (m, 1H), 3.078 (q, J=13.6 Hz, J=9.6 Hz, 1H), 2.567~2.743 (m, 8H), 2.473~2.533 (m, 1H), 2.099~2.176 (m, 2H), 2.003~2.074 (m, 1H), 1.924~1.964 (m, 1H), 1.862~1.897 (m, 1H).

Example 1-30

4-(Benzyl(methyl)amino)-2-((dimethylamino) methyl)-1-(3-methoxyphenyl) cyclohexan-1-ol

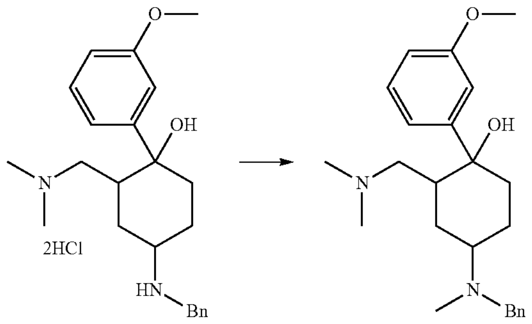

Add 4-(benzylamino)-2-((dimethylamino)methyl)-1-(3-methoxyphenyl) cyclohexan-1-ol dihydrochloride (4.2 g, 9.51 g) to a 100 ml single-necked bottle mmol, 1 eq.), aqueous formaldehyde solution (8%, 28.56 g, 76.10 mmol, 8 eq.), formic acid (3.5 g, 76.10 mmol, 8 eq.), warm to 85° C. and stir. TLC (DCM:MeOH=10:1) after 10 h showed the reaction was complete. Adjust the pH to 9~10 with 2 mol/L NaOH, and extract with ethyl acetate (20+20+20+20 ml). The organic phases were combined, washed with water (20 ml), washed with saturated sodium chloride (20 ml), dried over anhydrous magnesium sulfate, suction filtered, and the filtrate was evaporated under reduced pressure to obtain 3.55 g of light yellow liquid. Yield: 97.5%. $^1$H NMR (400 MHz, $CD_3OD$), δ 7.322~7.398 (m, 4H), 7.226~7.288 (m, 2H), 7.120 (s, 1H), 7.009 (s, 1H), 6.760 (d, J=8.4 Hz, 1H), 3.817 (s, 3H), 3.725 (s, 2H), 2.724 (m, 1H), 2.426 (d, J=13.6 Hz, 1H), 2.341 (s, 3H), 2.193~2.288 (m, 1H), 2.115 (s, 6H), 2.073~2.115 (m, 1H), 1.951~1.982 (m, 1H), 1.867~1.902 (m, 1H), 1.787 (m, 3H), 1.576~1.642 (m, 1H).

Example 1-31

4-(Benzyl(methyl)amino)-2-((dimethylamino)methyl)-1-(3-methoxyphenyl) cyclohexyl benzoate

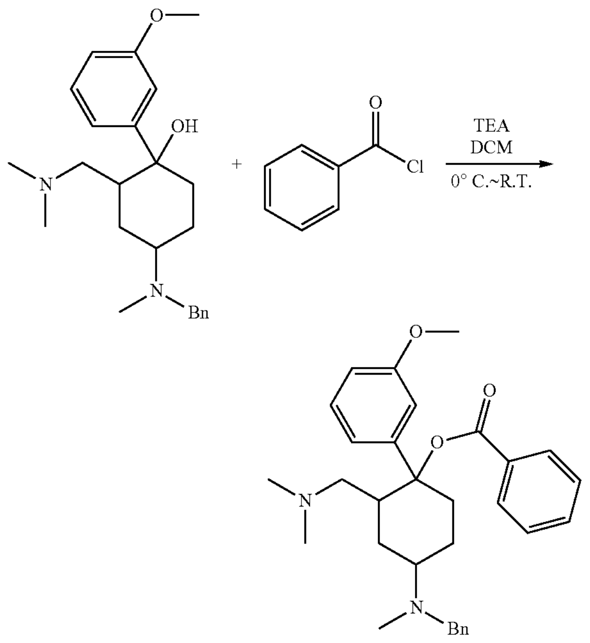

A 100 ml three-necked flask accompanied by a thermometer and a nitrogen balloon was charged with 4-(benzyl(methyl)amino)-2-((dimethylamino)methyl)-1-(3-methoxyphenyl) cyclohexan-1-ol (3.5 g, 9.15 mmol, 1 eq.), dichloromethane (35 ml), triethylamine (2.78 g, 27.45 mmol, 3 eq.) and cooled to 10° C. in an ice water bath. Next, add benzoyl chloride (2.57 g, 18.3 mmol, 2 eq.) to dichloromethane (3 ml) solution (no significant warming was observed). After dropwise addition, the ice water bath was withdrawn and stirred. 6 h later TLC (DCM:MeOH=10:1) showed complete reaction. Add water (50 ml) and adjust pH 8~9 with 2 mol/L NaOH. dichloromethane extraction (40+40+20 ml). The organic phases were combined, washed with water (40 ml), dried over anhydrous magnesium sulfate, filtered and the filtrate was evaporated under reduced pressure to give 6.6 g of light yellow liquid. Add water (100 ml), hydrochloric acid (2 mol/L, 12 ml). PE extraction (50+50+50 ml). The organic phases were combined and washed twice with hydrochloric acid (0.5 mol/L, 25 ml). All acid-water layers were combined and pH 9~10 adjusted with 2 mol/L NaOH. ethyl acetate extraction (50+50+50 ml). The ethyl acetate layer was combined, washed with saturated sodium chloride (50 ml), dried with anhydrous magnesium sulfate, filtered, and the filtrate was evaporated under reduced pressure to yield 5.07 g of colorless liquid. Purified with ethyl acetate (containing 1‰ TEA), silica gel column chromatography, yielded 4.73 g colorless liquid. Yield: 93%. $^1$H NMR (400 MHz, $CD_3OD$), δ 8.117 (d, J=8 Hz, 2H), 7.589~7.627 (m, 1H), 7.474~7.518 (m, 2H), 7.292~7.342 (m, 4H), 7.208~7.259 (m, 2H), 6.757~6.794 (m, 2H), 6.715~6.725 (m, 1H), 3.760 (s, 3H), 3.634 (s, 2H), 3.292~3.338 (m, 1H), 2.776 (m, 1H), 2.505~2.559 (m, 1H), 2.354~2.374 (m, 1H), 2.224 (s, 3H), 2.091~2.130 (m, 1H), 2.027~2.052 (m, 7H), 1.906~1.934 (m, 1H), 1.775~1.800 (m, 1H), 1.491~1.588 (m, 1H).

Example 1-32

2-((Dimethylamino)methyl)-1-(3-methoxyphenyl)-4-(dimethylamino)cyclohexyl benzoate

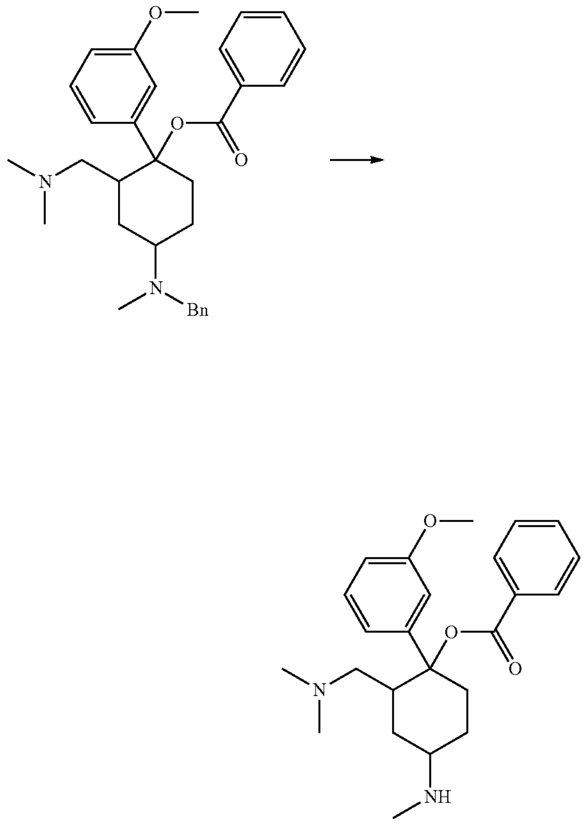

250 ml single-necked bottle with 4-(benzyl(methyl)amino)-2-((dimethylamino)methyl)-1-(3-methoxyphenyl) cyclohexyl benzoate (4.5 g, 9.25 mmol), methanol (45 ml), stirred to dissolve, 15% $Pd(OH)_2/C$ (0.45 g), stirred overnight at room temperature with hydrogen (13.5 h), about two-thirds of the material remaining. The reaction was not complete after two additions of hydrogen balloon, 15% $Pd(OH)_2/C$ (0.45 g) was added and two more additions of hydrogen balloon, TLC (DCM:MeOH=10:1) showed complete reaction. The 15% $Pd(OH)_2/C$ was filtered off and the filter cake was washed with methanol (30 ml). The filtrates were combined and evaporated under reduced pressure. The residue obtained was added with dichloromethane (50 ml), dried with anhydrous magnesium sulfate and filtered, and the filtrate was evaporated under reduced pressure to give 3.6 g of colorless liquid. Yield: 98%. $^1$H NMR (400 MHz, $CD_3OD$), δ 8.095 (d, J=Hz, 2H), 7.591 (s, 1H), 7.483 (s, 2H), 7.215~7.266 (m, 1H), 6.756~6.798 (m, 2H), 6.723 (s, 1H), 3.763 (s, 3H), 3.305 (d, J=15.2 Hz, 1H), 2.819 (m, 1H), 2.642 (m, 2H), 2.509 (s, 3H), 2.367~2.430 (m, 2H), 1.920~1.151 (m, 2H), 2.009 (s, 6H), 1.818 (m, 1H), 1.686 (m, 1H), 1.363~1.423 (m, 1H).

Example 1-33

2-((Dimethylamino)methyl)-1-(3-methoxyphenyl)-4-(N-methylbenzenesulfonylamino)cyclohexyl benzoate

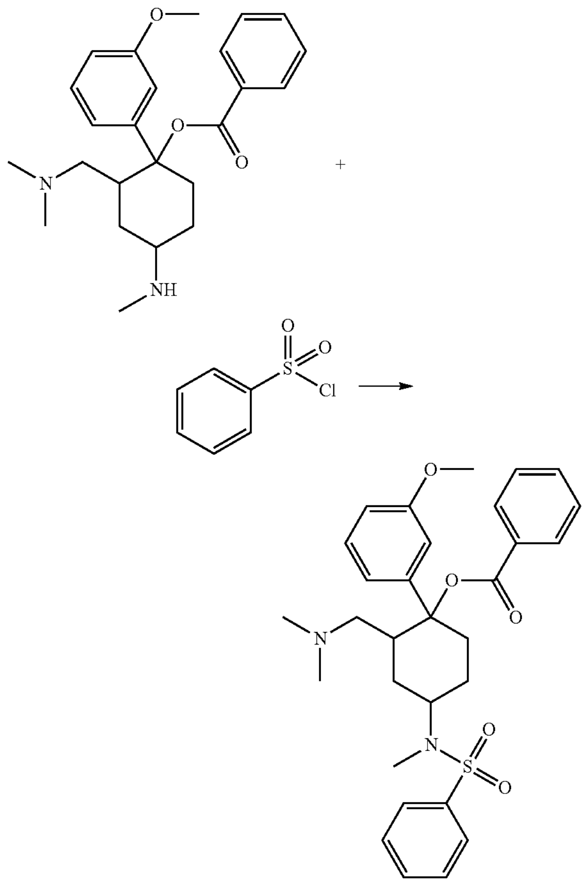 [SMILES: CNC1CCC(OC(=O)c2ccccc2)(c2cccc(OC)c2)C(CN(C)C)C1 ; O=S(=O)(Cl)c1ccccc1 ; COc1cccc(C2(OC(=O)c3ccccc3)CCC(N(C)S(=O)(=O)c3ccccc3)CC2CN(C)C)c1]

Add 2-((dimethylamino)methyl)-1-(3-methoxyphenyl)-4-(dimethylamino) cyclohexyl benzoate (0.5 g, 1.26 mmol, 1 eq.), dichloromethane (5 ml), triethylamine (0.191 g, 1.89 mmol, 1.5 eq.), benzenesulfonyl chloride (0.245 g, 1.39 mmol, 1.1 eq.), stirred at room temperature. Overnight (14 h), TLC (DCM:MeOH=10:1) showed a small amount of starting material, additional triethylamine (64 ml, 0.5 eq.), benzenesulfonyl chloride (111.4 mg, 0.5 eq.) were added. After 5 h, a small amount of raw materials remained, and triethylamine (1 eq.) and benzenesulfonyl chloride (1 eq.) were added. Overnight, with a small amount of starting material remaining, additional pyridine (0.1 g, 1 eq.) was added. A small amount of raw material remains. Next, add saturated sodium bicarbonate (30 ml), extract with dichloromethane (20+20+20 ml), combine the organic phases, wash with water (15 ml), dry over anhydrous magnesium sulfate, filter with suction, and evaporate the filtrate under reduced pressure to obtain 1.04 g Brown-black viscous substance. Purified by silica gel column chromatography (DCM-DCM:MeOH=200:1, plus 0.5% c triethylamine), 0.5 g of brownish yellow liquid was obtained. Yield: 74%. $^1$H NMR (400 MHz, $CDCl_3$), δ 8.065 (d, J=7.6 Hz, 2H), 7.845 (d, J=7.6 Hz, 2H), 7.482~7.614 (m, 6H), 7.214~7.269 (m, 1H), 6.792 (d, J=8.4 Hz, 1H), 6.733 (d, J=8 Hz, 1H), 6.684 (s, 1H), 4.114~4.138 (m, 2H), 3.766 (s, 3H), 3.239 (d, J=14.4 Hz, 1H), 2.700 (s, 3H), 2.483~2.538 (m, 1H), 2.085~2.156 (m, 2H), 2.001 (s, 6H), 1.756~1.899 (m, 2H), 1.502 (m, 2H), 1.253~1.284 (m, 1H).

Example 1-34

N-(3-((Dimethylamino)methyl)-4-hydroxy-4-(3-methoxyphenyl)cyclohexyl)-N-methylbenzenesulfonamide

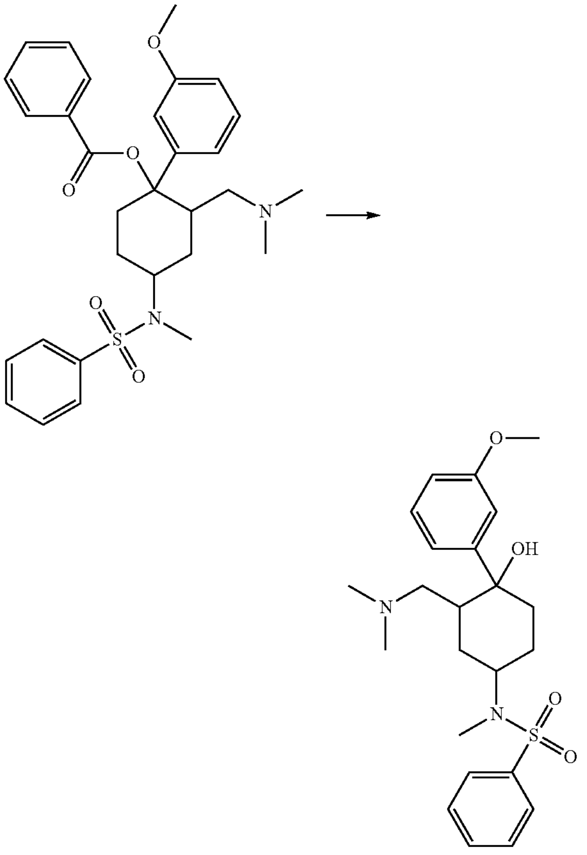 [SMILES: COc1cccc(C2(OC(=O)c3ccccc3)CCC(N(C)S(=O)(=O)c3ccccc3)CC2CN(C)C)c1 ; COc1cccc(C2(O)CCC(N(C)S(=O)(=O)c3ccccc3)CC2CN(C)C)c1]

A 50 ml single-necked vial with a nitrogen balloon was charged with 2-((dimethylamino)methyl)-1-(3-methoxyphenyl)-4-(N-methylbenzenesulfonylamino) cyclohexyl benzoate (0.47 g, 0.88 mmol, 1 eq.), THF (5 ml), dissolved with stirring, stirred in an ice-water bath, and lithium tetrahydroaluminum (50 mg, 1.5 eq.) was added. 1.5 h later TLC (DCM:MeOH=25:1) showed a small amount of new spots. DCM:MeOH=25:1) showed a small amount of new spot formation, supplemented with lithium tetrahydroaluminum (50 mg), withdrawn from the ice water bath and stirred. Overnight, there was still a small amount of raw material, supplemented with lithium tetrahydroaluminum (50 mg), and TLC showed basically complete reaction after 1 h. Add water (150 ul), 2 mol/L NaOH (300 ul), water (450 ul) dropwise under ice water bath, stirred for 10 min, and filtered, and the filter cake was drenched with ethyl acetate. The filtrate was combined and evaporated under reduced pressure to yield 0.41 g of colorless mucilage. Purified by silica gel column chromatography, 0.26 g of yellow mucilage was obtained. Yield: 68.4%.

Example 1-35

N-(3-((Dimethylamino)methyl)-4-hydroxy-4-(3-methoxyphenyl)cyclohexyl)-N-methylbenzenesulfonamide hydrochloride

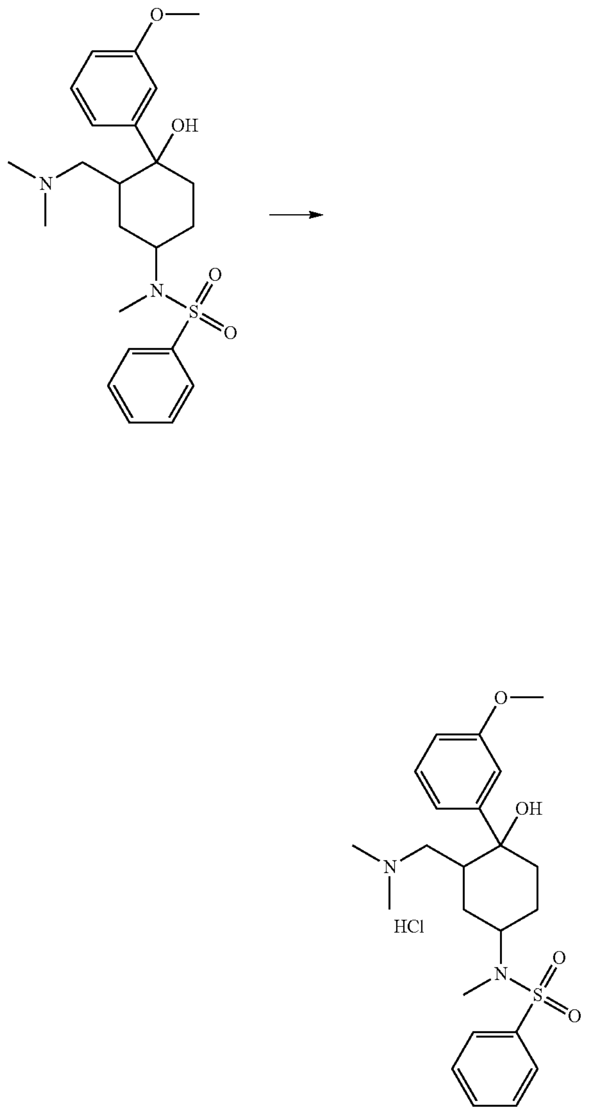

50 ml single-necked vial with N-(3-((dimethylamino) methyl)-4-hydroxy-4-(3-methoxyphenyl) cyclohexyl)-N-methylbenzenesulfonamide (0.28 g, 0.65 mmol, 1 eq.), DCM (3 ml), stirred to dissolve, add HCl/Dioxane (0.24 ml, 0.98 mmol, 1.5 eq.), precipitated as a solid. MTBE (6 ml) was added and stirred for 1 h. The filter cake was drenched with MTBE and evaporated under reduced pressure to give 0.256 g of a white solid. Yield: 84%. $^1H$ NMR (400 MHz, $CD_3OD$), δ 7.915 (d, J=7.6 Hz, 2H), 7.586~7.678 (m, 3H), 7.297 (t, J=8 Hz, 1H), 7.051~7.088 (m, 2H), 7.831 (d, J=8 Hz, 1H), 4.134~4.197 (t, 1H), 3.799 (s, 3H), 2.976~3.033 (m, 1H), 2.858 (s, 3H), 2.685 (s, 3H), 2.586~2.607 (m, 4H), 2.447~2.503 (t, 1H), 1.868~2.075 (m, 3H), 1.674~1.711 (m, 2H), 1.201~1.236 (m, 1H). LC-MS-$ESI^+$: $[M+H]^+$ 433.2

Example 1-36

4-((3-Chloro-N-methylphenyl)sulfonamido)-2-((dimethylamino)methyl)-1-(3-methoxyphenyl) cyclohexyl benzoate

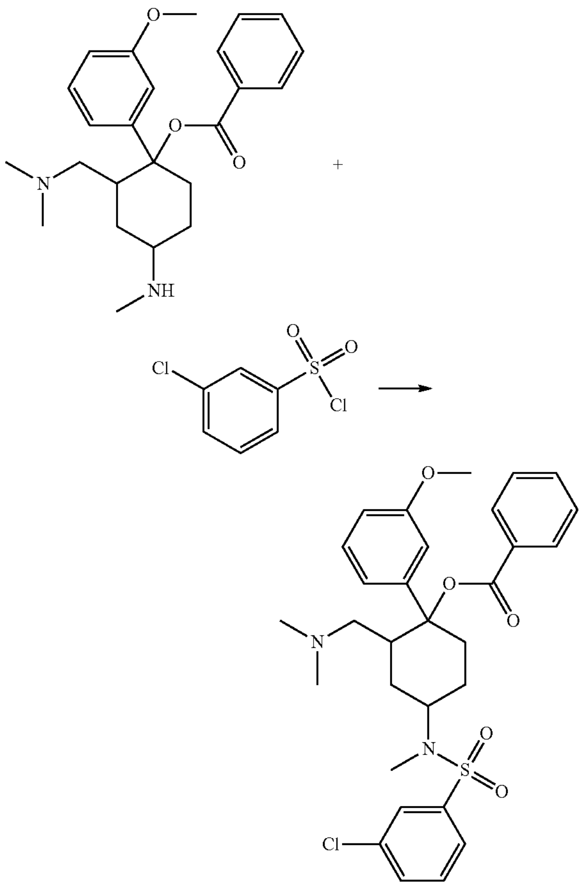 [SMILES: CNC1CCC(OC(=O)c2ccccc2)(c2cccc(OC)c2)C(CN(C)C)C1 ; O=S(=O)(Cl)c1cccc(Cl)c1 ; COc1cccc(C2(OC(=O)c3ccccc3)CCC(N(C)S(=O)(=O)c3cccc(Cl)c3)CC2CN(C)C)c1]

A 50 ml single port flask was charged with benzoic acid 2-((dimethylamino) methyl)-1-(3-methoxyphenyl)-4-(dimethylamino) cyclohexyl ester (0.5 g, 1.26 mmol, 1 eq.), dichloromethane (5 ml), triethylamine (0.382 g, 3.78 mmol, 3 eq.), stirred on an ice water bath, m-chlorophenylsulfonyl chloride (0.4 g, 1.89 mmol, 1.5 eq.) in DCM (1 ml), and stirred on an ice cold water bath. mL), water (20 ml), dichloromethane (15 ml), mix, stand, layer, and aliquot. Aqueous dichloromethane extraction (15+10 ml). The organic phases were combined, washed with water (20 ml), dried over anhydrous magnesium sulfate, suction filtered, and the filtrate was evaporated under reduced pressure to obtain 0.77 g of buffy gum. Silica gel column chromatography purification (DCM:MeOH=200:1 with 0.5% c TEA) afforded 0.47 g of the pale yellow viscous product. Yield: 65.3%. $^1H$ NMR (400 MHz, $CDCl_3$), δ 8.067 (d, J=8 Hz, 2H), 7.827 (s, 1H), 7.723 (d, J=8 Hz, 1H), 7.616 (t, J=7.6 Hz, 1H), 7.427~7.540 (m, 4H), 7.217~7.267 (m, 1H), 6.793 (d, J=8.4 Hz, 1H), 6.734 (d, J=8 Hz, 1H), 6.686 (s, 1H), 4.138 (m, 1H), 3.766 (s, 3H), 3.266 (d, J=14.4 Hz, 1H), 2.710 (s, 3H), 2.488 (t, J=11.2 Hz, 1H), 2.134~2.214 (m, 1H), 1.993 (s, 6H), 1.770~1.919 (m, 4H), 1.512~1.545 (m, 2H).

Example 1-37

3-Chloro-N-(3-((dimethylamino)methyl)-4-hydroxy-4-(methoxyphenyl)cyclohexyl)-N-methylbenzenesulfonamide

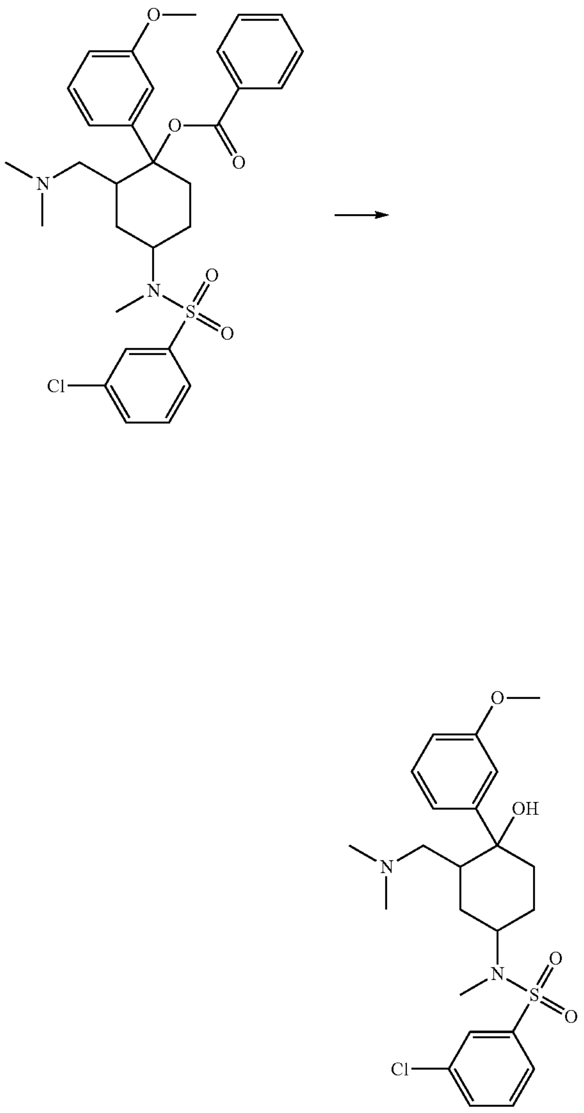

A 50 ml single port bottle was charged with benzoic acid 4-((3-chloro-n-methylphenyl) sulfonamido)-2-((dimethylamino) methyl)-1-(3-methoxyphenyl) cyclohexyl ester (0.45 g, 0.79 mmol, 1 eq.), THF (10 ml), lithium aluminum hydride (150 mg, 3.95 mmol, 5 eq.) and raised to 50° C. for reaction. TLC (DCM:MeOH=10:1) after 1.5 h showed complete response. Under an ice water bath, water (150 μl)、2 mol/L NaOH (300 μl), water (450 μl), stirred for about 30 min, and suction filtered. Cake dichloromethane was eluted. The filtrates were combined and the solvent was evaporated under reduced pressure to obtain 0.44 g of a colorless liquid. Silica gel column chromatography purification (DCM: MeOH=200:1 with 0.5% C TEA) afforded 164 mg of the colorless viscosity. Yield: 46.6%.

Example 1-38

3-Chloro-N-(3-((dimethylamino)methyl)-4-hydroxy-4-(methoxyphenyl)cyclohexyl)-N-methylbenzenesulfonamide hydrochloride

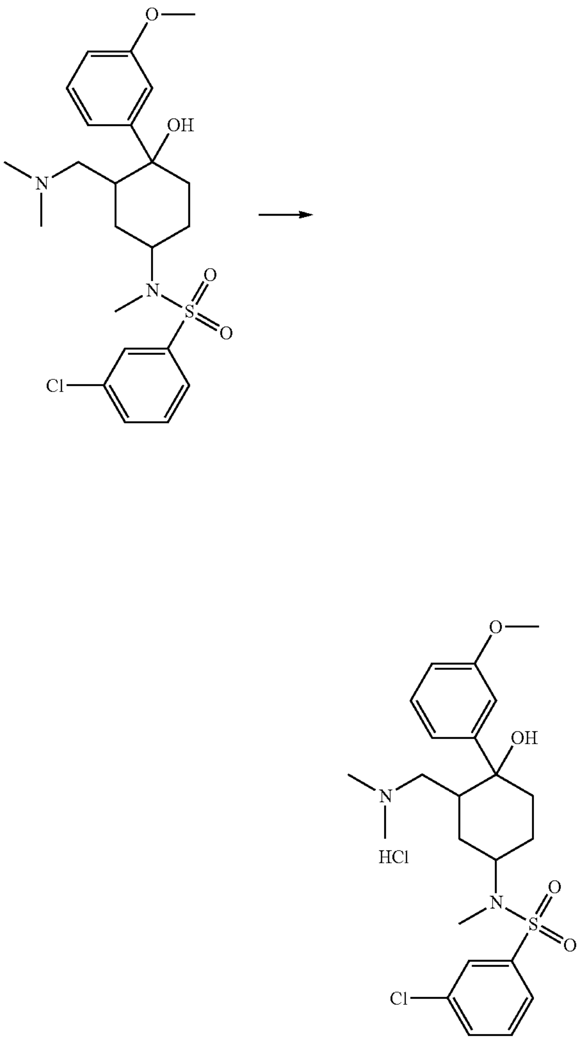

A 50 ml single port bottle was charged with 3-chloro-N-(3-((dimethylamino) methyl)-4-hydroxy-4-(methoxyphenyl) cyclohexyl)-N-methylbenzenesulfonamide (0.164 g, 0.4 mmol, 1 eq.), DCM (2 ml), dissolved by stirring, and HCl/dioxane (0.24 ml, 0.98 mmol, 1.5 eq.) was added and the solid was slowly eluted. Addition of MTBE (6 ml), stirring for 1 h, suction filtration, elution of cake MTBE, and evaporation to dryness under reduced pressure provided 0.166 g of a white like solid. Yield: 87.4%. $^1$H NMR (400 MHz, $CD_3OD$), δ 7.924 (s, 1H), 7.853 (d, J=7.6 Hz, 1H), 7.678 (d, J=8 Hz, 1H), 7.586~7.825 (t, 1H), 7.282~7.322 (t, 1H), 7.057~7.093 (m, 2H), 6.835 (d, J=7.6 Hz, 1H), 4.158~4.221 (t, 1H), 3.802 (s, 3H), 2.984~3.042 (q, 1H), 2.874 (s, 3H), 2.688 (s, 3H), 2.570~2.600 (m, 4H), 2.472~2.527 (m, 1H), 1.912~2.110 (m, 3H), 1.720 (d, J=12 Hz, 1H), 1.657 (d, J=12 Hz, 1H), 1.275 (d, J=12 Hz, 1H). LC-MS-ESI$^+$: $[M+H]^+$ 467.3.

Example 1-39

2-((Dimethylamino)methyl)-1-(3-methoxyphenyl)-4-(N-methylthiophene-2-ylsulfonamido)cyclohexyl benzoate

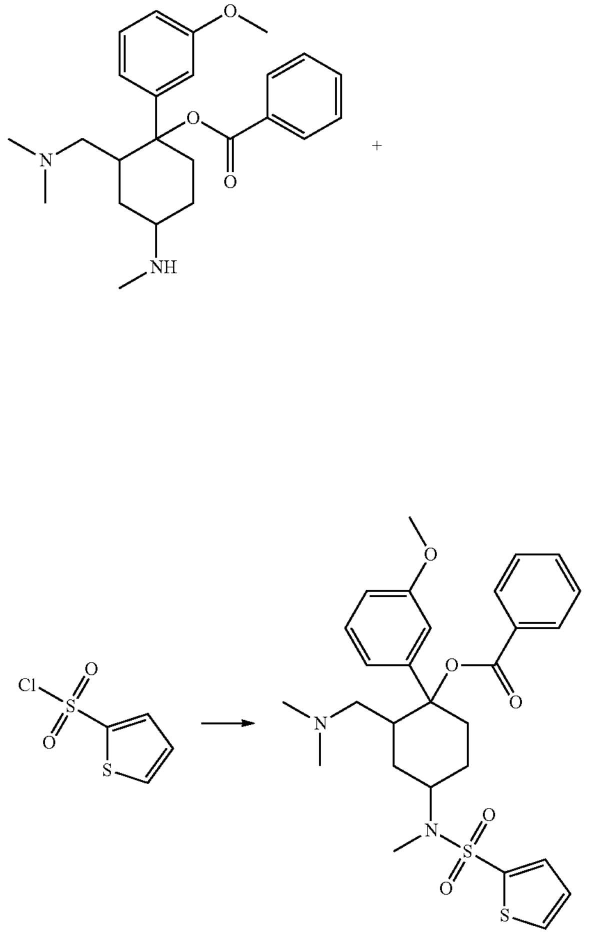

A 50 ml single port bottle was charged with a mixture of 2-((dimethylamino)methyl)-1-(3-methoxyphenyl)-4-(dimethylamino)cyclohexyl benzoate (0.5 g, 1.26 mmol, 1 eq.), dichloromethane (5 ml), triethylamine (0.382 g, 3.78 mmol, 3 eq.), and DCM (1 ml) supplemented with thiophene-2-ylsulfonyl chloride (0.35 g, 1.89 mmol, 1.5 eq.) by stirring on an ice water bath, water (20 ml), dichloromethane (15 ml), mix, stand, layer, and aliquot. Aqueous dichloromethane extraction (15+10 ml). The organic phases were combined, washed with water (20 ml), dried over anhydrous magnesium sulfate, suction filtered, and the filtrate was evaporated under reduced pressure to obtain 0.7 g of a brownish black viscous. Column chromatography on silica gel to purify 0.36 g of the light yellow viscous product. Yield: 52.7%. $^1$H NMR (400 MHz, $CDCl_3$), δ 8.076 (d, J=7.6 Hz, 2H), 7.545~7.643 (m, 3H), 7.474~7.512 (t, 3H), 7.219~7.267 (m, 1H), 7.088 (s, 1H), 6.794 (d, J=8.4 Hz, 1H), 6.737 (d, J=7.6 Hz, 1H), 6.688 (s, 1H), 4.157 (m, 1H), 3.767 (s, 3H), 3.255 (d, J=14.8 Hz, 1H), 2.740 (s, 3H), 2.530 (t, J=11.2 Hz, 1H), 2.127~2.167 (m, 1H), 2.017 (s, 6H), 2.017~2.067 (m, 1H), 1.767~1.945 (m, 3H), 1.512 (m, 2H).

Example 1-40

N-(3-((Dimethylamino)methyl)-4-hydroxy-4-(3-methoxyphenyl)cyclohexyl)-N-methylthiophene-2-sulfonamide

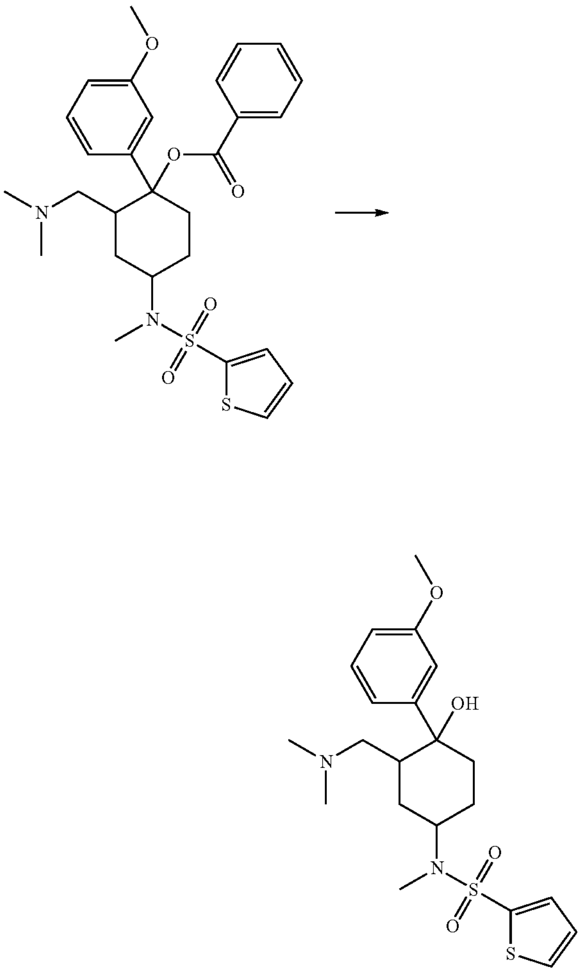

A 100 ml single port flask was charged with benzoic acid 2-((dimethylamino) methyl)-1-(3-methoxyphenyl)-4-(N-methylthiophene-2-ylsulfonamido) cyclohexyl ester (0.32 g, 0.59 mmol, 1 eq.), THF (5 ml), stirred on ice water bath, lithium aluminum hydride (70 mg, 1.77 mmol, 3 eq.), stirred naturally to room temperature overnight (13 h), and TLC (DCM:MeOH=10:1) revealed the presence of about half of the starting material. Ice water bath cooled, supplemented with lithium aluminum hydride (70 mg, 1.77 mmol, 3 eq.). Overnight, TLC showed that there was still a small amount of starting material, which was supplemented with lithium aluminum hydride (70 mg, 1.77 mmol, 3 eq.). Overnight, still with a small amount of starting material. mmol/L NaOH (420 μL), water (630 μL) and stirred for 30 min under ice water bath, then the filtrate was evaporated under reduced pressure to obtain 0.36 g colorless liquid. Silica gel column chromatography (EA:PE=1:2) to obtain 0.25. Plate purification was prepared to obtain 124 mg of the viscous material. Yield: 48%.

Example 1-41

N-(3-((Dimethylamino)methyl)-4-hydroxy-4-(3-methoxyphenyl) cyclohexyl)-N-methylthiophene-2-sulfonamide hydrochloride

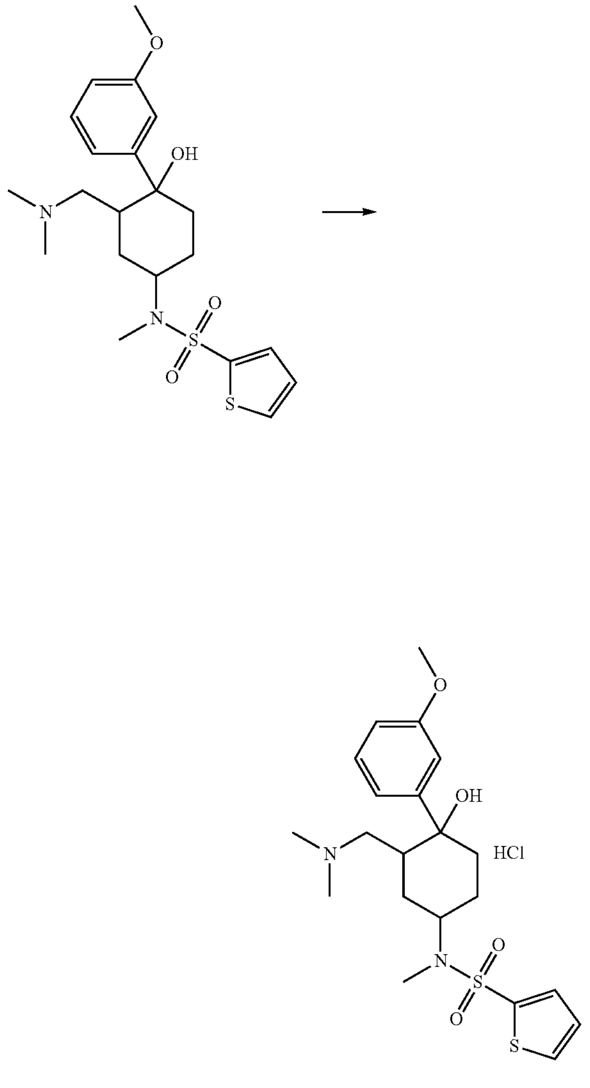

A 50 ml single port flask was charged with N-(3-((dimethylamino) methyl)-4-hydroxy-4-(3-methoxyphenyl) cyclohexyl)-N-methylthiophene-2-sulfonamide (0.124 g, 0.3 mmol, 1 eq.), DCM (2 ml), dissolved with stirring, and HCl/dioxane (0.113 ml, 0.45 mmol, 1.5 eq.) was added, and no solid was isolated. MTBE (6 ml) was added, stirred for 1.5 h, and the filter was aspirated, and the cake MTBE was eluted and evaporated to dryness under reduced pressure to yield 110 mg of a white like solid. Yield: 77%. $^1H$ NMR (400 MHz, $CD_3OD$), δ 7.817 (d, J=4.8 Hz, 1H), 7.686 (s, 1H), 7.300 (d, J=8 Hz, 1H), 7.201 (t, J=8.8 Hz, 1H), 7.053~7.092 (m, 2H), 6.821~6.846 (m, 1H), 4.124~4.187 (t, 1H), 3.800 (s, 3H), 2.987~3.044 (q, 1H), 2.888 (s, 3H), 2.577~2.643 (m, 7H), 2.450~2.507 (t, 1H), 1.88~2.077 (m, 3H), 1.710 (d, J=12 Hz, 2H), 1.245 (d, J=12 Hz, 1H). LC-MS-ESI$^+$: $[M+H]^+$ 439.2.

Example 1-42

2-((Dimethylamino)methyl)-1-(3-methoxyphenyl)-4-((N-methyl-1-benzyl)sulfonamido) cyclohexyl benzoate

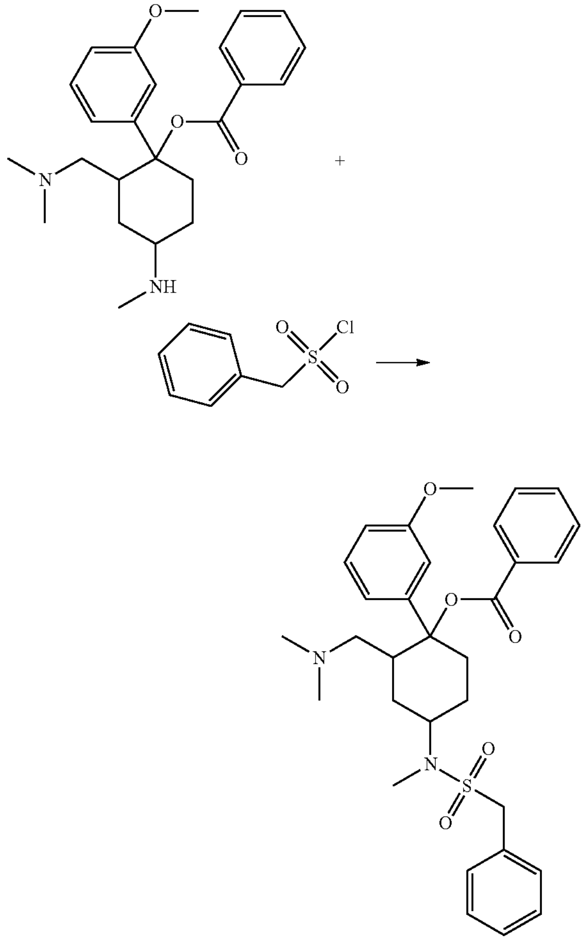

2-((Dimethylamino) methyl)-1-(3-methoxyphenyl)-4-(dimethylamino) cyclohexyl benzoate (0.5 g, 1.26 mmol, 1 eq.), dichloromethane (12 ml), tea (0.382 g, 3.78 mmol, 3 eq.), DMAP (154 mg, 1.26 mmol, 1 eq.) were added to 50 ml single mouth bottle. Benzylsulfonyl chloride (0.36 g, 1.89 mmol, 1.5 eq.) was added under stirring in an ice water bath. After stirring for 5 min, remove the ice water bath and stir until TLC (DCM:MeOH=10:1) showed that the reaction is complete. The volatile material was evaporated under reduced pressure and purified by silica gel column chromatography (EA:PE=4:5~1:1 with 0.5% c triethylamine) to give 266 mg of light yellow mucilage. Yield: 38.3%. $^1H$ NMR (400 MHz, $CDCl_3$), δ 8.085 (d, J=7.6 Hz, 2H), 7.609~7.629 (m, 1H), 7.484~7.523 (m, 2H), 7.426~7.444 (m, 2H), 7.355~7.37 (m, 3H), 7.215~7.270 (m, 1H), 6.793 (d, J=8.4 Hz, 1H), 6.715 (d, J=8 Hz, 1H), 6.669 (s, 1H), 4.248 (s, 2H), 3.869 (m, 1H), 3.763 (s, 3H), 3.236 (d, J=14.4 Hz, 1H), 2.594 (s, 3H), 1.867~2.175 (m, 4H), 1.513~1.605 (m, 2H), 1.260~1.283 (m, 2H). LC-MS-ESI$^+$: $[M+H]^+$ 551.4.

Example 1-43

N-(3-((Dimethylamino)methyl)-4-hydroxy-4-(3-methoxyphenyl)cyclohexyl)-N-methyl-1-phenyl-methanesulfonamide

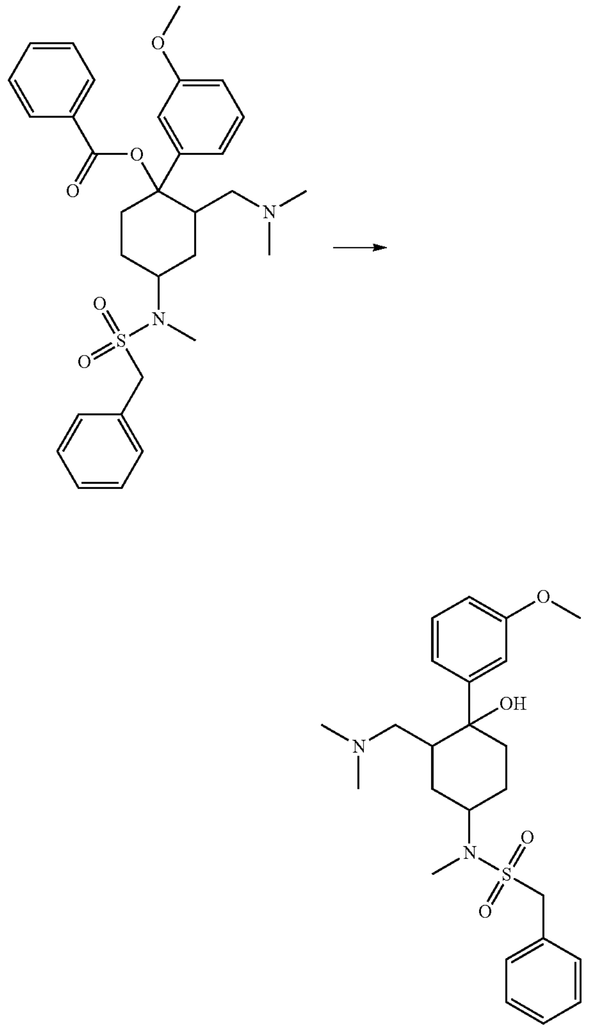

A 50 ml single port bottle with a nitrogen balloon was charged with 2-((dimethylamino)methyl)-1-(3-methoxyphenyl)-4-((N-methyl-1-benzyl)sulfonamido)cyclohexyl benzoate (0.38 g, 0.7 mmol, 1 eq.), THF (4 ml), dissolved by stirring, and stirred in an ice water bath, adding lithium aluminum tetrahydride (80 mg, 3 eq.). Stirring was obtained in an ice water bath after 10 min and TLC (DCM: MeOH=20:1) after 3 h showed that about half of the starting material was left, lithium aluminum tetrahydride (80 mg) was added and the ice water bath was stirred. TLC after 4 h showed the basic response was complete. Water (160 μL), 2 mol/L NaOH (320 μL), water (480 μL) was added dropwise under ice water bath, stirred for 20 min, aspirated and filtered, and then the cake was eluted with ethyl acetate. The filtrates were combined and evaporated under reduced pressure to obtain 0.37 g of a colorless viscous substance. Plate purification was prepared to give 70 mg of the viscous.

Example 1-44

2-((Dimethylamino)methyl)-1-(3-methoxyphenyl)-4-((N-methyl-1-benzyl)sulfonylamino) cyclohexyl benzoate hydrochloride Salt

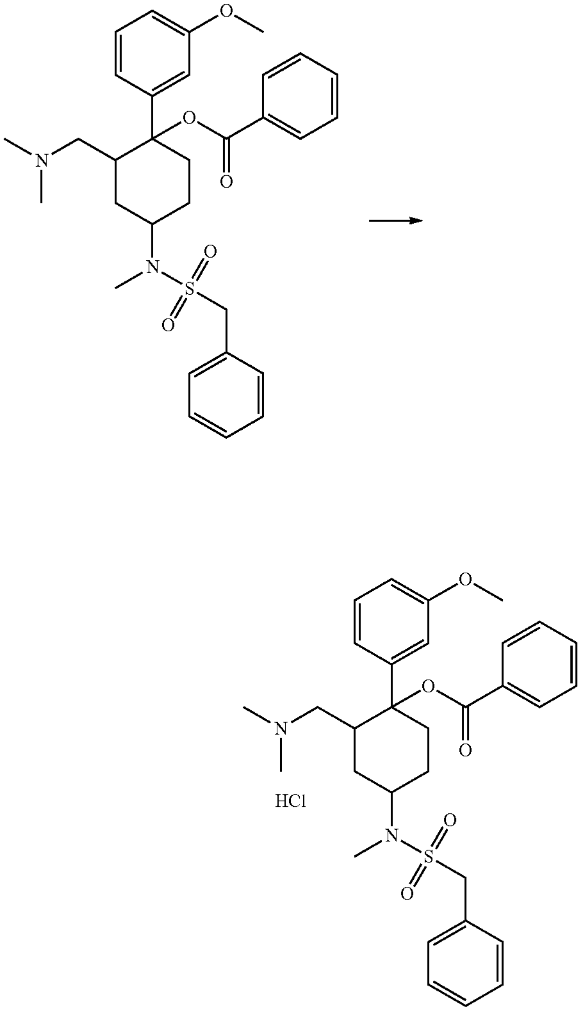

A 50 ml single port flask was charged with N-(3-((dimethylamino)methyl)-4-hydroxy-4-(3-methoxyphenyl) cyclohexyl)-N-methyl-1-phenylmethanesulfonamide (0.164 g, 0.3 mmol, 1 eq.), DCM (2 ml), dissolved by stirring, and HCl/dioxane (0.113 ml, 0.45 mmol, 1.5 eq.) was added, and no solid precipitated. Addition of MTBE (9 ml), stirring for 1.5 h, suction filtration, elution of cake MTBE, and evaporation to dryness under reduced pressure afforded 98 mg of a white like solid. Yield: 56%. $^1H$ NMR (400 MHz, $CD_3OD$), δ 8.153 (d, J=7.6 Hz, 2H), 7.701 (t, J=7.6 Hz, 1H), 7.554~7.593 (t, 2H), 7.452~7.468 (m, 2H), 7.367~7.381 (m, 3H), 7.301~7.341 (t, 1H), 6.906 (d, J=8.4 Hz, 1H), 6.856 (d, J=7.6 Hz, 1H), 6.808 (s, 1H), 4.359~4.439 (q, 2H), 4.007~4.038 (m, 1H), 3.762 (s, 3H), 3.346~3.406 (m, 1H), 3.177~3.217 (m, 1H), 2.874 (d, J=6.8 Hz, 1H), 2.779 (s, 3H), 2.649 (s, 3H), 2.469 (s, 3H), 2.417 (m, 1H), 2.271~2.338 (m, 1H). 2.084~2.214 (m, 2H), 1.539~1.596 (m, 2H). LC-MS-ESI$^+$: $[M+H]^+$ 551.3.

Example 1-45

4-((1-(3-Chlorophenyl)-N-methyl)sulfonylamino)-2-((dimethylamino)methyl)-1-(3-methoxyphenyl)cyclohexyl benzoate

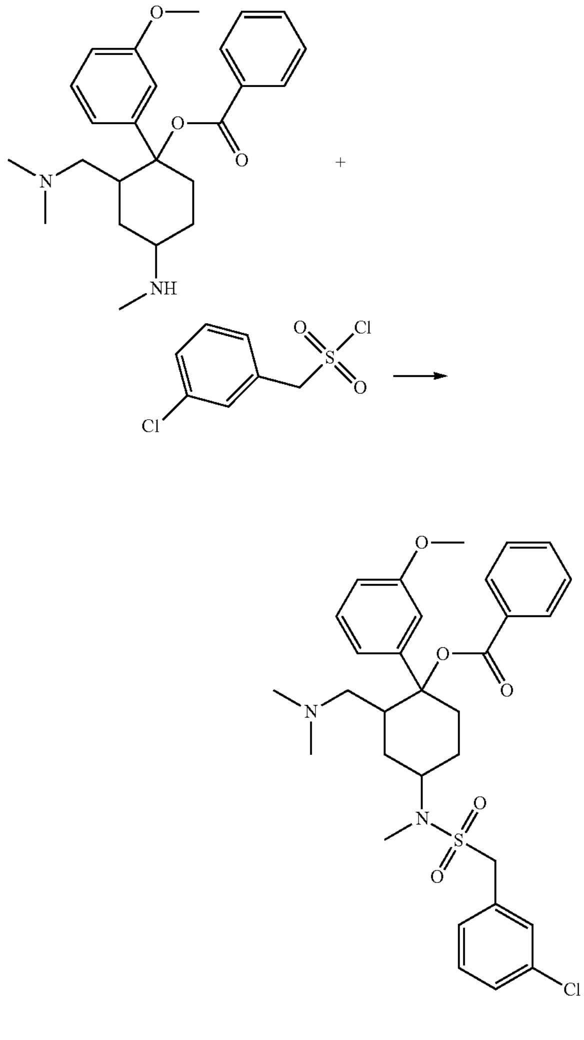

A 50 ml single port flask was charged with 2-((dimethylamino)methyl)-1-(3-methoxyphenyl)-4-(dimethylamino) cyclohexyl benzoate (0.5 g, 1.26 mmol, 1 eq.), dichloromethane (12 ml), TEA (0.382 g, 3.78 mmol, 3 eq.), DMAP (154 mg, 1.26 mmol, 1 eq.), and stirred in an ice water bath. m-chlorobenzylsulfonyl chloride (0.43 g, 1.89 mmol, 1.5 eq.) was added and stirred for 5 min. Overnight (12 h), TLC (DCM:MeOH=10:1) showed essentially complete reaction. Add water (20 ml), adjust pH 8~9 with 2 mol/L NaOH solution, dichloromethane extraction (25+25+10 ml), organic phases were combined, washed with water (15 ml), dried with anhydrous magnesium sulfate, filtered, and the filtrate was evaporated under reduced pressure to yield 0.9 g of yellow mucilage. Purified by silica gel column chromatography (EA:PE=1:1, plus 0.5% c triethylamine), yielding 0.9 g yellow liquid. Purified by silica gel column chromatography (DCM:MeOH=150:1, with 0.5% c TEA) to give 174 mg of light yellow liquid. Yield: 23.6%.

Example 1-46

4-((1-(3-Chlorophenyl)-N-methyl)sulfonylamino)-2-((dimethylamino)methyl)-1-(3-methoxyphenyl)cyclohexyl benzoate hydrochloride

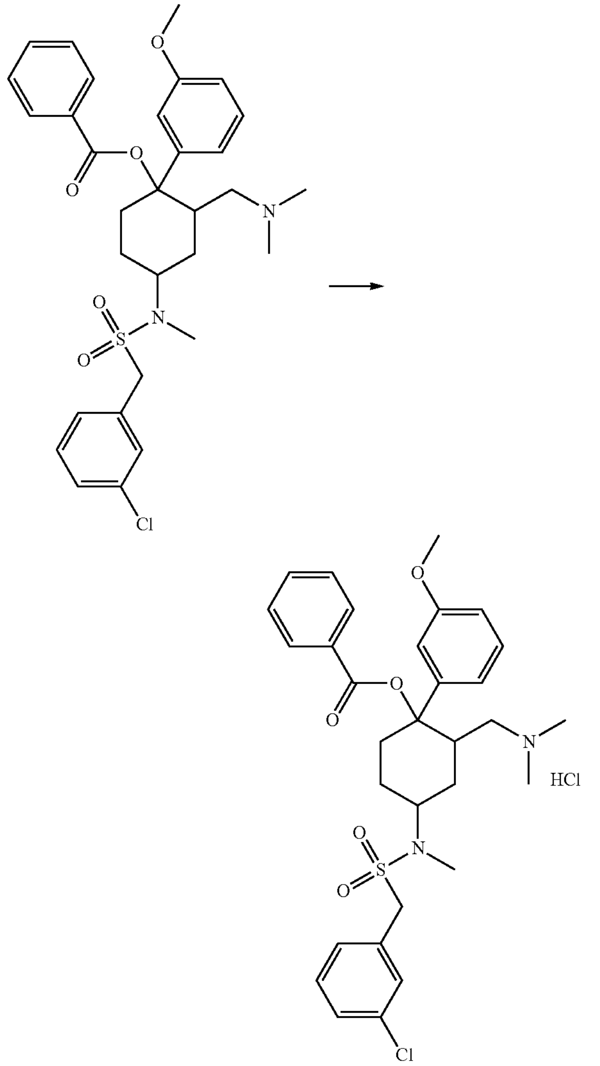

A 50 ml single port bottle was charged with 4-((1-(3-chlorophenyl)-N-methyl)sulfonamido)-2-((dimethylamino) methyl)-1-(3-methoxyphenyl) cyclohexyl benzoate (0.174 g, 0.3 mmol, 1 eq.), DCM (2 ml), dissolved by stirring, and HCl/dioxane (0.113 ml, 0.45 mmol, 1.5 eq.) was added, and no solid precipitated. Addition of MTBE (12 ml), stirring for 2.5 h, suction filtration, elution of cake MTBE, and evaporation to dryness under reduced pressure afforded 168 mg of a white like solid. Yield: 90.3%. $^1H$ NMR (400 MHz, $CD_3OD$), δ 8.162 (d, J=7.6 Hz, 2H), 7.704 (t, J=7.6 Hz, 1H), 7.577 (t, J=7.6 Hz, 2H), 7.508 (s, 1H), 7.379~7.411 (m, 3H), 7.306~7.345 (t, 1H), 6.820~6.920 (m, 3H), 4.376~4.460 (q, 2H), 4.076 (m, 1H), 3.765 (s, 3H), 3.355~3.412 (t, 1H), 3.214~3.252 (m, 1H), 2.893 (d, J=13.2 Hz, 1H), 2.779 (s, 3H), 2.692 (s, 3H), 2.315~2.477 (m, 5H), 2.156~2.242 (m, 2H), 1.629 (m, 2H). LC-MS-ESI$^+$: $[M+H]^+$ 585.3.

Example 1-47

N-Benzyl-N-(3-((dimethylamino)methyl)-4-hydroxy-4-(3-methoxyphenyl)cyclohexyl) benzenesulfonamide

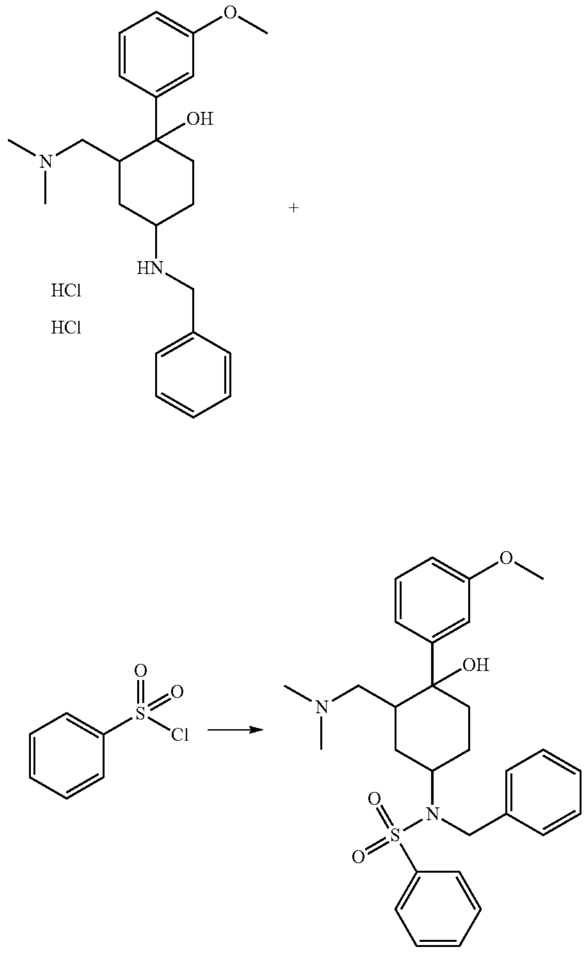

A 50 ml three port bottle containing nitrogen, thermometer was charged with 4-(benzylamino)-2-((dimethylamino) methyl)-1-(3-methoxyphenyl) cyclohex-1-ol dihydrochloride (1 g, 2.3 mmol, 1 eq.), dichloromethane (10 ml), triethylamine (1.05 g, 10.35 mmol, 4.5 eq.), and stirred in an ice water bath. 5° C. was added a solution of benzenesulfonyl chloride (0.6 g, 3.4 mmol, 1.5 eq.) in dichloromethane (1 ml). Keep stirring. A small amount of starting material remained after 4.5 h. Triethylamine (0.223 g, 1 eq.), benzenesulfonyl chloride (0.2 g, 0.5 eq.), and TLC (DCM: MeOH=10:1) after 5.5 h showed complete reaction. ml), water (30 ml), dichloromethane (15 ml), mix, stand, layer, and aliquot. Aqueous dichloromethane extraction (25+15 ml). The organic phases were combined and water was washed (20 ml), saturated sodium bicarbonate was washed (20 ml), anhydrous magnesium sulfate was dried, suction filtered, and the filtrate was evaporated under reduced pressure to yield 1.06 g of foam. Ethyl acetate/Pet ether (2:1, 12 ml) crystallized to afford 0.84 g of a white solid. Yield: 71.8%.

Example 1-48

N-Benzyl-N-(3-((dimethylamino)methyl)-4-hydroxy-4-(3-methoxyphenyl)cyclohexyl) benzenesulfonamide hydrochloride

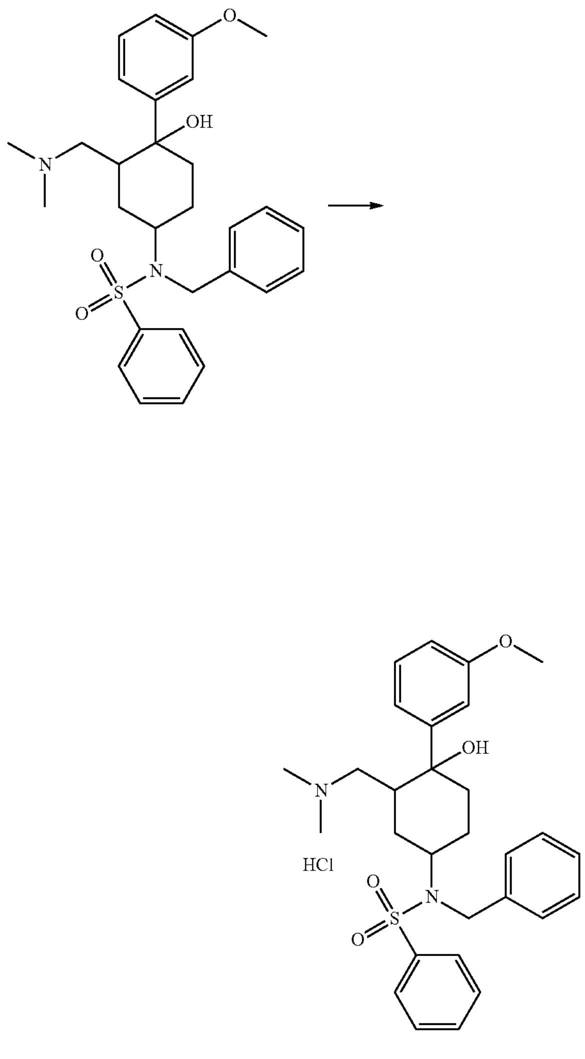

A 100 ml single port flask was charged with N-benzyl-N-(3-((dimethylamino) methyl)-4-hydroxy-4-(3-methoxyphenyl) cyclohexyl) benzenesulfonamide (0.4 g, 0.79 mmol, 1 eq.), DCM (3 ml) dissolved by stirring, and HCl/dioxane (0.3 ml, 1.19 mmol, 1.5 eq.) was added, and no solid precipitated. MTBE (12 ml) was added, and the solid was precipitated and stirred for 1 h. Filtration was aspirated, cake MTBE was eluted, and evaporated to dryness under reduced pressure to yield 0.37 g of a white solid. Yield: 86%. $^1$H NMR (400 MHz, $CD_3OD$), δ 7.937 (d, J=7.6 Hz, 2H), 7.573~7.673 (m, 3H), 7.478 (d, J=7.8 Hz, 2H), 7.33 (t, J=7.6 Hz, 2H), 7.252~7.292 (m, 2H), 7.001~7.037 (m, 2H), 6.811 (d, J=8.4 Hz, 1H), 4.498~4.615 (q, 2H), 4.128 (t, J=11.6 Hz, 1H), 3.779 (s, 3H), 2.800~2.857 (t, 1H), 2.469~2.590 (m, 7H), 2.343~2.371 (m, 1H), 1.826~2.005 (m, 3H), 1.642 (d, J=12.0 Hz, 1H), 1.347 (d, J=10.8 Hz, 1H. LC-MS-ESI$^+$: $[M+H]^+$ 509.3.

Example 1-49

N-Benzyl-3-chloro-N-(3-((dimethylamino)methyl)-4-hydroxy-4-(3-methoxyphenyl)cyclohexyl) benzenesulfonamide

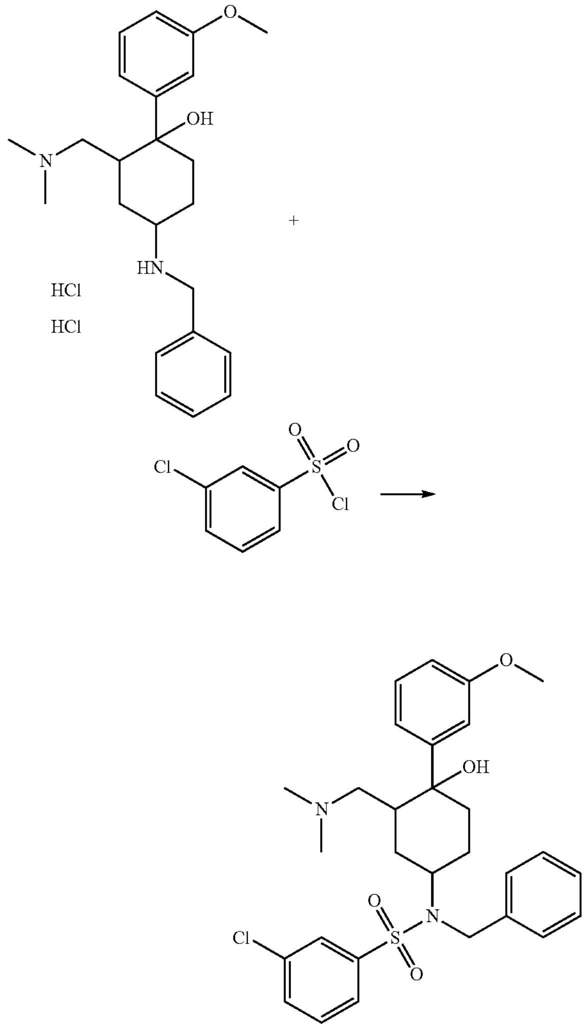

A 50 ml single port flask was charged with 4-(benzylamino)-2-((dimethylamino) methyl)-1-(3-methoxyphenyl) cyclohex-1-ol dihydrochloride (0.5 g, 1.132 mmol, 1 eq.), dichloromethane (5 ml), triethylamine (0.573 g, 5.66 mmol, 5 eq.), and stirred on ice with m-chlorophenylsulfonyl chloride (0.48 g, 2.265 mmol, 2 eq.) and held on ice. After overnight (12 h), TLC (DCM:MeOH=10:1) after 5.5 h showed that the reaction was complete, extracted with water (15 ml), dichloromethane (15 ml), mixed, allowed to stand, layered, and aliquoted. Aqueous dichloromethane extraction (15 ml). The organic phases were combined, water washed (10 ml), dried over anhydrous magnesium sulfate, suction filtered, and the filtrate evaporated under reduced pressure to obtain 0.55 g of a light yellow viscous substance. Silica gel column chromatography purification (DCM~DCM: MeOH=200:1 with 0.5% c triethylamine) provided 0.46 g of a white foam. Yield: 75%.

Example 1-50

N-benzyl-3-chloro-N-(3-((dimethylamino)methyl)-4-hydroxy-4-(3-methoxyphenyl)cyclohexyl) benzenesulfonamide hydrochloride

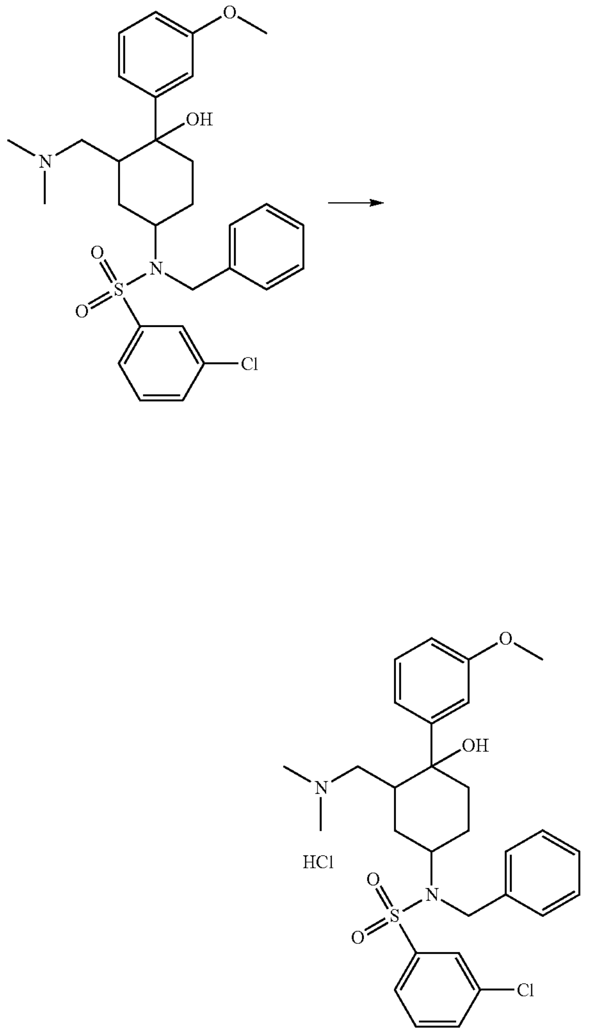

A 50 ml single port flask was charged with n-benzyl-3-chloro-N-(3-((dimethylamino)methyl)-4-hydroxy-4-(3-methoxyphenyl) cyclohexyl) benzenesulfonamide (0.42 g, 0.78 mmol, 1 eq.), DCM (3 ml) dissolved by stirring, and HCl/dioxane (0.29 ml, 1.16 mmol, 1.5 eq.) was added, and no solid precipitated. MTBE (6 ml) was added, and the solid was precipitated and stirred for 1 h. Filtration was aspirated. Filter cake was washed with MTBE, and evaporated to dryness under reduced pressure to yield 0.437 g of a white solid. Yield: 97%. $^1$H NMR (400 MHz, $CD_3OD$), δ 7.842 (d, J=9.6 Hz, 2H), 7.647 (d, J=8 Hz, 1H), 7.566 (t, J=8 Hz, 1H), 7.457 (d, J=7.6 Hz, 2H), 7.262~7.347 (m, 4H), 7.015~7.043 (m, 2H), 6.819 (d, J=8 Hz, 1H), 4.514~4.607 (q, 2H), 4.173 (t, J=12 Hz, 1H), 3.785 (s, 3H), 2.833~2.890 (m, 1H), 2.525~2.559 (m, 7H), 2.368~2.422 (t, 1H), 1.866~2.024 (m, 4H), 1.659~1.695 (m, 2H), 1.413 (d, J=10.8 Hz, 1H). LC-MS-ESI$^+$: $[M+H]^+$ 543.3.

Example 1-51

N-Benzyl-N-(3-((dimethylamino)methyl)-4-hydroxy-4-(3-methoxyphenyl)cyclohexyl)thiophene-2-sulfonamide

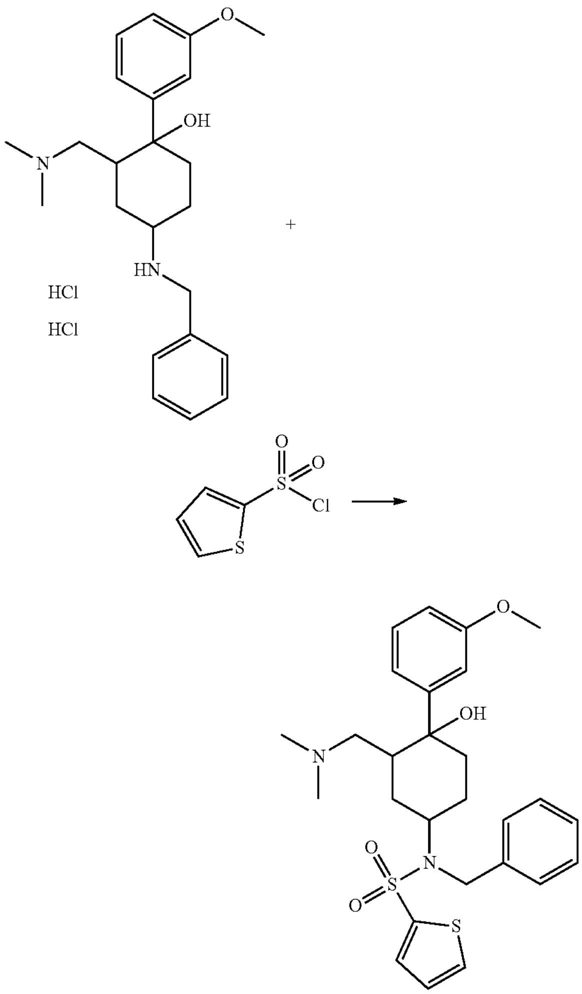

A 50 ml three port bottle containing nitrogen, thermometer was charged with 4-(benzylamino)-2-((dimethylamino)methyl)-1-(3-methoxyphenyl) cyclohex-1-ol dihydrochloride (0.5 g, 1.132 mmol, 1 eq.), dichloromethane (5 ml), triethylamine (0.573 g, 5.66 mmol, 5 eq.), and stirred on ice with water bath. Plus thiophene-2-sulfonyl chloride (0.414 g, 2.265 mmol, 2 eq.). Keep stirring. TLC (DCM: MeOH=10:1) after 5.5 h showed complete response. ml), saturated sodium bicarbonate (25 ml), dichloromethane (5 ml), mixed, allowed to stand, layered, and aliquoted. Aqueous dichloromethane extraction (15 ml). The organic phases were combined, washed with water (10 ml), dried over anhydrous magnesium sulfate, suction filtered, and the filtrate was evaporated under reduced pressure to obtain 0.59 g of brownish black viscous. Silica gel column chromatography purification (DCM~DCM:MeOH=200:1, with 0.5% c triethylamine) provided 0.45 g of a pale yellow solid. Yield: 78.5%.

Example 1-52

N-Benzyl-N-(3-((dimethylamino)methyl)-4-hydroxy-4-(3-methoxyphenyl)cyclohexyl)thiophene-2-sulfonamide hydrochloride

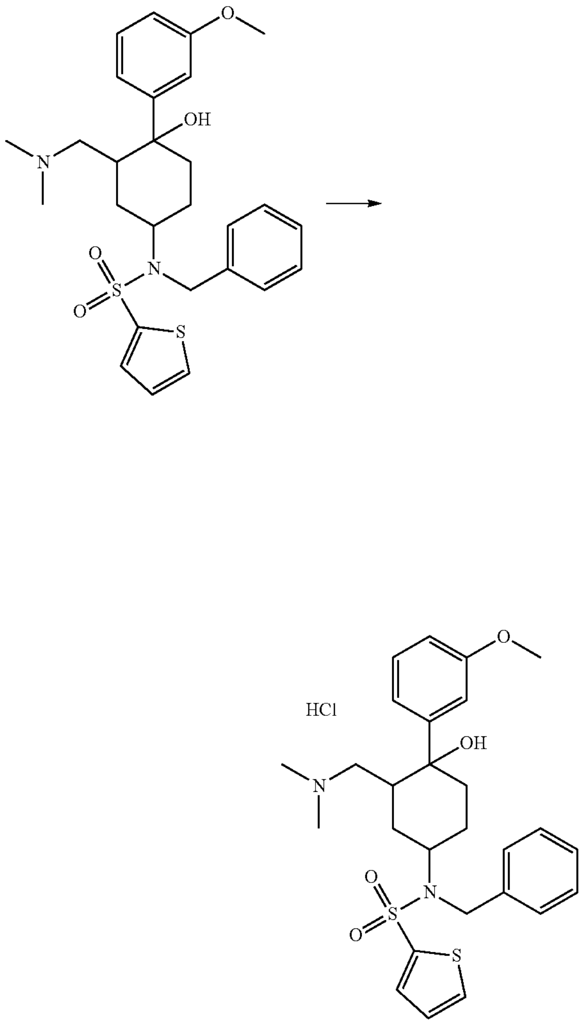

A 50 ml single port flask was charged with N-benzyl-N-(3-((dimethylamino) methyl)-4-hydroxy-4-(3-methoxyphenyl) cyclohexyl) thiophene-2-sulfonamide (0.3 g, 0.6 mmol, 1 eq.), DCM (2 ml), dissolved by stirring, and HCl/dioxane (0.113 ml, 0.45 mmol, 1.5 eq.) was added, and the solid was slowly eluted. MTBE (6 ml) was added, stirred for 1 h, and the filter was aspirated, and the cake MTBE was eluted and evaporated to dryness under reduced pressure to afford 298 mg of a white like solid. Yield: 95%. $^1H$ NMR (400 MHz, $CD_3OD$), δ 7.817~7.833 (m, 1H), 7.715~7.729 (m, 1H), 7.495 (d, J=7.6 Hz, 2H), 7.351 (t, J=7.6 Hz, 2H), 7.257~7.295 (t, 2H), 7.190 (t, J=8.4 Hz, 1H), 7.004~7.032 (m, 2H), 6.802~6.829 (m, 1H), 7.474~7.614 (q, 2H), 4.115~4.145 (m, 1H), 3.780 (s, 3H), 2.808~2.864 (q, 1H), 2.495~2.593 (m, 7H), 2.324~2.379 (m, 1H), 1.832~2.023 (m, 3H), 1.659~1.693 (m, 2H), 1.368~1.390 (m, 1H). LC-MS-ESI$^+$: $[M+H]^+$ 515.3.

Example 1-53

1,4-Dioxaspiro[4.5]dec-8-ol

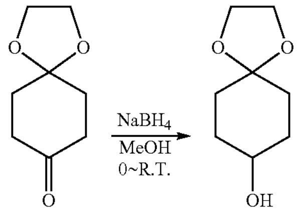

A 250 ml three port bottle with thermometer was charged with 1,4-dioxaspiro [4.5] decan-8-one (10 g, 64.03 mmol, 1 eq.), MeOH (80 ml), stirred, and a small amount was left undissolved, and sodium borohydride (0.61 g+0.6 g, 3.2 mol, 0.5 eq.) was added twice under ice water bath. After that, stirred in an ice withdrawal water bath, and after 0.5 h TLC (DCM:MeOH=100:1, color development with 2,4-dinitrophenylhydrazine) showed complete reaction. Water (40 ml) was added and methanol was evaporated under reduced pressure and ethyl acetate extracted (50+50+25+25 ml). The organic phases were combined, dried over anhydrous magnesium sulfate, suction filtered, and the filtrate was evaporated under reduced pressure to afford 10.02 g of a colorless liquid. Yield: 98.9%. Without purification and used directly in the next step.

Example 1-54

1,4-Dioxaspiro[4.5]dec-8-ylmethanesulfonate

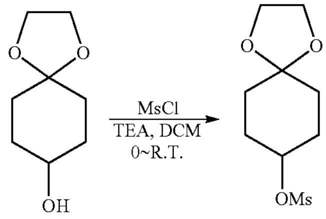

A 250 ml single port bottle with a thermometer, constant pressure dropping funnel was charged with 1,4-dioxaspiro [4.5] dec-8-ol (10 g, 63.21 mmol, 1 eq.), dichloromethane (100 ml), triethylamine (8.32 g, 82.17 mmol, 1.3 eq.), and stirred in an ice water bath at 30° C. with methanesulfonyl chloride (8.69 g, 75.85 mmol, 1.2 eq.). All drops were added and the ice bath stirred. Overnight (14 h), TLC (DCM: MeOH=100:1, 2,4-dinitrophenylhydrazine color development) showed complete reaction. Water (80 ml) was added without warming, and the solution was mixed, allowed to stand, layered, and aliquoted. Aqueous dichloromethane extraction (50+20 ml). The organic phases were combined, washed with water (20 ml), dried over anhydrous magnesium sulfate, suction filtered, and the filtrate was evaporated under reduced pressure to yield 14.73 g of a yellow like solid. Ethyl acetate and petroleum ether (30 ml: 60 ml) crystallised from 9.13 g of a white solid. The mother liquor crystallized from ethyl acetate and petroleum ether (10 ml: 20 ml) to a 3.32 g white like solid. A total of 12.45 g of white like solid was obtained. Yield: 83.3%. $^1$H NMR (400 MHz, $CDCl_3$), δ 4.822~4.875 (m, 1H), 3.927~3.981 (m, 4H), 3.023 (s, 3H), 1.945~2.049 (m, 4H), 1.617~1.681 (m, 4H).

Example 1-55

8-(Benzylthio)-1,4-dioxaspiro [4.5]decane

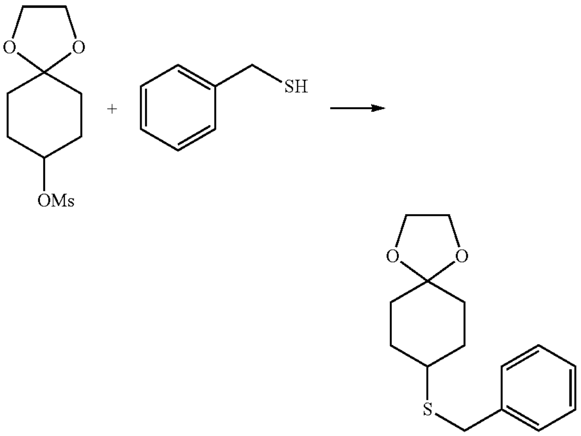

A 100 ml three port bottle with thermometer, constant pressure dropping funnel, and nitrogen balloon was cooled with benzylthiol (3.16 g, 25.44 mmol, 1.2 eq.), DMF (20 ml), and ice water bath, and NaH (0.3+0.3+0.42 g, 25.44 mmol, 1.2 eq., internal temperature <20° C.) was added three times. After stirring for 10 min, a solution of 1,4-dioxaspiro [4.5] dec-8-ylmethanesulfonate (5 g, 21.2 mmol, 1 eq.) in DMF (10 ml) was added dropwise. All was added dropwise, and the reaction was raised to 50° C. TLC (DCM:MeOH=100:1) after 2 h showed complete response. Ml), water (100 ml), and dichloromethane extraction (50 ml×4). The organic phases were combined, washed (50×3 ml), dried over anhydrous magnesium sulfate, suction filtered, and the filtrate evaporated under reduced pressure to yield 12.15 g of a light yellow liquid. Silica gel column chromatography purification (PE~EA:PE=100:1~50:1) afforded 4.74 g colorless liquid in 85% yield. The nuclear magnetic map revealed the presence of isomers in a ratio of approximately 4:1. $^1$H NMR (400 MHz, $CDCl_3$), δ 7.215~7.347 (m, 5H), 3.926 (s, 4H), 3.743 (s, 2H), 2.582~2.680 (m, 1H), 1.918~1.974 (m, 2H), 1.785~1.834 (m, 2H), 1.623~1.716 (m, 2H), 1.483~1.553 (m, 2H).

Example 1-56

8-(Benzylsulfonyl)-1,4-dioxospiro [4.5]decane

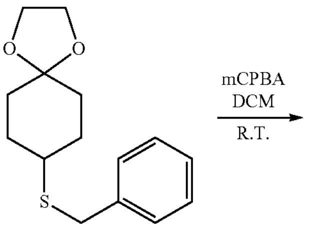

-continued

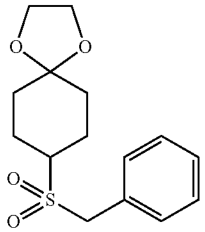

A 100 ml three port bottle with a thermometer was charged with the starting material 8-(benzylthio)-1,4-dioxaspiro [4.5] decane (4.5 g, 17.02 mmol, 1 eq.), DCM (45 ml), cooled in an ice water bath, and m-chloroperoxybenzoic acid (4.41 g, 25.53 mmol, 1.5 eq.) in four portions at 30° C. After that, stirring with a water bath of ice withdrawal. TLC (DCM and DCM:MeOH=100:1) after 1 h revealed the generation of two points. m-chloroperoxybenzoic acid supplementation (1.61 g, 0.55 eq.). Overnight. m-chloroperoxybenzoic acid supplementation (1.06 g, 15% remaining). Showed no sulfoxide after 12 h, forming sulfone. pH 8~9 was adjusted by adding 2 mmol/L NaOH (40 ml). Mix, allow to stand, layer, and aliquot. Aqueous dichloromethane (40+20 ml) extraction. The organic phases were combined and water washed (40 ml). Anhydrous magnesium sulfate was dried, suction filtered, and the filtrate was evaporated under reduced pressure to yield 5.16 g of a white solid. Ethyl acetate (15 ml) was added, dissolved under reflux, petroleum ether (15 ml) was added, a large amount of solid precipitated, ethyl acetate (7.5 ml) was added, and there was still part undissolved. Stirring cooling. After 5 h suction filtration, the cake was eluted with ethyl acetate:PE (3:2, 2 ml) and evaporated to dryness under reduced pressure to afford 4.08 g of a white like solid. Yield: 81%. LC-MS-ESI$^+$: $[M+H]^+$ 297.3. $[M+Na]^+$319.3. $[2M+Na]^+$615.5. $^1H$ NMR (400 MHz, $CDCl_3$), δ 7.387~7.438 (m, 5H), 4.217 (s, 2H), 3.941 (s, 4H), 2.720~2.790 (m, 1H), 2.117~2.156 (m, 2H), 1.876~2.011 (m, 4H), 1.465~1.543 (m, 2H).

Example 1-57

4-Benzylsulfonyl)cyclohex-1-one

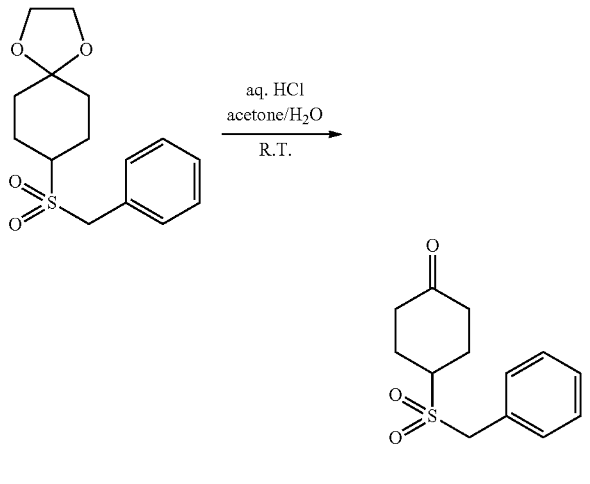

A 100 ml single port flask was charged with 8-(benzylsulfonyl)-1,4-dioxaspiro [4.5] decane (4.6 g, 15.52 mmol, 1 eq.), acetone (45 ml), dissolved by stirring, and water (11 ml) was added and clarified. Plus 2 mol/L hydrochloric acid (7.76 ml, 15.52 mmol, 1 eq.). After stirring at 50° C. overnight (12 h), TLC (DCM:MeOH=100:1) showed a small amount of starting material supplemented with 2 mol/L hydrochloric acid (7.76 ml, 15.52 mmol, 1 eq.), and after 6 h TLC showed complete reaction. The pH 8 to 9 was adjusted with 2 mol/L NaOH under an ice water bath, the solid was precipitated, water (120 ml) was added, stirred for 10 min, and then the filter cake was washed and evaporated to dryness under reduced pressure to obtain 3.06 g white like solid. The filtrate was evaporated off acetone under reduced pressure and extracted with dichloromethane (50+50 ml). The organic phases were combined, washed with water (20 ml), dried over anhydrous magnesium sulfate, suction filtered, and the filtrate was evaporated under reduced pressure to yield 1.3 g of a white solid and ethyl acetate was crystallized (10 ml) to yield 0.6 g of a white solid. The resulting solid was combined with the above solids and purified by column chromatography (PE~DCM~DCM:MeOH=100:1) to afford 3.4 g of a white like solid in 85% yield. $^1H$ NMR (400 MHz, $CDCl_3$), δ 7.408~7.460 (m, 5H), 4.301 (s, 2H), 3.092~3.164 (m, 1H), 2.582~2.632 (m, 2H), 2.265~2.401 (m, 4H), 2.082~2.198 (m, 2H).

Example 1-58

4-(Benzylsulfonyl)-2-((dimethylamino)methyl)cyclohexyl-1-one

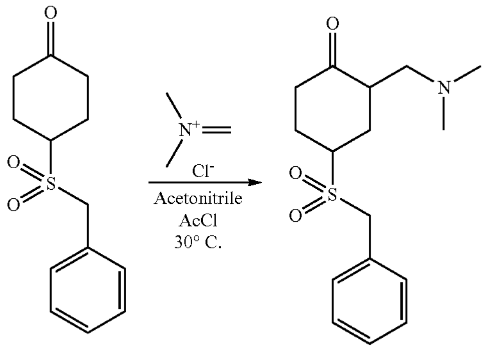

A 100 ml single port bottle was charged with 4-(benzylsulfonyl) cyclohex-1-one (0.9 g, 3.56 mmol, 1 eq.), acetonitrile (9 ml), salt (0.35 g, 3.74 mmol, 1.05 eq.), acetyl chloride (14 mg, 0.18 mmol, 0.05 eq.), and stirred at 30° C. TLC (DCM:MeOH=50:1) after 12 h showed that the basic reaction was complete. Saturated sodium bicarbonate solution (15 ml) was added and pH 8~9 adjusted with 2 mol/L NaOH. Acetonitrile was evaporated off under reduced pressure and dichloromethane extracted (15+15+5 ml). The organic phases were combined, washed with water (5 ml), dried over anhydrous magnesium sulfate, and the filtrate was evaporated under reduced pressure to afford 1.17 g of a colorless viscous substance. Yield: 95.12%. Without purification and used directly in the next step.

Example 1-59

4-(Benzylsulfonyl)-2-((dimethylamino)methyl)-1-(3-methoxyphenyl)cyclohexane-1-ol

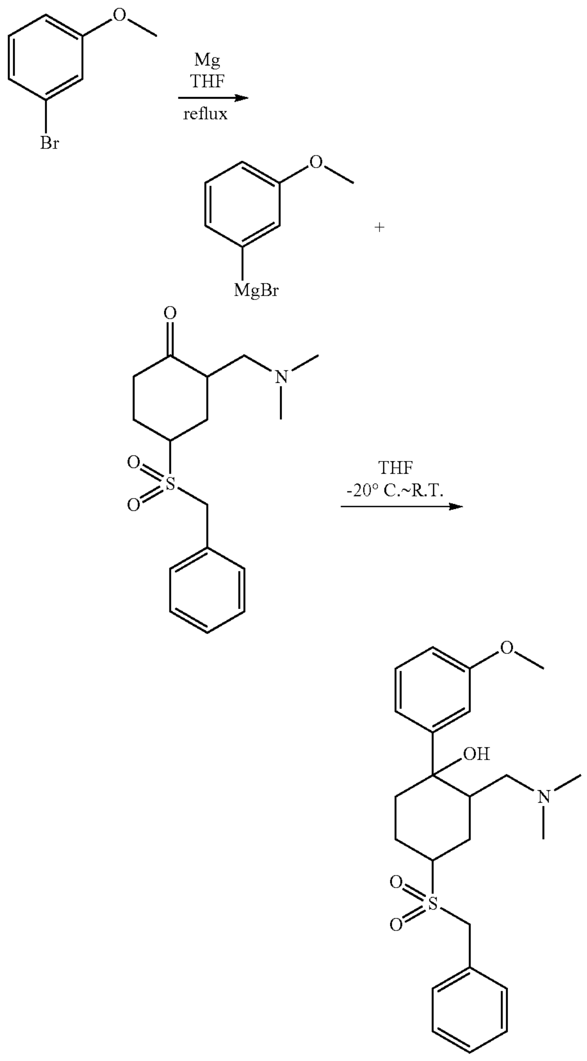

A 100 ml three port bottle with magnesium chips (0.14 g, 5.67 mmol, 1.5 eq.), THF (5 ml) accompanied by a thermometer, constant pressure dropping funnel, condensation tube and nitrogen balloon. A solution of about half m-bromoanisole (1.06 g, 5.67 mmol, 1.5 eq.) in THF (5 ml) was added and the reaction was initiated by warm reflux. After the reaction was to be initiated, the heating was stopped. Pending on m-bromoanisole being consumed completely, add remaining m-bromoanisole dropwise until complete. All drops were added, the temperature was refluxed for 10 min and heating was stopped. After cooling to room temperature, an ice salt bath was cooled to −22° C. and 4-(benzylsulfonyl)-2-((dimethylamino) methyl) cyclohexyl-1-one (1.17 g, 3.78 mmol, 1 eq.) in THF (5 ml) was added dropwise at 20° C. All drops were added and stirring was kept for 1 h. TLC (DCM:MeOH=10:1) after 1 h showed complete response. 20° C. the reaction was poured into saturated ammonium chloride solution (20 ml), THF was evaporated under reduced pressure and ethyl acetate was extracted (20+20+10 ml). The organic phases were combined and washed with 2 mol/L hydrochloric acid (2+2+2+2 ml) and 12 mol/L hydrochloric acid (2+1 ml). The acid layers were combined and adjusted to pH 8~9 with 2 mol/L NaOH. Dichloromethane extraction (20+20+20 ml). The organic phases were combined, washed with water (10 ml), dried over anhydrous magnesium sulfate, suction filtered, and the filtrate was evaporated under reduced pressure to obtain 0.7 g of a colorless viscous substance. The organic layers were combined, adjusted pH to 8~9, and ethyl acetate extracted. Anhydrous magnesium sulfate was dried, suction filtered, and the filtrate was evaporated under reduced pressure and combined with the above to give 1.2 g of a light yellow viscous substance. Silica gel column chromatography purified to give 0.81 g of viscous material. Further silica gel column chromatography purification (DCM~DCM: MeOH=200:1) afforded 300 mg of the viscous material. Yield: 12.6%. $^1$H NMR (400 MHz, $CD_3OD$), δ 7.467~7.500 (m, 2H), 7.390~7.441 (m, 3H), 7.273 (t, J=8 Hz, 1H), 7.078 (s, 1H), 7.024 (d, J=7.6 Hz, 1H), 6.816 (dd, J1=8 Hz, J2=2 Hz, 1H), 4.451 (s, 2H), 3.795 (s, 3H), 3.253~3.283 (m, 1H), 2.717 (dd, J1=13.2 Hz, J2=9.2 Hz, 1H), 2.355 (d, J=12.4 Hz, 1H), 2.304 (s, 6H), 2.177~2.260 (m, 2H), 2.029~2.144 (m, 2H), 1.948~2.029 (m, 2H), 1.833~1.876 (m, 1H), 1.280~1.335 (m, 1H). LC-MS-ESI$^+$: $[M+H]^+$ 418.2.

Example 1-60

4-(Benzylsulfonyl)-2-((dimethylamino)methyl)-1-(3-methoxyphenyl)cyclohexane-1-ol hydrochloride

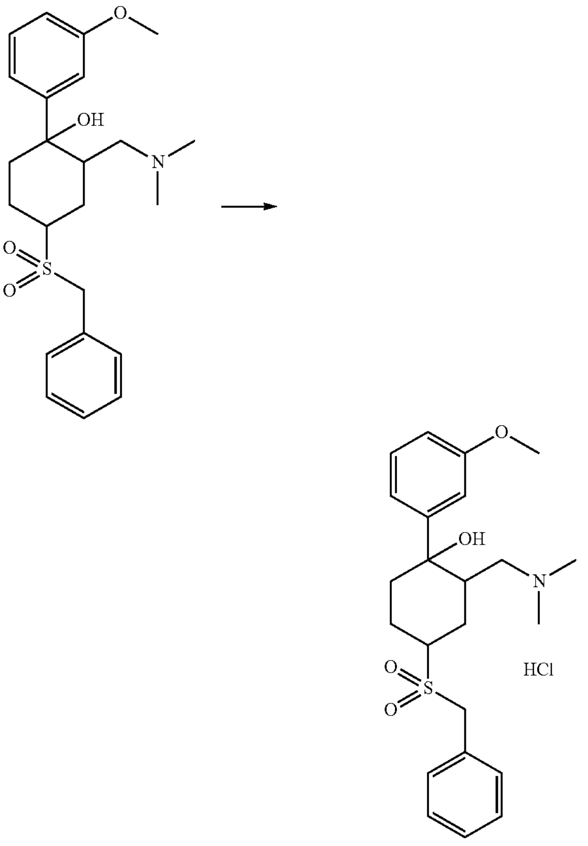

A 50 ml single port flask was charged with 4-(benzenesulfonyl)-2-((dimethylamino) methyl)-1-(3-methoxyphenyl) cyclohexane-1-ol (0.42 g, 0.65 mmol, 1 eq.), DCM (3 ml) and partially dissolved by stirring, methanol (0.25 ml) was added, and HCl/dioxane (0.25 ml, 0.97 mmol, 1.5 eq.) was added, and no solid precipitated. MTBE (12 ml) was added, and the solid was precipitated and stirred for 1.5 h. Filtration was aspirated, cake MTBE was eluted, and evaporated to dryness under reduced pressure to afford 0.223 g of a white solid. Yield: 76%. $^1$H NMR (400 MHz, $CD_3OD$), δ 7.474~7.520 (m, 1H), 7.379~7.412 (m, 3H), 7.307 (t, J=8 Hz, 1H), 7.033~7.084 (m, 2H), 7.840 (d, J=8.4 Hz, 1H), 4.364~4.445 (m, 2H), 3.804 (s, 3H), 3.360~4.442 (m, 1H), 2.961~3.173 (m, 2H), 2.617~2.708 (m, 6H), 2.325~2.381 (m, 1H), 1.984~2.103 (m, 2H), 1.743~1.827 (m, 4H). 13C NMR (150 MHz, $CD_3OD$) δ 161.51, 149.60, 135.23, 133.91, 132.14, 132.03, 131.09, 130.85, 130.56, 129.58, 129.52, 118.18, 113.23, 112.35, 74.63, 61.31, 59.69, 55.73, 53.16, 46.20, 42.62, 42.37, 40.33, 35.47, 29.91. LC-MS-ESI$^+$: $[M+H]^+$ 418.2.

Example 1-61

Ethyl 1,4-dioxospiro [4.5]decane-8-carboxylate

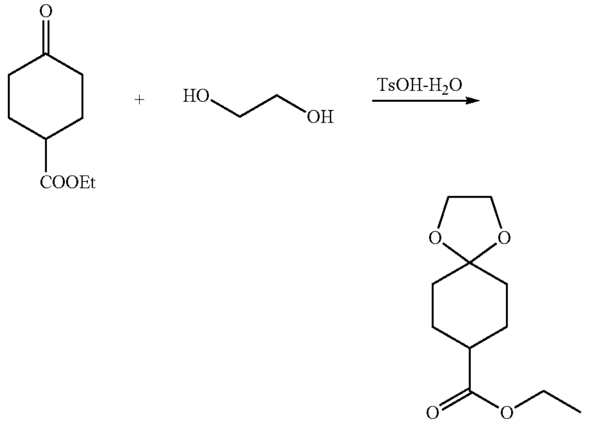

A 250 ml single port flask was charged with ethyl 4-oxocyclohexane-1-carboxylate (20 g, 117.5 mmol, 1 eq.), toluene (200 ml), ethylene glycol (29.17 g, 470 mmol, 4 eq.), p-toluenesulfonic acid monohydrate (2.24 g, 11.75 mmol, 0.1 eq.), and stirred at 30° C. TLC (DCM, 2,4-dinitrophenylhydrazine color development) after 23 h showed complete response. Add saturated sodium bicarbonate solution, and then adjust the pH to 8~9 with 2 mol/L NaOH solution. Mix, allow to stand, layer, and aliquot. Aqueous ethyl acetate extraction (100+100 ml). The organic phases were combined, water washed (50 ml), dried over anhydrous magnesium sulfate, suction filtered, and the filtrate was evaporated under reduced pressure to afford 26 g of a colorless liquid. Yield: 96.9%. $^1$H NMR (400 MHz, $CDCl_3$), δ 4.252 (q, J=7.2 Hz, 2H), 3.947 (s, 3H), 2.305~2.368 (m, 1H), 1.917~1.963 (m, 2H), 1.753~1.822 (m, 4H), 1.518~1.594 (m, 2H), 1.249 (t, J=7.6 Hz, 3H).

Example 1-62

(1,4-Dioxaspiro[4.5]dec-8-yl)methanol

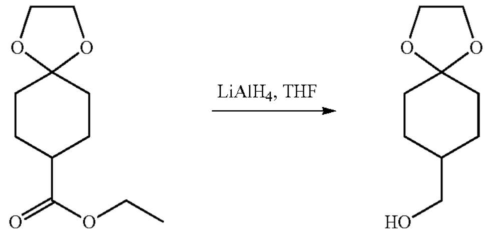

A 500 ml three port bottle with a nitrogen balloon, thermometer and constant pressure dropping funnel was charged with lithium aluminum hydride (4.3 g, 111.7 mmol, 1 eq.), THF (180 ml). Ice water bath cooled, and a solution of ethyl 1,4-dioxaspiro [4.5] decane-8-carboxylate (25.5 g, 111.7 mmol, 1 eq.) in THF (80 ml) was added dropwise at 15° C. All drops were added, stirred for 5 min, and stirring was removed from the ice water bath. After 3 h both TLC (DCM:MeOH=100:1) and LC-MS showed that the starting material was left, supplemented with $LiAlH_4$ (0.7 g, 0.16 eq. Overnight (14 h), the reaction was complete. 2 mmol/L NaOH (10 ml), water (15 ml) were added dropwise at 20° C., the mixture was stirred for 30 min, the solution was aspirated and the filtrate was evaporated under reduced pressure. The resulting liquid plus dichloromethane (200 ml) was dissolved, dried over anhydrous magnesium sulfate, suction filtered, and the filtrate was evaporated under reduced pressure to obtain 18.5 g of colorless liquid. Yield: 96.2%. $^1$H NMR (400 MHz, $CDCl_3$), δ 3.949 (s, 4H), 3.492 (d, J=6.4 Hz, 2H), 1.753~1.182 (m, 4H), 1.510~1.588 (m, 3H), 1.218~1.320 (m, 2H).

Example 1-63

(1,4-Dioxaspiro[4.5]dec-8-yl)methyl methanesulfonate

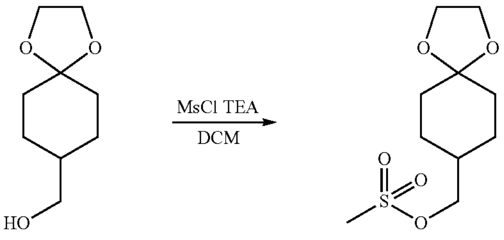 [SMILES: OCC1CCC2(CC1)OCCO2 ; CS(=O)(=O)OCC1CCC2(CC1)OCCO2]

A 500 ml three port bottle with a nitrogen balloon, constant pressure dropping funnel, and thermometer was charged with (1,4-dioxaspiro [4.5] dec-8-yl) methanol (18 g, 104.52 mmol, 1 eq.), dichloromethane (180 ml), triethylamine (13.75 g, 135.88 mmol, 1.3 eq.). An ice water bath was stirred and methanesulfonyl chloride (14.37 g, 125.42 mmol, 1.2 eq.) was added dropwise at 10° C. All drops were added and the ice bath stirred. TLC (DCM:MeOH=100:1) after 1.5 h showed complete response. Water (150 ml) was added, mixed, allowed to stand, layered, and aliquoted. Aqueous DCM extraction (100+30 ml). The organic phases were combined, washed with water (50+50 ml), dried over anhydrous magnesium sulfate, suction filtered, and the filtrate was evaporated under reduced pressure to yield 26.1 g of an off white solid like material. Yield: 99.8%. $^1$H NMR (400 MHz, $CDCl_3$), δ 4.064 (d, J=6.4 Hz, 2H), 3.947 (s, 4H), 3.009 (s, 3H), 2.138~2.243 (m, 1H), 1.774~1.991 (m, 4H), 1.519~1.597 (m, 2H), 1.229~1.400 (m, 2H).

Example 1-64

8-((Phenylthio)methyl)-1,4-dioxospiro[4.5]decane

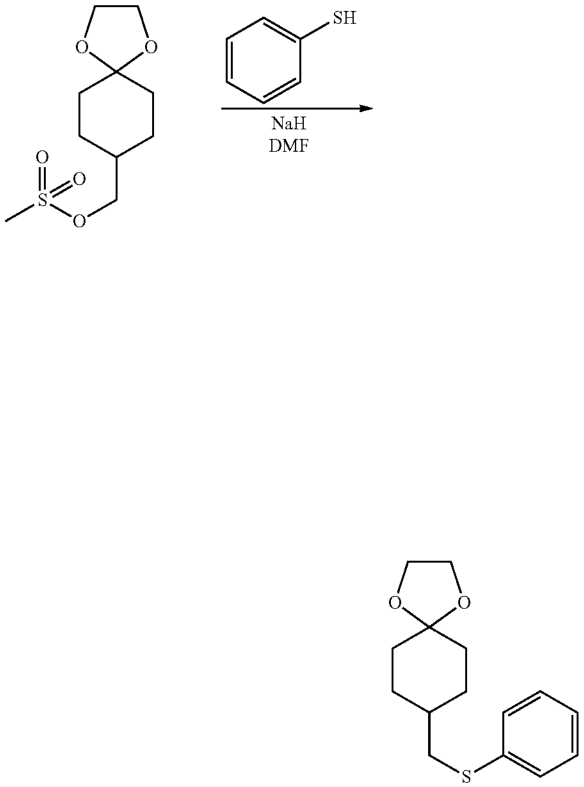

A 50 ml single port bottle containing thiophenol (1.06 g, 9.6 mmol, 1.2 eq.), DMF (6 ml) with a nitrogen balloon, thermometer and NAH (0.384 g, 9.6 mmol, 1.2 eq.) at 20° C. was stirred for 10 min. A solution of (1,4-dioxaspiro [4.5] dec-8-yl) methyl methanesulfonate (2 g, 8 mmol, 1 eq.) in DMF (6 ml) was added dropwise at 20° C. without noticeable warming. All drops were added and raised to 50° C. for agitation. TLC (DCM) after 1 h showed complete response. Water (50 ml), ethyl acetate extraction (25+25+20 ml). The organic phases were combined, washed with water (50+50+50 ml), dried over anhydrous magnesium sulfate, suction filtered, and the filtrate evaporated under reduced pressure to yield 2.33 g of a pale yellow liquid. Silica gel column chromatography purification (PE~PE:DCM=1:1~DCM) afforded 2.04 g colorless liquid. Yield: 96.2%. $^1$H NMR (400 MHz, $CDCl_3$), δ 7.251~7.362 (m, 5H), 3.937 (s, 4H), 2.851 (d, J=6.8 Hz, 2H), 2.317~2.418 (m, 1H), 1.898~1.932 (m, 2H), 1.754 (d, J=9.2 Hz, 2H), 1.482~1.588 (m, 2H), 1.319~1.389 (m, 2H).

Example 1-65

8-((Benzenesulfonyl)methyl)-1,4-dioxaspiro[4.5]decane

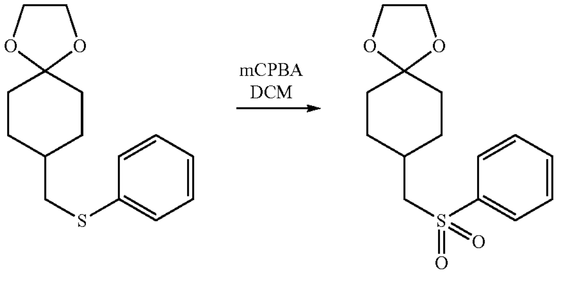 [SMILES: c1ccc(SCC2CCC3(CC2)OCCO3)cc1 ; O=S(=O)(CC1CCC2(CC1)OCCO2)c1ccccc1]

A 100 ml three port bottle accompanied by a thermometer was charged with 8-((phenylthio) methyl)-1,4-dioxaspiro [4.5] decane (1.94 g, 7.34 mmol, 1 eq.), dichloromethane (20 ml), dissolved by stirring, and m-chloroperoxybenzoic acid (3.05 g, 15.04 mmol, 2.05 eq.) was added portionwise at 30° C. to give a small amount of bubbling. A large amount of white solid precipitated after about 10 min, which was harder to stir, and DCM (10 ml) was added. Room temperature overnight (14 h.). pH≈10 was adjusted with 2 mol/L NaOH solution (9 ml). Dichloromethane extraction (20+10 ml), organic phase merging, water washing (20 ml), anhydrous magnesium sulfate drying, suction and filtration, the filtrate was evaporated under reduced pressure to obtain 2.23 g of solid like material. Ethyl acetate (5 ml) was added and dissolved under reflux with warming, petroleum ether (10 ml) was added, stirred overnight (12 h) with cooling, and then filtered, and the filter cake was evaporated to dryness under reduced pressure with ethyl acetate/petroleum ether (EA/PE=1:2, 0.5 ml) to afford 1.76 g of a white solid. Yield: 80%. $^1$H NMR (400 MHz, $CDCl_3$), δ 7.905~7.957 (m, 2H), 7.622~7.692 (m, 1H), 7.557~7.662 (m, 2H), 3.886~3.947 (m, 4H), 3.022 (d, J=3.2 Hz, 2H), 3.380~3.413 (m, 1H), 1.894~1.937 (m, 2H), 1.704~1.735 (m, 2H), 1.517~1.592 (m, 2H), 1.350~1.452 (m, 2H).

Example 1-66

4-((Benzenesulfonyl)methyl)cyclohexan-1-one

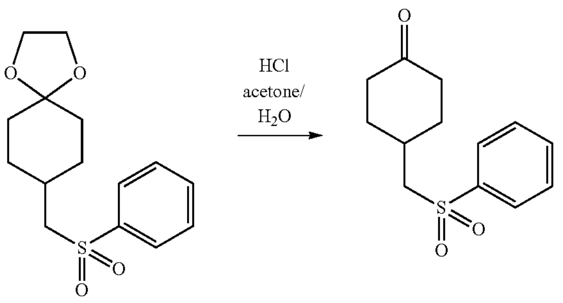 [SMILES: O=S(=O)(CC1CCC2(CC1)OCCO2)c1ccccc1 ; O=C1CCC(CS(=O)(=O)c2ccccc2)CC1]

A 100 ml single port bottle was charged with 8-((phenylsulfonyl) methyl)-1,4-dioxaspiro [4.5]decane (2 g, 6.75 mmol, 1 eq.), acetone (10 ml), water (2.5 ml), 2 mol/L hydrochloric acid solution (6.75 ml, 13.5 mmol, 2 eq.), and stirred at 50° C. 6 h to stop heating. Stirred at room temperature for 42 h. A large amount of solid was precipitated. The acetone was evaporated under reduced pressure, water (25 ml) was added, pH≈9 was adjusted with 2 mol/L NaOH, and the filter was aspirated and cake water was washed (10 ml). Oven dried (100° C., 4 h) to obtain 1.48 g of a light yellow solid. Ethyl acetate and petroleum ether (1:2, 6 ml) crystallised to give 1.43 g of an off white solid. The filtrate was dichloromethane extracted (30+15 ml). The organic phases were combined, dried over anhydrous magnesium sulfate, suction filtered, and the filtrate was evaporated under reduced pressure to yield 0.14 g of solid like material in. Yield: 78%. $^1$H NMR (400 MHz, $CD_3OD$), δ 7.947 (d, J=7.2 Hz, 2H), 7.692 (t, J=7.2 Hz, 1H), 7.603 (t, J=8 Hz, 2H), 3.086 (d, J=6.4 Hz, 2H), 2.482~2.570 (m, 1H), 2.379~2.412 (m, 3H), 2.268~2.317 (m, 2H), 1.532~1.637 (m, 3H).

Example 1-67

2-((Dimethylamino)methyl)-4-((benzenesulfonyl) methyl)cyclohexan-1-one

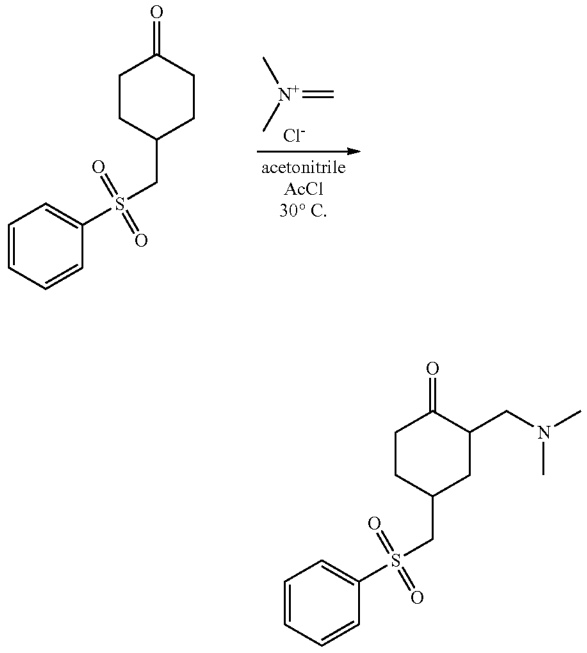

A 100 ml single port bottle was charged with 4-((phenylsulfonyl) methyl) cyclohex-1-one (1.4 g, 5.864 mmol, 1 eq.), acetonitrile (15 ml), salt (0.603 g, 6.45 mmol, 1.1 eq.), acetyl chloride (23 mg, 0.293 mmol, 0.05 eq.), and stirred at 30° C. TLC (DCM:MeOH=50:1) after 24 h showed that the basic reaction was complete. Acetonitrile was evaporated under reduced pressure, added water (25 ml), and adjusted to pH 8~9 with 2 mol/L NaOH. Dichloromethane extraction (20+20 ml). The organic phases were combined, washed with water (20 ml), dried over anhydrous magnesium sulfate, and the filtrate was distilled under reduced pressure to afford 1.7 g yellow liquid. Yield: 94%. Without purification and used directly in the next step.

Example 1-68

2-((Dimethylamino)methyl)-1-(3-methoxyphenyl)-4-((benzenesulfonyl)methyl)cyclohexan-1-ol

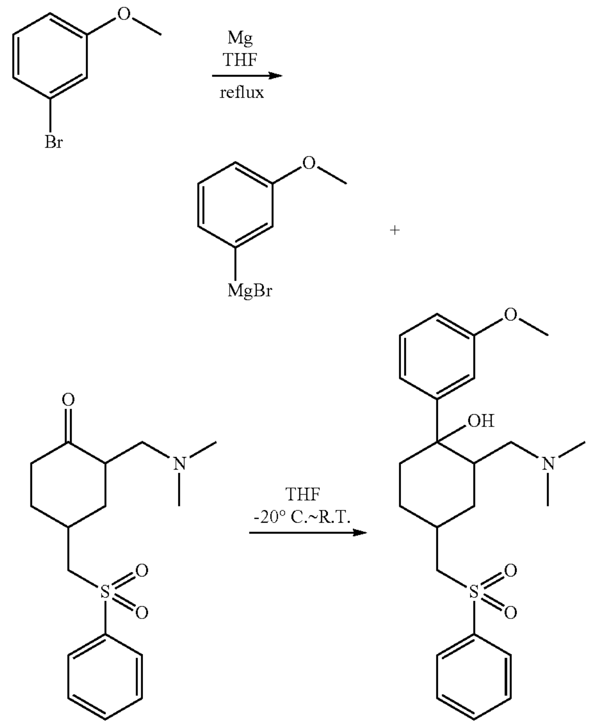

A 100 ml three port bottle with magnesium chips (0.2 g, 8.25 mmol, 1.5 eq.), THF (8 ml) accompanied by a thermometer, constant pressure dropping funnel, condensation tube and nitrogen balloon. A solution of about half m-bromoanisole (1.54 g, 8.25 mmol, 1.5 eq.) in THF (8 ml) was added and the reaction was initiated by warm reflux. After the reaction was to be initiated, the heating was stopped. Pending on m-bromoanisole being consumed completely, add remaining m-bromoanisole dropwise until complete. All drops were added, the temperature was refluxed for 10 min and heating was stopped. After cooling to room temperature with an ice salt bath cooled to −20° C. and 2-((dimethylamino) methyl)-4-((phenylsulfonyl) methyl) cyclohex-1-one (1.7 g, 5.5 mmol, 1 eq.) in THF (8 ml) was added dropwise at −15° C. All drops were added and stirring was kept for 1.5 h. LC-MS revealed minor amounts of starting material, as did TLC (DCM:MeOH=10:1). The reaction was poured into saturated ammonium chloride solution (30 ml), THF was evaporated under reduced pressure and ethyl acetate was extracted (20+20 ml). The organic phases were combined, water washed (10 ml), dried over anhydrous magnesium sulfate, suction filtered, and the filtrate was evaporated under reduced pressure to yield 1.7 g yellow liquid. Column chromatography purification (DCM~DCM: MeOH=200:1 plus one thousandth of TEA) afforded 0.81 g of a colorless viscosity. Yield: 35%. $^1$H NMR (400 MHz, $CD_3OD$), δ 7.96~7.99 (m, 2H), 7.71~7.75 (m, 1H), 7.64~7.67 (m, 2H), 7.20~7.26 (m, 1H), 7.04~7.08 (m, 1H), 6.99 (d, J=8 Hz, 1H), 6.76 (d, J=8 Hz, 1H), 3.78 (s, 3H), 3.17~3.28 (m, 2H), 2.23~2.28 (m, 1H), 2.12 (s, 1H), 1.97~2.02 (m, 7H), 1.87~1.97 (m, 2H), 1.79~1.83 (m, 3H), 1.47~1.66 (m, 3H).

Example 1-69

2-((Dimethylamino)methyl)-1-(3-methoxyphenyl)-4-((benzenesulfonyl)methyl)cyclohexan-1-ol hydrochloride

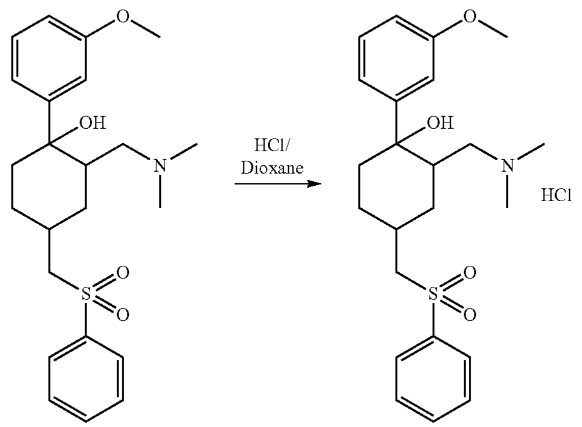 [SMILES: COc1cccc(C2(O)CCC(CS(=O)(=O)c3ccccc3)CC2CN(C)C)c1 ; COc1cccc(C2(O)CCC(CS(=O)(=O)c3ccccc3)CC2CN(C)C)c1 ; Cl]

A 50 ml single port flask was charged with 2-((dimethylamino) methyl)-1-(3-methoxyphenyl)-4-((phenylsulfonyl) methyl) cyclohex-1-ol (0.75 g, 1.8 mmol, 1 eq.), DCM (3 ml), MeOH (0.25 ml), dissolved by stirring, and MTBE (3.5 ml) was added and clarified. HCl in dioxane (0.68 ml, 2.7 mmol, 1.5 eq.) was added, slowly turning turbid and gradually precipitating solids, and MTBE (3.5 ml) was added. Filtration was aspirated after stirring for 1 h, and the cake MTBE was eluted and dried under reduced pressure to afford 0.82 g of a white like solid. Yield: 100%. $^1$H NMR (400 MHz, $CD_3OD$), δ 7.973~7.995 (m, 2H), 7.736~7.773 (m, 1H), 7.651~7.690 (m, 2H), 7.298 (t, J=8 Hz, 1H), 7.050~7.132 (m, 2H), 6.831 (d, J=8 Hz, 1H), 3.800 (s, 3H), 3.655 (s, 2H), 2.942~2.995 (m, 2H), 2.607~2.741 (m, 7H), 2.296~2.342 (m, 2H), 1.974~2.050 (m, 2H), 1.820 (d, J=13.6 Hz, 1H), 1.616~1.745 (m, 3H). $^{13}$C NMR (150 MHz, $CD_3OD$) δ 161.47, 149.81, 141.53, 135.13, 130.81, 130.70, 128.88, 118.24, 113.19, 112.32, 75.06, 68.15, 62.72, 61.52, 55.73, 46.19, 42.77, 42.65, 40.88, 33.38, 33.18, 28.72. LC-MS-ESI$^+$: [M+H]$^+$ 418.2.

Example 1-70

Preparation of Membrane Receptors

CHO cells expressing p opioid receptor, δ opioid receptor and κ opioid receptor were cultured in 10 $cm^2$ culture dishes (F-12 medium+10% neonatal bovine serum) for several days, and the culture fluid was aspirated after the cells had grown to the bottom of the dishes; 3 ml of PBS/EDTA solution (0.1M NaCl, 0.01M $NaH_2PO4$, 0.04% EDTA) was added to digest the cells for 3-5 min. Add ice-cold homogenate (50 mM HEPES PH 7.4, 3 mM MgCl, 1 mM EGTA) to the centrifuge tube, transfer the solution and sediment to a homogenizer and homogenize; then transfer the homogenate to a centrifuge tube and centrifuge at 18000 rpm. Centrifuge for 15 min, two times; the obtained precipitate was homogenized with appropriate amount of 50 mM Tris-HCl, pH 7.4 buffer and divided into centrifuge tubes and stored at −70° C. in the refrigerator until use.

Competition Binding Assay

The total binding tube was spiked with 20-30 μg of the expressed membrane receptor protein and [13H]-labeled ligand (1-2 nM), the corresponding non-specific binding tube was spiked with 1 μM of the corresponding ligand, and the sample tubes were spiked with various screened opioid ligands in a final volume of 100 al, incubated at 30° C. for 30 min, and the reaction was terminated in ice water. The reaction was terminated by incubation in ice-cold water for 30 min at 30° C. The samples were filtered under negative pressure through GF/C (whatman) glass fiber filter paper on a Millipore sample collector. The reaction was rinsed three times with 4 ml of 50 mMV Tris-HCl (pH 7.4), the filter paper was dried and placed in 0.5 ml Eppendorf tubes with 0.5 ml of lipophilic scintillation solution, the radioactivity was measured by PERKIN ELMER PRI-CARB 2910 liquid scintillation counter and the inhibition rate was calculated.

Inhibition rate (or binding rate)=(total binding rate dpm−sample tube dpm)/(total binding tube dpm−non-specific binding tube dpm)×100%

$IC_{50}$ was calculated using Prism 5.0 software. the Ki value was calculated as follows, Ki=IC50/(1+[IL]/Kd), [lL] is the concentration of the added labeled ligand and Kd is the equilibrium dissociation parameter of the labeled ligand.

Table 1-1 showed the affinity constants Ki values of representative compounds for opioid receptors, expressed as the mean±standard deviation of three independent measurements.

TABLE 1-1

Opioid receptor binding rate or Ki at 10 μM concentration of compound

| | | Binding rate (%) or Ki (nM) | | |
|---|---|---|---|---|
| Compound | Structure | μOR | δOR | κOR |
| tramadol | 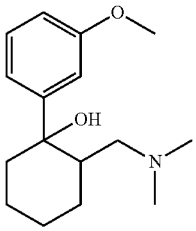 [SMILES: COc1cccc(C2(O)CCCCC2CN(C)C)c1] | 6.0 ± 0.4% | 0% | 0% |

TABLE 1-1-continued

| Opioid receptor binding rate or Ki at 10 μM concentration of compound | | | | |
|---|---|---|---|---|
| | | Binding rate (%) or Ki (nM) | | |
| Compound | Structure | μOR | δOR | κOR |
| 2((Dimethylamino) methyl)-1-(3-methoxyphenyl)-4-(phenylsulfonyl) cyclohexyl benzoate hydrochloride | 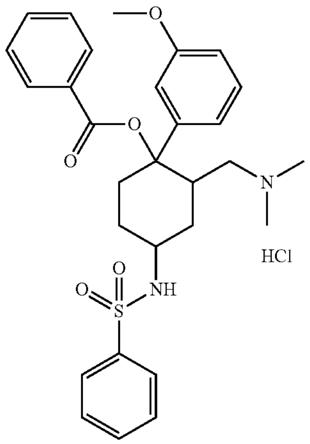 [SMILES: COc1cccc(C2(OC(=O)c3ccccc3)CCC(NS(=O)(=O)c3ccccc3)CC2CN(C)C)c1 ; Cl] | 80.9 ± 4.4% | 17.4 ± 2.5% | 51.5 ± 6.6% |
| N-(3-((Dimethylamino) methyl)-4-hydroxy-4-(3-methoxyphenyl) cyclohexyl) benzenesulfonamide hydrochloride | 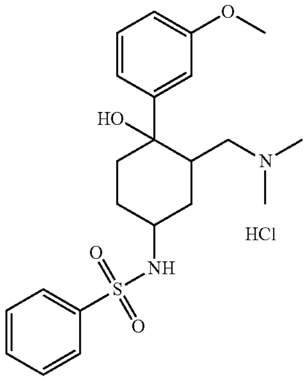 [SMILES: COc1cccc(C2(O)CCC(NS(=O)(=O)c3ccccc3)CC2CN(C)C)c1 ; Cl] | 75.8 ± 4.1% | 38.0 ± 2.43% | 25.8 ± 7.9% |
| 4-((3-Chlorophenyl) sulfonylamino)-2-((dimethylamino) methyl)-1-(3-methoxyphenyl) cyclohexyl benzoate hydrochloride | 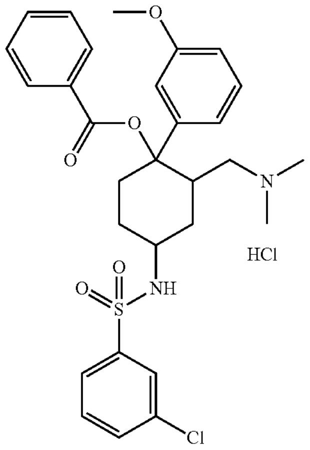 [SMILES: COc1cccc(C2(OC(=O)c3ccccc3)CCC(NS(=O)(=O)c3cccc(Cl)c3)CC2CN(C)C)c1 ; Cl] | 70.4 ± 3.0% | 18.8 ± 8.6% | 39.0 ± 5.5% |

TABLE 1-1-continued

| Opioid receptor binding rate or Ki at 10 μM concentration of compound | | | | |
|---|---|---|---|---|
| | | Binding rate (%) or Ki (nM) | | |
| Compound | Structure | μOR | δOR | κOR |
| 3-Chloro-N-(3-((dimethylamino)methyl)-4-hydroxy-4-(3-methoxyphenyl)cyclohexyl)benzenesulfonamide hydrochloride | 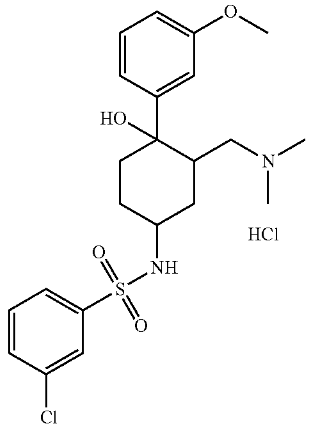 [SMILES: COc1cccc(C2(O)CCC(NS(=O)(=O)c3cccc(Cl)c3)CC2CN(C)C)c1 ; Cl] | 79.7 ± 4.6% | 14.5 ± 5.8% | 35.9 ± 5.7% |
| N-(3-((Dimethylamino)methyl)-4-hydroxy-4-(3-methoxyphenyl)cyclohexyl)thiophene-2-sulfonamide hydrochloride | 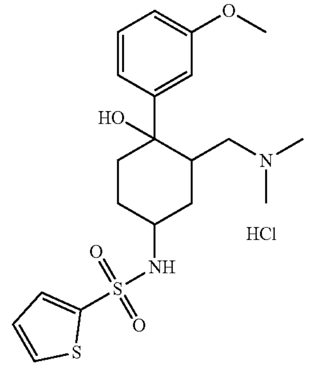 [SMILES: COc1cccc(C2(O)CCC(NS(=O)(=O)c3cccs3)CC2CN(C)C)c1 ; Cl] | 57.0 ± 4.8% | 0% | 37.0 ± 6.8% |
| N-(3-((Dimethylamino)methyl)-4-hydroxy-4-(3-methoxyphenyl)cyclohexyl)-1-benzenesulfonamide hydrochloride | 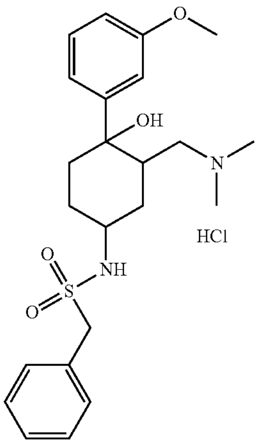 [SMILES: COc1cccc(C2(O)CCC(NS(=O)(=O)Cc3ccccc3)CC2CN(C)C)c1 ; Cl] | 99.5 ± 1.6% | 37.2 ± 12.1% | 28.8 ± 4.5% |

TABLE 1-1-continued

| Opioid receptor binding rate or Ki at 10 μM concentration of compound | | | | |
|---|---|---|---|---|
| | | Binding rate (%) or Ki (nM) | | |
| Compound | Structure | μOR | δOR | κOR |
| 1-(3-Chlorophenyl)-N-(3-((dimethylamino)methyl)-4-hydroxy-4-(3-methoxyphenyl)cyclohexyl)methanesulfonamide hydrochloride | 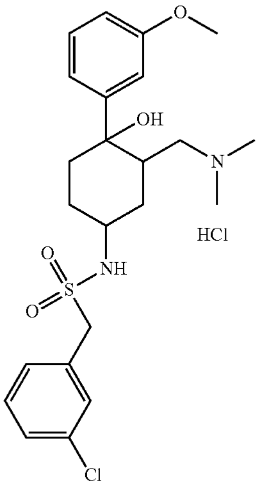 [SMILES: COc1cccc(C2(O)CCC(NS(=O)(=O)Cc3cccc(Cl)c3)CC2CN(C)C)c1 ; Cl] | 83.2 ± 5.6% | 12.0 ± 4.4% | 60.7 ± 6.8% |
| N-(3-((Dimethylamino)methyl)-4-hydroxy-4-(3-methoxyphenyl)cyclohexyl)-N-methylbenzenesulfonamide hydrochloride | 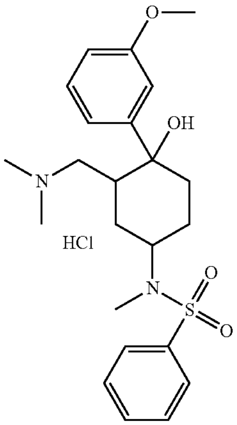 [SMILES: COc1cccc(C2(O)CCC(N(C)S(=O)(=O)c3ccccc3)CC2CN(C)C)c1 ; Cl] | 86.7 ± 1.6% | 0% | 46.7 ± 9.2% |
| 3-Chloro-N-(3-((dimethylamino)methyl)-4-hydroxy-4-(methoxyphenyl)cyclohexyl)-N-methylbenzenesulfonamide hydrochloride | 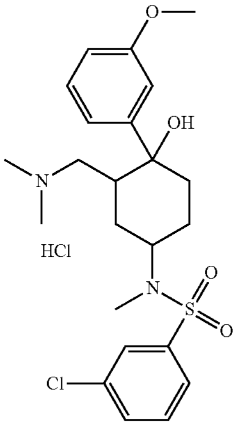 [SMILES: COc1cccc(C2(O)CCC(N(C)S(=O)(=O)c3cccc(Cl)c3)CC2CN(C)C)c1 ; Cl] | 90.0 ± 2.0% | 13.8 ± 3.0% | 66.6 ± 4.8% |

TABLE 1-1-continued

| Compound | Structure | μOR | δOR | κOR |
| --- | --- | --- | --- | --- |
| | | Opioid receptor binding rate or Ki at 10 μM concentration of compound | | |
| | | Binding rate (%) or Ki (nM) | | |
| N-(3-((Dimethylamino)methyl)-4-hydroxy-4-(3-methoxyphenyl)cyclohexyl)-N-methylthiophene-2-sulfonamide hydrochloride | 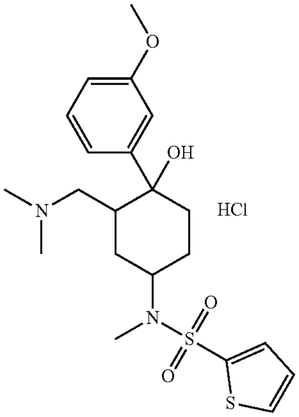 [SMILES: COc1cccc(C2(O)CCC(N(C)S(=O)(=O)c3cccs3)CC2CN(C)C)c1 ; Cl] | 62.0 ± 6.8% | 0% | 51.4 ± 7.5% |
| 2-((Dimethylamino)methyl)-1-(3-methoxyphenyl)-4-((N-methyl-1-phenylmethyl)sulfonylamino)cyclohexyl benzoate hydrochloride | 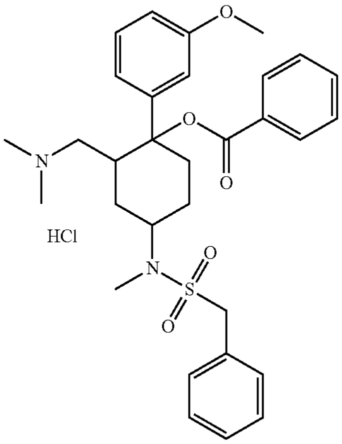 [SMILES: COc1cccc(C2(OC(=O)c3ccccc3)CCC(N(C)S(=O)(=O)Cc3ccccc3)CC2CN(C)C)c1 ; Cl] | 81.2 ± 4.2% | 30.1 ± 14.9% | 35.7 ± 3.0% |
| 4-((1-(3-Chlorophenyl)-N-methyl)sulfonylamino)-2-((dimethylamino)methyl)-1-(3-methoxyphenyl)cyclohexyl benzoate hydrochloride | 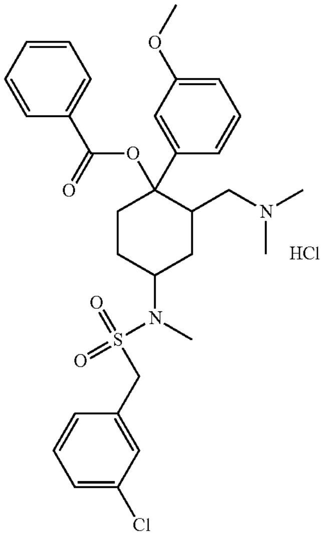 [SMILES: COc1cccc(C2(OC(=O)c3ccccc3)CCC(N(C)S(=O)(=O)Cc3cccc(Cl)c3)CC2CN(C)C)c1 ; Cl] | 89.8 ± 4.6% | 4.8% | 25.5 ± 6.1% |

TABLE 1-1-continued

| Opioid receptor binding rate or Ki at 10 μM concentration of compound | | | | |
|---|---|---|---|---|
| | | Binding rate (%) or Ki (nM) | | |
| Compound | Structure | μOR | δOR | κOR |
| N-Benzyl-N-(3-((dimethylamino)methyl)-4-hydroxy-4-(3-methoxyphenyl)cyclohexyl)benzenesulfonamide hydrochloride | 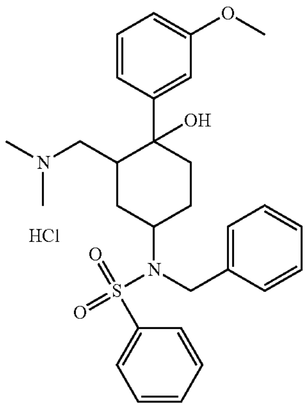 [SMILES: COc1cccc(C2(O)CCC(N(Cc3ccccc3)S(=O)(=O)c3ccccc3)CC2CN(C)C)c1 ; Cl] | 70.5 ± 2.3% | 9.53% | 84.7 ± 2.1% |
| N-Benzyl-3-chloro-N-(3-((dimethylamino)methyl)-4-hydroxy-4-(3-methoxyphenyl)cyclohexyl)benzenesulfonamide hydrochloride | 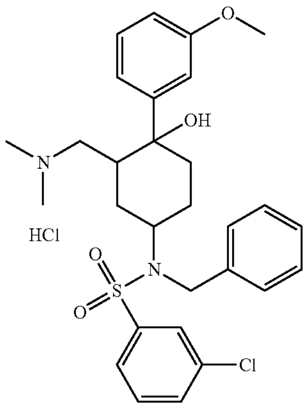 [SMILES: COc1cccc(C2(O)CCC(N(Cc3ccccc3)S(=O)(=O)c3cccc(Cl)c3)CC2CN(C)C)c1 ; Cl] | 85.8 ± 3.2% | 5.1% | 9.81 ± 0.32 nM |
| N-Benzyl-N-(3-((dimethylamino)methyl)-4-hydroxy-4-(3-methoxyphenyl)cyclohexyl)thiophene-2-sulfonamide hydrochloride | 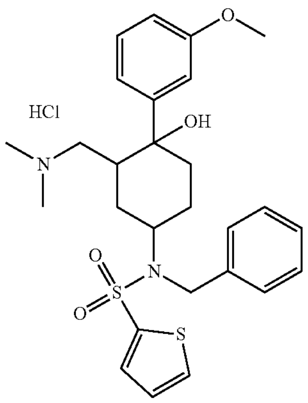 [SMILES: COc1cccc(C2(O)CCC(N(Cc3ccccc3)S(=O)(=O)c3cccs3)CC2CN(C)C)c1 ; Cl] | 68.4 ± 3.4% | 0% | 71.2 ± 2.7% |

TABLE 1-1-continued

| Opioid receptor binding rate or Ki at 10 μM concentration of compound | | | | |
|---|---|---|---|---|
| | | Binding rate (%) or Ki (nM) | | |
| Compound | Structure | μOR | δOR | κOR |
| 4-(Benzylsulfonyl)-2-((dimethylamino)methyl)-1-(3-methoxyphenyl)cyclohexane-1-ol hydrochloride | 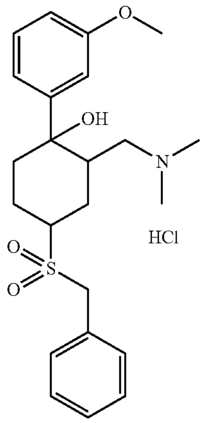 [SMILES: COc1cccc(C2(O)CCC(S(=O)(=O)Cc3ccccc3)CC2CN(C)C)c1 ; Cl] | 98.6 ± 1.2% | 44.0 ± 7.85% | 47.7 ± 3.1% |
| 2-((Dimethylamino)methyl)-1-(3-methoxyphenyl)-4-((phenylsulfonyl)methyl)cyclohexane-1-ol hydrochloride | 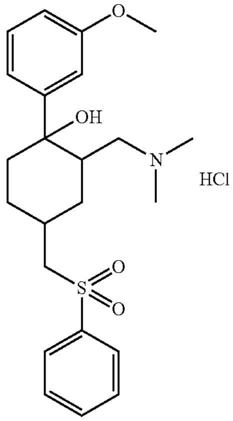 [SMILES: COc1cccc(C2(O)CCC(CS(=O)(=O)c3ccccc3)CC2CN(C)C)c1 ; Cl] | 86.9 ± 2.0% | 9.3% | 34.6 ± 5.1% |

In the column of "Binding rate (%) or Ki (nM)" in Table 1-1, the values expressed in percentage referred to the binding rate, and the values in nM referred to Ki.

From Table 1-1, the compounds of the present invention had higher affinity for opioid receptors than for tramadol, and higher affinity for δ or κ opioid receptors than or comparable to tramadol, with higher affinity generally implying stronger analgesic effects.

Example 1-71

In Vivo Hot Plate Method Analgesia Test

Female mice weighing about 20 g were placed on a hot plate apparatus preheated to 55° C., and the latency of the hindfoot response of the mice was used as the pain threshold indicator. Animals were screened before the experiment, and those with response latency less than 5 s or more than 30 s were excluded. To prevent foot scalding, the maximum observation time was set at 60 s. The basal pain threshold was the average of two measurements, with a 5-min interval between measurements. pain thresholds were measured at 15 m, 30 m, 60 m and 120 m after intraperitoneal injection in each group of mice. The percentage effective analgesia (% MPE) was calculated according to the following formula: percentage effective analgesia (% MPE) (post-dose latency−pre-dose latency)/(60−pre-dose latency)×100%. $ED_{50}$ values were calculated based on the effective percentage of analgesia using the software Graphpad prism 5.0 software.

TABLE 1-2

| Maximum percentage effective analgesic or $ED_{50}$ values of compound hot plate at 5 mg/kg dose | | |
|---|---|---|
| Compound | Stucture | % MPE or $ED_{50}$ |
| Tramadol | 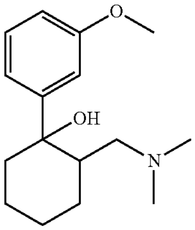 [SMILES: COc1cccc(C2(O)CCCCC2CN(C)C)c1] | 64.5% (50 mg/kg dose, no analgesic effect of tramadol at 5 mg/kg dose) |
| 2-((Dimethylamino)methyl)-1-(3-methoxyphenyl)-4-(phenylsulfonyl)cyclohexyl benzoate hydrochloride | 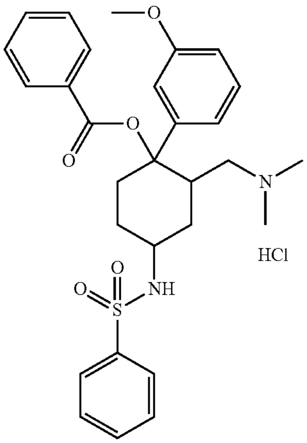 [SMILES: COc1cccc(C2(OC(=O)c3ccccc3)CCC(NS(=O)(=O)c3ccccc3)CC2CN(C)C)c1 ; Cl] | 26.4% |
| N-(3-((Dimethylamino)methyl)-4-hydroxy-4-(3-methoxyphenyl)cyclohexyl)benzenesulfonamide hydrochloride | 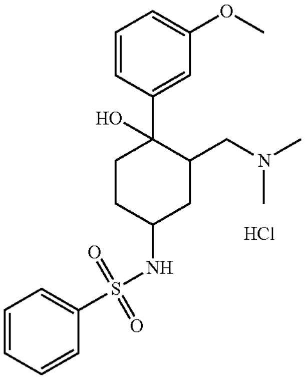 [SMILES: COc1cccc(C2(O)CCC(NS(=O)(=O)c3ccccc3)CC2CN(C)C)c1 ; Cl] | 10.3% |
| 4-((3-Chlorophenyl)sulfonylamino)-2-((dimethylamino)methyl)-1-(3-methoxyphenyl)cyclohexyl benzoate hydrochloride | 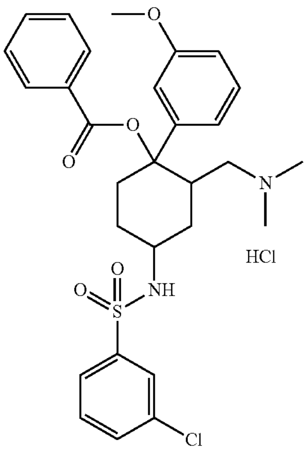 [SMILES: COc1cccc(C2(OC(=O)c3ccccc3)CCC(NS(=O)(=O)c3cccc(Cl)c3)CC2CN(C)C)c1 ; Cl] | 11.6% |

TABLE 1-2-continued

Maximum percentage effective analgesic or $ED_{50}$ values of compound hot plate at 5 mg/kg dose

| Compound | Stucture | % MPE or $ED_{50}$ |
| --- | --- | --- |
| 3-Chloro-N-(3-((dimethylamino)methyl)-4-hydroxy-4-(3-methoxyphenyl)cyclohexyl)benzenesulfonamide hydrochloride | 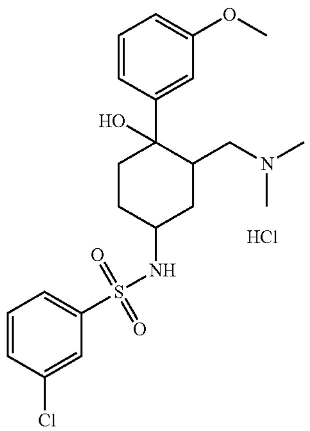 [SMILES: COc1cccc(C2(O)CCC(NS(=O)(=O)c3cccc(Cl)c3)CC2CN(C)C)c1 ; Cl] | 11.7% |
| N-(3-((Dimethylamino)methyl)-4-hydroxy-4-(3-methoxyphenyl)cyclohexyl)thiophene-2-sulfonamide hydrochloride | 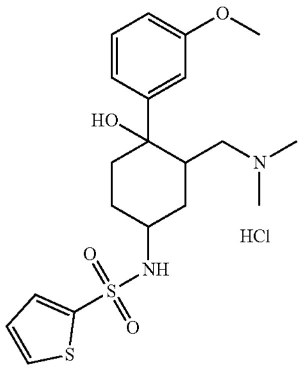 [SMILES: COc1cccc(C2(O)CCC(NS(=O)(=O)c3cccs3)CC2CN(C)C)c1 ; Cl] | 19.5% |
| N-(3-((Dimethylamino)methyl)-4-hydroxy-4-(3-methoxyphenyl)cyclohexyl)-1-benzenesulfonamide hydrochloride | 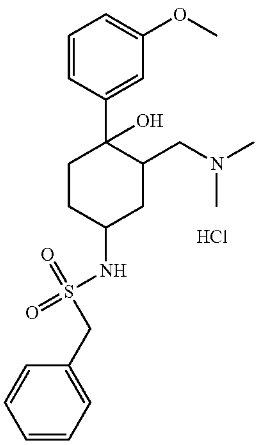 [SMILES: COc1cccc(C2(O)CCC(NS(=O)(=O)Cc3ccccc3)CC2CN(C)C)c1 ; Cl] | 100% $ED_{50}$ = 3.4 mg/kg |

TABLE 1-2-continued

<table>
<tr><th colspan="3">Maximum percentage effective analgesic or $ED_{50}$ values of compound hot plate at 5 mg/kg dose</th></tr>
<tr><th>Compound</th><th>Stucture</th><th>% MPE or $ED_{50}$</th></tr>
<tr><td>1-(3-Chlorophenyl)-N-(3-((dimethylamino)methyl)-4-hydroxy-4-(3-methoxyphenyl)cyclohexyl)methanesulfonamide hydrochloride</td><td>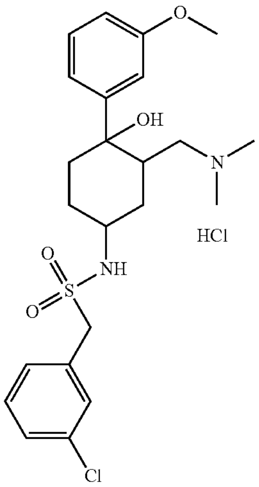 [SMILES: COc1cccc(C2(O)CCC(NS(=O)(=O)Cc3cccc(Cl)c3)CC2CN(C)C)c1 ; Cl]</td><td>15.2%</td></tr>
<tr><td>N-(3-((Dimethylamino)methyl)-4-hydroxy-4-(3-methoxyphenyl)cyclohexyl)-N-methylbenzenesulfonamide hydrochloride</td><td>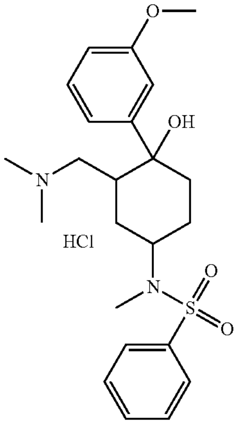 [SMILES: COc1cccc(C2(O)CCC(N(C)S(=O)(=O)c3ccccc3)CC2CN(C)C)c1 ; Cl]</td><td>15.8%</td></tr>
<tr><td>3-Chloro-N-(3-((dimethylamino)methyl)-4-hydroxy-4-(methoxyphenyl)cyclohexyl)-N-methylbenzenesulfonamide hydrochloride</td><td>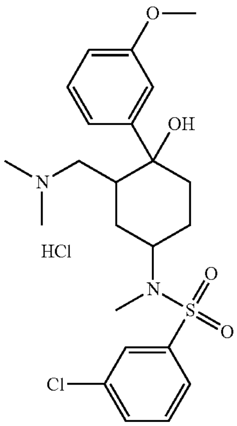 [SMILES: COc1cccc(C2(O)CCC(N(C)S(=O)(=O)c3cccc(Cl)c3)CC2CN(C)C)c1 ; Cl]</td><td>20.2%</td></tr>
</table>

TABLE 1-2-continued

| Maximum percentage effective analgesic or $ED_{50}$ values of compound hot plate at 5 mg/kg dose | | |
|---|---|---|
| Compound | Stucture | % MPE or $ED_{50}$ |
| N-(3-((Dimethylamino)methyl)-4-hydroxy-4-(3-methoxyphenyl)cyclohexyl)-N-methylthiophene-2-sulfonamide hydrochloride | 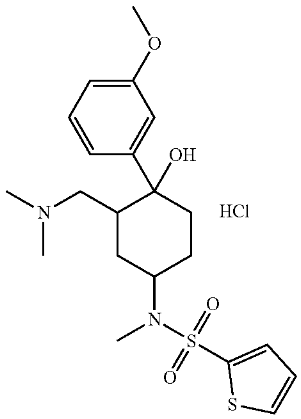 [SMILES: COc1cccc(C2(O)CCC(N(C)S(=O)(=O)c3cccs3)CC2CN(C)C)c1 ; Cl] | 14.3% |
| 2-((Dimethylamino)methyl)-1-(3-methoxyphenyl)-4-((N-methyl-1-phenylmethyl)sulfonylamino)cyclohexyl benzoate hydrochloride | 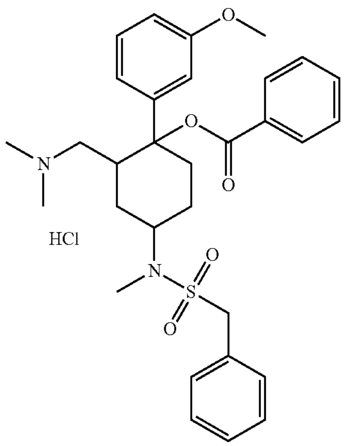 [SMILES: COc1cccc(C2(OC(=O)c3ccccc3)CCC(N(C)S(=O)(=O)Cc3ccccc3)CC2CN(C)C)c1 ; Cl] | 37.2% |
| 4-((1-(3-Chlorophenyl)-N-methyl)sulfonylamino)-2-((dimethylamino)methyl)-1-(3-methoxyphenyl)cyclohexyl benzoate hydrochloride | 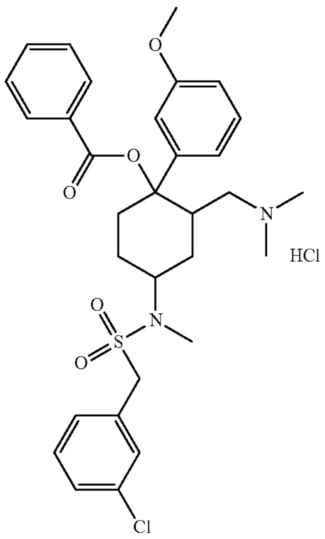 [SMILES: COc1cccc(C2(OC(=O)c3ccccc3)CCC(N(C)S(=O)(=O)Cc3cccc(Cl)c3)CC2CN(C)C)c1 ; Cl] | 0% |

TABLE 1-2-continued

| Maximum percentage effective analgesic or $ED_{50}$ values of compound hot plate at 5 mg/kg dose | | |
|---|---|---|
| Compound | Stucture | % MPE or $ED_{50}$ |
| N-Benzyl-N-(3-((dimethylamino)methyl)-4-hydroxy-4-(3-methoxyphenyl)cyclohexyl)benzenesulfonamide hydrochloride | 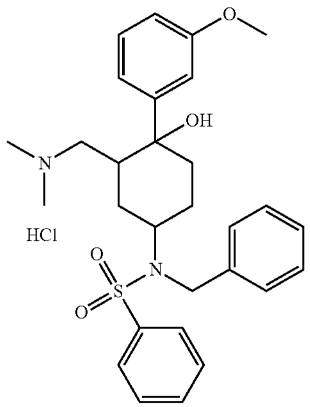 [SMILES: COc1cccc(C2(O)CCC(N(Cc3ccccc3)S(=O)(=O)c3ccccc3)CC2CN(C)C)c1 ; Cl] | 0% |
| N-Benzyl-3-chloro-N-(3-((dimethylamino)methyl)-4-hydroxy-4-(3-methoxyphenyl)cyclohexyl)benzenesulfonamide hydrochloride | 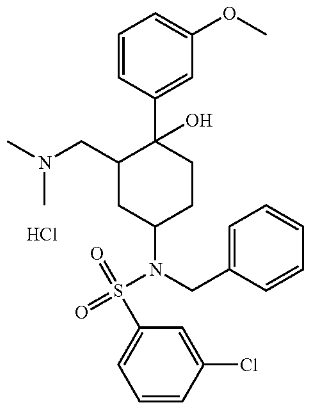 [SMILES: COc1cccc(C2(O)CCC(N(Cc3ccccc3)S(=O)(=O)c3cccc(Cl)c3)CC2CN(C)C)c1 ; Cl] | 6% |
| N-Benzyl-N-(3-((dimethylamino)methyl)-4-hydroxy-4-(3-methoxyphenyl)cyclohexyl)thiophene-2-sulfonamide hydrochloride | 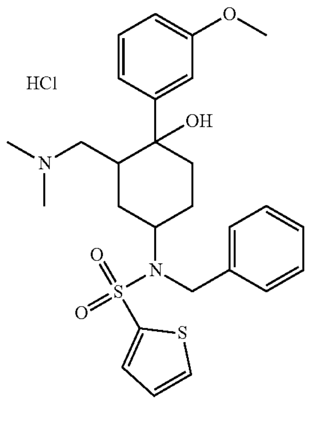 [SMILES: COc1cccc(C2(O)CCC(N(Cc3ccccc3)S(=O)(=O)c3cccs3)CC2CN(C)C)c1 ; Cl] | 22.8% |

TABLE 1-2-continued

| Maximum percentage effective analgesic or $ED_{50}$ values of compound hot plate at 5 mg/kg dose | | |
|---|---|---|
| Compound | Stucture | % MPE or $ED_{50}$ |
| 4-(Benzylsulfonyl)-2-((dimethylamino)methyl)-1-(3-methoxyphenyl)cyclohexane-1-ol hydrochloride | 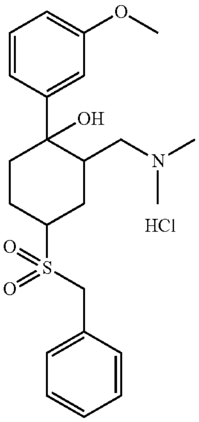 [SMILES: COc1cccc(C2(O)CCC(S(=O)(=O)Cc3ccccc3)CC2CN(C)C)c1 ; Cl] | 21.7% |
| 2-((Dimethylamino)methyl)-1-(3-methoxyphenyl)-4-((phenylsulfonyl)methyl)cyclohexane-1-ol hydrochloride | 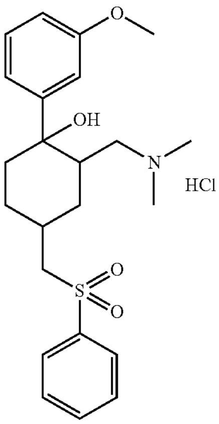 [SMILES: COc1cccc(C2(O)CCC(CS(=O)(=O)c3ccccc3)CC2CN(C)C)c1 ; Cl] | 22.4% |

In the column "% MPE or ED50", the value expressed as a percentage refered to % MPE, and the value in mg/kg refered to ED50.

As can be seen from Tables 1-2, the analgesic effect of the compounds of the present invention at a dose of 5 mg/kg was comparable to or stronger than that of tramadol.

Example 2

The present invention is illustrated by the following examples, which are for illustration only and do not limit the scope of the invention. Compounds of formula FWBH can be prepared as described in the general synthetic routes and examples below.

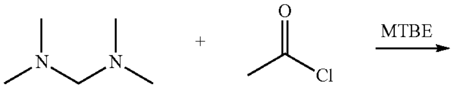

-continued

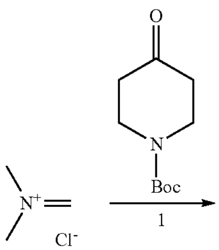
2
1

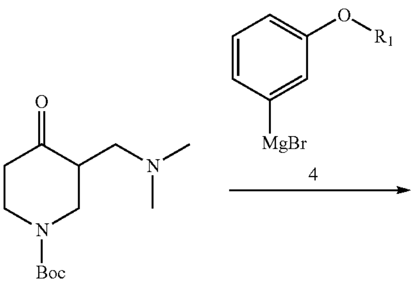
3
4

-continued

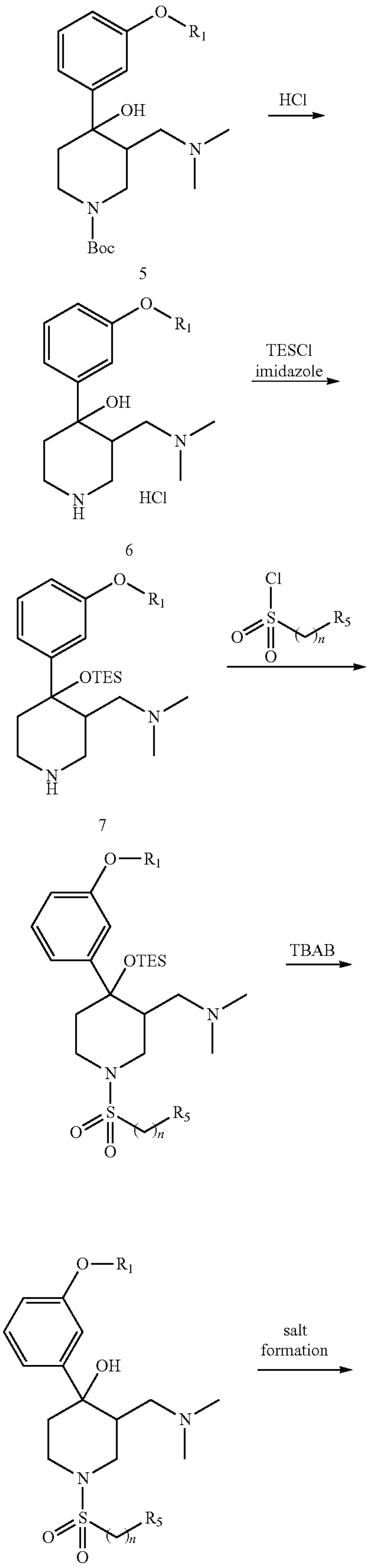

5
6
7
(I) salt.

Example 2-1

Preparation of Intermediate 2

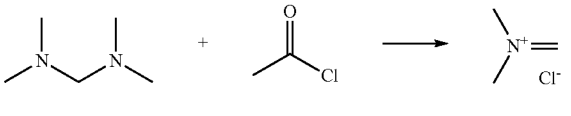
2

N,N,N',N'-tetramethylmethanediamine (60 g, 587.2 mmol, 1 eq.), methyl tert-butyl ether (500 ml) were added to 1 L three-neck bottle with nitrogen balloon, thermometer and constant pressure dropping funnel, cooled to 0° C., and acetyl chloride (46.1 g, 587.2 mmol, 1 eq., about 20 min) was added dropwise at 30° C. After the dropwise addition was completed, stirred for 30 minutes, filtered with suction, added acetonitrile (100 ml) and MTBE (25 ml) to the filter cake, stirred for 10 minutes, filtered with suction, and evaporated the filter cake to dryness under reduced pressure (55° C.) to obtain 46 g of off-white solid (It is easy to absorb moisture), and the yield was 83.7%.

Example 2-2

Preparation of Intermediate 3:

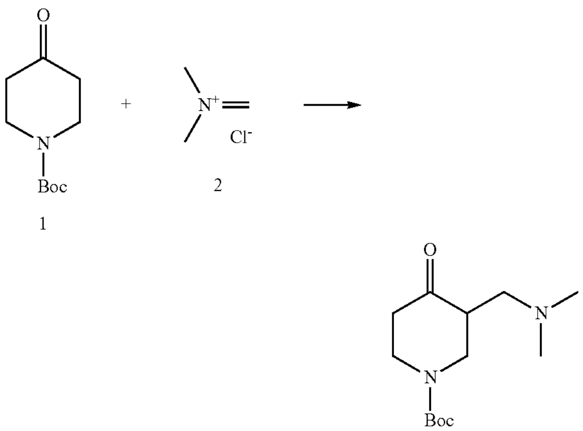
1
2
3

Boc-piperidone (35 g, 175.66 mmol, 1 eq.) and acetonitrile (350 mL) were added to a 1 L single-neck flask with a thermometer and nitrogen balloon, stirred to dissolve, and then Intermediate 2 (19.72 g, 210.8 mmol, 1.2 eq.) was added. The internal temperature was 30-35° C. for 24 h, and TLC showed that the reaction was basically complete after 24 h. The acetonitrile was evaporated under reduced pressure, DCM (300 mL) was added, and then saturated sodium bicarbonate (250 mL) was added, mixed, stood, layered and separated. The aqueous phase was extracted with DCM (200+100 mL). The organic phases were combined, washed with water (50 mL), dried over anhydrous magnesium sulfate, filtered with suction, and the filtrate was evaporated under reduced pressure to obtain 43.3 g of a reddish-brown viscous liquid with a yield of 93.5%.

Example 2-3

Preparation of Intermediate 5:

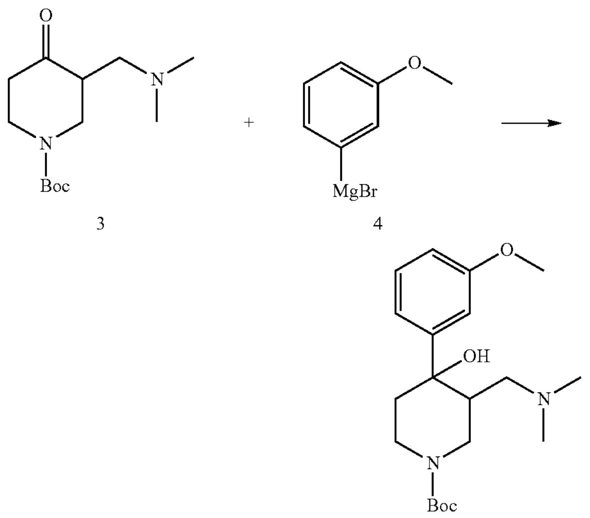

3 4 5

Magnesium turnings (11 g, 451.68 mmol, 3 eq.), THF (300 mL), 3 grains of iodine, a small amount of m-bromoanisole (84.5 g, 451.68 mmol, 3 eq.) in THF (70 mL) were added to a 1 L four-necked flask with a nitrogen balloon, a constant pressure dropping funnel, a condenser tube and a thermometer, the temperature was raised and refluxed. When the yellow color faded, heating was stopped. The THF solution of m-bromoanisole was slowly added dropwise (about 1 h) until the addition was complete. After the dropwise addition was completed, the stirring was naturally lowered to room temperature. After 30 min, a solution of Intermediate 3 (37.76 g, 1 eq.) in THF (100 mL) was added dropwise at 25° C. After the dropwise addition was completed, the ice water bath was removed and the mixture was stirred at room temperature overnight (18 h). The reaction solution was poured into a mixture of ammonium chloride aqueous solution (200 mL) and ice (about 100 g), stirred for 5 min, and THF was evaporated under reduced pressure (30° C.). Ethyl acetate (300 mL) was added, stirred, allowed to stand, layered and separated. The aqueous phase was extracted with ethyl acetate (300 mL). The organic phases were combined, washed with water (100 mL), dried over anhydrous magnesium sulfate, filtered with suction, and the filtrate was evaporated under reduced pressure to obtain 76.5 g of a yellow liquid, which was purified by column chromatography to obtain 21.4 g of a light yellow viscous liquid with a yield of 38.9%. (two steps, based on boc-piperidone). $^1$H NMR (400 MHz, $CD_3OD$), δ 7.26 (t, J=8 Hz, 1H), 7.04~7.05 (m, 1H), 6.98 (d, J=8 Hz, 1H), 6.81 (dd, J=8 Hz, J=4 Hz, 1H), 4.20~4.25 (m, 1H), 3.96~4.00 (m, 1H), 3.79 (s, 3H), 3.35 (s, 1H), 3.03~3.22 (m, 2H), 2.31~2.37 (m, 1H), 2.07~2.11 (m, 1H), 2.04 (s, 6H), 1.94~2.01 (m, 1H), 1.78~1.81 (m, 1H), 1.58~1.62 (m, 1H), 1.50 (s, 9H).

Example 2-4

Preparation of Intermediate 6:

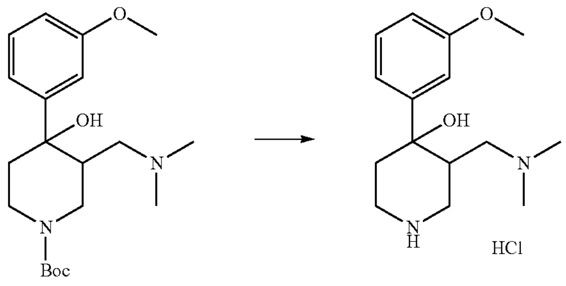

5 6

Boc-amino alcohol (9.5 g, 26.06 mmol, 1 eq.) and methanol (76 mL) were added to a 250 mL one-neck flask, stirred, and a solution of HCl/1,4-dioxane (16.3 mL, 65.15 mmol, 2.5 eq.) was added dropwise, the internal temperature rose to about 36° C. After stirring for 2 hours, TLC showed substantial raw material. The temperature was raised to 50° C. and stirred, after 2 hours TLC showed that the reaction was substantially complete. MTBE (150 mL) was added and stirred with solid gradually precipitated, which was stirred overnight (24 h). Then they were suction filtered, the filter cake was rinsed with MTBE (20 mL), and rotary-evaporated under reduced pressure and rotary-dried to obtain 8.63 g of off-white solids with a yield of 98.3%. $^1$H NMR (400 MHz, $CD_3OD$), δ 7.38 (t, J=8 Hz, 1H), 7.15~7.16 (m, 1H), 7.12 (d, J=8 Hz, 1H), 6.92 (dd, $J_1$=8 Hz, $J_2$=4 Hz, 1H), 3.83 (s, 3H), 3.75 (dd, $J_1$=12 Hz, $J_2$=4 Hz, 1H), 3.41~3.43 (m, 3H), 3.09~3.15 (m, 1H), 2.85~2.92 (m, 1H), 2.75 (s, 3H), 2.75~2.78 (m, 1H), 2.57 (s, 3H), 2.54~2.62 (m, 1H), 1.89~1.94 (m, 1H).

Example 2-5

Preparation of Intermediate 7:

Aminoalcohol hydrochloride (10 g, 33.22 mmol, 1 eq.), imidazole (20.35 g, 298.98 mmol, 9 eq.), DCM (100 mL) were added to a 250 mL three-necked bottle with a nitrogen balloon, a constant pressure dropping funnel and a thermometer, stirred to dissolve. After cooling, triethylchlorosilane (35.06 g, 232.6 mmol, 7 eq.) was added dropwise at 10° C. After the dropwise addition was completed, the mixture was stirred for 5 min, and the ice water bath was removed and stirred overnight (26 h). TLC (DCM:MeOH=10:1 and 4:1) showed that the reaction was complete. Under an ice-water bath, the reaction solution was slowly poured into saturated aqueous sodium bicarbonate solution (100 mL), stirred for 10 minutes, and extracted with dichloromethane (25 mL). The aqueous phase was extracted with dichloromethane. The organic phases were combined, washed with water (20 mL), dried over anhydrous magnesium sulfate, filtered with suction, and the filtrate was evaporated under reduced pressure to obtain 36.72 g of light yellow liquid, which was purified by aluminum oxide column chromatography to obtain 10.2 g of light yellow liquid, yield 81%. LC-MS: $ESI^+[M+H]^+$ 379.1.

Example 2-6

General Method for the Condensation of Intermediate 7 with Sulfonyl Chloride:

Intermediate 7 (1 eq.), DCM (10 mL), TEA (2 eq.) were added to a 100 mL single-neck flask, stirred under an ice-water bath, and sulfonyl chloride (1 eq.) was added. Stirred for a certain time at 30° C. Water (30 mL), DCM was added, mixed, allowed to stand, layered, and separated. The aqueous phase was extracted with DCM (20 mL). The organic phases were combined and washed with water, which was evaporate under reduced pressure to obtain light yellow liquid. The liquid was used directly in the next step without further purification.

Example 2-7

General Procedure for Removing Protecting Group TES:

Raw material (1 eq.), THF was added to a 50 mL single-neck flask, stirred to dissolve, and TBAF (1.5 eq.) was added and stirred under room temperature. The reaction was monitored by LC-MS until the completion of reaction. The THF was evaporated under reduced pressure, sodium bicarbonate solution (30 mL) was added, and the mixture was extracted with DCM. The organic phases were combined, washed with water, dried over anhydrous magnesium sulfate, filtered with suction, and the filtrate was evaporated under reduced pressure to obtain a liquid. The target product was purified by column chromatography.

Example 2-8

General Method of Salt Formation:

Raw material (1 eq.), dichloromethane was added to a 50 mL single-neck flask, stirred to dissolve, and methyl tert-butyl ether was added. A solution of HCl in 1,4-dioxane (1.2 eq.) was added with solid precipitated, stirred for a certain period of time, filtered with suction, rinsed with methyl tert-butyl ether on the filter cake, and drained by an oil pump to obtain the target product.

Example 2-9

1-(Benzylsulfonyl)-3-((dimethylamino)methyl)-4-(3-methoxyphenyl)piperidin-4-ol hydrochloride (FWBH6)

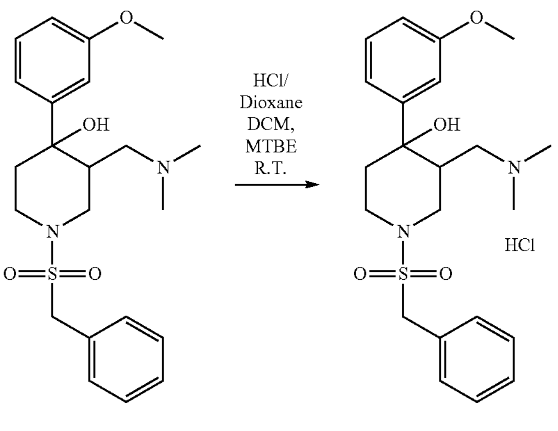 [SMILES: COc1cccc(C2(O)CCN(S(=O)(=O)Cc3ccccc3)CC2CN(C)C)c1 ; COc1cccc(C2(O)CCN(S(=O)(=O)Cc3ccccc3)CC2CN(C)C)c1 ; Cl]

FWBH6 was obtained by salifying 1-(benzylsulfonyl)-3-((dimethylamino)methyl)-4-(3-methoxyphenyl) piperidin-4-ol, yield: 95.8%. $^1$H NMR (400 MHz, CDOD), δ 7.50 (dd, $J_1$=8 Hz, $J_2$=4 Hz, 1H), 7.36~7.44 (m, 3H), 7.33 (t, J=8 Hz, 1H), 7.07 (s, 1H), 70.03 (d, J=8 Hz, 1H), 6.85~6.87 (m, 1H), 4.45 (s, 2H), 3.79~3.83 (m, 4H), 3.52~3.57 (m, 1H), 3.12~3.20 (m, 2H), 2.95~3.01 (m, 1H), 2.60~2.69 (m, 1H), 2.60 (s, 6H), 2.29~2.35 (m, 1H), 2.13~2.21 (m, 1H), 1.65~1.70 (m, 1H). LC-MS-ESI$^+$: [M+H]$^+$ 419.3.

Example 2-10

1-((3-Chlorobenzyl)sulfonyl)-3-((dimethylamino)methyl)-4-(3-methoxyphenyl)piperidin-4-ol hydrochloride (FWBH7)

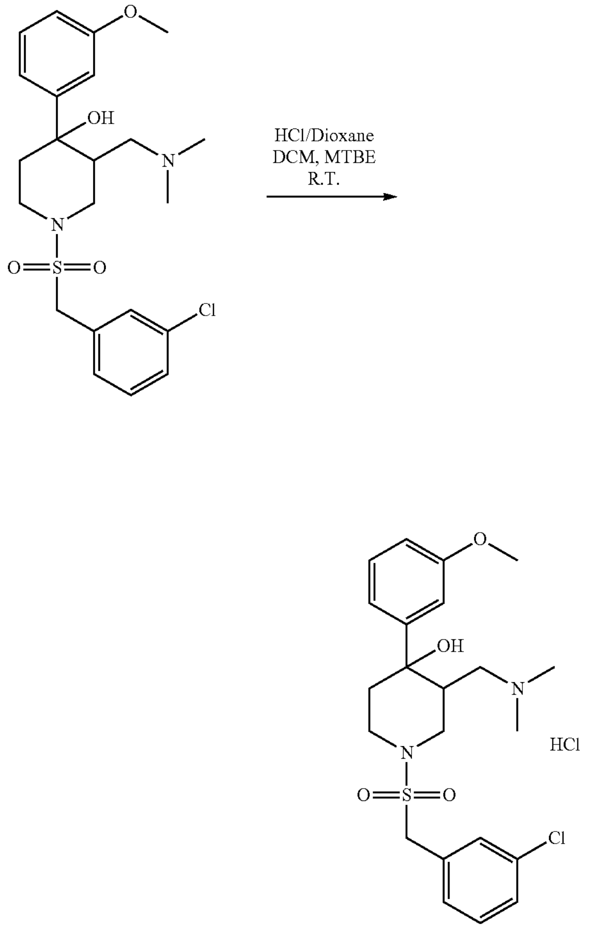

FWBH7 was obtained by salifying 1-((3-chlorobenzyl)sulfonyl)-3-((dimethylamino)methyl)-4-(3-methoxyphenyl)piperidin-4-ol, yield: 92.1%. $^1$H NMR (400 MHz, CDOD), δ 7.56~7.57 (m, 1H), 7.41~7.47 (m, 3H), 7.34 (t, J=8 Hz, 1H), 7.10~7.11 (m, 1H), 7.05 (d, J=12 Hz, 1H), 6.88 (dd, $J_1$=8 Hz, $J_2$=4 Hz, H), 4.49 (t, 2H), 3.89 (dd, $J_1$=12 Hz, $J_2$=4 Hz, 1H), 3.82 (s, 3H), 3.56~3.61 (m, 1H), 3.18~3.25 (m, 2H), 2.99~3.05 (m, 1H), 2.71 (s, 6H), 2.69~2.73 (m, 1H), 2.53 (s, 3H), 2.34~2.41 (m, 1H), 2.15~2.23 (m, 1H), 1.68~1.73 (m, 1H). LC-MS-ESI$^+$: [M+H]$^+$ 453.2.

Example 2-11

3-((Dimethylamino)methyl)-4-(3-methoxyphenyl)-1-((4-methylbenzyl)sulfonyl)piperidin-4-ol hydrochloride (FWBH8)

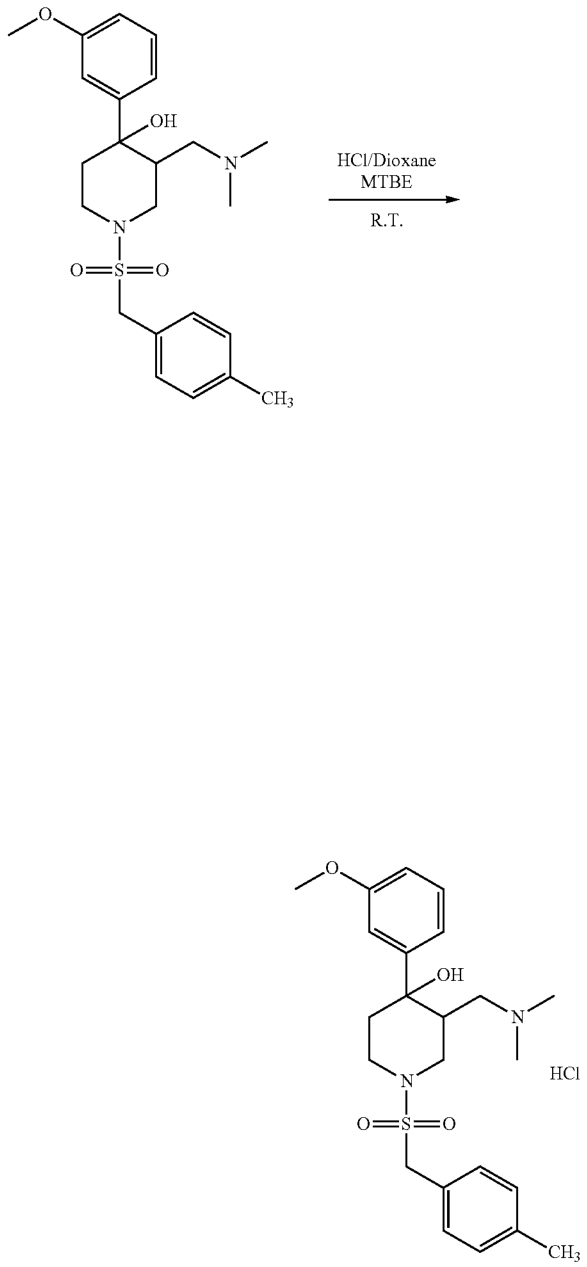

FWBH8 was obtained by salifying 3-((dimethylamino) methyl)-4-(3-methoxyphenyl)-1-((4-methylbenzyl) sulfonyl)piperidin-4-ol, and obtaining Rate: 96.8%. $^1$H NMR (400 MHz, $CD_3OD$), δ 7.31~7.38 (m, 3H), 7.23~7.26 (m, 2H), 7.02~7.07 (m, 2H), 6.87 (dd, J=8 Hz, J=4 Hz, 1H), 4.40 (s, 2H), 3.81 (s, 3H), 3.75~3.82 (m, 1H), 3.51~3.56 (m, 1H), 3.12~3.21 (m, 3H), 2.95~3.01 (m, 1H), 2.66~2.70 (m, 1H), 2.60 (s, 6H), 2.35 (s, 3H), 2.28~2.37 (m, 1H), 2.13~2.21 (m, 1H), 1.65~1.70 (m, 1H). LC-MS-ESI$^+$: $[M+H]^+$ 433.3.

Example 2-12

3-((Dimethylamino)methyl)-4-(3-methoxyphenyl)-1-(phenethylsulfonyl)piperidin-4-ol hydrochloride (FWBH9)

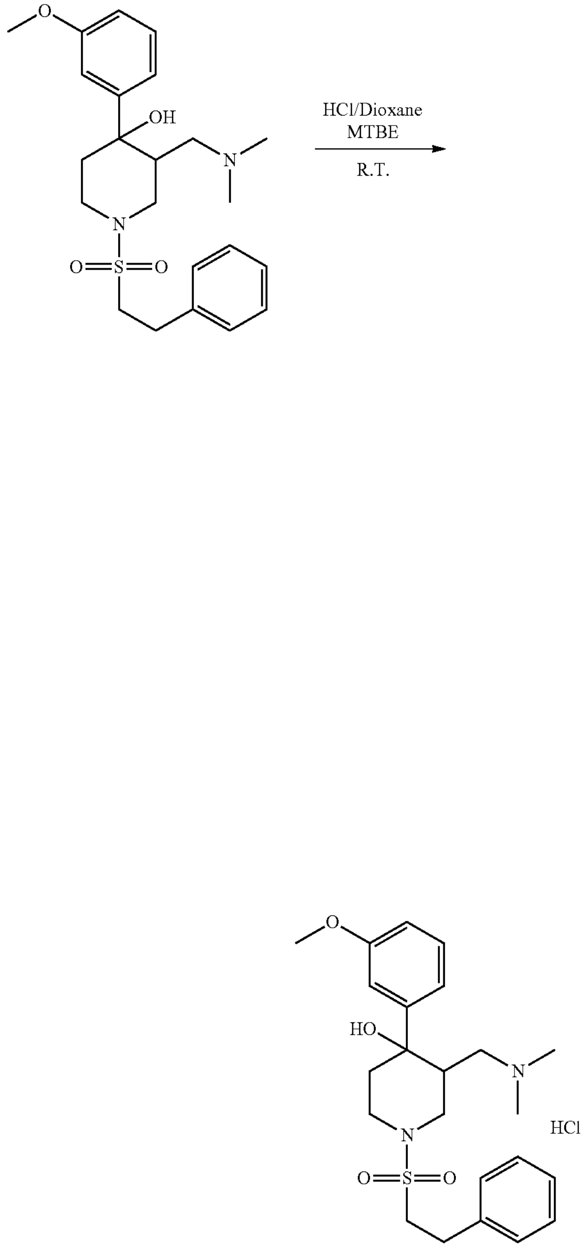

FWBH9 was obtained by salifying 3-((dimethylamino) methyl)-4-(3-methoxyphenyl)-1-(phenethylsulfonyl) piperidin-4-ol, yield: 87.2%. $^1$H NMR (400 MHz, $CD_3OD$), δ 7.23~7.37 (m, 6H), 7.11 (s, 1H), 7.07 (d, J=8 Hz, 1H), 6.88 (dd, $J_1$=8 Hz, $J_2$=4 Hz, H), 3.86~3.91 (m, 1H), 3.82 (s, 3H), 3.70 (d, J=12 Hz, 1H), 3.39~3.43 (m, 2H), 3.10~3.27 (m, 4H), 3.01~3.06 (m, 1H), 2.69~2.74 (m, 1H), 2.65 (s, 6H), 2.41~2.46 (m, 1H), 2.21~2.29 (m, 1H), 1.76 (dd, $J_1$=12 Hz, $J_2$=4 Hz, H). LC-MS-ESI$^+$: $[M+H]^+$ 433.3.

Example 2-13

3-((Dimethylamino)methyl)-4-(3-methoxyphenyl)-1-((3-(trifluoromethyl)benzyl)sulfonyl) piperidin-4-ol hydrochloride (FWBH10)

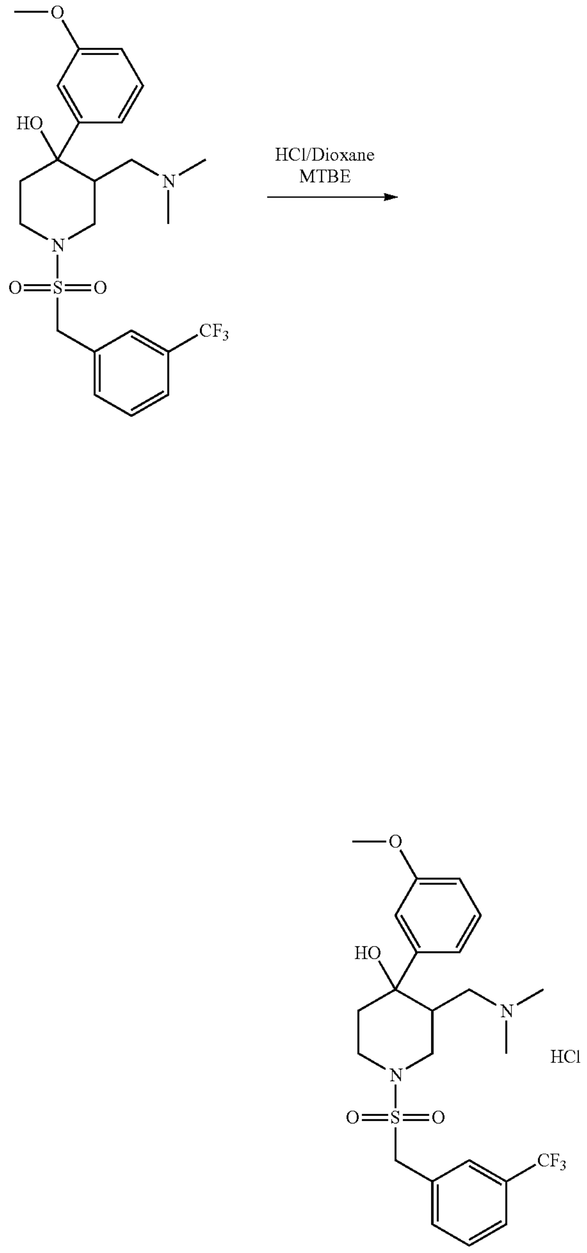

FWBH10 was obtained by salifying 3-((dimethylamino)methyl)-4-(3-methoxyphenyl)-1-((3-(trifluoromethyl)benzyl)sulfonyl)piperidin-4-ol, yield: 90.6%. $^{1}H$ NMR (400 MHz, $CD_3OD$), δ 7.70~7.81 (m, 3H), 7.83 (t, J=8 Hz, 1H), 7.33 (t, J=8 Hz, 1H), 7.04~7.10 (m, 2H), 6.87 (d, J=8 Hz, 1H), 4.57 (s, 2H), 3.82~3.87 (m, 1H), 3.81 (s, 3H), 3.58~3.61 (m, 1H), 3.18~3.25 (m, 2H), 2.96~3.04 (m, 1H), 2.69~2.73 (m, 1H), 2.62 (s, 6H), 2.39 (m, 1H), 2.18~2.26 (m, 1H), 1.70~1.74 (m, 1H). LC-MS-ESI$^{+}$: $[M+H]^{+}$ 487.2.

Example 2-14

1-((4-Chlorobenzyl)sulfonyl)-3-((dimethylamino)methyl)-4-(3-methoxyphenyl)piperidin-4-ol hydrochloride (FWBH11)

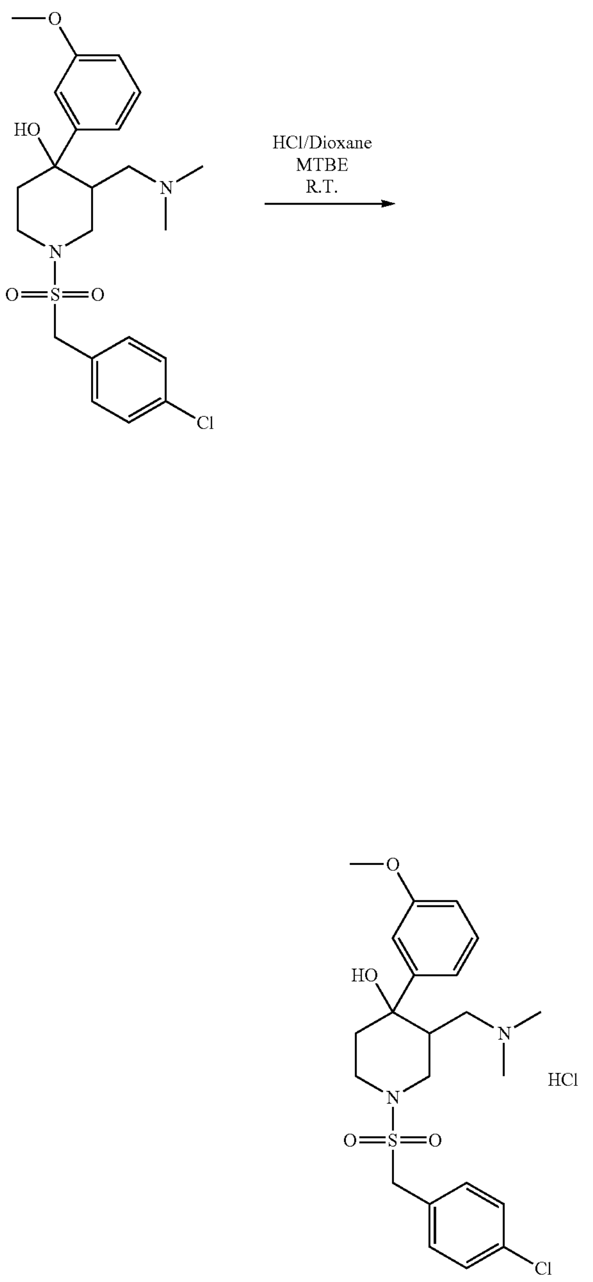

FWBH11 was obtained by salifying 1-((4-chlorobenzyl)sulfonyl)-3-((dimethylamino)methyl)-4-(3-methoxyphenyl)piperidin-4-ol, yield: 68.4%. $^{1}H$ NMR (400 MHz, $CD_3OD$), δ 7.41~7.50 (m, 4H), 7.30~7.37 (m, 1H), 7.04~7.09 (m, 2H), 6.85~6.88 (m, 1H), 4.44~4.46 (m, 2H), 3.80~3.84 (m, 4H), 3.59 (m, 1H), 3.14~3.24 (m, 3H), 2.96~3.03 (m, 1H), 2.69~2.71 (m, 4H), 2.54 (s, 3H), 2.35 (s, 1H), 2.16~2.23 (m, 1H), 1.68~1.72 (m, 1H). LC-MS-ESI$^{+}$: $[M+H]^{+}$ 453.2.

Example 2-15

3-((Dimethylamino)methyl)-1-((4-fluorobenzyl)sulfonyl)-4-(3-methoxyphenyl)piperidin-4-ol hydrochloride (FWBH12)

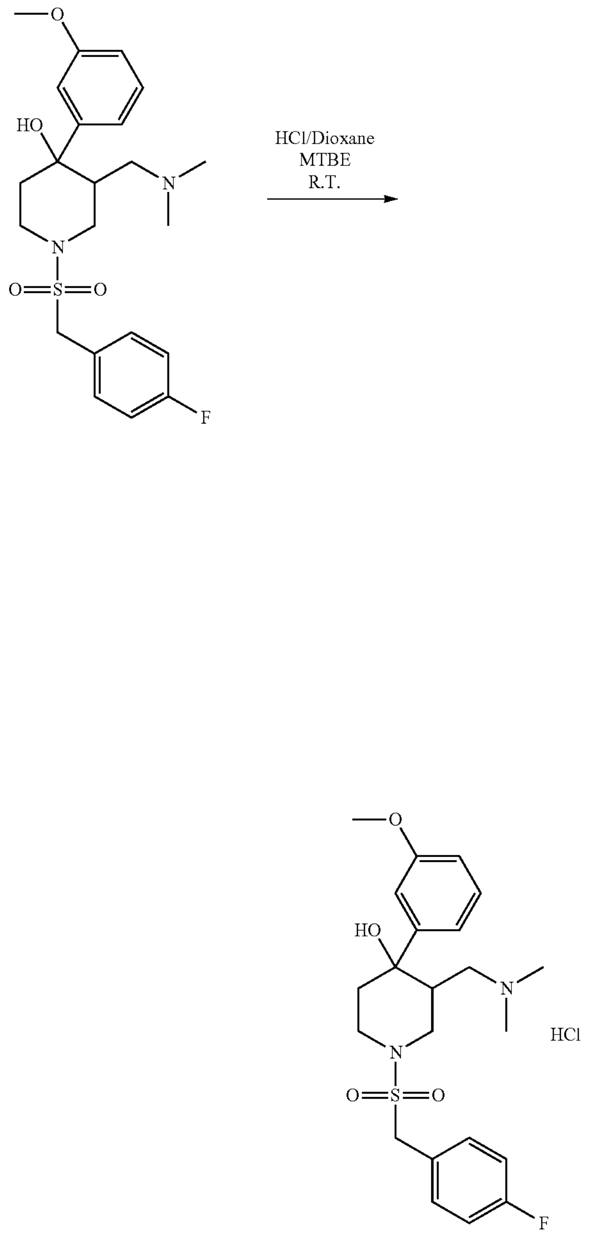

FWBH12 was obtained by salifying 3-((dimethylamino)methyl)-1-((4-fluorobenzyl)sulfonyl)-4-(3-methoxyphenyl)piperidin-4-ol in yield: 98.33%. $^{1}$H NMR (400 MHz, $CD_3OD$), δ 7.50~7.54 (m, 2H), 7.31~7.35 (m, 1H), 7.14~7.19 (m, 2H), 7.09 (s, 1H), 7.05 (d, J=8 Hz, 1H), 6.87 (d, J=8 Hz, 1H), 4.45 (s, 2H), 3.82~3.84 (m, 1H), 3.81 (s, 3H), 3.54~3.59 (m, 1H), 3.15~3.21 (m, 1H), 2.97~3.03 (m, 1H), 2.68~2.72 (m, 1H), 2.62 (s, 6H), 2.34~2.40 (m, 1H), 2.16~2.24 (m, 1H), 1.67~1.72 (m, 1H). LC-MS-ESI$^+$: $[M+H]^+$ 437.2.

Example 2-16

1-((3-Bromobenzyl)sulfonyl)-3-((dimethylamino)methyl)-4-(3-methoxyphenyl)piperidin-4-ol hydrochloride (FWBH13)

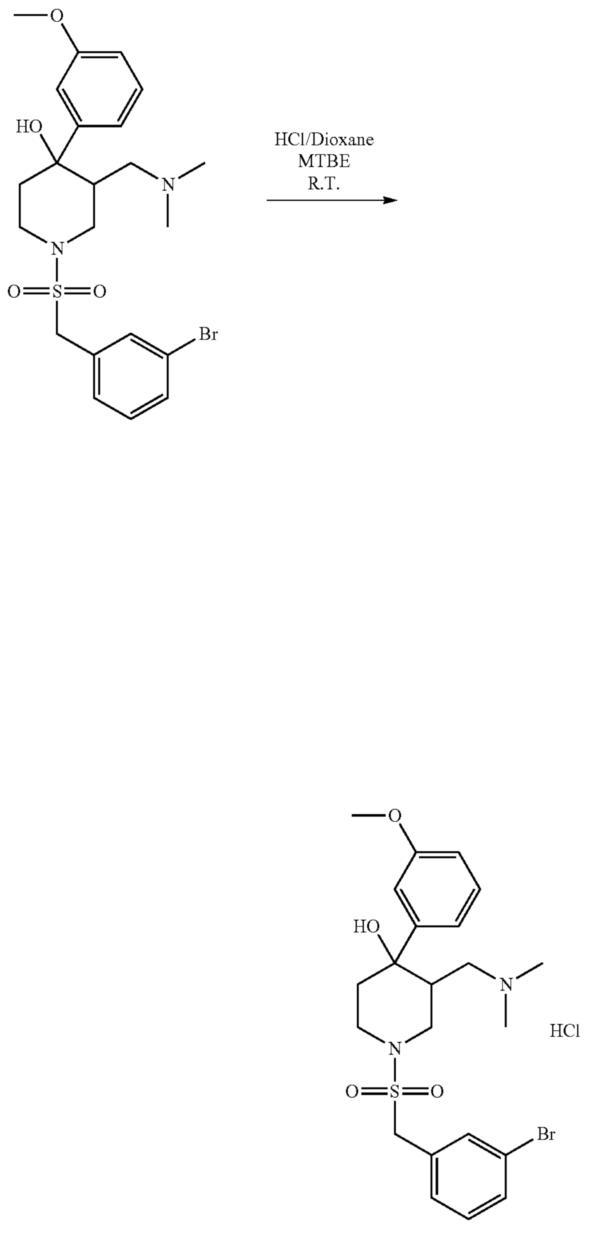

FWBH13 was obtained by salifying 1-((3-bromobenzyl)sulfonyl)-3-((dimethylamino)methyl)-4-(3-methoxyphenyl)piperidin-4-ol in yield: 85%. $^{1}$H NMR (400 MHz, CD3OD), δ 7.57~7.58 (m, 1H), 7.43 (d, J=8 Hz, 1H), 7.35 (d, J=8 Hz, 1H), 7.18~7.24 (m, 2H), 6.90~6.98 (m, 2H), 6.72~6.76 (m, 1H), 4.33 (s, 2H), 3.68~3.75 (m, 1H), 3.67 (s, 3H), 3.45 (dd, $J_1$=16 Hz, $J_2$=8 Hz, 1H), 3.03~3.11 (m, 2H), 2.84~2.90 (m, 1H), 2.54~2.59 (m, 1H), 2.48 (s, 6H), 2.19~2.24 (m, 1H), 2.01~2.09 (m, 1H), 1.55~1.59 (m, 1H). LC-MS-ESI$^+$: $[M+H]^+$ 497.2.

Example 2-17

3-((Dimethylamino)methyl)-1-((2-fluorobenzyl)sulfonyl)-4-(3-methoxyphenyl)piperidin-4-ol hydrochloride (FWBH14)

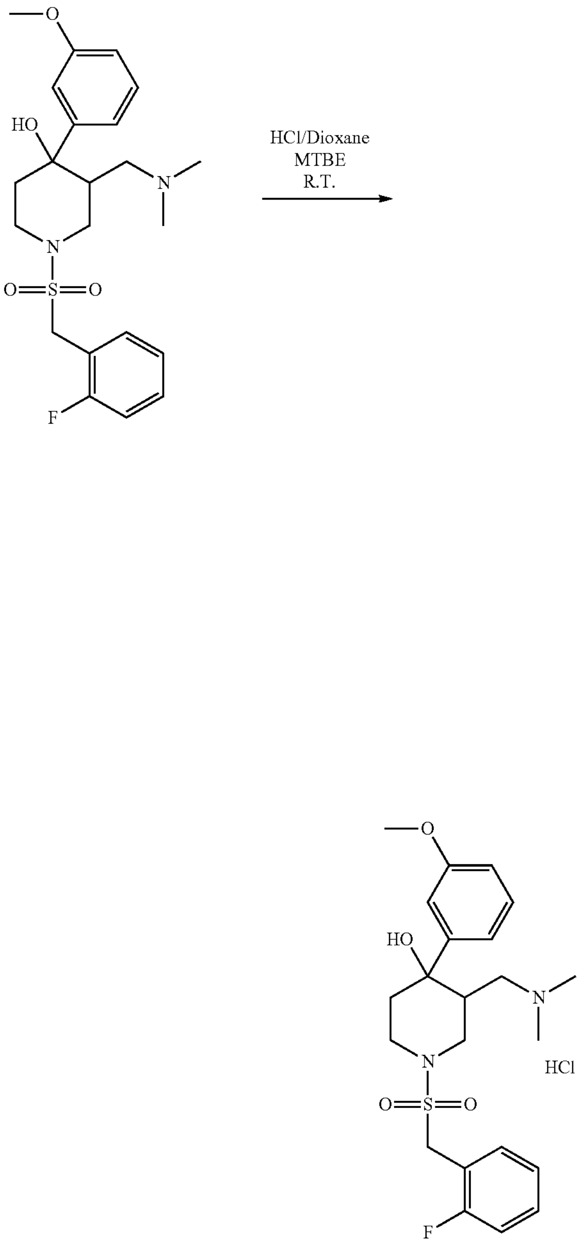

FWBH14 was obtained by salifying 3-((dimethylamino)methyl)-1-((2-fluorobenzyl)sulfonyl)-4-(3-methoxyphenyl)piperidin-4-ol, yield: 94%. $^1$H NMR (400 MHz, $CD_3OD$), δ 7.54~7.60 (m, 1H), 7.41~7.49 (m, 1H), 7.32~7.38 (m, 1H), 7.19~7.29 (m, 2H), 7.04~7.11 (m, 2H), 6.86~6.91 (m, 1H), 4.52 (s, 2H), 3.82~3.87 (m, 1H), 3.81 (s, 3H), 3.54~3.57 (m, 1H), 3.20~3.27 (m, 2H), 2.99~3.06 (m, 1H), 2.67~2.73 (m, 1H), 2.62 (s, 6H), 2.36~2.41 (m, 1H), 2.15~2.25 (m, 1H), 1.61~1.74 (m, 1H). LC-MS-ESI$^+$: $[M+H]^+$ 437.2.

Example 2-18

1-(Butylsulfonyl)-3-((dimethylamino)methyl)-4-(3-methoxyphenyl)piperidin-4-ol hydrochloride (FWBH15)

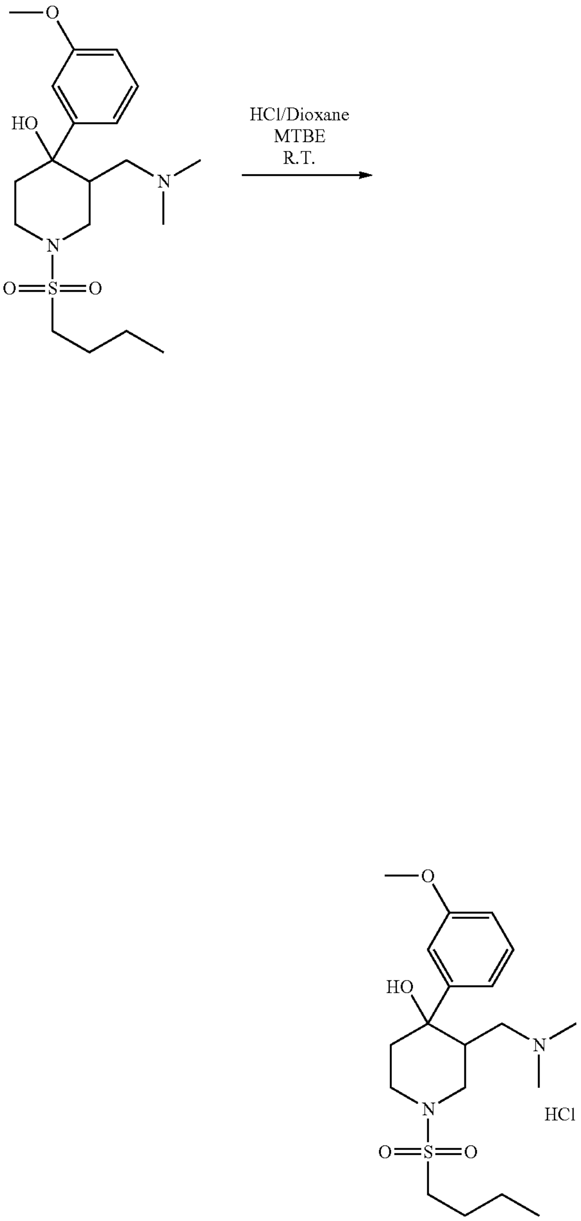

FWBH15 was obtained by salifying 1-(butylsulfonyl)-3-((dimethylamino)methyl)-4-(3-methoxyphenyl)piperidin-4-ol, yield: 88.6%. $^1$H NMR (400 MHz, $CD_3OD$), δ 7.32~7.39 (m, 1H), 7.08~7.15 (m, 2H), 6.86~6.92 (m, 1H), 3.87~3.91 (m, 1H), 3.81 (s, 3H), 3.67~3.72 (m, 1H), 3.20~3.27 (m, 1H), 3.03~3.16 (m, 3H), 2.70~2.77 (m, 1H), 2.65 (s, 6H), 2.45~2.50 (m, 1H), 2.25~2.33 (m, 1H), 1.76~1.84 (m, 3H), 1.46~1.56 (m, 2H), 0.91~1.04 (m, 3H). LC-MS-ESI$^+$: $[M+H]^+$ 385.2.

Example 2-19

3-((Dimethylamino)methyl)-4-(3-methoxyphenyl)-1-((3-nitrobenzyl)sulfonyl)piperidin-4-ol hydrochloride (FWBH22)

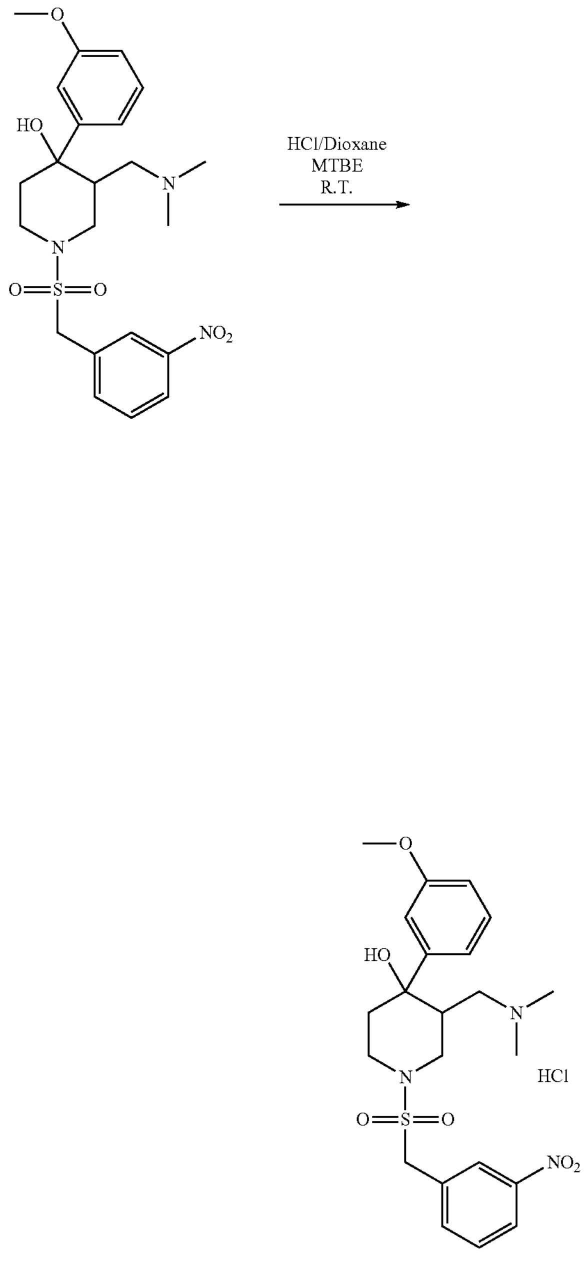

FWBH22 was obtained by salifying 3-((dimethylamino)methyl)-4-(3-methoxyphenyl)-1-((3-nitrobenzyl)sulfonyl)piperidin-4-ol, yield: 98.4%. $^{1}$H NMR (400 MHz, $CD_3OD$), δ 8.28~8.34 (m, 2H), 7.74~7.80 (m, 2H), 7.32~7.40 (m, 1H), 7.05~7.13 (m, 2H), 6.86~6.92 (m, 1H), 4.62~4.66 (m, 2H), 3.81~3.88 (m, 4H), 3.60~3.69 (m, 2H), 3.18~3.27 (m, 3H), 2.98~3.08 (m, 1H), 2.64~2.74 (m, 7H), 2.40~2.48 (m, 1H), 2.19~2.28 (m, 1H), 1.70~1.77 (m, 1H). LC-MS-ESI$^{+}$: $[M+H]^{+}$ 464.2.

Example 2-20

3-((Dimethylamino)methyl)-4-(3-methoxyphenyl)-1-(phenylsulfonyl)piperidin-4-ol hydrochloride (FWBH16)

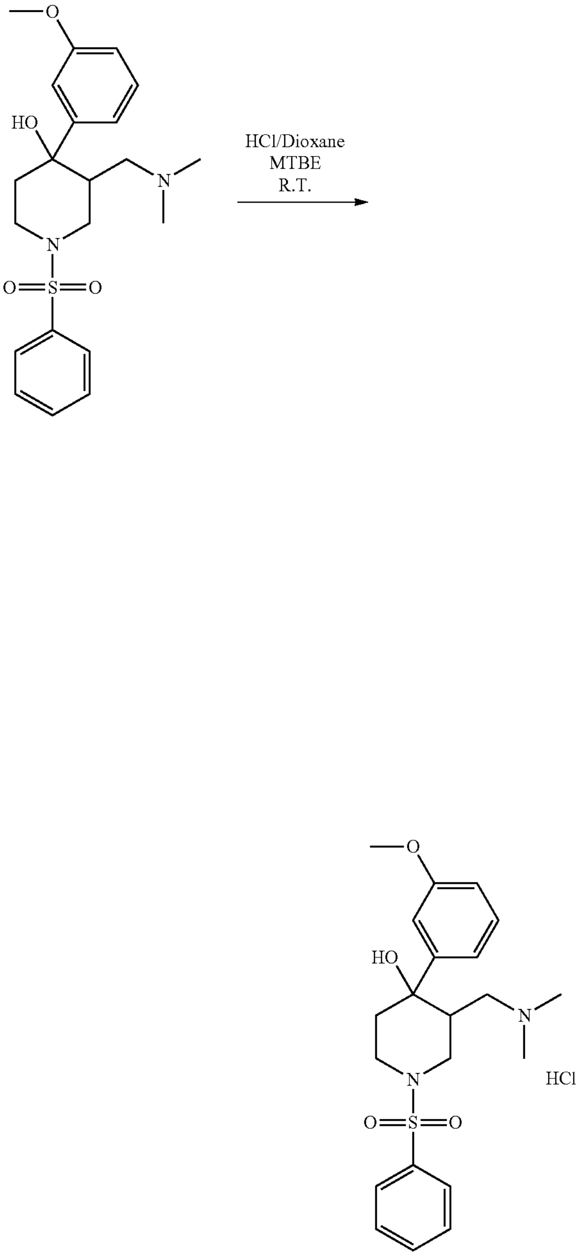

FWBH16 was obtained by salifying 3-((dimethylamino)methyl)-4-(3-methoxyphenyl)-1-(phenylsulfonyl)piperidin-4-ol, yield: 92.3%. $^{1}$H NMR (400 MHz, $CD_3OD$), δ 7.89 (d, J=8 Hz, 1H), 7.72~7.76 (m, 1H), 7.65~7.69 (m, 2H), 7.32 (t, J=8 Hz, 1H), 7.02~7.06 (m, 2H), 6.84~6.87 (m, 1H), 3.98 (dd, $J_1$=12 Hz, $J_2$=4 Hz, 1H), 3.79 (s, 3H), 3.71~3.73 (m, 1H), 2.95~3.01 (m, 1H), 2.53~2.77 (m, 10H), 2.29~2.36 (m, 1H), 1.73~1.77 (m, 1H). LC-MS-ESI$^{+}$: $[M+H]^{+}$ 405.2.

Example 2-21

3-((Dimethylamino)methyl)-4-(3-methoxyphenyl)-1-((4-(trifluoromethyl)benzyl)sulfonyl) piperidin-4-ol hydrochloride (FWBH17)

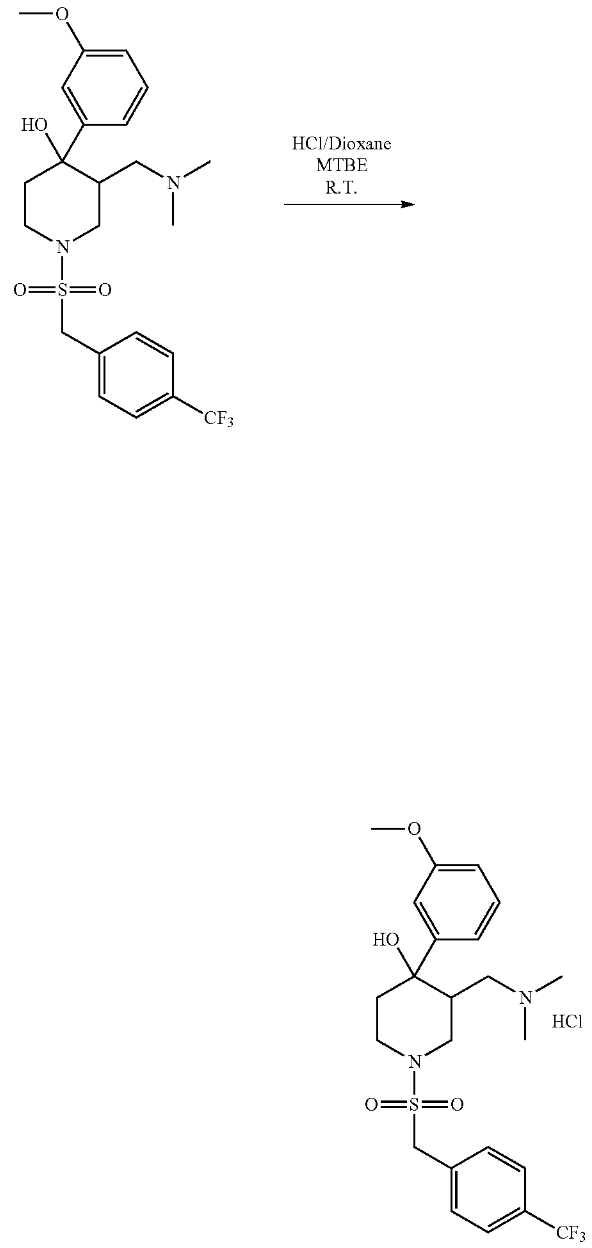

FWBH17 was obtained by salifying 3-((dimethylamino)methyl)-4-(3-methoxyphenyl)-1-((4-(trifluoromethyl)benzyl)sulfonyl)piperidin-4-ol, yield: 98.5%. $^{1}H$ NMR (400 MHz, $CD_3OD$), δ 7.69~7.75 (m, 4H), 7.31~7.36 (m, 1H), 7.04~7.10 (m, 2H), 6.86~6.89 (m, 1H), 4.56 (s, 2H), 3.82~3.88 (m, 1H), 3.81 (s, 3H), 3.58~3.62 (m, 1H), 3.22 (t, J=8 Hz, 2H), 2.98~3.05 (m, 1H), 2.69~2.74 (m, 1H), 2.63 (s, 6H), 2.35~2.41 (m, 1H), 2.17~2.25 (m, 1H), 1.69~1.74 (m, 1H). LC-MS-ESI$^{+}$: $[M+H]^{+}$ 487.2.

Example 2-22

3-((Dimethylamino)methyl)-1-(ethylsulfonyl)-4-(3-methoxyphenyl)piperidin-4-ol hydrochloride (FWBH18)

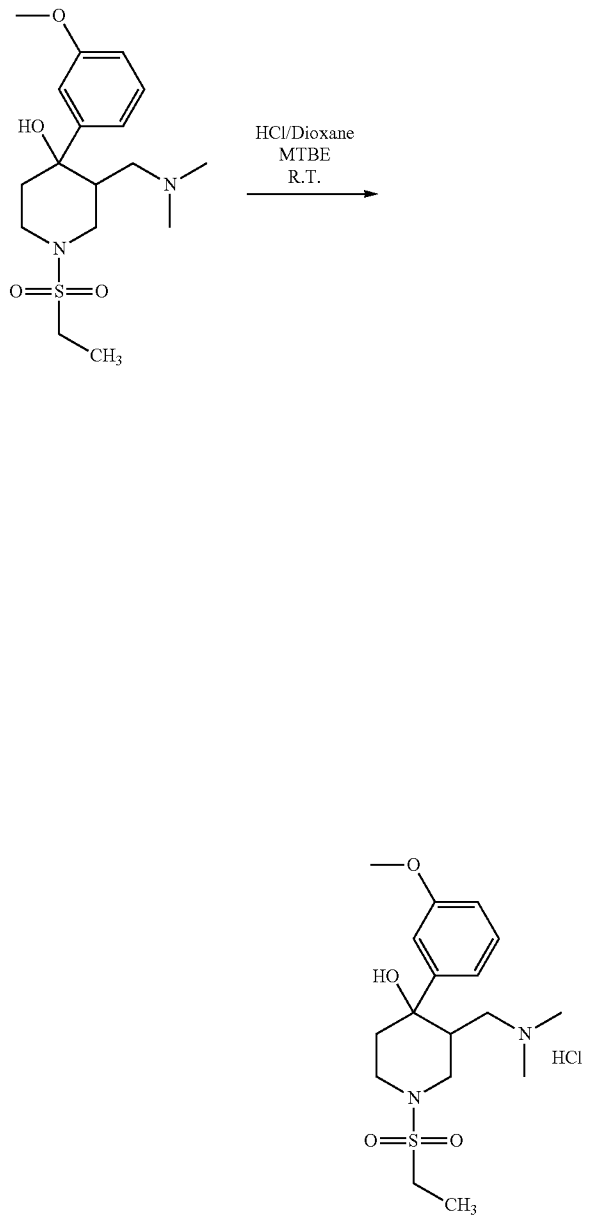

FWBH18 was obtained by salifying 3-((dimethylamino)methyl)-1-(ethylsulfonyl)-4-(3-methoxyphenyl)piperidin-4-ol, yield: 98.7%. $^{1}H$ NMR (400 MHz, $CD_3OD$), δ 7.34 (t, J=8 Hz, 1H), 7.13 (s, 1H), 7.09 (d, J=8 Hz, 1H), 6.88 (dd, $J_1$=8 Hz, $J_2$=4 Hz, 1H), 3.91 (dd, $J_1$=12 Hz, $J_2$=8 Hz, 1H), 3.82 (s, 3H), 3.70 (dd, $J_1$=12 Hz, $J_2$=4 Hz, 1H), 3.22~3.36 (m, 2H), 3.13~3.18 (m, 2H), 3.03~3.09 (m, 1H), 2.74 (s, 3H), 2.70~2.73 (m, 1H), 2.58 (s, 3H), 2.45~2.51 (m, 1H), 2.25~2.33 (m, 1H), 1.75~1.80 (m, 1H), 1.37 (t, J=8 Hz, 3H). LC-MS-ESI$^{+}$: $[M+H]^{+}$ 357.3.

Example 2-23

3-((Dimethylamino)methyl)-4-(3-methoxyphenyl)-1-(propylsulfonyl)piperidin-4-ol hydrochloride (FWBH19)

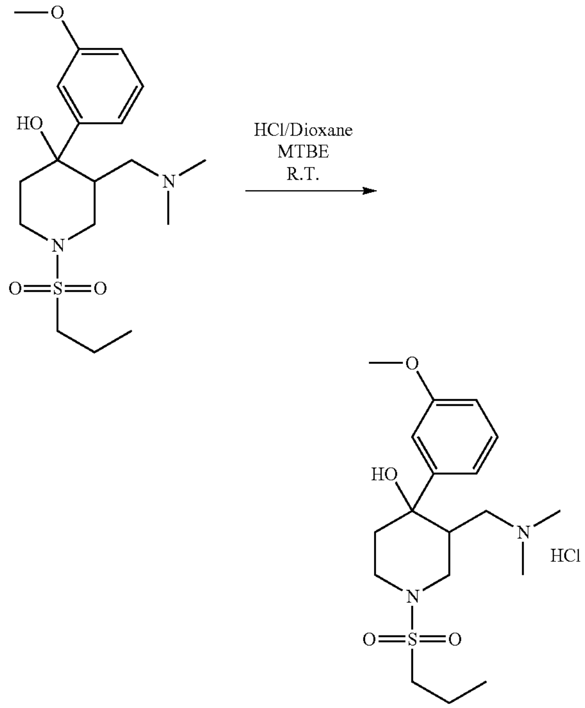

FWBH19 was obtained by salifying 3-((dimethylamino)methyl)-4-(3-methoxyphenyl)-1-(propylsulfonyl)piperidin-4-ol, yield: 80%. $^1$H NMR (400 MHz, $CD_3OD$), δ 7.32~7.36 (m, 1H), 7.08~7.13 (m, 2H), 6.88 (dd, $J_1$=8 Hz, $J_2$=4 Hz, 1H), 3.87~3.91 (m, 1H), 3.81 (s, 3H), 3.66~3.71 (m, 1H), 3.19~3.33 (m, 2H), 3.03~3.12 (m, 3H), 2.61~2.75 (m, 7H), 2.45~2.51 (m, 1H), 2.25~2.33 (m, 1H), 1.82~1.89 (m, 2H), 1.76~1.81 (m, 1H), 1.08~1.12 (m, 3H). LC-MS-ESI$^+$: $[M+H]^+$ 371.2.

Example 2-24

3-((Dimethylamino)methyl)-1-(isopropylsulfonyl)-4-(3-methoxyphenyl)piperidin-4-ol hydrochloride (FWBH20)

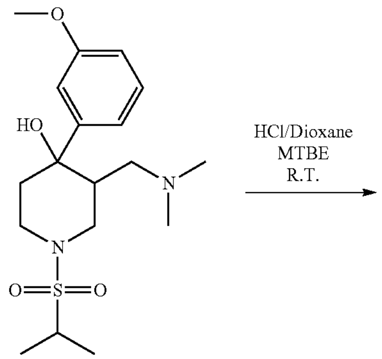

-continued

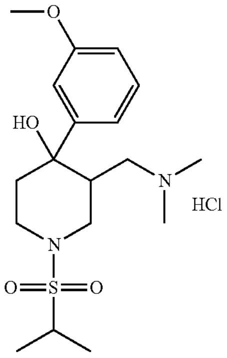

FWBH20 was obtained by salifying 3-((dimethylamino)methyl)-1-(isopropylsulfonyl)-4-(3-methoxyphenyl)piperidin-4-ol, yield: 85.5%. $^1$H NMR (400 MHz, $CD_3OD$), δ 7.34 (t, J=8 Hz, 1H), 7.04~7.11 (m, 2H), 6.88 (dd, $J_1$=8 Hz, $J_2$=4 Hz, 1H), 3.89~3.93 (m, 1H), 3.81 (s, 3H), 3.70~3.75 (m, 1H), 3.34~3.44 (m, 3H), 3.03~3.09 (m, 1H), 2.61~2.73 (m, 7H), 2.41~2.45 (m, 1H), 2.22~2.30 (m, 1H), 1.71~1.76 (m, 1H), 1.37 (d, J=4 Hz, 6H). LC-MS-ESI$^+$: $[M+H]^+$ 371.3.

Example 2-25

1-(Allylsulfonyl)-3-((dimethylamino)methyl)-4-(3-methoxyphenyl)piperidin-4-ol hydrochloride (FWBH21)

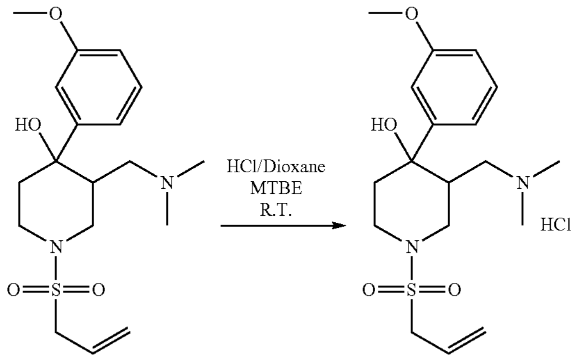

FWBH21 was obtained by salifying 1-(allylsulfonyl)-3-((dimethylamino)methyl)-4-(3-methoxyphenyl)piperidin-4-ol, yield: 89%. $^1$H NMR (400 MHz, $CD_3OD$), δ 7.32~7.36 (m, 1H), 7.07~7.12 (m, 2H), 6.88 (dd, $J_1$=8 Hz, $J_2$=4 Hz, 1H), 5.91~6.02 (m, 1H), 5.45~5.53 (m, 2H), 3.94 (d, J=8 Hz, 3H), 3.82 (s, 3H), 3.70~3.75 (m, 1H), 3.25~3.39 (m, 3H), 3.02~3.08 (m, 1H), 2.74 (s, 3H), 2.57 (s, 3H), 2.42~2.47 (m, 1H), 2.23~2.31 (m, 1H), 1.77 (dd, $J_1$=16 Hz, $J_2$=4 Hz, 1H). LC-MS-ESI$^+$: $[M+H]^+$ 369.2.

Example 2-26

(1R,4S)-1-(((3-((Dimethylamino)methyl)-4-hydroxy-4-(3-methoxyphenyl)piperidin-1-yl)sulfonyl)methyl)-7,7-Dimethylbicyclo[2.2.1]heptan-2-one hydrochloride (FWBH24)

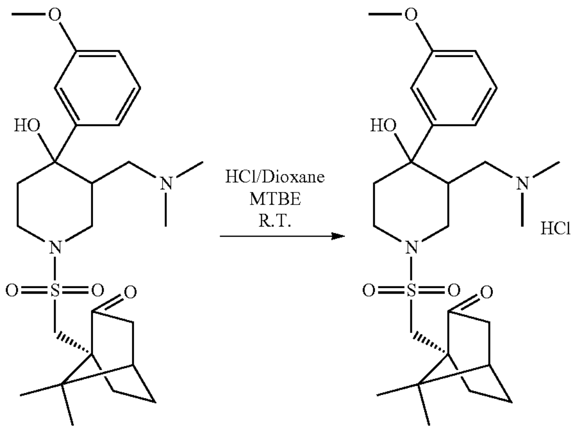

FWBH24 was obtained by salifying (1R,4S)-1-(((3-((dimethylamino)methyl)-4-hydroxy-4-(3-methoxyphenyl)piperidin-1-yl)sulfonyl)methyl)-7,7-Dimethylbicyclo[2.2.1]heptan-2-one, yield: 84.4%. $^1$H NMR (400 MHz, $CD_3OD$), δ 7.32~7.37 (m, 1H), 7.07~7.13 (m, 2H), 6.88 (dd, $J_1$=8 Hz, $J_2$=4 Hz, H), 3.92~3.95 (m, 1H), 3.82 (s, 3H), 3.73~3.77 (m, 1H), 3.46 (t, J=16 Hz, 1H), 3.20~3.35 (m, 2H), 2.96~3.12 (m, 2H), 2.39~2.75 (m, 10H), 2.24~2.35 (m, 1H), 2.06~2.14 (m, 2H), 1.98 (dd, $J_1$=20 Hz, $J_2$=4 Hz, 1H), 1.80 (dd, $J_1$=12 Hz, $J_2$=4 Hz, 1H), 1.62~1.70 (m, 1H), 1.45~1.53 (m, 1H), 1.15 (d, J=4 Hz, 3H), 0.93 (d, J=4 Hz, 3H). LC-MS-ESI$^+$: $[M+H]^+$ 479.3.

Example 2-27

3-((Dimethylamino)methyl)-1-((((1R,4S)-2-hydroxy-7,7-dimethylbicyclo[2.2.1]hept-1-yl)methyl)sulfonic acid acyl)-4-(3-methoxyphenyl)piperidin-4-ol hydrochlorid (FWBH26)

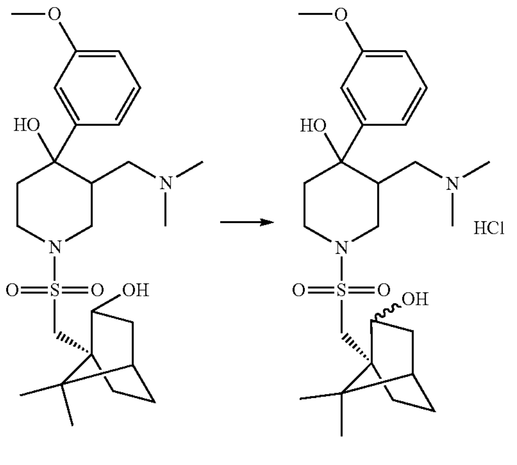

FWBH26 was obtained by salifying 3-((dimethylamino)methyl)-1-((((1R,4S)-2-hydroxy-7,7-dimethylbicyclo[2.2.1]hept-1-yl)methyl)sulfonic acid acyl)-4-(3-methoxyphenyl)piperidin-4-ol, yield: 84.2%. $^1$H NMR (400 MHz, $CD_3OD$), δ 7.32~7.39 (m, 1H), 7.09~7.17 (m, 2H), 6.87~6.93 (m, 1H), 4.03~4.07 (m, 1H), 3.92~3.97 (m, 1H), 3.72~3.86 (m, 4H), 3.46~3.52 (m, 1H), 3.18~3.35 (m, 2H), 3.05~3.10 (m, 1H), 2.05~2.77 (m, 8H), 2.28~2.36 (m, 1H), 1.73~1.86 (m, 5H), 1.43~1.48 (m, 1H), 1.08~1.23 (m, 5H), 0.99~1.00 (m, 1H), 0.90~0.95 (m, 3H). LC-MS-ESI$^+$: $[M+H]^+$ 481.3.

Example 2-28

3-((Dimethylamino)methyl)-4-(3-methoxyphenyl)-1-(methylsulfonyl)piperidin-4-ol hydrochloride (FWBH23)

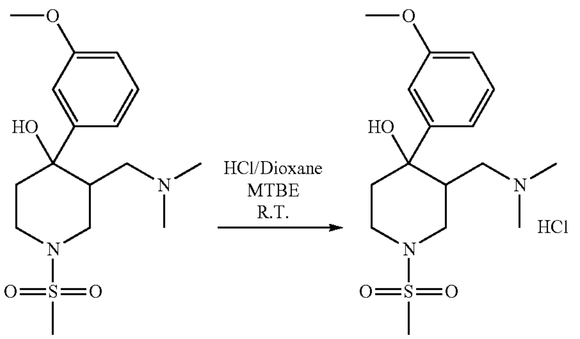

FWBH23 was obtained from 3-((Dimethylamino)methyl)-4-(3-methoxyphenyl)-1-(methylsulfonyl) piperidin-4-ol as a salt, yield: 94.0%. $^1$H NMR (400 MHz, $CD_3OD$), δ 7.34 (t, J=8 Hz, 1H), 7.09~7.14 (m, 2H), 6.86~6.89 (m, 1H), 3.88 (dd, J1=8 Hz, J2=4 Hz, 1H), 3.82 (s, 3H), 3.65~3.70 (m, 1H), 3.11~3.25 (m, 2H), 3.03~3.09 (m, 1H), 2.95 (s, 3H), 2.72~2.78 (m, 1H), 2.65 (s, 6H), 2.49~2.55 (m, 1H), 2.29~2.37 (m, 1H), 1.79~1.84 (m, 1H). LC-MS-ESI$^+$: $[M+H]^+$ 343.2.

Example 2-29

(1S,4R)-1-(((3-((Dimethylamino)methyl)-4-hydroxy-4-(3-methoxyphenyl)piperidin-1-yl)sulfonyl)methyl)-7,7-dimethylbicyclo[2.2.1]heptan-2-one hydrochloride (FWBH25)

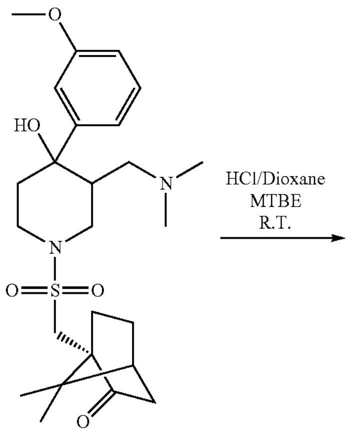

-continued

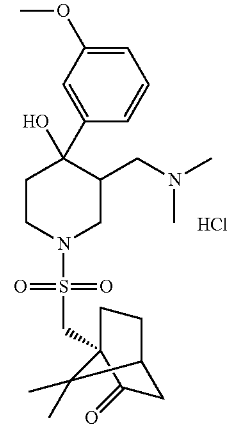

FWBH25 was obtained from (1S,4R)-1-(((3-((Dimethylamino)methyl)-4-hydroxy-4-(3-methoxyphenyl)piperidin-1-yl)sulfonyl)methyl)-7,7-dimethylbicyclo[2.2.1]heptan-2-one as a salt, yield: 76.3%. $^1H$ NMR (400 MHz, $CD_3OD$), δ 7.34 (t, J=8 Hz, 1H), 7.07~7.13 (m, 2H), 7.86~7.89 (m, 1H), 3.95 (d, J=12 Hz, 1H), 3.82 (s, 3H), 3.74 (t, J=8 Hz, 1H), 3.42~3.50 (m, 1H), 3.20~3.35 (m, 2H), 3.06~3.12 (m, 1H), 2.97~3.03 (m, 1H), 2.68~2.74 (m, 7H), 2.39~2.57 (m, 3H), 2.23~2.35 (m, 1H), 2.06~2.15 (m, 2H), 1.98 (dd, $J_1$=20 Hz, $J_2$=4 Hz, 1H), 1.80 (d, J=16 Hz, 1H), 1.62~1.70 (m, 1H), 1.45~1.53 (m, 1H), 1.14 (d, J=8 Hz, 3H), 0.93 (d, J=8 Hz, 3H). LC-MS-$ESI^+$: $[M+H]^+$ 479.3.

Example 2-30

3-((Dimethylamino)methyl)-1-((((1S,4R)-2-hydroxy-7,7-dimethylbicyclo[2.2.1]hept-1-yl)methyl)sulfonyl)-4-(3-methoxyphenyl)piperidin-4-ol hydrochloride (FWBH27)

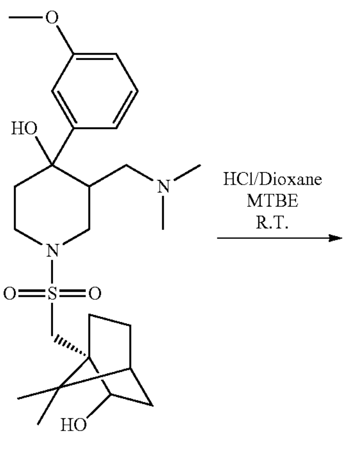

-continued

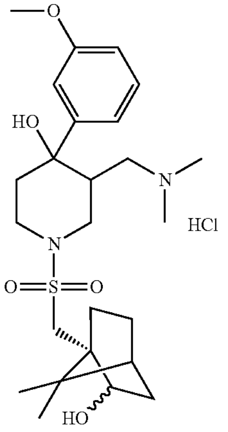

FWBH27 was obtained from 3-((Dimethylamino)methyl)-1-((((1S,4R)-2-hydroxy-7,7-dimethylbicyclo[2.2.1]hept-1-yl)methyl)sulfonyl)-4-(3-methoxyphenyl)piperidin-4-ol as a salt, yield: 88.6%. $^1H$ NMR (400 MHz, $CD_3OD$), δ 7.32~7.38 (m, 1H), 7.09~7.14 (m, 2H), 6.89 (dd, $J_1$=8 Hz, $J_2$=4 Hz, 1H), 4.02~4.07 (m, 1H), 3.93~3.99 (m, 1H), 3.82 (s, 3H), 3.72~3.78 (m, 1H), 3.46~3.52 (m, 1H), 3.18~3.30 (m, 2H), 3.05~3.11 (m, 1H), 2.87~2.93 (m, 1H), 2.50~2.75 (m, 8H), 2.28~2.36 (m, 1H), 1.73~1.86 (m, 5H), 1.43~1.148 (m, 1H), 0.91~1.20 (m, 8H). LC-MS-$ESI^+$: $[M+H]^+$ 481.3.

Example 2-31

1-(Phenylsulfonyl)-3-((dimethylamino)methyl)-4-(3-(trifluoromethoxy)phenyl)piperidin-4-ol hydrochloride (FWBH29)

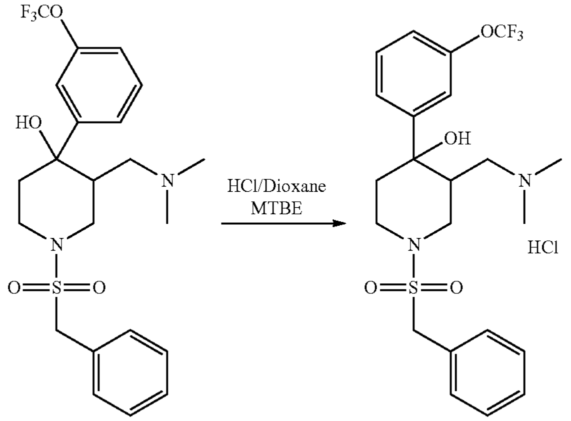 [SMILES: CN(C)CC1CN(S(=O)(=O)Cc2ccccc2)CCC1(O)c1cccc(OC(F)(F)F)c1 ; CN(C)CC1CN(S(=O)(=O)Cc2ccccc2)CCC1(O)c1cccc(OC(F)(F)F)c1 ; Cl]

By replacing 3-(methoxy) phenylmagnesium bromide in Example 3 with 3-(trifluoromethoxy)phenylmagnesium bromide, 1-(benzylsulfonyl)-3-((dimethylamino)methyl)-4-(3-methoxyphenyl)piperidin-4-ol can be prepared by the same route as for the preparation of 1-(benzylsulfonyl)-3-((dimethylamino)methyl)-4-(3-(trifluoromethoxy)phenyl)piperidin-4-ol. FWBH29 was obtained from 1-(Phenylsulfonyl)-3-((dimethylamino)methyl)-4-(3-(trifluoromethoxy)phenyl)piperidin-4-ol as a salt, yield: 91.4%. $^1H$ NMR (400 MHz, $CD_3OD$), δ 7.49~7.55 (m, 4H), 7.47 (s, 1H), 7.39~7.44 (m, 3H), 7.25 (d, J=8 Hz, 1H), 4.46 (s, 2H), 3.82 (dd, $J_1$=12 Hz, $J_2$=4 Hz, 1H), 3.54~3.59 (m, 1H), 3.12~3.21 (m, 2H), 3.00~3.07 (m, 1H), 2.58~2.63 (m, 7H), 2.35~2.41 (m, 1H), 2.13~2.22 (m, 1H), 1.68~1.73 (m, 1H). LC-MS-ESI$^+$: $[M+H]^+$ 473.2.

Example 2-32

1-(1-(Benzylsulfonyl)-4-(difluoromethoxy)-4-(3-methoxyphenyl)piperidin-3-yl)-N,N-dimethylaminomethanamine

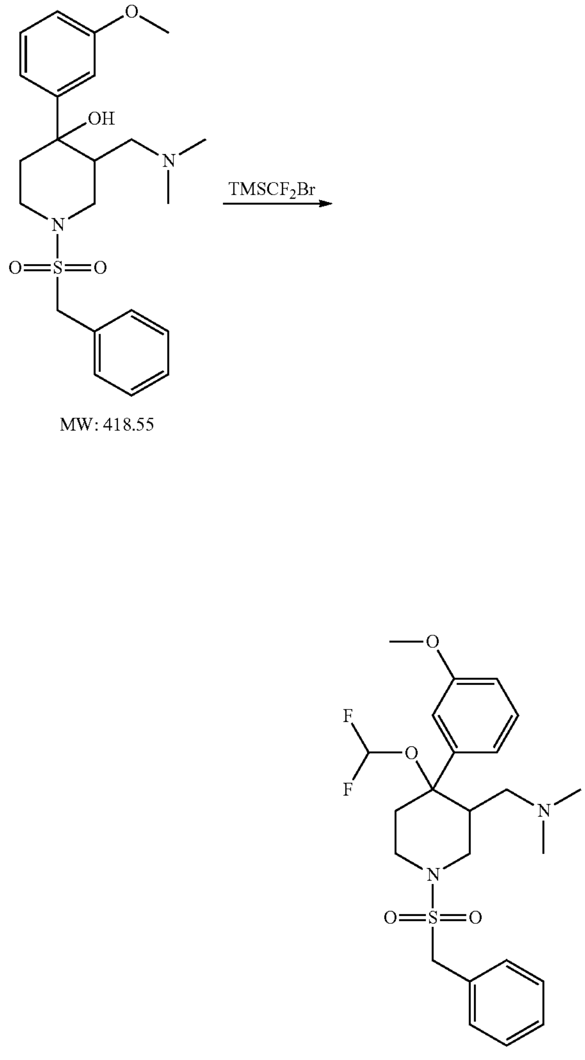

A 25 mL single-neck flask was added with raw material (100 mg, 0.24 mmol, 1 eq), dichloromethane (0.5 mL), water (0.5 mL), KOAc (188.43 mmol, 1.92 mmol, 8 eq), and $TMSCF_2Br$ (195 mg, 0.96 mmol, 4 eq). The solid was precipitated with stirring at room temperature and supplemented with dichloromethane (0.5 mL) and water (0.5 mL). The reaction was monitored by LC-MS. The filter cake was washed with water and dried to give about 115 mg off-white solid. Methanol and ethyl acetate (0.4 mL:0.6 mL) were used to crystalize to give 90 mg off-white solid in 80.4% yield.

1-(1-(benzylsulfonyl)-4-(difluoromethoxy)-4-(3-methoxyphenyl)piperidin-3-yl)-N,N-dimethylaminomethanamine hydrochloride (FWBH30)

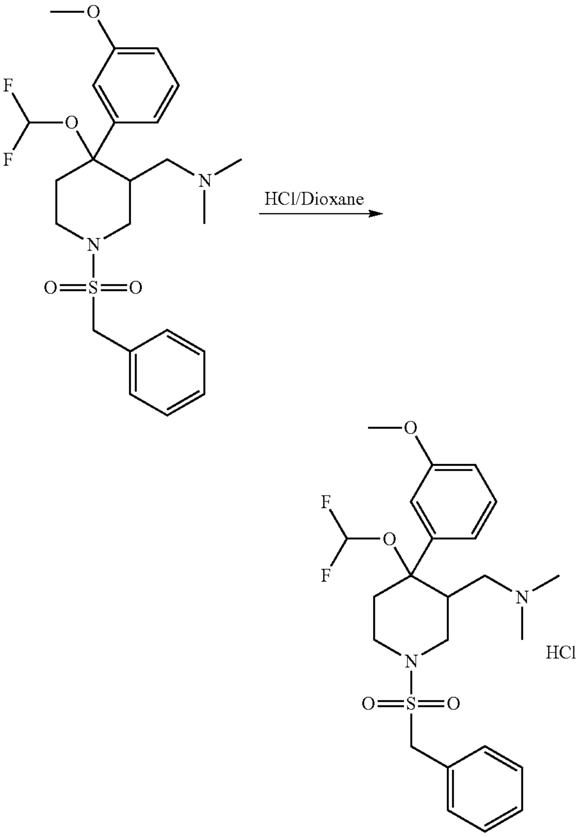

FWBH30 was obtained from 1-(1-(benzylsulfonyl)-4-(difluoromethoxy)-4-(3-methoxyphenyl) piperidin-3-yl)-N,N-dimethylaminomethanamine as a salt, yield: 84%. $^1$H NMR (400 MHz, $CD_3OD$), δ 7.485~7.501 (m, 2H), 7.339~7.421 (m, 4H), 7.107~7.148 (m, 2H), 6.890~6.914 (m, 2H), 6.838 (s, J=58.4 Hz, 1H), 4.456 (s, 2H), 3.823 (s, 3H), 3.765 (d, J=13.2 Hz, 2H), 3.564 (d, J=12.8 Hz, 1H), 3.117~3.362 (m, 2H), 2.977 (s, 3H), 2.637 (s, 3H), 2.482~2.504 (m, 1H), 2.326~2.395 (m, 1H), 1.715 (d, J=14.8 Hz, 1H). LC-MS-ESI$^+$: $[M+H]^+$ 469.2.

Example 2-33

Preparation of Membrane Receptors:

CHO cells expressing p opioid receptor, δ opioid receptor and κ opioid receptor were cultured in a 10 $cm^2$ culture dish (F-12 medium+10% neonatal bovine serum) for several days, and the culture fluid was aspirated after the cells grew to the bottom of the dish. 3 mL PBS/EDTA solution (0.1 M NaCl, 0.01 M $NaH_2PO_4$, 0.04% EDTA) was added to digest the cells for 3~5 min, blew with a pipette to completely dislodge the cells. The cells were collected in a 40 mL centrifuge tube, centrifuged at 5000 rpm for 5 min. The supernatant was removed and the ice-cold homogenate (50 mM HEPES pH 7.4, 3 mM $MgCl_2$, 1 mM EGTA) was added to the centrifuge tube. The solution and the precipitate were transferred to a homogenizer. Then the homogenate was transferred to a centrifuge tube and centrifuged at 18000 rpm for 15 min. The precipitate was centrifuged twice at 18000 rpm for 15 min. The obtained precipitate was homogenized by adding appropriate amount of 50 mM Tris-HCl, pH 7.4 buffer and divided into centrifuge tubes and stored at −70° C. in the refrigerator until use.

Competition Binding Test:

The total binding tube was added with 20-30 μg of expressed membrane receptor protein and [3H]-labeled ligand (1-2 nM). The corresponding non-specific binding tube was added with 1 μM of the corresponding ligand, and the sample tubes were added with various screened opioid ligands in a final volume of 100 μL. All of them were incubated for 30 min at 30° C., and the reaction was terminated in ice water. The samples were filtered under negative pressure through GF/C (Whatman) glass fiber filter paper on a Millipore sample collector. The reaction was rinsed three times with 4 mL of 50 mM Tris-HCl (pH 7.4), the filter paper was dried and placed in 0.5 mL Eppendorf tubes with 0.5 mL of lipophilic scintillation solution. The radioactivity was measured by PERKIN ELMER PRI-CARB 2910 liquid scintillation counter and the inhibition rate was calculated.

Inhibition rate (or binding rate)=(total binding rate (dpm)−sample tube (dpm)/(total binding tube (dpm)−non-specific binding tube (dpm))×100%

$IC_{50}$ was calculated using GraphPad Prism 5.0 software. Ki values were calculated according to the following formula, $Ki=IC_{50}/(1+[IL]/Kd)$, [IL] is the concentration of the added labeled ligand and Kd is the equilibrium dissociation parameter of the labeled ligand.

Table 2-1 showed the Ki values of affinity constants of representative compounds for opioid receptors, expressed as the mean±standard deviation of three independent measurements.

TABLE 2-1

Opioid receptor binding rate or Ki at 1 μM concentration of compound

| Compound | Stucture | Binding rate (%) or Ki (nM) | | |
|---|---|---|---|---|
| | | μOR | δOR | κOR |
| Tramadol | 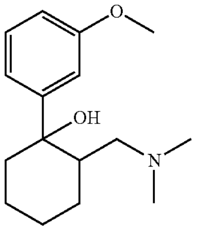 [SMILES: COc1cccc(C2(O)CCCCC2CN(C)C)c1] | 6.0 ± 0.4% | 0% | 0% |
| 3-((Dimethylamino)methyl)-4-(3-methoxyphenyl)-1-(phenylsulfonyl)piperidin-4-ol hydrochloride (FWBH16) | 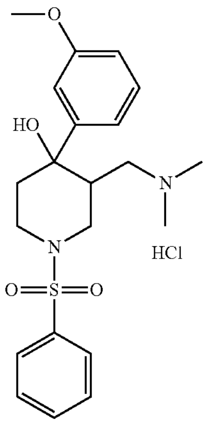 | 87.71 ± 9.37 nM | 40.53 ± 1.66% | 32.64 ± 0.55% |
| 3-((Dimethylamino)methyl)-4-(3-methoxyphenyl)-1-(phenylethylsulfonyl) piperidin-4-ol hydrochloride (FWBH9) | 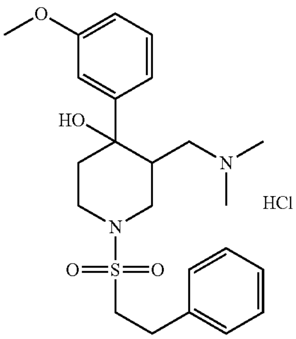 | 1.79 ± 2.0 nM | 0% | 8.41 ± 1.66% |

TABLE 2-1-continued

Opioid receptor binding rate or Ki at 1 μM concentration of compound

| Compound | Stucture | Binding rate (%) or Ki (nM) | | |
|---|---|---|---|---|
| | | μOR | δOR | κOR |
| 1-(Phenylsulfonyl)-3-((dimethylamino)methyl)-4-(3-methoxyphenyl)piperidin-4-ol hydrochloride (FWBH6) | 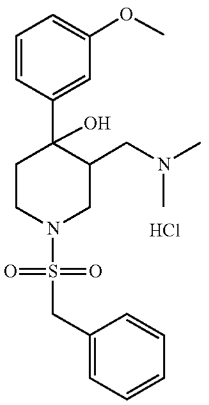 [SMILES: COc1cccc(C2(O)CCN(S(=O)(=O)Cc3ccccc3)CC2CN(C)C)c1 ; Cl] | 0% | >10000 nM | >10000 nM |
| 3-((Dimethylamino)methyl)-4-(3-methoxyphenyl)-1-((4-methylbenzyl)sulfonyl) piperidin-4-ol hydrochloride (FWBH8) | 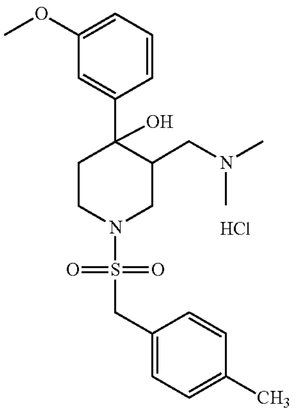 | 246.7 ± 49.44 nM | 11.88 ± 1.31% | 28.98 ± 0.32% |
| 3-((Dimethylamino)methyl)-1-((4-fluorobenzyl)sulfonyl)-4-(3-methoxyphenyl)piperidin-4-ol hydrochloride (FWBH12) | 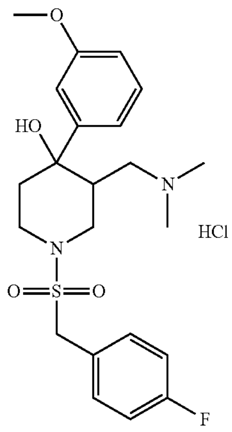 | 39.18 ± 6.13 nM | 1107.5 ± 28.5 nM | 45.92 ± 2.11% |

TABLE 2-1-continued

| Opioid receptor binding rate or Ki at 1 μM concentration of compound | | | | |
|---|---|---|---|---|
| | | Binding rate (%) or Ki (nM) | | |
| Compound | Stucture | μOR | δOR | κOR |
| 3-((Dimethylamino)methyl)-1-((2-fluorobenzyl)sulfonyl)-4-(3-methoxyphenyl)piperidin-4-ol hydrochloride (FWBH14) | 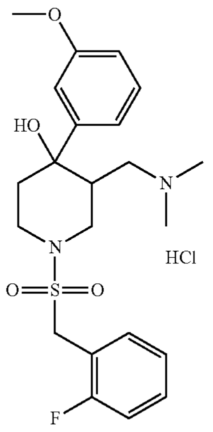 | 29.60 ± 2.53 nM | 40.76 ± 2.66% | 17.56 ± 6.34% |
| 1-(3-Bromobenzyl)sulfonyl)-3-((dimethylamino)methyl)-4-(3-methoxyphenyl)piperidin-4-ol hydrochloride (FWBH13) | 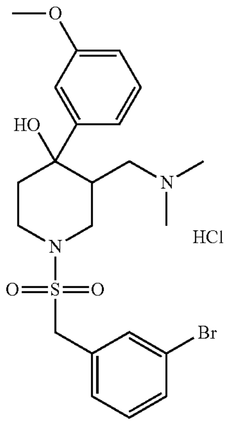 [SMILES: COc1cccc(C2(O)CCN(S(=O)(=O)Cc3cccc(Br)c3)CC2CN(C)C)c1 ; Cl] | 18.17 ± 4.37 nM | 15.09 ± 2.47% | 42.07 ± 2.29% |
| 1-((3-Chlorobenzyl)sulfonyl)-3-((dimethylamino)methyl)-4-(3-methoxyphenyl)piperidin-4-ol hydrochloride (FWBH7) | 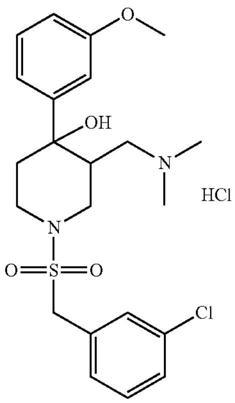 [SMILES: COc1cccc(C2(O)CCN(S(=O)(=O)Cc3cccc(Cl)c3)CC2CN(C)C)c1 ; Cl] | 21.9 ± 2.4% | 28.8 ± 0.04% | 0% |

TABLE 2-1-continued

| Opioid receptor binding rate or Ki at 1 μM concentration of compound | | | | |
|---|---|---|---|---|
| | | Binding rate (%) or Ki (nM) | | |
| Compound | Stucture | μOR | δOR | κOR |
| 1-((4-Chlorobenzyl)sulfonyl)-3-((dimethylamino)methyl)-4-(3-methoxyphenyl)piperidin-4-ol hydrochloride (FWBH11) | 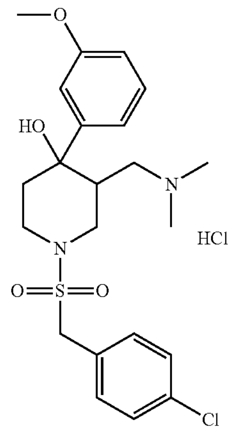 [SMILES: COc1cccc(C2(O)CCN(S(=O)(=O)Cc3ccc(Cl)cc3)CC2CN(C)C)c1 ; Cl] | 711.7 ± 3.65 nM | 50.91 ± 1.58% | 36.65 ± 3.32% |
| 3-((Dimethylamino)methyl)-4-(3-methoxyphenyl)-1-((3-(trifluoromethyl)benzyl) sulfonyl)piperidin-4-ol hydrochloride (FWBH10) | 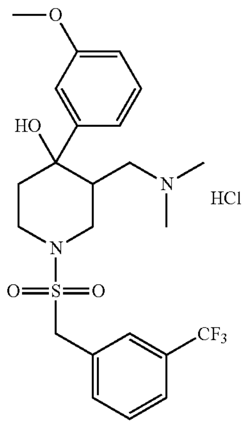 [SMILES: COc1cccc(C2(O)CCN(S(=O)(=O)Cc3cccc(C(F)(F)F)c3)CC2CN(C)C)c1 ; Cl] | 4.68 ± 0.12 nM | 3654.5 ± 1245.5 nM | 30.13 ± 0.70% |
| 3-((Dimethylamino)methyl)-4-(3-methoxyphenyl)-1-((4-(trifluoromethyl)benzyl) sulfonyl)piperidin-4-ol hydrochloride (FWBH17) | 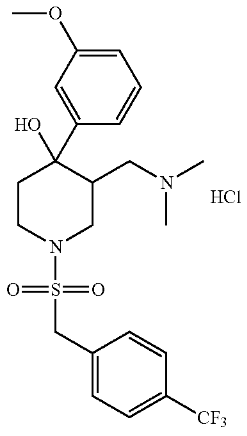 [SMILES: COc1cccc(C2(O)CCN(S(=O)(=O)Cc3ccc(C(F)(F)F)cc3)CC2CN(C)C)c1 ; Cl] | 261.4 ± 35.26 nM | 29.29 ± 1.66% | 25.42 ± 5.93% |

TABLE 2-1-continued

| Opioid receptor binding rate or Ki at 1 μM concentration of compound | | | | |
|---|---|---|---|---|
| | | Binding rate (%) or Ki (nM) | | |
| Compound | Stucture | μOR | δOR | κOR |
| 3-((Dimethylamino)methyl)-4-(3-methoxyphenyl)-1-((3-nitrobenzyl)sulfonyl) piperidin-4-ol hydrochloride (FWBH22) | 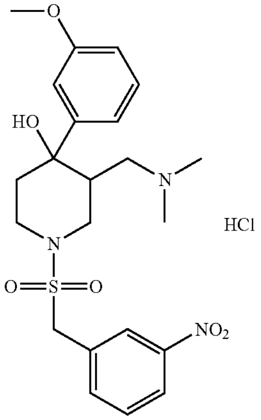 [SMILES: COc1cccc(C2(O)CCN(S(=O)(=O)Cc3cccc([N+](=O)[O-])c3)CC2CN(C)C)c1 ; Cl] | 211.7 ± 9.00 nM | 10.16 ± 3.19% | 32.67 ± 3.1% |
| 3-((Dimethylamino)methyl)-4-(3-methoxyphenyl)-1-(methylsulfonyl)piperidin-4-ol hydrochloride (FWBH23) | 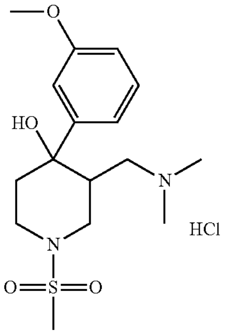 | 192.1 ± 15.01 nM | 16.01 ± 1.99% | 14.34 ± 3.33% |
| 3-((Dimethylamino)methyl)-1-(ethylsulfonyl)-4-(3-methoxyphenyl)piperidin-4-ol hydrochloride (FWBH18) | 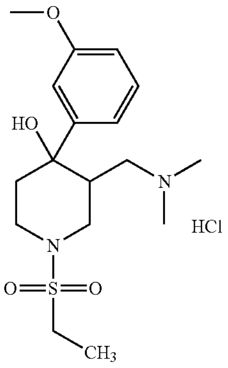 | 180.2 ± 11.72 nM | 23.99 ± 0.49% | 13.50 ± 2.22% |
| 3-((Dimethylamino)methyl)-4-(3-methoxyphenyl)-1-(propylsulfonyl)piperidin-4-ol hydrochloride (FWBH19) | 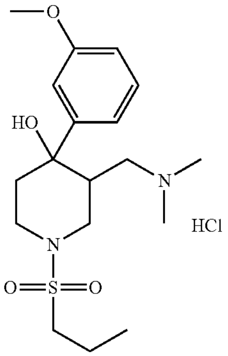 | 133.1 ± 3.1 nM | 17.48 ± 4.38% | 19.08 ± 10.31% |

TABLE 2-1-continued

| Opioid receptor binding rate or Ki at 1 μM concentration of compound | | | | |
|---|---|---|---|---|
| | | Binding rate (%) or Ki (nM) | | |
| Compound | Stucture | μOR | δOR | κOR |
| 3-((Dimethylamino)methyl)-1-(isopropylsulfonyl)-4-(3-methoxyphenyl)piperidin-4-ol hydrochloride (FWBH20) | 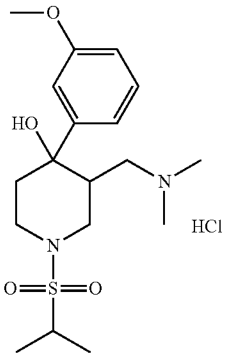 | 254.9 ± 5.30 nM | 20.81 ± 1.91% | 6.88 ± 4.38% |
| 1-(Allylsulfonyl)-3-((dimethylamino)methyl)-4-(3-methoxyphenyl)piperidin-4-ol hydrochloride (FWBH21) | 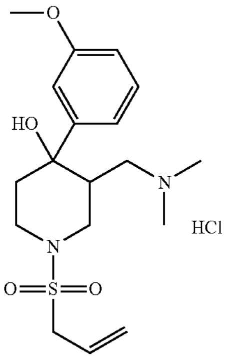 | 40.39 ± 4.99 nM | 31.52 ± 0.21% | 17.06% ± 0.10% |
| 1-(Butylsulfonyl)-3-((dimethylamino)methyl)-4-(3-methoxyphenyl)piperidin-4-ol hydrochloride (FWBH15) | 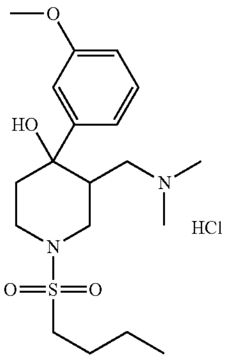 | 34.85 ± 9.40 nM | 27.21 ± 1.43% | 9.86 ± 2.67% |
| (1R,4S)-1-(((3-((Dimethylamino)methyl)-4-hydroxy-4-(3-methoxyphenyl)piperidin-1-yl)sulfonyl)methyl)-7,7-dimethylbicyclo[2.2.1]heptan-2-one hydrochloride (FWBH24) | 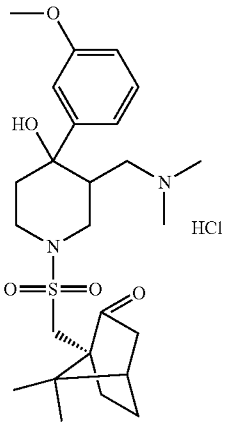 | 65.08 ± 5.36 nM | 11.05 ± 1.30% | 433.2 ± 15.3 nM |

TABLE 2-1-continued

| Opioid receptor binding rate or Ki at 1 μM concentration of compound | | | | |
|---|---|---|---|---|
| | | Binding rate (%) or Ki (nM) | | |
| Compound | Stucture | μOR | δOR | κOR |
| 3-((Dimethylamino)methyl)-1-(((1R,4S)-2-hydroxy-7,7-dimethylbicyclo[2.2.1]hept-1-yl)methyl)sulfonyl)-4-(3-methoxyphenyl)piperidin-4-ol hydrochloride (FWBH26) | 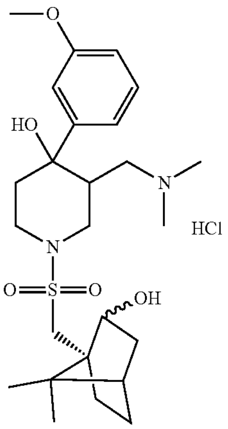 | 11.50 ± 1.60 nM | 9.15 ± 1.92% | 8.2 ± 3.1 nM |
| (1S,4R)-1-(((3-((Dimethylamino)methyl)-4-hydroxy-4-(3-methoxyphenyl)piperidin-1-yl)sulfonyl)methyl)-7,7-dimethylbicyclo[2.2.1]heptan-2-one hydrochloride (FWBH25) | 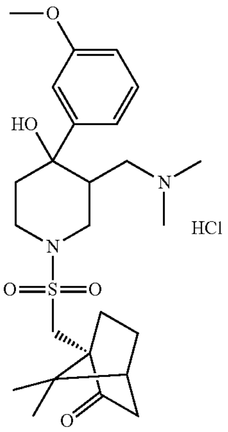 | 50.79 ± 1.56 nM | 14.29 ± 8.63% | 54.0 ± 20.9 nM |
| 3-((Dimethylamino)methyl)-1-((((1S,4R)-2-hydroxy-7,7-dimethylbicyclo[2.2.1]hept-1-yl)methyl)sulfonyl)-4-(3-methoxyphenyl)piperidin-4-ol hydrochloride (FWBH27) | 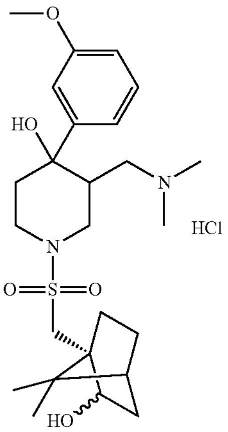 | 32.47 ± 3.30 nM | 24.76 ± 0.77% | 27.7 ± 3.9 nM |

TABLE 2-1-continued

| Opioid receptor binding rate or Ki at 1 μM concentration of compound | | | | |
|---|---|---|---|---|
| | | Binding rate (%) or Ki (nM) | | |
| Compound | Stucture | μOR | δOR | κOR |
| 1-(Benzylsulfonyl)-3-((dimethylamino)methyl)-4-(3-(trifluoromethoxy)phenyl) piperidin-4-ol hydrochloride (FWBH29) | 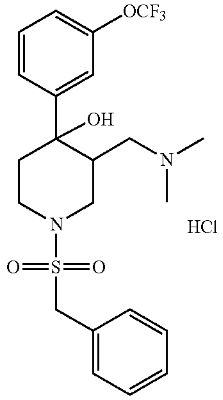 [SMILES: CN(C)CC1CN(S(=O)(=O)Cc2ccccc2)CCC1(O)c1cccc(OC(F)(F)F)c1 ; Cl] | 64.55 ± 1.76 nM | 40.77 ± 2.23% | 21.36 ± 0.36% |
| 1-(1-(Benzylsulfonyl)-4-(difluoromethoxy)-4-(3-methoxyphenyl)piperidin-3-yl)-N,N-dimethylaminomethanamine hydrochloride (FWBH30) | 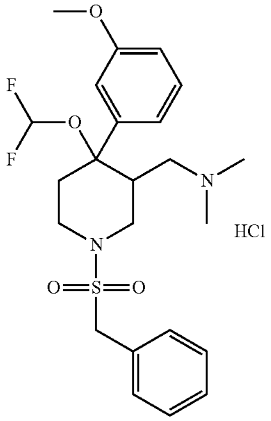 [SMILES: COc1cccc(C2(OC(F)F)CCN(S(=O)(=O)Cc3ccccc3)CC2CN(C)C)c1 ; Cl] | 22.6 ± 9.8%[a] | 0%[a] | 15.5 ± 4.1%[a] |

[a]Inhibition rate or binding rate at 0.1 μM.

In the column "Binding rate (%) or Ki (nM)" in Table 1, the values expressed as percentages refer to the binding rate and the values in nM refer to Ki. As can be seen from Table 1, the compounds of the present invention all exhibit stronger or comparable opioid receptor affinity than tramadol.

Example 2-34

In Vivo Hot Plate Analgesia Test

Female mice weighing about 20 g were placed on a hot plate apparatus preheated to 55° C., and the latency of the hindfoot response of the mice was used as the pain threshold indicator. Animals were selected before the experiment, and those with response latency less than 5 s or greater than 30 s were excluded. To prevent foot scalding, the maximum observation time was set at 60 s. The basal pain threshold was the average of two measurements, with a 5-min interval between measurements. pain thresholds were measured at 15 min, 30 min, 60 min and 120 min after intraperitoneal administration in each group of mice. The percentage of analgesic effectiveness (% MPE) was calculated according to the following equation. Percentage of effective analgesia (% MPE)_(Pre-dose incubation period−Incubation period after drug administration)/(60-Pre-dose incubation period)× 100%. $ED_{50}$ values were calculated based on the effective percentage of analgesia using GraphPad prism 5.0 software.

TABLE 2-2

Maximum percentage effective analgesic or $ED_{50}$ values of compound hot plate at 5 mg/kg dose

| Compound | Structure | % MPE or $ED_{50}$ (5 mg/kg) |
| --- | --- | --- |
| Tramadol | 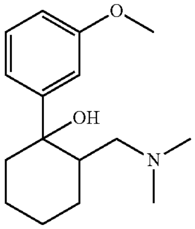 [SMILES: COc1cccc(C2(O)CCCCC2CN(C)C)c1] | 64.5% (no analgesic effect at 5 mg/kg or 50 mg/kg dose) |
| 3-((Dimethylamino)methyl)-4-(3-methoxyphenyl)-1-(phenylsulfonyl)piperidin-4-ol hydrochloride (FWBH16) | 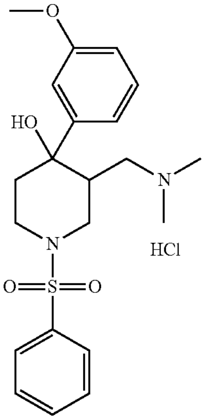 | 100% |
| 3-((Dimethylamino)methyl)-4-(3-methoxyphenyl)-1-(phenylethylsulfonyl)piperidin-4-ol hydrochloride (FWBH9) | 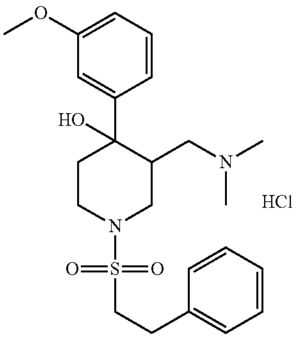 | 100% |
| 1-(Phenylsulfonyl)-3-((dimethylamino)methyl)-4-(3-methoxyphenyl)piperidin-4-ol hydrochloride (FWBH6) | 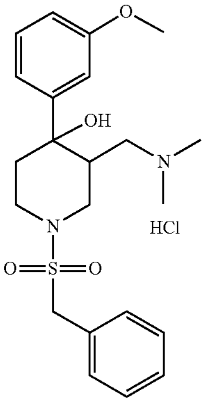 [SMILES: COc1cccc(C2(O)CCN(S(=O)(=O)Cc3ccccc3)CC2CN(C)C)c1 ; Cl] | 1.1 mg/kg |

TABLE 2-2-continued

| Maximum percentage effective analgesic or $ED_{50}$ values of compound hot plate at 5 mg/kg dose | | |
|---|---|---|
| Compound | Structure | % MPE or $ED_{50}$ (5 mg/kg) |
| 3-((Dimethylamino)methyl)-4-(3-methoxyphenyl)-1-((4-methylbenzyl)sulfonyl)piperidin-4-ol hydrochloride (FWBH8) | 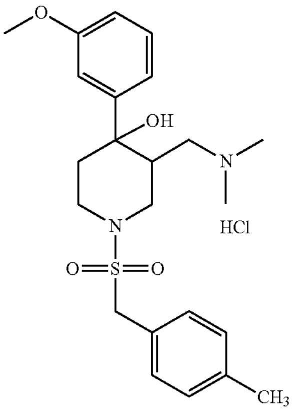 | 17.36% |
| 3-((Dimethylamino)methyl)-1-((4-fluorobenzyl)sulfonyl)-4-(3-methoxyphenyl)piperidin-4-ol hydrochloride (FWBH12) | 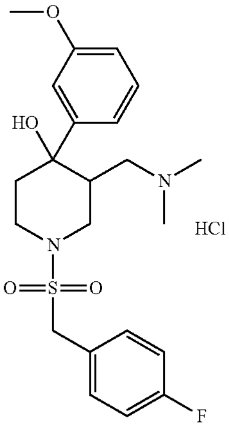 | 332.92% |
| 3-((Dimethylamino)methyl)-1-((2-fluorobenzyl)sulfonyl)-4-(3-methoxyphenyl)piperidin-4-ol hydrochloride (FWBH14) | 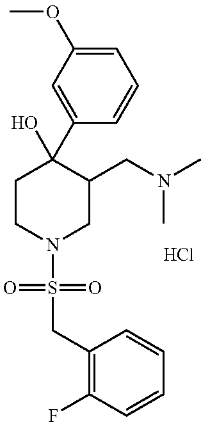 | 81.20% |

TABLE 2-2-continued

| Maximum percentage effective analgesic or $ED_{50}$ values of compound hot plate at 5 mg/kg dose | | |
|---|---|---|
| Compound | Structure | % MPE or $ED_{50}$ (5 mg/kg) |
| 1-((3-Bromobenzyl)sulfonyl)-3-((dimethylamino)methyl)-4-(3-methoxyphenyl)piperidin-4-ol hydrochloride (FWBH13) | 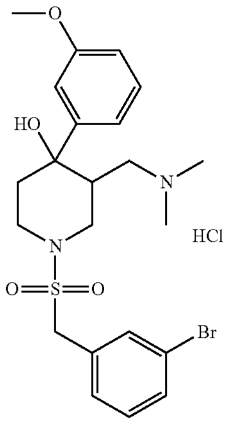 [SMILES: COc1cccc(C2(O)CCN(S(=O)(=O)Cc3cccc(Br)c3)CC2CN(C)C)c1 ; Cl] | 81.71% |
| 1-((3-Chlorobenzyl)sulfonyl)-3-((dimethylamino)methyl)-4-(3-methoxyphenyl)piperidin-4-ol hydrochloride (FWBH7) | 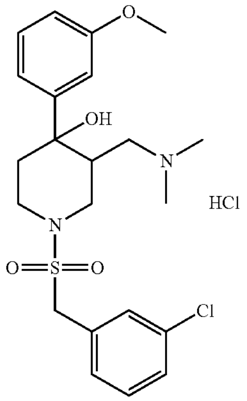 [SMILES: COc1cccc(C2(O)CCN(S(=O)(=O)Cc3cccc(Cl)c3)CC2CN(C)C)c1 ; Cl] | 1.58 mg/kg |
| 1-((4-Chlorobenzyl)sulfonyl)-3-((dimethylamino)methyl)-4-(3-methoxyphenyl)piperidin-4-ol hydrochloride (FWBH11) | 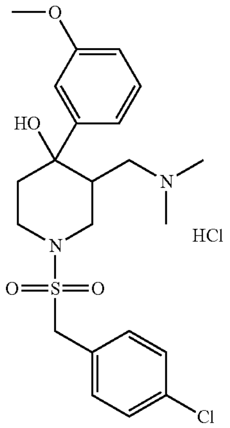 [SMILES: COc1cccc(C2(O)CCN(S(=O)(=O)Cc3ccc(Cl)cc3)CC2CN(C)C)c1 ; Cl] | 55.49% |

TABLE 2-2-continued

| Maximum percentage effective analgesic or $ED_{50}$ values of compound hot plate at 5 mg/kg dose | | |
|---|---|---|
| Compound | Structure | % MPE or $ED_{50}$ (5 mg/kg) |
| 3-((Dimethylamino)methyl)-4-(3-methoxyphenyl)-1-((3-(trifluoromethyl)benzyl)sulfonyl) piperidin-4-ol hydrochloride (FWBH10) | 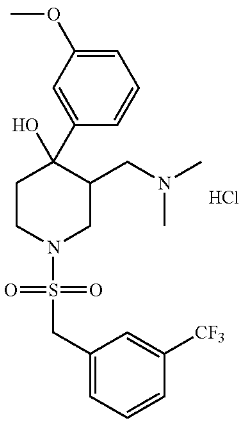 [SMILES: COc1cccc(C2(O)CCN(S(=O)(=O)Cc3cccc(C(F)(F)F)c3)CC2CN(C)C)c1 ; Cl] | 72.41% |
| 3-((Dimethylamino)methyl)-4-(3-methoxyphenyl)-1-((4-(trifluoromethyl)benzyl)sulfonyl) piperidin-4-ol hydrochloride (FWBH17) | 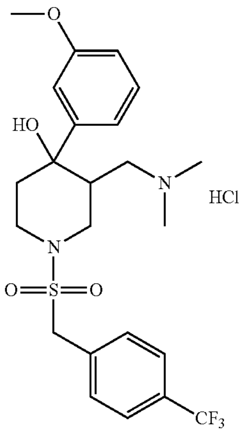 [SMILES: COc1cccc(C2(O)CCN(S(=O)(=O)Cc3ccc(C(F)(F)F)cc3)CC2CN(C)C)c1 ; Cl] | 48.32% |
| 3-((Dimethylamino)methyl)-4-(3-methoxyphenyl)-1-((3-nitrobenzyl)sulfonyl)piperidin-4-ol hydrochloride (FWBH22) | 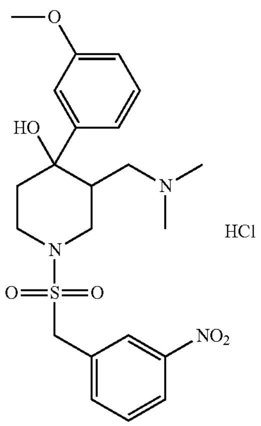 [SMILES: COc1cccc(C2(O)CCN(S(=O)(=O)Cc3cccc([N+](=O)[O-])c3)CC2CN(C)C)c1 ; Cl] | 41.43% |

TABLE 2-2-continued

| Maximum percentage effective analgesic or $ED_{50}$ values of compound hot plate at 5 mg/kg dose | | |
|---|---|---|
| Compound | Structure | % MPE or $ED_{50}$ (5 mg/kg) |
| 3-((Dimethylamino)methyl)-4-(3-methoxyphenyl)-1-(methylsulfonyl)piperidin-4-ol hydrochloride (FWBH23) | 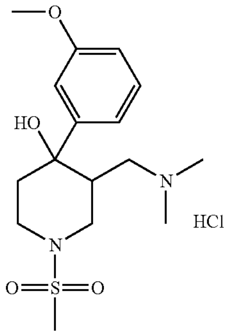 | 16.87% |
| 3-((Dimethylamino)methyl)-1-(ethylsulfonyl)-4-(3-methoxyphenyl)piperidin-4-ol hydrochloride (FWBH18) | 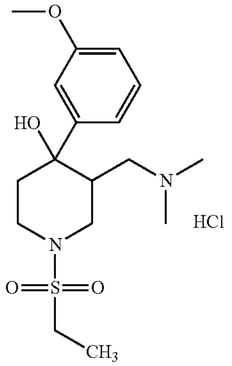 | 15.57% |
| 3-((Dimethylamino)methyl)-4-(3-methoxyphenyl)-1-(propylsulfonyl)piperidin-4-ol hydrochloride (FWBH19) | 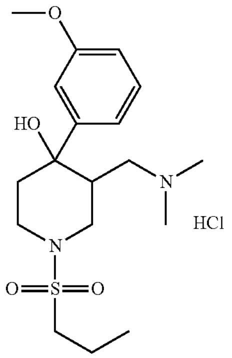 | 17.04% |
| 3-((Dimethylamino)methyl)-1-(isopropylsulfonyl)-4-(3-methoxyphenyl)piperidin-4-ol hydrochloride (FWBH20) | 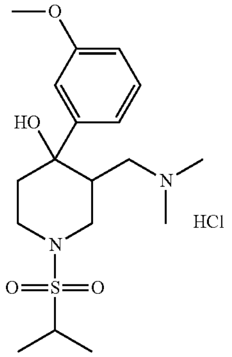 | 0% |

TABLE 2-2-continued

| Maximum percentage effective analgesic or $ED_{50}$ values of compound hot plate at 5 mg/kg dose | | |
|---|---|---|
| Compound | Structure | % MPE or $ED_{50}$ (5 mg/kg) |
| 1-(Allylsulfonyl)-3-((dimethylamino)methyl)-4-(3-methoxyphenyl)piperidin-4-ol hydrochloride (FWBH21) | 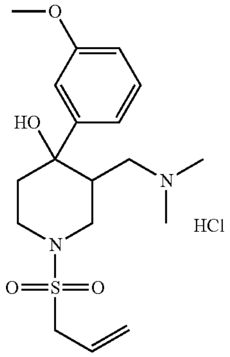 | 18.80% |
| 1-(Butylsulfonyl)-3-((dimethylamino)methyl)-4-(3-methoxyphenyl)piperidin-4-ol hydrochloride (FWBH15) | 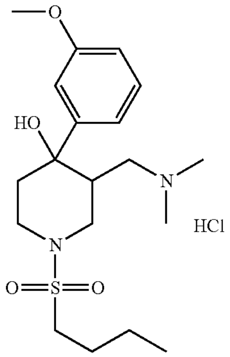 | 93.73% |
| (1R,4S)-1-(((3-((Dimethylamino)methyl)-4-hydroxy-4-(3-methoxyphenyl)piperidin-1-yl)sulfonyl)methyl)-7,7-dimethylbicyclo[2.2.1]heptan-2-one hydrochloride (FWBH24) | 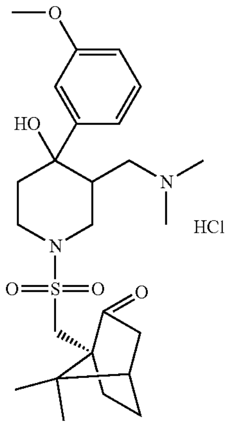 | 54.81% |

TABLE 2-2-continued

| Maximum percentage effective analgesic or $ED_{50}$ values of compound hot plate at 5 mg/kg dose | | |
|---|---|---|
| Compound | Structure | % MPE or $ED_{50}$ (5 mg/kg) |
| 3-((Dimethylamino)methyl)-1-((((1R,4S)-2-hydroxy-7,7-dimethylbicyclo[2.2.1]hept-1-yl)methyl)sulfonyl)-4-(3-methoxyphenyl)piperidin-4-ol hydrochloride (FWBH26) | 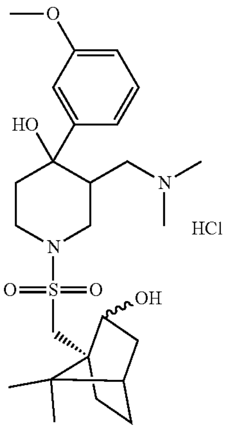 | 44.91% |
| (1S,4R)-1-((3-((Dimethylamino)methyl)-4-hydroxy-4-(3-methoxyphenyl)piperidin-1-yl)sulfonyl)methyl)-7,7-dimethylbicyclo[2.2.1]heptan-2-one hydrochloride (FWBH25) | 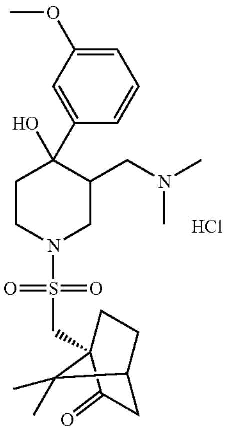 | 6.03% |
| 3-((Dimethylamino)methyl)-1-((((1S,4R)-2-hydroxy-7,7-dimethylbicyclo[2.2.1]hept-1-yl)methyl)sulfonyl)-4-(3-methoxyphenyl)piperidin-4-ol hydrochloride (FWBH27) | 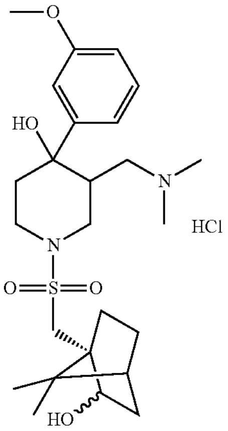 | 12.21 |

TABLE 2-2-continued

Maximum percentage effective analgesic or $ED_{50}$ values of compound hot plate at 5 mg/kg dose

| Compound | Structure | % MPE or $ED_{50}$ (5 mg/kg) |
|---|---|---|
| 1-(Benzylsulfonyl)-3-((dimethylamino)methyl)-4-(3-(trifluoromethoxy)phenyl)piperidin-4-ol hydrochloride (FWBH29) | 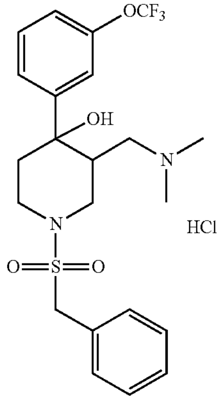 [SMILES: CN(C)CC1CN(S(=O)(=O)Cc2ccccc2)CCC1(O)c1cccc(OC(F)(F)F)c1 ; Cl] | 20.2% |
| 1-(1-(Benzylsulfonyl)-4-(difluoromethoxy)-4-(3-methoxyphenyl)piperidin-3-yl)-N,N-dimethylaminomethanamine hydrochloride (FWBH30) | 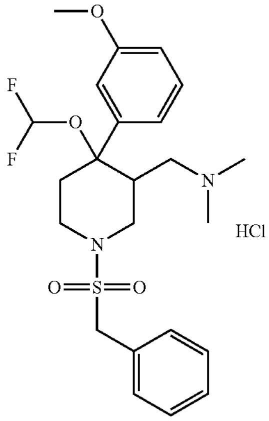 [SMILES: COc1cccc(C2(OC(F)F)CCN(S(=O)(=O)Cc3ccccc3)CC2CN(C)C)c1 ; Cl] | 8.38% |

In the column of "% MPE or $ED_{50}$" in Table 2-2, the value expressed as a percentage refers to % MPE, and the value in mg/kg refers to $ED_{50}$.

As can be seen from Table 2-2, the compounds of the present invention all exhibited stronger analgesic effects in vivo than tramadol.

EXAMPLE 3

The following examples are illustrative, but not limiting, of the inventions described herein. Compounds (FWBF) can be prepared utilizing the following general synthesis route or descriptions of the embodiments.

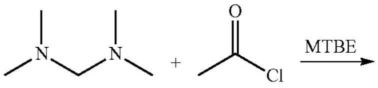

-continued

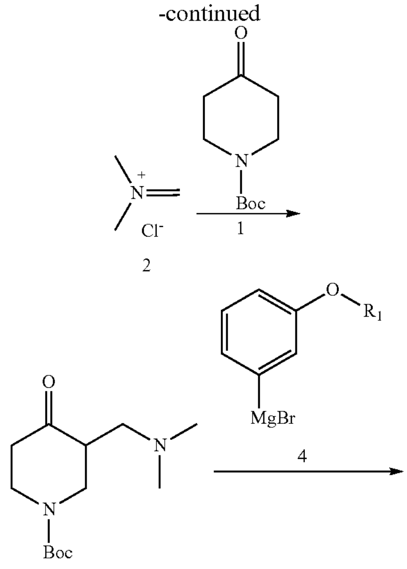
1
2
3
4

-continued

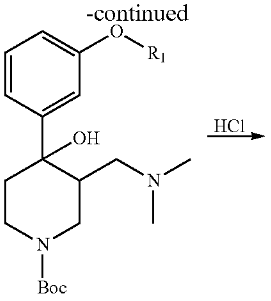

5

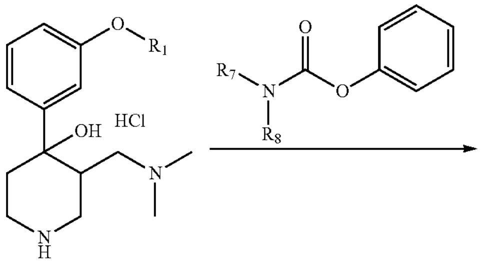

6

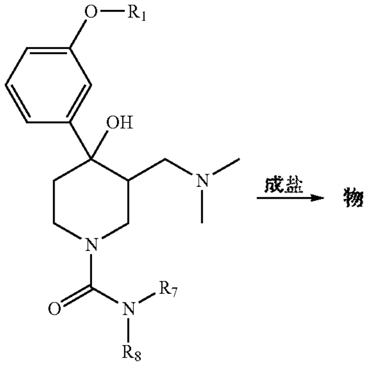

Example 3-1

Preparation of Intermediate 2:

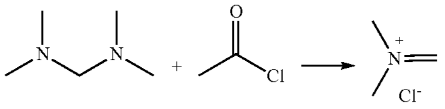

2

To a three-necked 1 L flask equipped with a nitrogen gas balloon, thermometer and constant pressure dropping funnel were added N,N,N',N'-Tetramethyldiaminomethane (60 g, 587.2 mmol, 1 eq.), tert-butyl methyl ether (500 ml), the solution was cooled to 0° C. and acetyl chloride (46.1 g, 587.2 mmol, 1 eq.) was added while maintaining the internal temperature below 30° C. over about 20 minutes. The obtained solution was stirred for 30 min and the precipitated solid was collected by filtration, washed with cold tert-butyl methyl ether, and dried under reduced pressure to give 46 g of off-white solid (yield 83.7%).

Example 3-2

Preparation of Intermediate 3:

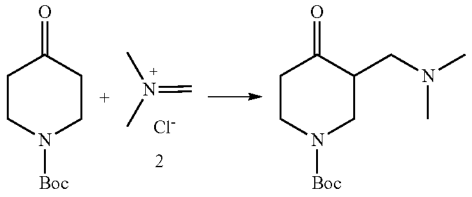

1 3

Intermediate 2 (19.72 g, 210.8 mmol, 1.2 eq.) was added to the solution of tert-butyl 4-oxopiperidine-1-carboxylate (35 g, 175.66 mmol, 1 eq.) dissolved in acetonitrile (350 mL) in a round bottle equipped with a thermometer and nitrogen gas balloon and stirred under the inner temperature of 30-35° C. for 24 h. After the completion of the reaction monitored by thin-layer chromatography, acetonitrile was removed under reduced pressure. Then, DCM (300 mL) was added followed by saturated $NaHCO_3$ solution (250 mL). The layers were separated, and the water phase was extracted with DCM (200+100 mL) twice. Organic layers were combined, washed with water (50 mL), dried over anhydrous magnesium sulfate. The organic phase was filtered, and evaporated under reduced pressure to afford 43.3 g of reddish syrup (yield 93.5%).

Example 3-3

Preparation of Intermediate 5:

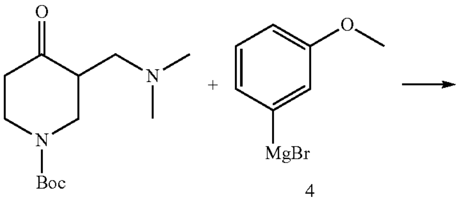

3 4

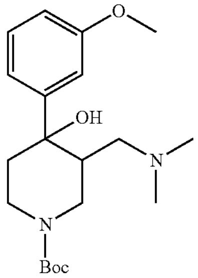

5

To a three-necked 1 L flask equipped with a nitrogen gas balloon, constant pressure dropping funnel, thermometer and a condenser tube were added magnesium (11 g, 451.68 mmol, 3 eq.), THF (300 mL), iodine (3 pellets), and the solution of 1-bromo-3-methoxybenzene (84.5 g, 451.68 mmol, 3 eq.) in THF (70 mL). The mixture was heated to reflux to initiate the reaction. After the yellow color was faded, the reaction was stopped heating and the remaining solution of 1-bromo-3-methoxybenzene was added dropwise (over 1 h). The reaction was then stirred and cooled to room temperature naturally. Intermediate 3 (37.76 g, 1 eq.) was added after 30 min at 25° C. After addition, the reaction mixture was stirred at room temperature overnight (18 h), followed by being poured into mixture solution of saturated $NH_4Cl$ solution (200 mL) with ice (100 g) and stirred for 5 min. Then, THF was removed under reduced pressure and the resulting solution was extracted with ethyl acetate (300 mL) twice. Organic layers were combined, washed with brine (100 mL), dried over anhydrous magnesium sulfate, and evaporated under reduced pressure to give a yellowish oil (21.4 g, yield 38.9% over 2 steps). $^1H$ NMR (400 MHz, $CD_3OD$), δ 7.26 (t, J=8 Hz, 1H), 7.04~7.05 (m, 1H), 6.98 (d, J=8 Hz, 1H), 6.81 (dd, J=8 Hz, J=4 Hz, 1H), 4.20~4.25 (m, 1H), 3.96~4.00 (m, 1H), 3.79 (s, 3H), 3.35 (s, 1H), 3.03~3.22 (m, 2H), 2.31~2.37 (m, 1H), 2.07~2.11 (m, 1H), 2.04 (s, 6H), 1.94~2.01 (m, 1H), 1.78~1.81 (m, 1H), 1.58~1.62 (m, 1H), 1.50 (s, 9H).

Example 3~4

Preparation of Intermediate 6:

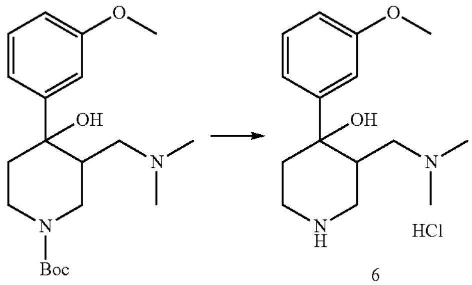

5 6

Boc-amino alcohol (9.5 g, 26.06 mmol, 1 eq.) was dissolved in methanol (76 mL) in a 250 mL single-necked bottle and stirred followed by adding HCl/1,4-dioxane solution (16.3 mL, 65.15 mmol, 2.5 eq.). The solution was heated to 36° C. and stirred for 2 h then heated to 50° C. and the reaction was completed after stirring for 2 h monitored by TLC. MTBE was added into the solution and solid was precipitated. The mixture was then stirred for 24 h followed by filtration. The solid was washed with MTBE and dried under reduce pressure to afford 8.63 g off-white solid (yield 98.3). $^1H$ NMR (400 MHz, $CD_3OD$), δ 7.38 (t, J=8 Hz, 1H), 7.15~7.16 (m, 1H), 7.12 (d, J=8 Hz, 1H), 6.92 (dd, J1=8 Hz, J2=4 Hz, 1H), 3.83 (s, 3H), 3.75 (dd, J1=12 Hz, J2=4 Hz, 1H), 3.41~3.43 (m, 3H), 3.09~3.15 (m, 1H), 2.85~2.92 (m, 1H), 2.75 (s, 3H), 2.75~2.78 (m, 1H), 2.57 (s, 3H), 2.54~2.62 (m, 1H), 1.89~1.94 (m, 1H).

Example 3-5

General Procedure for Condensation:

Intermediate 6 (1 eq.) was added to a 100 mL round bottle, followed by phenyl carbamate (1 eq., Tetrahedron Letters. 2014 55:1540-1543), DCM, triethylamine (1.5 eq.) and stirred at room temperature. The reaction was quenched after completion monitored by TLC. Water and $NaHCO_3$ solution were added and extracted by DCM. The organic phase was combined, washed with water, dried with anhydrous $MgSO_4$, filtered and then the organic solution was evaporated under reduced pressure to give crude product, which was subjected to silica gel column chromatography to give the target product.

Example 3-6

General Procedure for Salt Form:

The free organic base (1 eq.) was added to a 100 mL round bottle followed by DCM and stirred to give clear solution. MTBE was added, and then HCl/1,4-dioxane (1.2 eq.) was added dropwise. Solid was precipitated and the mixture was then stirred and filtrated. The solid was washed with MTBE, dried under reduced pressure from oil pump to afford corresponding product.

Example 3-7

3-((Dimethylamino)methyl)-4-hydroxy-4-(3-methoxyphenyl)-N-phenylpiperidine-1-carboxamide hydrochloride (FWBF1)

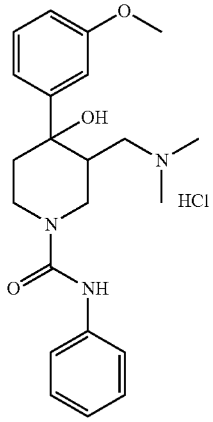 [SMILES: COc1cccc(C2(O)CCN(C(=O)Nc3ccccc3)CC2CN(C)C)c1 ; Cl]

Referring to the method of preparing phenyl (4-chlorophenyl) carbamate in Example 9, phenyl N-phenylcarbamate can be obtained from the reaction of phenyl chloroformate with aniline, and then reacted with intermediate 6 to obtain the target product in a 2-step yield of 32%. $^1H$ NMR (400 MHz, $CD_3OD$), δ 7.44~7.47 (m, 2H), 7.25~7.35 (m, 3H), 7.01~7.15 (m, 2H), 6.68~6.88 (m, 1H), 4.43~4.48 (m, 1H), 4.09~4.14 (m, 1H), 3.81 (s, 3H), 3.37~3.45 (m, 1H), 3.20~3.30 (m, 1H), 3.00~3.06 (m, 1H), 2.65~2.75 (m, 7H), 2.37~2.44 (m, 1H), 2.18~2.26 (m, 1H), 1.72~1.76 (m, 1H). LC-MS-ESI$^+$: $[M+H]^+$ 384.3.

Example 3-8

N-(3-Chlorophenyl)-3-((dimethylamino)methyl)-4-hydroxy-4-(3-methoxyphenyl) piperidine-1-carboxamide hydrochloride (FWBF2)

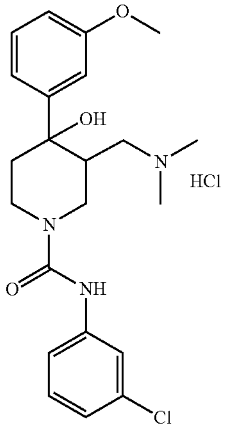 [SMILES: COc1cccc(C2(O)CCN(C(=O)Nc3cccc(Cl)c3)CC2CN(C)C)c1 ; Cl]

Referring to the preparation of phenyl (4-chlorophenyl) carbamate in Example 9, phenyl N-(3-chlorophenyl) carbamate can be obtained from the reaction of phenyl chloroformate with 3-chloroaniline, and then reacted with intermediate 6 to form a salt to obtain the target product in 2-step yield of 64%. $^1H$ NMR (400 MHz, $CD_3OD$), δ 7.64~7.65 (m, 1H), 7.37~7.39 (m, 1H), 7.33 (t, J=8 Hz, 1H), 7.22~7.26 (t, 1H), 7.4~7.15 (m, 1H), 7.09 (d, J=4 Hz, 1H), 7.01 (dd, J=8 Hz, J=4 Hz, 1H), 6.86 (dd, J=8 Hz, J=4 Hz, 1H), 4.43~4.68 (m, 1H), 4.08~4.12 (m, 1H), 3.81 (s, 3H), 3.38~3.45 (m, 1H), 3.24~3.34 (m, 1H), 3.01~3.06 (m, 1H), 2.72~2.75 (m, 4H), 2.57 (s, 3H), 2.38~2.44 (m, 1H), 2.17~2.25 (m, 1H), 1.71~1.76 (m, 1H). LC-MS-ESI$^+$: $[M+H]^+$ 418.2.

Example 3-9

N-(4-Chlorophenyl)-3-((dimethylamino)methyl)-4-hydroxy-4-(3-methoxyphenyl) piperidine-1-carboxamide hydrochloride (FWBF4)

Phenyl (4-chlorophenyl) carbamate

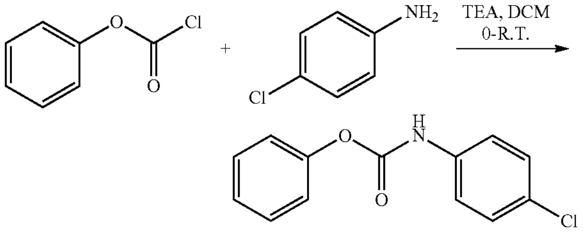

To a 50 mL three-necked flask equipped with a nitrogen gas balloon, and a thermometer were added phenyl chloroformate (2.46 g, 15.68 mmol, 1 eq.) and dichloromethane (15 ml). The solution was cooled to 0° C. and triethylamine (1.90 g, 18.82 mmol, 2 eq.) were added. A solution of p-chloroaniline (2 g, 15.68 mmol, 1 eq.) in dichloromethane (6 mL) was added dropwise at 5° C. The reaction temperature was kept at 5° C. and monitored by TLC (EA:PE=1:3). Additional phenyl chloroformate (0.246 g, 0.1 eq.) was added and the reaction was then completed after 2 h, monitored by TLC. Water (30 mL) was added to form solid precipitation and the mixture was stirred and filtrated. The solid was washed with DCM (20 mL). The liquid was separated and the water phase was extracted by DCM (20 mL). The organic phase was combined, washed with water (20 mL) and dried with anhydrous $MgSO_4$, and the solvent was removed under reduced pressure to afford 3.7 g off-white solid, which was subjected to silica gel column chromatography (EA:PE=1:3) to give 2.7 g off-white solid. Yield: 54%. $^1H$ NMR (400 MHz, $CDCl_3$), δ 7.34~7.45 (m, 4H), 7.23~7.30 (m, 3H), 7.11~7.20 (m, 2H). LC-MS-ESI$^+$: $[M+H]^+$ 248.1, $[M+Na]^+$270.1.

N-(4-Chlorophenyl)-3-((dimethylamino)methyl)-4-hydroxy-4-(3-methoxyphenyl) piperidine-1-carboxamide hydrochloride (FWBF4)

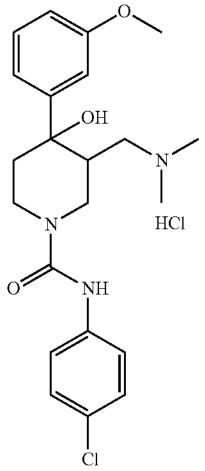 [SMILES: COc1cccc(C2(O)CCN(C(=O)Nc3ccc(Cl)cc3)CC2CN(C)C)c1 ; Cl]

The target product was obtained by the reaction of phenyl (4-chlorophenyl)carbamate with intermediate 6 followed by salt formation in a two-step yield of 42%. $^1H$ NMR (400 MHz, $CD_3OD$), δ 7.33 (d, J=4 Hz, 2H), 7.18 (t, J=8 Hz, 1H), 7.11 (d, J=4 Hz, 2H), 6.99 (s, 1H), 6.94 (d, J=4 Hz, 1H), 6.72 (dd, J1=8 Hz, J2=4 Hz, 1H), 4.29 (dd, J1=12 Hz, J2=4 Hz, H), 3.93~3.97 (m, 1H), 3.66 (s, 3H), 3.27 (t, J=12 Hz, 1H), 3.08~3.16 (m, 1H), 2.86~2.92 (m, 1H), 2.57~2.60 (m, 4H), 2.4 (s, 3H), 2.25~02.28 (m, 1H), 2.03~2.11 (m, 1H), 1.59 (d, J=8 Hz, 1H). LC-MS-ESI$^+$: $[M+H]^+$ 418.2. LC-MS-ESI$^-$: $[M+H]^-$ 416.2.

Example 3-11

N-(3,5-Bis(trifluoromethyl)phenyl)-3-((dimethylamino)methyl)-4-hydroxy-4-(3-methoxyphenyl) piperidine-1-carboxamide hydrochloride (FWBF10)

Phenyl (3,5-bis(trifluoromethyl)phenyl)carbamate

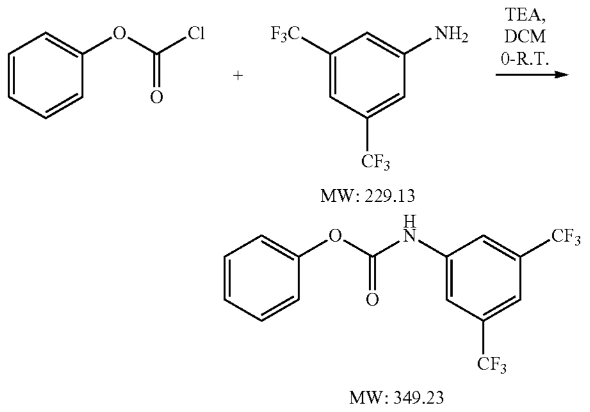

To a 100 mL three-necked flask equipped with a thermometer was added 3,5-di(trifluoromethyl)aniline (2 g, 8.73 mmol, 1 eq.), THF (20 mL), water (20 mL) and sodium bicarbonate (0.88 g, 10.48 mmol, 2 eq.). The mixture was cooled to 0° C. in ice water bath and a solution of phenyl chloroformate (1.44 g, 9.17 mmol, 1.05 eq.) in THF (10 ml) was added dropwise at 5° C. Then the ice water bath was removed. The reaction was completed after 1 h, monitored by TLC (EA:PE=1:4). THF was removed under reduced pressure. Then the mixture was extracted with EA (30+20 mL), the organic layers was combined and washed with water (20 mL), dried with anhydrous $MgSO_4$ and filtered. Then EA was removed under reduced pressure to give 3.1 g off-white solid. PE was added and the mixture was stirred for 2 h and filtrated. The solid was dried under reduced pressure to afford 2.6 g off-white solid. Yield: 85%. $^1$H NMR (400 MHz, $CDCl_3$), δ 7.96~8.00 (m, 2H), 7.61~7.63 (m, 1H), 7.40~7.46 (m, 2H), 7.26~7.34 (m, 2H), 7.18~7.22 (m, 2H).

N-(3,5-Bis(trifluoromethyl)phenyl)-3-((dimethylamino)methyl)-4-hydroxy-4-(3-methoxyphenyl) piperidine-1-carboxamide hydrochloride (FWBF10)

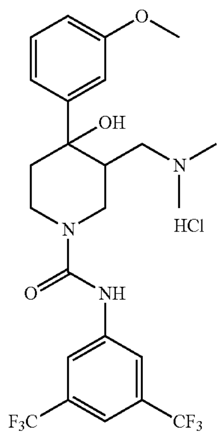 [SMILES: COc1cccc(C2(O)CCN(C(=O)Nc3cc(C(F)(F)F)cc(C(F)(F)F)c3)CC2CN(C)C)c1 ; Cl]

The target product was obtained by the reaction of phenyl (3,5-bis(trifluoromethyl)phenyl) carbamate with intermediate 6 followed by salt formation in a two-step yield of 21.2%. $^1$H NMR (400 MHz, $CD_3OD$), δ 8.22 (s, 2H), 7.55 (s, 1H), 7.31~7.35 (m, 1H), 7.10~7.12 (m, 1H), 6.87 (d, J=8 Hz, 1H), 4.51~4.54 (m, 1H), 4.13~4.17 (m, 1H), 3.82 (s, 3H), 3.42~3.49 (m, 1H), 3.28~3.35 (m, 1H), 3.18~3.24 (m, 1H), 3.03~3.08 (m, 1H), 2.74~2.78 (m, 4H), 3.58 (s, 3H), 2.44 (m, 1H), 2.21~2.29 (m, 1H). LC-MS-ESI$^+$: [M+H]$^+$ 520.3. LC-MS-ESI$^-$: [M+H]$^-$ 518.3; [M+Cl$^-$]$^-$ 554.3.

Example 3-12

N-(3,4-dichlorophenyl)-3-((dimethylamino)methyl)-4-hydroxy-4-(3-methoxyphenyl) piperidine-1-carboxamide (FWBF5)

Phenyl (3,4-dichlorophenyl)-carbamate

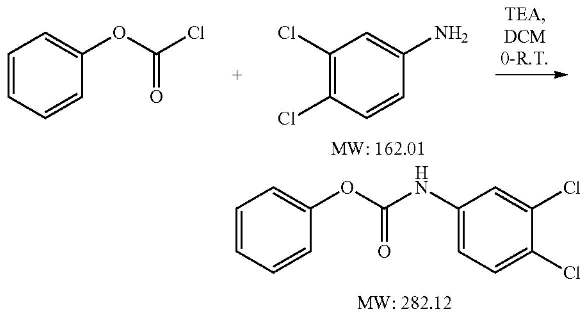

To a 100 mL three-necked flask equipped with a thermometer was added phenyl chloroformate (1.93 g, 12.34 mmol, 1 eq.) and dichloromethane (15 mL). The mixture was then cooled to 0° C. and triethylamine (1.31 g, 12.34 mmol, 1.05 eq.) was added. A solution of 3,4-dichloroaniline (2 g, 12.34 mmol, 1 eq.) in DCM (5 mL) was added dropwise at 10° C. Then the ice water bath was removed and there was a little material left after 38 h monitored by TLC (EA:PE=1:3). Triethylamine (0.67 g, 0.5 eq.), phenyl chloroformate (0.96 g, 0.5 eq.) and DMAP (75 mg, 0.05 eq.) were added. After 24 h, There was still some material left monitored by TLC. Water (30 mL) was added followed by DCM (30 mL) and the mixture was stirred, filtrated and the solid was washed with DCM (20 mL). The liquid was combined, separated and the water layer was extracted with DCM (20 mL). The organic layer was combined and washed with water, dried with anhydrous $MgSO_4$ and the solvent was removed under reduced pressure to give 3.8 g brown oil, which was subjected to silica gel column chromatography to afford 2.3 g off-white solid. Yield: 66.1%.

N-(3,4-dichlorophenyl)-3-((dimethylamino)methyl)-4-hydroxy-4-(3-methoxyphenyl)piperidine-1-carboxamide hydrochloride (FWBF5)

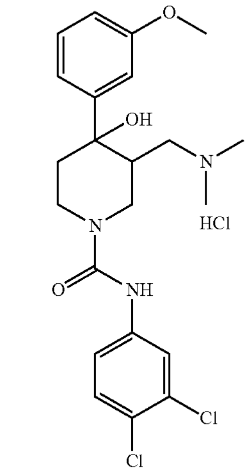 [SMILES: COc1cccc(C2(O)CCN(C(=O)Nc3ccc(Cl)c(Cl)c3)CC2CN(C)C)c1 ; Cl]

The target product was obtained from the reaction of (3,4-dichlorophenyl)carbamate with intermediate 6 and then salt formation, with a two-step yield of 28%. $^1$H NMR (400 MHz, $CD_3OD$), δ 7.67~7.69 (m, 1H), 7.23~7.29 (m, 2H), 7.16~7.23 (m, 1H), 7.00 (s, 1H), 6.95 (d, J=16 Hz, 1H), 6.72 (d, J=16 Hz, 1H), 4.30 (d, J=12 Hz, 1H), 3.96 (d, J=12 Hz, 1H), 3.67 (s, 3H), 3.28 (t, J=12 Hz, 1H), 2.52~2.61 (m, 7H), 2.26 (m, 1H), 2.04~2.11 (m, 1H), 1.60 (d, J=12 Hz, 1H). LC-MS-ESI$^+$: [M+H]$^+$ 452.2, 454.2. LC-MS-ESI$^-$: [M+H]$^-$ 450.2, 452.1.

Example 3-13

N-((3S,5S,7S)-adamantan-1-yl)-3-((dimethylamino)methyl)-4-hydroxy-4-(3-methoxyphenyl) piperidine-1-carboxamide hydrochloride (FWBF14)

Phenyl ((3S,5S,7S)-adamantan-1-yl)carbamate

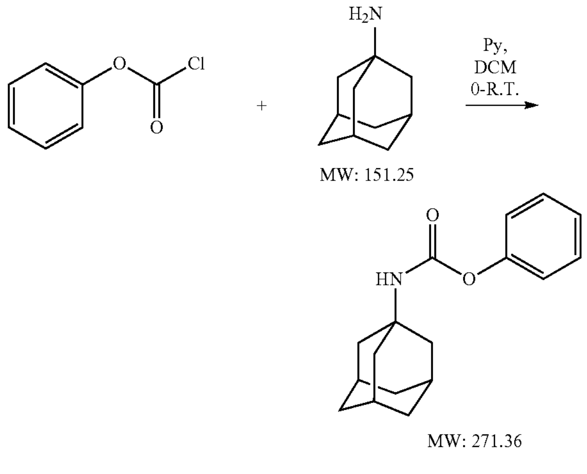

To a 100 mL three-necked flask equipped with a thermometer was added amantadine (1.5 g, 9.92 mmol, 1 eq.), THF (15 mL), water (15 mL) and sodium bicarbonate (0.88 g, 10.48 mmol, 2 eq.). The mixture was cooled to 0° C. in ice water bath and a solution of phenyl chloroformate (1.63 g, 10.41 mmol, 1.05 eq.) in THF (5 mL) was added dropwise at 5° C. Then the ice water bath was removed. The reaction was completed after 1 h, monitored by TLC (EA:PE=1:6). 3 h later LC-MS and TLC (EA:PE=1:6) showed that there was raw material remaining. Sodium bicarbonate (0.25 g, 0.3 eq.) and phenyl chloroformate (0.25 mL, 0.2 eq.) were added. 6 h later LC-MS showed that there was still raw material, and sodium bicarbonate (0.42 g, 0.5 eq.) and phenyl chloroformate (0.372 ml, 0.3 eq.) were added. The reaction was completed overnight monitored by LC-MS. THF was removed under reduced pressure. Then the mixture was extracted with EA (30+30 mL), the organic layers was combined and washed with water (10 mL), dried with anhydrous $MgSO_4$ and filtered. Then EA was removed under reduced pressure to give 2.81 g off-white solid. PE was added and the mixture was stirred for 7 h and filtrated. The solid was dried under reduced pressure to afford 2.02 g off-white solid. Yield: 75%. $^1$H NMR (400 MHz, $CDCl_3$), δ 7.18~7.25 (m, 2H), 6.96~7.15 (m, 3H), 4.75 (s, 1H), 1.97 (s, 3H), 1.86~1.89 (m, 6H), 1.53~1.58 (m, 6H). LC-MS-ESI$^+$: [M+H]$^+$ 300.2, [M+Na]$^+$322.2, [2M+Na]$^+$621.4.

N-((3S,5S,7S)-adamantan-1-yl)-3-((dimethylamino)methyl)-4-hydroxy-4-(3-methoxyphenyl) piperidine-1-carboxamide hydrochloride (FWBF14)

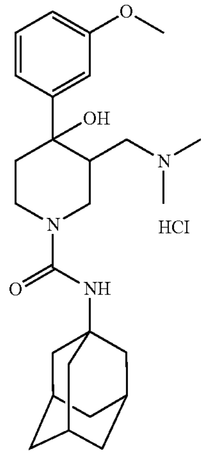

The target product was obtained from the reaction of Phenyl ((3S,5S,7S)-adamantan-1-yl)carbamate with intermediate 6 and then salt formation, with a two-step yield of 45.2%. $^1$H NMR (400 MHz, $CD_3OD$), δ 7.17~7.22 (m, 1H), 6.90~6.97 (m, 2H), 6.71~6.75 (m, 1H), 4.06 (d, J=12 Hz, 1H), 3.73 (d, J=16 Hz, 1H), 3.67 (s, 3H), 3.07~3.12 (m, 1H), 2.95 (t, J=12 Hz, 1H), 2.83~2.89 (m, 1H), 2.56~2.62 (m, 4H), 2.42 (s, 3H), 2.18 (m, 1H), 1.99~2.04 (m, 1H), 1.94 (s, 9H), 1.59 (s, 6H), 1.54 (d, J=12 Hz, 1H), 1.17 (t, J=8 Hz, 1H). LC-MS-ESI$^+$: [M+H]$^+$ 442.4.

Example 3-14

3-((Dimethylamino)methyl)-4-hydroxy-4-(3-methoxyphenyl)-N-(3,4,5-trichlorophenyl) piperidine-1-carboxamide hydrochloride (FWBF6)

Phenyl (3,4,5-trichlorophenyl)carbamate

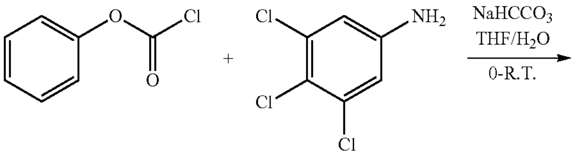

MW: 196.46

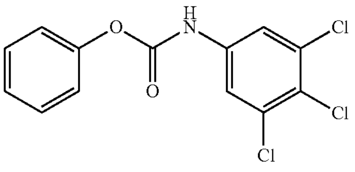

MW: 316.56

To a 100 mL three-necked flask equipped with a thermometer was added 3,4,5-trichloroaniline (2 g, 10.18 mmol, 1 eq.), THF (20 mL), sodium bicarbonate (1.03 g, 12.22 mmol, 1.2 eq.) in water (20 ml). The mixture was cooled to 0° C. in ice water bath and a solution of phenyl chloroformate (1.67 g, 10.69 mmol, 1.05 eq.) in THF (10 mL) was added dropwise at 5° C. Then the ice water bath was removed. The reaction was completed after 1 h, monitored by TLC. THF was removed under reduced pressure. Then the mixture was extracted with EA (40+30 mL), the organic layers was combined and washed with brine, dried with anhydrous $MgSO_4$ and filtered. Then EA was removed under reduced pressure to give 3.2 g brown solid, which was then recrystallized with the solution of PE:EA=1:3 (10 mL) to give 1.2 g off-white solid. The liquid was crystallized with 10 mL solution of EA:PE=10:1 to give 1.1 g off-white solid. The combined yield is 71.4%. $^{1}H$ NMR (400 MHz, $CDCl_3$), δ 7.96~8.00 (m, 2H), 7.42~7.43 (m, 2H), 7.25~7.30 (m, 2H), 7.11~7.15 (m, 1H), 7.02~7.06 (m, 2H), 6.87 (s, 1H). LC-MS-ESI$^+$: $[M+Na]^+$338.0, 340.0.

3-((Dimethylamino)methyl)-4-hydroxy-4-(3-methoxyphenyl)-N-(3,4,5-trichlorophenyl) piperidine-1-carboxamide hydrochloride (FWBF6)

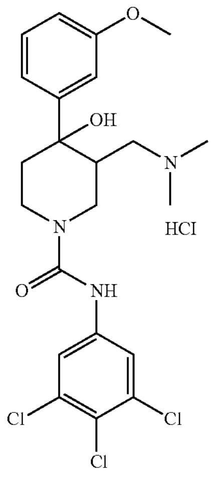

The target product was obtained from the reaction of Phenyl (3,4,5-trichlorophenyl)carbamate with intermediate 6 and then salt formation, with a two-step yield of 70%. $^{1}H$ NMR (400 MHz, $CD_3OD$), δ 7.64 (s, 2H), 7.18 (d, J=8 Hz, 1H), 6.99 (s, 1H), 6.94 (d, J=4 Hz, 1H), 6.71 (d, J=4 Hz, 1H), 3.3 (d, J=4 Hz, 1H), 3.96 (dd, J1=16 Hz, J2=4 Hz, 1H), 3.68 (s, 3H), 3.26 (t, J=12 Hz, 1H), 3.10~3.16 (m, 1H), 2.86~2.91 (m, 1H), 2.43~2.60 (m, 7H), 2.23~2.29 (m, 1H), 2.07 (m, J1=12 Hz, J2=4 Hz, 1H), 1.59 (d, J=12 Hz, 1H). LC-MS-ESI$^+$: $[M+H]^+$ 486.1, 488.1. LC-MS-ESI$^-$: $[M+H]^-$ 484.1, 486.1.

Example 3-15

3-((Dimethylamino)methyl)-4-hydroxy-4-(3-methoxyphenyl)-N-(naphthalen-2-yl)piperidine-1-carboxamide hydrochloride (FWBF11) Phenyl (2-naphthyl)carbamate

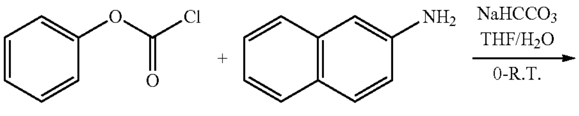

MW: 143.19

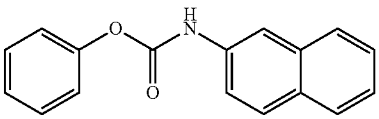

MW: 263.30

To a 100 mL three-necked flask equipped with a thermometer was added 2-naphthylamine (2 g, 13.97 mmol, 1 eq.), THF (20 mL), sodium bicarbonate (1.41 g, 14.67 mmol, 1.2 eq.) in water (20 ml). The mixture was cooled to 0° C. in ice water bath and a solution of phenyl chloroformate (1.84 g, 14.67 mmol, 1.05 eq.) in THF (10 mL) was added dropwise at 5° C. Then the ice water bath was removed. The reaction was completed after 1.5 h, monitored by TLC. THF was removed under reduced pressure. Then the mixture was extracted with EA (50+25 mL), the organic layers was combined and washed with brine, dried with anhydrous $MgSO_4$ and filtered. Then EA was removed under reduced pressure to give 3.5 g brown solid, which was then recrystallized with the solution of PE:EA=1:2 (45 mL) to give 3.0 g off-white solid. Yield: 81.5%. $^1$H NMR (400 MHz, CDCl3), δ 8.07 (s, 1H), 7.76~7.86 (m, 3H), 7.39~7.50 (m, 5H), 7.22~7.29 (m, 3H), 7.13 (m, 1H). LC-MS-ESI$^+$: [M+H]$^+$ 264.1, [M+H]$^+$ 286.10

3-((Dimethylamino)methyl)-4-hydroxy-4-(3-methoxyphenyl)-N-(naphthalen-2-yl)piperidine-1-carboxamide hydrochloride (FWBF11)

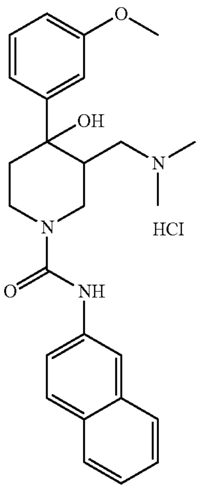

It is obtained by the reaction of phenyl (2-naphthyl) carbamate and intermediate 6 and then salt formation, with 45% yield. $^1$H NMR (400 MHz, $CD_3OD$), δ 7.83 (s, 1H), 7.59~7.65 (m, 3H), 7.47~7.51 (m, 1H), 7.26~7.30 (m, 1H), 7.17~7.23 (m, 2H), 6.94~7.02 (m, 1H), 6.73 (d, J=8 Hz, 1H), 4.36 (d, J=12 Hz, 1H), 4.03 (d, J=12 Hz, 1H), 3.68 (s, 3H), 3.29~3.36 (m, 1H), 3.06~3.21 (m, 1H), 2.92 (t, J=12 Hz, 1H), 2.51~2.63 (m, 7H), 2.30 (m, 1H), 2.08~2.16 (m, 1H), 1.63 (d, J=8 Hz, 1H). LC-MS-ESI$^+$: [M+H]$^+$ 434.3. LC-MS-ESI$^-$: [M+H]$^-$ 432.4, [M+Cl$^-$]$^-$ 468.3.

Example 3-16

N-(3,4-difluorophenyl)-3-((dimethylamino)methyl)-4-hydroxy-4-(3-methoxyphenyl)piperidine-1-carboxamide hydrochloride (FWBF8)

Phenyl (3,4-difluorophenyl)carbamate

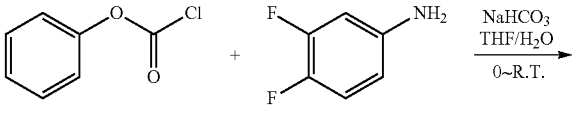

MW: 129.11

-continued

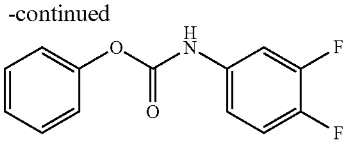

MW: 249.22

To a 100 mL three-necked flask equipped with a thermometer was added 3,4-difluoroaniline (2 g, 15.5 mmol, 1 eq.), THF (20 ml), water (20 ml), sodium bicarbonate (1.56 g, 18.6 mmol, 1.2 eq.). The mixture was cooled to 0° C. in ice water bath and a solution of phenyl chloroformate (2.55 g, 16.3 mmol, 1.05 eq.) in THF (10 mL) was added dropwise at 5° C. Then the ice water bath was removed. The reaction was completed after 2 h, monitored by TLC. THF was removed under reduced pressure. Then the mixture was extracted with EA (40+30 ml), the organic layers was combined and washed with brine, dried with anhydrous $MgSO_4$ and filtered. Then EA was removed under reduced pressure to give 4.3 g brown solid, which was then recrystallized with the solution of PE:EA=1:6 (10.5 mL) to give 3.18 g off-white solid. The liquid was crystallized with 2.5 mL solution of EA:PE=1:6 to give 0.18 g off-white solid. The combined yield is 87%. $^1$H NMR (400 MHz, $CDCl_3$), δ 7.32~7.38 (m, 1H), 7.25~7.30 (m, 2H), 7.11~7.17 (m, 1H), 7.03~7.09 (m, 2H), 6.96~7.00 (m, 1H), 6.86~6.93 (m, 2H). LC-MS-ESI$^+$: [M+H]$^+$ 250.1, [M+Na]$^+$272.1.

N-(3,4-difluorophenyl)-3-((dimethylamino)methyl)-4-hydroxy-4-(3-methoxyphenyl)piperidine-1-carboxamide hydrochloride (FWBF8)

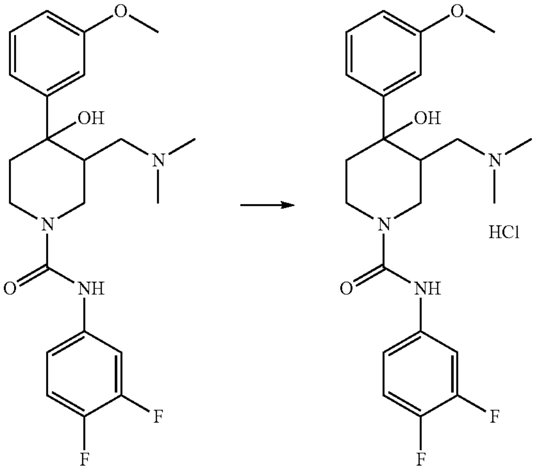 [SMILES: COc1cccc(C2(O)CCN(C(=O)Nc3ccc(F)c(F)c3)CC2CN(C)C)c1 ; COc1cccc(C2(O)CCN(C(=O)Nc3ccc(F)c(F)c3)CC2CN(C)C)c1 ; Cl]

It was obtained by the reaction of phenyl (3,4-difluorophenyl)carbamate with intermediate 6 and then salt formation, with a two-step yield of 35.6%. $^1$H NMR (400 MHz, $CD_3OD$), δ 7.51~7.56 (m, 1H), 7.33 (t, J=8 Hz, 1H), 7.17~7.19 (m, 1H), 7.09 (d, J=8 Hz, 1H), 6.86~6.88 (m, 1H), 4.39~4.43 (m, 1H), 4.05~4.10 (m, 1H), 3.81 (s, 3H), 3.41~3.48 (m, 1H), 3.25 (t, J=12 Hz, 1H), 3.02~3.07 (m, 1H), 2.66~2.75 (m, 7H), 2.39~2.42 (m, 1H), 2.18~2.26 (m, 1H), 1.74 (d, J=8 Hz, 1H). LC-MS-ESI$^+$: [M+H]$^+$ 420.3. LC-MS-ESI$^-$: [M+H]$^-$ 418.3, [M+Cl$^-$]$^-$ 454.3.

Example 3-17

3-((Dimethylamino)methyl)-N-(3-fluorophenyl)-4-hydroxy-4-(3-methoxyphenyl)piperidine-1-carboxamide hydrochloride (FWBF7)

Phenyl (3-fluorophenyl)carbamate

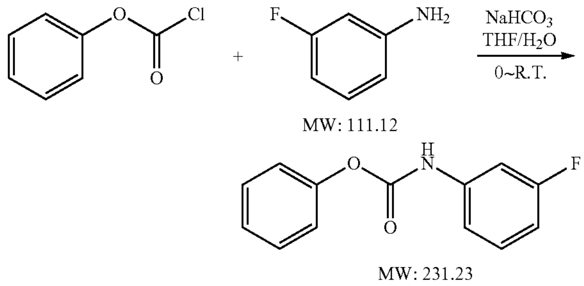

To a 100 mL three-necked flask equipped with a thermometer was added 3-fluoroaniline (2 g, 18.0 mmol, 1 eq.), THF (20 mL), water (20 mL), sodium bicarbonate (1.81 g, 21.6 mmol, 1.2 eq.). The mixture was cooled to 0° C. in ice water bath and a solution of phenyl chloroformate (2.96 g, 18.9 mmol, 1.05 eq.) in THF (10 mL) was added dropwise at 5° C. Then the ice water bath was removed. The reaction was completed after 1 h, monitored by TLC. THF was removed under reduced pressure. Then the mixture was extracted with EA (30+30 ml), the organic layers was combined and washed with brine, dried with anhydrous $MgSO_4$ and filtered. Then EA was removed under reduced pressure to give 4.78 g pink oil, which was then recrystallized with the solution of PE:EA=1:68 (5 mL) to give 1.1 g off-white solid. The liquid was crystallized with 2 mL solution of EA:PE=1:8 to give 3.53 g off-white solid. The combined yield is 85%. $^1$H NMR (400 MHz, $CDCl_3$), δ 7.21~7.28 (m, 3H), 7.08~7.14 (m, 2H), 7.02~7.05 (m, 2H), 6.91~6.95 (m, 2H), 6.62~6.68 (m, 1H). LC-MS-ESI$^+$: [M+H]$^+$ 232.1, [M+Na]$^+$254.1.

3-((Dimethylamino)methyl)-N-(3-fluorophenyl)-4-hydroxy-4-(3-methoxyphenyl)piperidine-1-carboxamide hydrochloride (FWBF7)

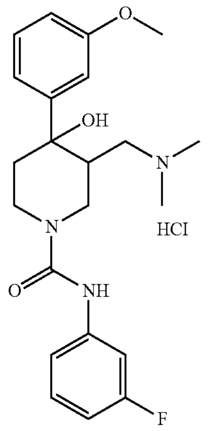

It was obtained from the reaction of phenyl (3-fluorophenyl)carbamate with intermediate 6 followed by salt formation, with a two-step yield of 35.7%. $^1$H NMR (400 MHz, $CD_3OD$), δ 7.265 (d, J=8 Hz, 1H), 7.16~7.20 (m, 1H), 7.09~7.12 (m, 2H), 6.99 (s, 1H), 6.94 (d, J=4 Hz, 1H), 6.72 (dd, J1=8 Hz, J2=4 Hz, 1H), 6.58~6.61 (m, 1H), 4.28~4.31 (m, 1H), 3.94~3.97 (m, 1H), 3.67 (s, 3H), 3.24~3.31 (m, 1H), 3.08~3.17 (m, 1H), 2.86~2.92 (m, 1H), 2.52~2.61 (m, 7H), 2.62 (m, 1H), 2.03~2.11 (m, 1H), 1.57~1.61 (m, 1H). LC-MS-ESI$^+$: [M+H]$^+$ 402.2. LC-MS-ESI: [M+H]$^-$ 400.3, [M+Cl$^-$]$^-$ 436.2.

Example 3-18

N-(3-chloro-4-fluorophenyl)-3-((dimethylamino)methyl)-4-hydroxy-4-(3-methoxyphenyl) piperidine-1-carboxamide hydrochloride (FWBF9)

Phenyl (3-chloro-4-fluorophenyl)carbamate

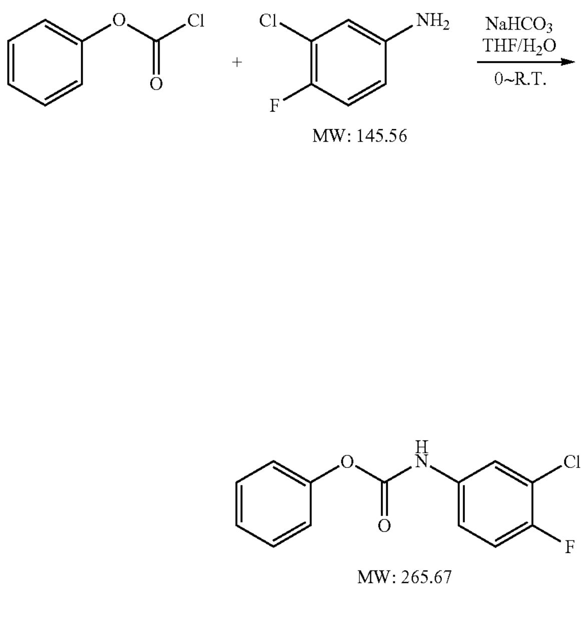

To a 100 mL three-necked flask equipped with a thermometer was added 3-chloro-4-fluoroaniline (2 g, 13.74 mmol, 1 eq.), THF (20 mL), water (20 mL), sodium bicarbonate (1.39 g, 16.49 mmol, 1.2 eq.). The mixture was cooled to 0° C. in ice water bath and a solution of phenyl chloroformate (2.26 g, 14.43 mmol, 1.05 eq.) in THF (10 mL) was added dropwise at 5° C. Then the ice water bath was removed. The reaction was completed after 1 h, monitored by TLC. THF was removed under reduced pressure. Then the mixture was extracted with EA (30+30 mL), the organic layers was combined and washed with brine, dried with anhydrous $MgSO_4$ and filtered. Then EA was removed under reduced pressure to give 3.67 g off-white solid. PE was added and the mixture was stirred for 2 h, filtrated and dried under reduced pressure to give 3.5 g off-white solid. Yield: 95.5%. $^1$H NMR (400 MHz, $CDCl_3$), δ 7.45~7.46 (m, 1H), 7.23~7.30 (m, 2H), 7.06~7.16 (m, 2H), 7.00~7.08 (m, 2H), 6.91~6.99 (m, 1H), 6.82 (s, 1H).

N-(3-chloro-4-fluorophenyl)-3-((dimethylamino)methyl)-4-hydroxy-4-(3-methoxyphenyl) piperidine-1-carboxamide hydrochloride (FWBF9)

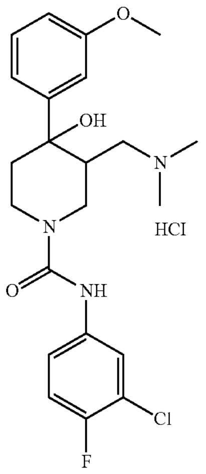

The target product was obtained by the reaction of phenyl (3-chloro-4-fluorophenyl)carbamate with intermediate 6 followed by salt formation in 60% yield in two steps. $^1$H NMR (400 MHz, $CD_3OD$), δ 7.706 (dd, $J_1$=6.8 Hz, $J_2$=2.8 Hz, 1H), 7.314~7.401 (m, 2H), 7.132~7.184 (m, 2H), 7.097 (d, J=7.6 Hz, 1H), 6.778 (dd, $J_1$=8 Hz, $J_2$=2.4 Hz, 1H), 4.411~4.458 (m, 1H), 4.087 (d, J=6.6 Hz, 1H), 3.819 (s, 3H), 3.403~3.472 (m, 1H), 3.230~3.351 (m, 1H), 3.018~3.075 (m, 1H), 2.720~2.758 (m, 4H), 2.585 (s, 3H), 2.378~2.432 (m, 1H), 2.183~2.262 (m, 1H), 1.719~1.767 (m, 1H). LC-MS-ESI$^+$: $[M+H]^+$ 436.2. LC-MS-ESI$^-$: $[M+H]^-$ 434.2.

Example 3-19

N-(3-Chlorophenyl)-3-((dimethylamino)methyl)-4-hydroxy-4-(3-methoxyphenyl)-N-methylpiperidine-1-carboxamide hydrochloride (FWBF3)

(3-Chlorophenyl)(methyl)carbamic acid p-nitrophenyl ester

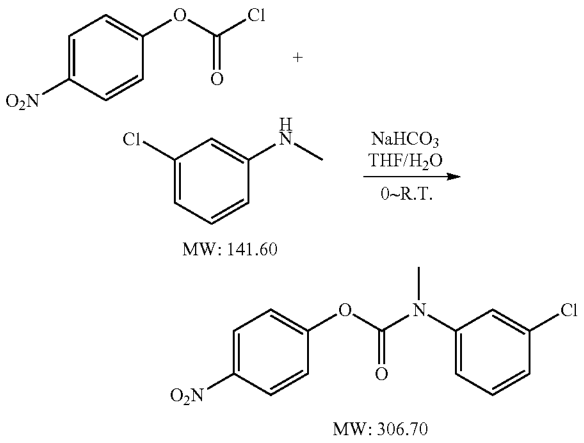

To a 50 mL three-necked flask equipped with a thermometer was added N-methyl 3-chloroaniline (1 g, 7.06 mmol, 1 eq.), THF (10 mL), sodium bicarbonate (0.712 g, 8.474, mmol, 1.2 eq.) and water (10 ml). The mixture was cooled to 0° C. in ice water bath and a solution of phenyl chloroformate (1.5 g, 7.42 mmol, 1.05 eq.) in THF (10 mL) was added dropwise at 5° C. Then the ice water bath was removed. The reaction was completed after 1 h, monitored by TLC. THF was removed under reduced pressure. Then the mixture was extracted with EA (15+15 mL), the organic layers was combined and washed with brine, dried with anhydrous $MgSO_4$ and filtered. Then EA was removed under reduced pressure to give 2.7 g brown oil. PE was added and the mixture was stirred for 2 h, filtrated and dried under reduced pressure to give 2.04 g off-white solid. Yield: 94%.

N-(3-Chlorophenyl)-3-((dimethylamino)methyl)-4-hydroxy-4-(3-methoxyphenyl)-N-methylpiperidine-1-carboxamide hydrochloride (FWBF3)

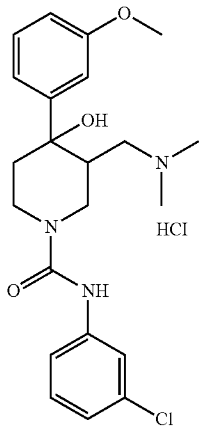

It was obtained from the reaction of (3-chlorophenyl)(methyl)carbamic acid p-nitrophenyl ester with intermediate 6 and then salt formation, with a two-step yield of 67.9%. $^1$H NMR (400 MHz, $CD_3OD$), δ 7.24~7.29 (m, 1H), 7.15~7.19 (m, 2H), 7.05 (d, J=4 Hz, 1H), 6.92 (s, 1H), 6.87 (s, J=8 Hz, 1H), 6.89~6.73 (m, 1H), 3.94 (d, J=12 Hz, 1H), 3.66 (s, 3H), 3.37 (d, J=12 Hz, 1H), 3.12 (s, 3H), 2.85~2.99 (m, 3H), 2.51~2.28 (m, 4H), 2.41 (s, 3H), 2.18 (s, 1H), 1.80~1.88 (m, 1H), 1.37 (d, J=16 Hz, 1H), 1.15~1.19 (m, 1H). LC-MS-ESI$^+$: $[M+H]^+$ 432.2.

Example 3-20

N-Benzyl-3-((dimethylamino)methyl)-4-hydroxy-4-(3-methoxyphenyl)piperidine-1-carboxamide hydrochloride (FWBF12)

Benzylcarbamic acid phenyl ester

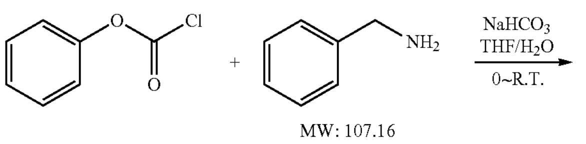

-continued

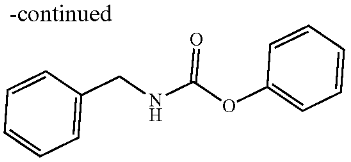

MW: 227.26

To a 100 mL three-necked flask equipped with a thermometer was added benzylamine (2 g, 18.67 mmol, 1 eq.), THF (20 mL), water (20 mL), sodium bicarbonate (3.14 g, 37.34 mmol, 2 eq.). The mixture was cooled to 0° C. in ice water bath and a solution of phenyl chloroformate (3.07 g, 19.61 mmol, 1.05 eq.) in THF (10 mL) was added dropwise at 5° C. Then the ice water bath was removed. The reaction was completed after 1 h, monitored by TLC. THF was removed under reduced pressure. Then the mixture was extracted with EA (15+15 mL), the organic layers was combined and washed with brine, dried with anhydrous $MgSO_4$ and filtered. Then EA was removed under reduced pressure to give 4.23 g off-white solid. PE was added and the mixture was stirred for 3 h, filtrated and dried under reduced pressure to give 3.9 g white solid. Yield: 92%. $^1$H NMR (400 MHz, $CDCl_3$), δ 7.31~7.41 (m, 7H), 7.11~7.26 (m, 3H), 5.37 (s, 1H), 4.44~4.51 (m, 2H). LC-MS-ESI$^+$: [M+H]$^+$ 227.1, [M+Na]$^+$250.1, [2M+Na]$^+$477.2.

N-Benzyl-3-((dimethylamino)methyl)-4-hydroxy-4-(3-methoxyphenyl)piperidine-1-carboxamide hydrochloride (FWBF12)

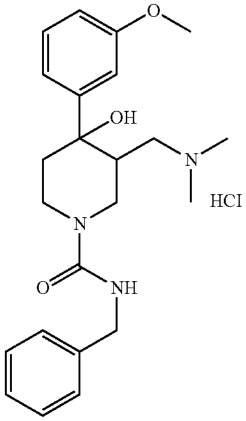

The target product was obtained by the reaction of benzylcarbamate with intermediate 6 and then formed a salt with a two-step yield of 54%. $^1$H NMR (400 MHz, $CD_3OD$), δ 7.15~7.21 (m, 5H), 7.07~7.10 (m, 1H), 6.95 (d, J=4 Hz, 1H), 6.87 (d, J=8 Hz, 1H), 6.71 (d, J=8 Hz, 1H), 4.26 (q, 2H), 4.13 (dd, J1=12 Hz, J2=4 Hz, 1H), 3.78 (d, J=8 Hz, 1H), 3.66 (s, 3H), 3.15~3.25 (m, 1H), 3.03 (t, J=12 Hz, 1H), 2.82~2.89 (m, 1H), 2.48~2.56 (m, 7H), 2.12~2.15 (m, 1H), 1.99 (m, J1=16 Hz, J2=4 Hz, 1H), 1.52~1.56 (m, 1H). LC-MS-ESI$^+$: [M+H]$^+$ 398.3.

Example 3-21

3-((Dimethylamino)methyl)-4-hydroxy-4-(3-methoxyphenyl)-N-((S)-1-phenylethyl)piperidine-1-carboxamide hydrochloride (FWBF13)

Phenyl (S)-(1-phenylethyl)carbamate

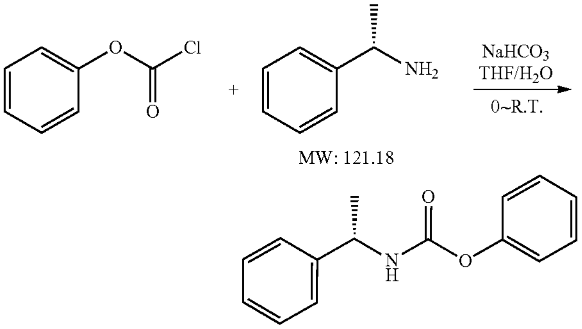

MW: 241.29

To a 100 mL three-necked flask equipped with a thermometer was added (S)-1-phenylethylamine (2 g, 16.5 mmol, 1 eq.), THF (20 mL), water (20 mL), sodium bicarbonate (1.66 g, 19.8 mmol, 1.2 eq.). The mixture was cooled to 0° C. in ice water bath and a solution of phenyl chloroformate (2.71 g, 17.33 mmol, 1.05 eq.) in THF (10 mL) was added dropwise at 5° C. Then the ice water bath was removed. The reaction was completed after 0.5 h, monitored by TLC. THF was removed under reduced pressure. Then the mixture was extracted with EA (40+30 mL), the organic layers was combined and washed with water (10 mL), dried with anhydrous $MgSO_4$ and filtered. Then EA was removed under reduced pressure to give 4.27 g off-white solid. PE (6 mL) was added and the mixture was stirred for 2 h, filtrated and dried under reduced pressure to give 3.74 g off-white solid. Yield: 94%. $^1$H NMR (400 MHz, $CDCl_3$), δ 7.26~7.41 (m, 7H), 6.97~7.21 (m, 3H), 5.34 (s, 1H), 4.89~4.97 (m, 1H), 1.55~1.60 (m, 3H). LC-MS-ESI$^+$: [M+H]$^+$ 242.2, [M+Na]$^+$264.2, [2M+Na]$^+$505.3.

3-((Dimethylamino)methyl)-4-hydroxy-4-(3-methoxyphenyl)-N-((S)-1-phenylethyl)piperidine-1-carboxamide hydrochloride (FWBF13)

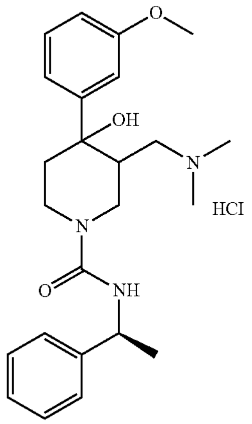

The target product was obtained from the reaction of phenyl (S)-(1-phenylethyl)carbamate with intermediate 6 and then formed a salt, with a two-step yield of 38.5%. $^1$H NMR (400 MHz, $CD_3OD$), δ 7.22~7.24 (m, 2H), 7.13~7.18 (m, 3H), 7.05 (s, 1H), 6.93 (d, J=12 Hz, 1H), 6.85 (dd, J1=16 Hz, J=4 Hz, 1H), 6.68~6.70 (m, 1H), 4.75~4.81 (m, 1H), 4.14 (d, J=16 Hz, 1H), 3.83 (d, J=16 Hz, 1H), 3.65 (s, 3H), 3.14~3.17 (m, 1H), 2.95~3.04 (m, 1H), 3.83 (t, J=12 Hz, 1H), 2.50~2.58 (m, 4H), 2.36~2.38 (d, 3H), 1.94~2.10 (m, 2H), 1.53 (d, J=16 Hz, 1H), 1.33~1.38 (m, 3H). LC-MS-ESI$^+$: $[M+H]^+$ 412.3. LC-MS-ESI$^-$: $[M+Cl^-]^-$ 446.2.

Example 3-22

N-(1-((3R,5R,7R)-adamantan-1-yl)ethyl)-3-((dimethylamino)methyl)-4-hydroxy-4-(3-methoxyphenyl) piperidine-1-carboxamide hydrochloride (FWBF15)

((3S,5S,7S)-adamantan-1-yl)carbamic acid phenyl ester

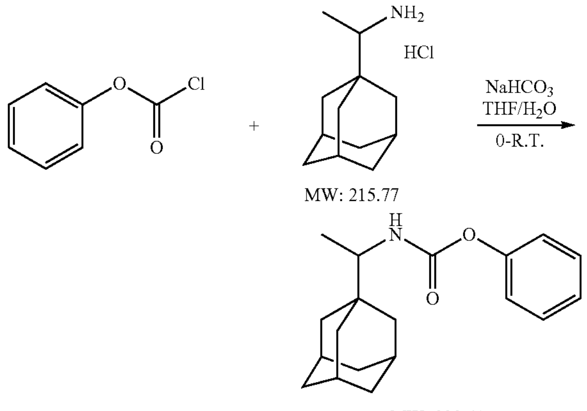

To a 100 mL three-necked flask equipped with a thermometer was added amantadine (2 g, 9.27 mmol, 1 eq.), THF (15 mL), water (20 mL), and sodium bicarbonate (1.71 g, 20.4 mmol, 2.2 eq.). The mixture was cooled to 0° C. in ice water bath and a solution of phenyl chloroformate (1.52 g, 9.73 mmol, 1.05 eq.) in THF (10 mL) was added dropwise at 5° C. Then the ice water bath was removed. The reaction was completed after 0.5 h, monitored by TLC. THF was removed under reduced pressure. Then the mixture was extracted with EA (70+30+10 mL), the organic layers was combined and washed with water (20 mL), dried with anhydrous $MgSO_4$ and filtered. Then EA was removed under reduced pressure to give 2.81 g off-white solid. PE (10 mL) was added and the mixture was stirred for 1 h, filtrated and dried under reduced pressure to give 2.62 g off-white solid. Yield: 93.5%. $^1$H NMR (400 MHz, $CDCl_3$), δ 7.333~7.394 (m, 2H), 7.128~7.200 (m, 3H), 4.883 (d, J=5 Hz, 1H), 3.436~3.477 (m, 1H), 2.018 (s, 3H), 1.506~1.746 (m, 12H), 1.109~1.158 (m, 3H). LC-MS-ESI$^+$: $[M+H]^+$ 300.2, $[M+Na]^+$322.2, $[2M+Na]^+$621.4.

N-(1-((3R,5R,7R)-adamantan-1-yl)ethyl)-3-((dimethylamino)methyl)-4-hydroxy-4-(3-methoxyphenyl) piperidine-1-carboxamide hydrochloride (FWBF15)

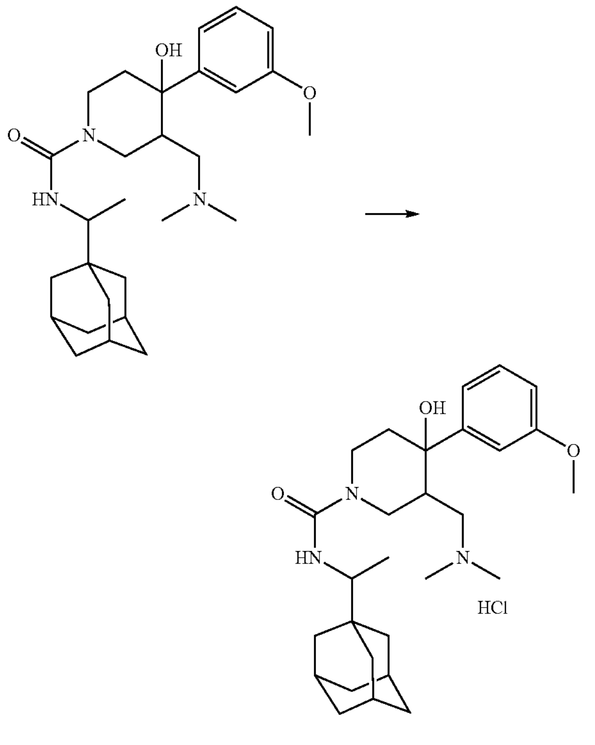

The target product was obtained by the reaction of ((3R,5R,7R)-adamantan-1-yl)carbamic acid phenyl ester with intermediate 6 after salt formation, with a two-step yield of 19%. $^1$H NMR (400 MHz, $CD_3OD$), δ 7.17 (t, J=8 Hz, 1H), 6.94 (d, J=4 Hz, 1H), 6.86~6.91 (m, 1H), 6.71 (dd, J1=8 Hz, J2=4 Hz, 1H), 4.15 (d, J=12 Hz, 1H), 3.80 (t, J=16 Hz, 1H), 3.65 (s, 3H), 3.43~3.50 (m, 1H), 3.15~3.23 (m, 1H), 3.00 (t, J=12 Hz, 1H), 2.82~2.91 (m, 1H), 2.53~2.59 (m, 4H), 2.39~2.43 (d, 3H), 2.15~2.17 (m, 1H), 2.01 (m, J1=16 Hz, J2=4 Hz, 1H), 1.84 (d, J=4 Hz, 3H), 1.50~1.62 (m, 7H), 1.45 (s, 6H), 0.94~0.97 (m, 1H). LC-MS-ESI$^+$: $[M+H]^+$ 470.4.

Example 3-23

Methyl 3-(3-((dimethylamino)methyl)-4-hydroxy-4-(3-methoxyphenyl)piperidine-1-carboxamide) thiophene-2-carboxylate hydrochloride (FWBF17)

Methyl 3-((phenoxycarbonyl)amino)thiophene-2-carboxylate

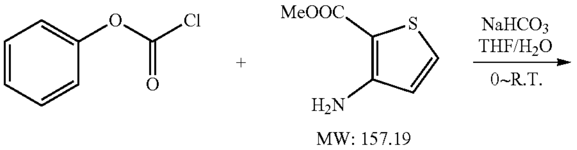

-continued

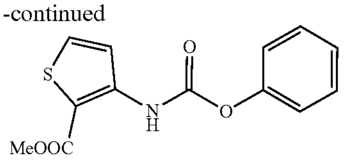

MW: 277.29

To a 100 mL three-necked flask equipped with a thermometer was added methyl 3-aminothiophene-1-carboxylate (2 g, 12.72 mmol, 1 eq.), THF (20 mL), water (20 mL), sodium bicarbonate (1.28 g, 15.26 mmol, 1.2 eq.). The mixture was cooled to 0° C. in ice water bath and a solution of phenyl chloroformate (2.09 g, 13.36 mmol, 1.05 eq.) in THF (10 mL) was added dropwise at 5° C. Then the ice water bath was removed. The reaction was still not completed after 2 h, monitored by TLC, and then sodium bicarbonate (0.32 g, 0.3 eq.) and benzyl chloroformate (0.4 g, 0.2 eq.) were added. After 1 h, the reaction was still not completed, so sodium bicarbonate (0.32 g, 0.3 eq.) and phenyl chloroformate (0.4 g, 0.2 eq.) were added and the mixture was stirred overnight. THF was removed under reduced pressure. Then the mixture was extracted with EA (50+30 mL), the organic layers was combined and washed with water (20 mL), dried with anhydrous $MgSO_4$ and filtered. Then EA was removed under reduced pressure to give 3.9 g off-white solid. PE (20 mL) was added and the mixture was stirred for 7 h, filtrated and dried under reduced pressure to give 3.1 g off-white solid. Yield: 88%. $^1$H NMR (400 MHz, $CDCl_3$), δ 9.90 (s, 1H), 7.89~7.91 (m, 1H), 7.47~7.52 (m, 1H), 7.39~7.46 (m, 2H), 7.24~7.31 (m, 1H), 7.19~7.23 (m, 2H), 2.93 (s, 3H).

Methyl 3-(3-((dimethylamino)methyl)-4-hydroxy-4-(3-methoxyphenyl)piperidine-1-carboxamide) thiophene-2-carboxylate hydrochloride (FWBF17)

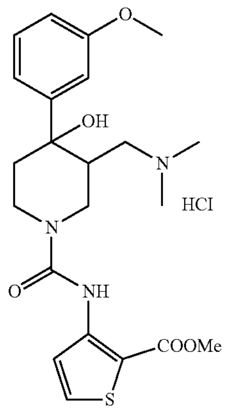

The target product was obtained by the reaction of methyl 3-((phenoxycarbonyl)amino)thiophene-2-carboxylate with Intermediate 6 and then salt formation, with a two-step yield of 76%. $^1$H NMR (400 MHz, $CD_3OD$), δ 7.77 (d, J=8 Hz, 1H), 7.54 (d, J=8 Hz, 1H), 7.18 (t, J=8 Hz, 1H), 6.99 (s, 1H), 6.94 (d, J=8 Hz, 1H), 7.72 (d, J=8 Hz, 1H), 4.20 (d, J=12 Hz, 1H), 3.85 (d, J=12 Hz, 1H), 3.74 (s, 3H), 3.67 (s, 3H), 3.44 (t, J=12 Hz, 1H), 3.15~3.17 (m, 2H), 2.93~2.99 (m, 1H), 2.59~2.62 (m, 4H), 2.53 (s, 3H), 2.31 (m, 1H), 2.09~2.16 (m, 1H), 1.65 (t, J=12 Hz, 1H). LC-MS-ESI$^+$: [M+H]$^+$ 448.3.

Example 3-24

3-((dimethylamino)methyl)-4-hydroxy-N-((1R,3S,5R,7S)-3-hydroxyadamantan-1-yl)-4-(3-methoxyphenyl)piperidine-1-carboxamide hydrochloride (FWBF16)

((1r,3s,5R,7S)-3-hydroxyadamantan-1-yl)benzyl carbamate

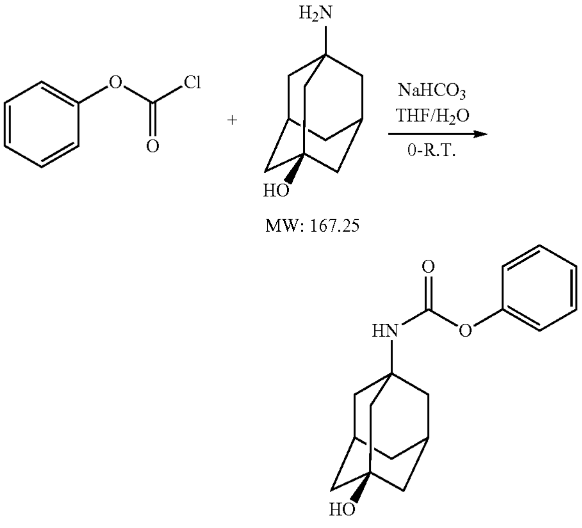

MW: 287.36

To a 100 mL three-necked flask equipped with a thermometer was added amantadine (1 g, 5.98 mmol, 1 eq.), THF (10 mL), water (10 mL), and sodium bicarbonate (0.6 g, 7.18 mmol, 1.2 eq.). The mixture was cooled to 0° C. in ice water bath and a solution of phenyl chloroformate (0.98 g, 6.28 mmol, 1.05 eq.) in THF (10 mL) was added dropwise at 5° C. Then the ice water bath was removed. The reaction was completed after 0.5 h, monitored by TLC. 1.5 h later LC-MS and TLC (EA:PE=1:4) showed that there was raw material remaining. Sodium bicarbonate (0.15 g, 0.3 eq.) and phenyl chloroformate (0.19 g, 0.2 eq.) were added. 6 h later LC-MS showed that there was still raw material, and sodium bicarbonate (0.15 g, 0.3 eq.) and phenyl chloroformate (0.19 g, 0.2 eq.) were added. Overnight, LC-MS confirmed complete reaction. THF was removed under reduced pressure. Then the mixture was extracted with EA (20+20 mL), the organic layers was combined and washed with water (10 mL), dried with anhydrous $MgSO_4$ and filtered. Then EA was removed under reduced pressure to give 2.1 g colorless oil. PE (12 mL) and EA (0.3 mL) were added and the mixture was stirred for 24 h, filtrated and dried under reduced pressure to give 1.51 g off-white solid. Yield: 87.8%. $^1$H NMR (400 MHz, $CDCl_3$), δ 7.35 (t, J=8 Hz, 2H), 7.19 (m, J=8 Hz, 1H), 7.11 (d, J=8 Hz, 2H), 4.99 (s, 1H), 2.30 (t, J=4 Hz, 2H), 1.99 (s, 2H), 1.93 (s, 4H), 1.70 (s, 4H), 1.52~1.61 (m, 3H).

3-((dimethylamino)methyl)-4-hydroxy-N-((1R,3S,5R,7S)-3-hydroxyadamantan-1-yl)-4-(3-methoxyphenyl)piperidine-1-carboxamide hydrochloride (FWBF16)

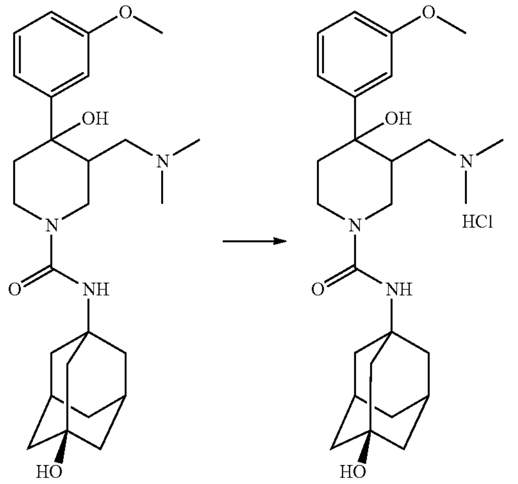

The target product was obtained from the reaction of ((1R,3S,5R,7S)-3-hydroxyadamantan-1-yl)carbamate with intermediate 6 and then salt formation with a two-step yield of 41.7%. $^1$H NMR (400 MHz, $CD_3OD$), δ 7.19 (d, J=8 Hz, 1H), 6.91~9.74 (m, 1H), 6.71~6.74 (m, 1H), 4.07 (d, J=16 Hz, 1H), 3.75 (d, J=12 Hz, 1H), 3.67 (s, 3H), 3.06~3.14 (m, 2H), 2.96 (t, J=12 Hz, 1H), 2.83~2.88 (m, 1H), 2.56~2.62 (m, 4H), 2.42 (s, 3H), 2.18 (m, 1H), 2.10 (s, 2H), 1.96~2.04 (m, 1H), 1.79~1.89 (m, 6H), 1.41~1.55 (m, 8H), 1.16~1.19 (m, 1H). LC-MS-ESI$^+$: [M+H]$^+$ 458.4. LC-MS-ESI$^-$: [M+Cl$^-$]$^-$ 492.4.

Example 3-25

Methyl 2-(3-((dimethylamino)methyl)-4-hydroxy-4-(3-methoxyphenyl)piperidine-1-carboxamide) thiophene-3-carboxylate hydrochloride (FWBF18) Methyl 2-((phenoxycarbonyl)amino)thiophene-3-carboxylate

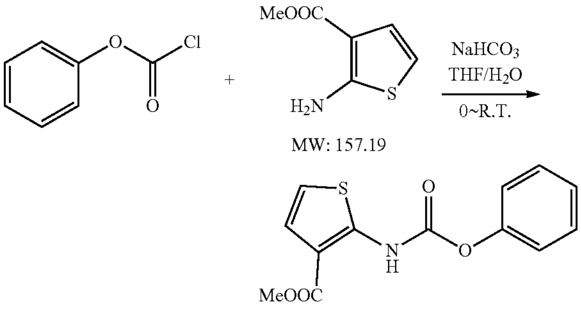

MW: 227.29

To a 100 ml three-necked flask equipped with a thermometer was added methyl 2-aminothiophene-3-carboxylate (2 g, 12.72 mmol, 1 eq.), THF (20 mL), water (20 mL), sodium bicarbonate (1.28 g, 15.26 mmol, 1.2 eq.). The mixture was cooled to 0° C. in ice water bath and a solution of phenyl chloroformate (2.09 g, 13.36 mmol, 1.05 eq.) in THF (10 mL) was added dropwise at 5° C. Then the ice water bath was removed. The reaction was still not completed after 2 h, monitored by TLC, and then sodium bicarbonate (0.33 g, 0.3 eq.) and benzyl chloroformate (0.5 g, 0.25 eq.) were added. After 1 h, the reaction was still not completed, so sodium bicarbonate (1.3 g, 1.2 eq.) and phenyl chloroformate (2.1 g, 1.05 eq.) were added and the mixture was stirred overnight. THF was removed under reduced pressure. Then the mixture was extracted with EA (50+30 m;), the organic layers was combined and washed with water (20 mL) and brine (20 mL) dried with anhydrous $MgSO_4$ and filtered. Then EA was removed under reduced pressure to give 7.09 g light yellow oil. PE (40 mL) and EA (0.5 mL) was added and the mixture was stirred for 24 h, filtrated and dried under reduced pressure to give 2.8 g grey solid. Yield: 79%. $^1$H NMR (400 MHz, $CDCl_3$), δ 10.57 (s, 1H), 7.39~7.43 (m, 2H), 7.19~7.29 (m, 4H), 6.75 (d, J=4 Hz, 1H), 3.91 (s, 3H).

Methyl 2-(3-((dimethylamino)methyl)-4-hydroxy-4-(3-methoxyphenyl)piperidine-1-carboxamide) thiophene-3-carboxylate hydrochloride (FWBF18)

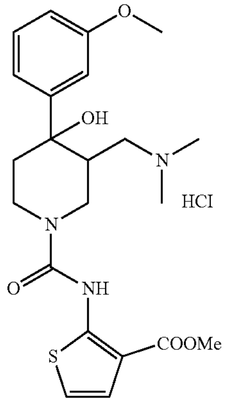

The target product was obtained by the reaction of methyl 2-((phenoxycarbonyl)amino)thiophene-3-carboxylate with Intermediate 6 and then salt formation, with a two-step yield of 82.4%. $^1$H NMR (400 MHz, $CD_3OD$), δ 7.19 (t, J=8 Hz, 1H), 7.05 (d, J=4 Hz, 1H), 7.00 (s, 1H), 6.95 (d, J=8 Hz, 1H), 6.73 (d, J=8 Hz, 1H), 6.64 (d, J=8 Hz, 1H), 4.19 (d, J=12 Hz, 1H), 3.80 (d, J=12 Hz, 1H), 3.74 (s, 3H), 3.67 (s, 3H), 3.44~3.47 (m, 1H), 3.19~3.26 (m, 1H), 2.95~3.10 (m, 1H), 2.58~2.63 (m, 7H), 2.33 (m, 1H), 2.11~2.19 (m, 1H), 1.68 (d, J=16 Hz, 1H). LC-MS-ESI$^+$: [M+H]$^+$ 448.3.

Example 3-26

3-((Dimethylamino)methyl)-4-hydroxy-4-(3-methoxyphenyl)-N-(thiophen-2-yl)piperidine-1-carboxamide hydrochloride (FWBF19) Phenyl thiophene-2-carbamate

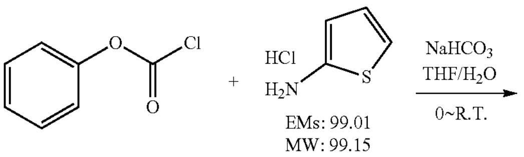

-continued

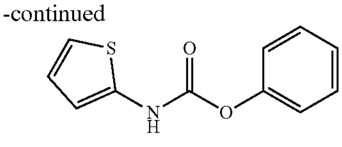

EMs: 219.04
MW: 219.26

To a 100 mL three-necked flask equipped with a thermometer was added 2-aminothiophene hydrochloride (0.617 g, 4.54 mmol, 1 eq.), THF (9 mL), water (6 mL), cooled in an ice-water bath, sodium bicarbonate (1.144 g, 13.62 mmol, 3 eq.). The mixture was cooled to 0° C. in ice water bath and a solution of phenyl chloroformate (0.75 g, 4.77 mmol, 1.05 eq.) in THF (10 ml) was added dropwise at 5° C. Then the ice water bath was removed. The reaction was completed after 16 h, monitored by TLC. THF was removed under reduced pressure. Then the mixture was extracted with EA (40+30 mL) and water (20 mL), the organic layers was combined and washed with brine (20 mL), dried with anhydrous $MgSO_4$ and filtered. Then EA was removed under reduced pressure to give 1.05 g black oil, which was subjected to silica gel column chromatography to give 0.43 g light purple solid. Yield: 39%. $^1H$ NMR (400 MHz, $CDCl_3$), δ 7.391 (t, J=8 Hz, 2H), 7.235 (d, J=7.6 Hz, 1H), 7.196 (d, J=8 Hz, 2H), 6.905 (d, J=5.6 Hz, 1H), 6.844~6.866 (t, 1H), 6.691~6.702 (m, 1H).

3-((Dimethylamino)methyl)-4-hydroxy-4-(3-methoxyphenyl)-N-(thiophen-2-yl)piperidine-1-carboxamide hydrochloride (FWBF19)

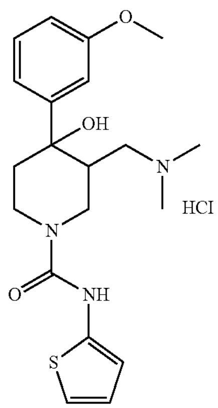

The target product was obtained from the reaction of benzyl thiophene-2-carbamate with intermediate 6 and then salt formation with a two-step yield of 80%. $^1H$ NMR (400 MHz, $CD_3OD$), δ 7.304~7.353 (m, 1H), 7.128~7.135 (m, 1H), 7.082 (d, J=7.6 Hz, 1H), 6.855~6.876 (m, 1H), 6.744~6.810 (m, 1H), 4.313~4.461 (m, 1H), 3.899~4.102 (m, 1H), 3.808 (s, 3H), 3.369~3.468 (m, 1H), 3.200~3.277 (m, 1H), 2.992~3.074 (m, 1H), 2.718~2.790 (m, 4H), 2.561~2.585 (d, 3H), 2.368~2.395 (m, 1H), 2.166~2.146 (m, 1H), 1.696~1.758 (m, 1H). LC-MS-ESI$^+$: $[M+H]^+$ 390.2. LC-MS-ESI$^-$: $[M+H]^-$ 388.2; $[M+Cl]^-$ 424.1.

Example 3-27

Preparation of Membrane Receptors

CHO cells expressing p opioid receptor, δ opioid receptor or κ opioid receptor were cultured in a 10 cm2 dish (F-12 medium+10% neonatal bovine serum) for several days, and the cells were grown to the bottom of the dish and the culture solution was aspirated; 3 ml of PBS/EDTA solution (0.1M NaCl, 0.01M $NaH_2PO4$, 0.04% EDTA) was added to digest the cells for 3-5 min. Ice-cold homogenate (50 mM HEPES PH 7.4, 3 mM MgCl, 1 mM EGTA) was added to the centrifuge tube. The solution and sediment were transferred to a homogenizer and homogenize. Then the homogenate was transferred to a centrifuge tube and centrifuge at 18000 rpm for 15 min, 2 times. The obtained precipitate was homogenized with 50 mM Tris-HCl, pH 7.4 buffer and divided into centrifuge tubes and stored at −70° C. in the refrigerator.

Competitive Binding Test

The total binding tube was added with the equivalent of 20-30 μg of expressed membrane receptor protein and [3H]-labeled ligand (1-2 nM). The corresponding non-specific binding tube was added with 1 μM of the corresponding ligand, and different concentrations of various screened opioid ligands were added to the sample tubes in a final volume of 100 μl, incubated at 30° C. for 30 min, and the reaction was terminated in ice water. The reaction was terminated by incubation in ice-cold water for 30 min at 30° C. The samples were filtered under negative pressure through GF/C (whatman) glass fiber filter paper on a Millipore sample collector. The reaction was rinsed three times with 4 ml of 50 mM Tris-HCl (pH 7.4). The filter paper was dried and placed in 0.5 ml Eppendorf tubes with 0.5 ml of lipophilic scintillation solution. The radioactivity was measured by PERKIN ELMER PRI-CARB 2910 liquid scintillation counter and the inhibition rate was calculated. The experiment was repeated more than three times, with three replicate tubes per group.

Inhibition rate=(total binding tube dpm−sample tube dpm)/(total binding tube dpm−non-specific binding tube dpm)×100%

$IC_{50}$ was calculated using Graphpad Prism 5.0 software. The Ki value was calculated according to the following equation. $Ki=IC_{50}/(1+[IL]/Kd)$. [IL] is the concentration of the added labeled ligand and Kd is the equilibrium dissociation parameter of the labeled ligand.

Table 3-1 showed the Ki values of affinity constants of representative compounds for opioid receptors, expressed as the mean±standard deviation of three independent measurements.

TABLE 3-1

| Opioid receptor binding rate or Ki at 1 μM concentration of compounds | | | | |
|---|---|---|---|---|
| | | Binding rate (%) or Ki (nM) | | |
| Compound | Structure | μOR | δOR | κOR |
| Tramadol | 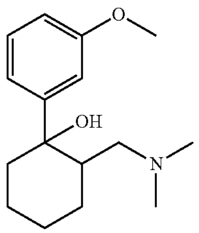 [SMILES: COc1cccc(C2(O)CCCCC2CN(C)C)c1] | 6.0% | 0% | 0% |
| 3-((Dimethylamino)methyl)-4-hydroxy-4-(3-methoxyphenyl)-N-phenylpiperidine-1-carboxamide hydrochloride (FWBF1) | 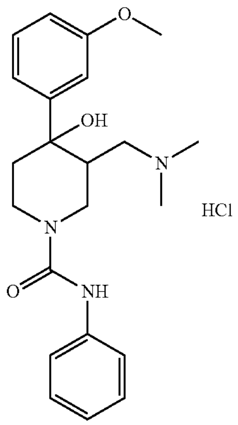 [SMILES: COc1cccc(C2(O)CCN(C(=O)Nc3ccccc3)CC2CN(C)C)c1 ; Cl] | 7.3 ± 0.5 nM | 849.4 ± 96.6 nM | 49.1 ± 6.9 nM |
| N-(3-Chlorophenyl)-3-((dimethylamino)methyl)-4-hydroxy-4-(3-methoxyphenyl)piperidine-1-carboxamide hydrochloride (FWBF2) | 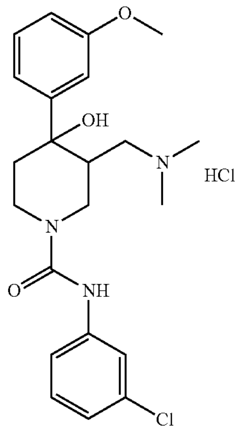 [SMILES: COc1cccc(C2(O)CCN(C(=O)Nc3cccc(Cl)c3)CC2CN(C)C)c1 ; Cl] | 14.1 ± 2.7 nM | 537 ± 69.3 nM | 718.6 ± 197.0 nM |
| N-(3-Chlorophenyl)-3-((dimethylamino)methyl)-4-hydroxy-4-(3-methoxyphenyl)-N-methylpiperidine-1 -carboxamide hydrochloride (FWBF3) | 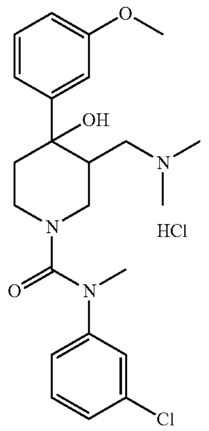 [SMILES: COc1cccc(C2(O)CCN(C(=O)N(C)c3cccc(Cl)c3)CC2CN(C)C)c1 ; Cl] | 8.7 ± 3.7% | 0% | 14.0 ± 9.7% |

TABLE 3-1-continued

| Opioid receptor binding rate or Ki at 1 μM concentration of compounds | | | | |
|---|---|---|---|---|
| | | Binding rate (%) or Ki (nM) | | |
| Compound | Structure | μOR | δOR | κOR |
| N-(4-Chlorophenyl)-3-((dimethylamino)methyl)-4-hydroxy-4-(3-methoxyphenyl)piperidine-1-carboxamide hydrochloride (FWBF4) | 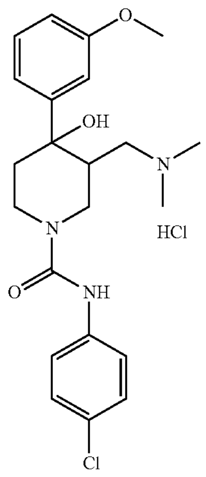 [SMILES: COc1cccc(C2(O)CCN(C(=O)Nc3ccc(Cl)cc3)CC2CN(C)C)c1 ; Cl] | 48.8 ± 3.9% | 0% | 22.1 ± 10.7% |
| N-(3,4-Dichlorophenyl)-3-((dimethylamino)methyl)-4-hydroxy-4-(3-methoxyphenyl)piperidine-1-carboxamide hydrochloride (FWBF5) | 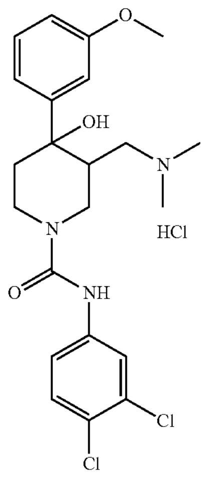 [SMILES: COc1cccc(C2(O)CCN(C(=O)Nc3ccc(Cl)c(Cl)c3)CC2CN(C)C)c1 ; Cl] | 46.0 ± 5.4% | 0% | 18.2 ± 1.9% |
| 3-((Dimethylamino)methyl)-4-hydroxy-4-(3-methoxyphenyl)-N-(3,4,5-trichlorophenyl)piperidine-1-carboxamide hydrochloride (FWBF6) | 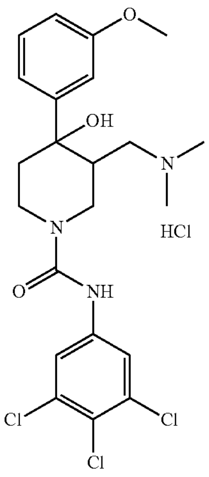 | 13.2 ± 8.0% | 0% | 0% |

TABLE 3-1-continued

| Opioid receptor binding rate or Ki at 1 μM concentration of compounds | | | | |
|---|---|---|---|---|
| | | Binding rate (%) or Ki (nM) | | |
| Compound | Structure | μOR | δOR | κOR |
| 3-((Dimethylamino)methyl)-N-(3-fluorophenyl)-4-hydroxy-4-(3-methoxyphenyl)piperidine-1-carboxamide hydrochloride (FWBF7) | 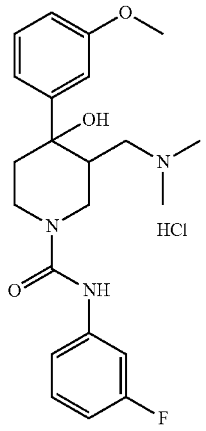 [SMILES: COc1cccc(C2(O)CCN(C(=O)Nc3cccc(F)c3)CC2CN(C)C)c1 ; Cl] | 36.7 ± 7.4% | 9.2 ± 7.8% | 0% |
| N-(3,4-difluorophenyl)-3-((dimethylamino)methyl)-4-hydroxy-4-(3-methoxyphenyl)piperidine-1-carboxamide hydrochloride (FWBF8) | 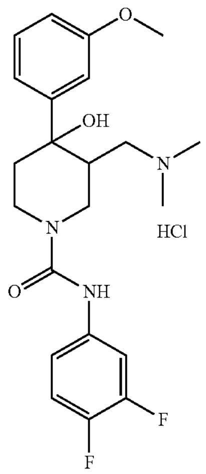 [SMILES: COc1cccc(C2(O)CCN(C(=O)Nc3ccc(F)c(F)c3)CC2CN(C)C)c1 ; Cl] | 13.6 ± 13.1% | 16.4 ± 10.6% | 0% |
| N-(3-chloro-4-fluorophenyl)-3-((dimethylamino)methyl)-4-hydroxy-4-(3-methoxyphenyl)piperidine-1-carboxamide hydrochloride (FWBF9) | 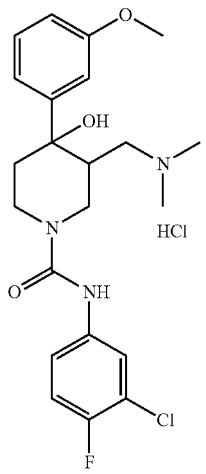 | 25.0 ± 13.3% | 21.6 ± 13.4% | 7.1 ± 5.0% |

TABLE 3-1-continued

| Opioid receptor binding rate or Ki at 1 μM concentration of compounds | | | | |
|---|---|---|---|---|
| | | Binding rate (%) or Ki (nM) | | |
| Compound | Structure | μOR | δOR | κOR |
| N-(3,5-Bis(trifluoromethyl) phenyl)-3-((dimethylamino)methyl)-4-hydroxy-4-(3-methoxyphenyl)piperidine-1-carboxamide hydrochloride (FWBF10) | 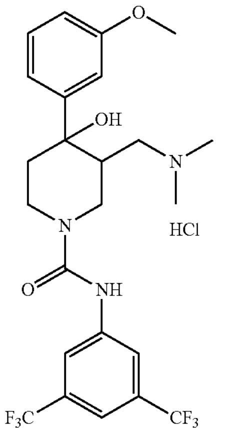 [SMILES: COc1cccc(C2(O)CCN(C(=O)Nc3cc(C(F)(F)F)cc(C(F)(F)F)c3)CC2CN(C)C)c1 ; Cl] | 0% | 0.9% | 8.6 ± 4.8% |
| 3-((Dimethylamino)methyl)-4-hydroxy-4-(3-methoxyphenyl)-N-(naphthalen-2-yl)piperidine-1-carboxamide hydrochloride (FWBF11) | 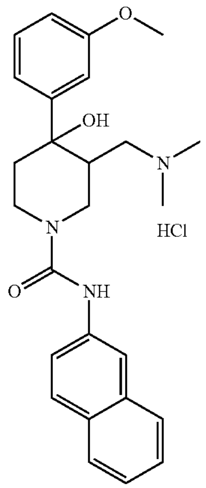 | 0.5% | 0% | 3.9% |
| N-Benzyl-3-((dimethylamino)methyl)-4-hydroxy-4-(3-methoxyphenyl)piperidine-1-carboxamide hydrochloride (FWBF12) | 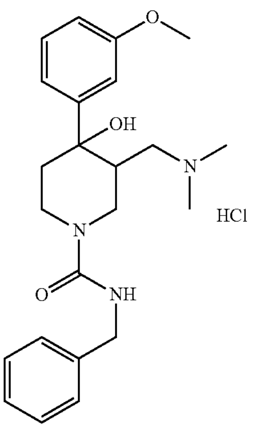 [SMILES: COc1cccc(C2(O)CCN(C(=O)NCc3ccccc3)CC2CN(C)C)c1 ; Cl] | 35.1 ± 4.4% | 2.6 ± 2.9% | 5.1 ± 4.0% |

TABLE 3-1-continued

| Opioid receptor binding rate or Ki at 1 μM concentration of compounds | | | | |
|---|---|---|---|---|
| | | Binding rate (%) or Ki (nM) | | |
| Compound | Structure | μOR | δOR | κOR |
| 3-((Dimethylamino)methyl)-4-hydroxy-4-(3-methoxyphenyl)-N-((S)-1-phenylethyl)piperidine-1-carboxamide hydrochloride (FWBF13) | 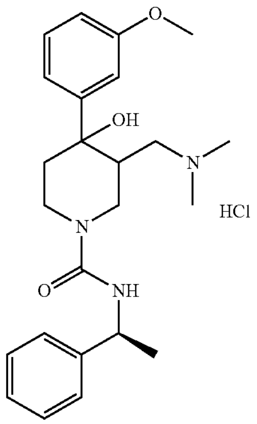 [SMILES: COc1cccc(C2(O)CCN(C(=O)N[C@@H](C)c3ccccc3)CC2CN(C)C)c1 ; Cl] | 20.5 ± 5.5% | 0% | 4.1 ± 6.7% |
| N-((3s,5s,7s)-adamantan-1-yl)-3-((dimethylamino)methyl)-4-hydroxy-4-(3-methoxyphenyl)piperidine-1-carboxamide hydrochloride (FWBF14) | 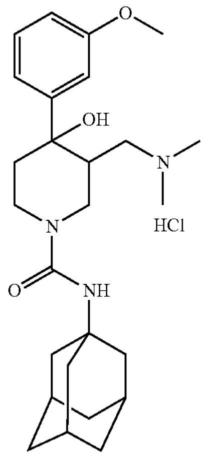 [SMILES: COc1cccc(C2(O)CCN(C(=O)NC34CC5CC(CC(C5)C3)C4)CC2CN(C)C)c1 ; Cl] | 13.5 ± 4.8% | 0% | 17.9 ± 4.8% |
| N-(1-((3r,5r,7r)-adamantan-1-yl)ethyl)-3-((dimethylamino)methyl)-4-hydroxy-4-(3-methoxyphenyl)piperidine-1-carboxamide hydrochloride (FWBF15) | 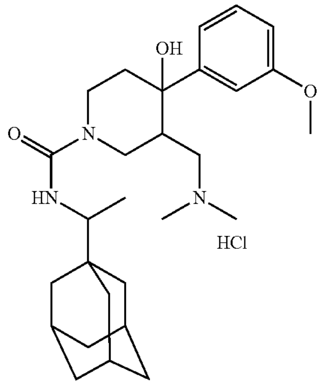 [SMILES: COc1cccc(C2(O)CCN(C(=O)NC(C)C34CC5CC(CC(C5)C3)C4)CC2CN(C)C)c1 ; Cl] | 32.8 ± 5.5% | 0% | 10.4 ± 10.2% |

TABLE 3-1-continued

| Opioid receptor binding rate or Ki at 1 μM concentration of compounds | | | | |
|---|---|---|---|---|
| | | Binding rate (%) or Ki (nM) | | |
| Compound | Structure | μOR | δOR | κOR |
| 3-((Dimethylamino)methyl)-4-hydroxy-N-((1r,3s,5R,7S)-3-hydroxyadamantan-1-yl)-4-(3-methoxyphenyl)piperidine-1-carboxamide hydrochloride (FWBF16) | 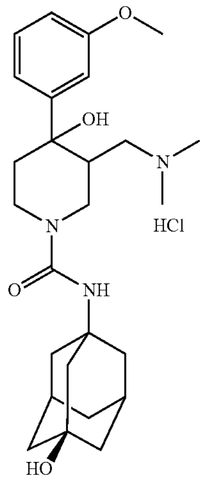 | 0% | 1.9% | 0% |
| Methyl 3-(3-((dimethylamino)methyl)-4-hydroxy-4-(3-methoxyphenyl)piperidine-1-carboxamide)thiophene-2-carboxylate hydrochloride (FWBF17) | 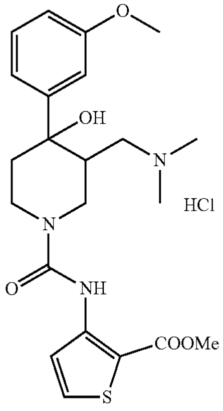 [SMILES: COC(=O)c1sccc1NC(=O)N1CCC(O)(c2cccc(OC)c2)C(CN(C)C)C1 ; Cl] | 10.2 ± 9.0% | 0% | 0% |
| Methyl 2-(3-((dimethylamino)methyl)-4-hydroxy-4-(3-methoxyphenyl)piperidine-1-carboxamide)thiophene-3-carboxylate hydrochloride (FWBF18) | 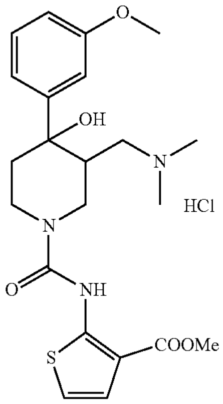 [SMILES: COC(=O)c1ccsc1NC(=O)N1CCC(O)(c2cccc(OC)c2)C(CN(C)C)C1 ; Cl] | 2.3% | 16.0 ± 12.4% | 9.2 ± 3.1% |

TABLE 3-1-continued

| Opioid receptor binding rate or Ki at 1 μM concentration of compounds | | | | |
|---|---|---|---|---|
| | | Binding rate (%) or Ki (nM) | | |
| Compound | Structure | μOR | δOR | κOR |
| 3-((Dimethylamino)methyl)-4-hydroxy-4-(3-methoxyphenyl)-N-(thiophen-2-yl)piperidine-1-carboxamide hydrochloride (FWBF19) | 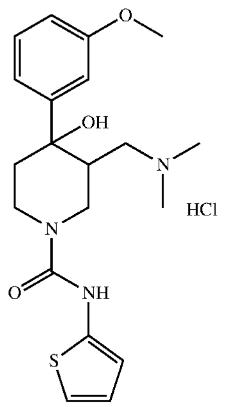 [SMILES: COc1cccc(C2(O)CCN(C(=O)Nc3cccs3)CC2CN(C)C)c1 ; Cl] | 0% | 38.2 ± 9.4% | 27.5 ± 6.4% |

In the column "Binding rate (%) or Ki (nM)" of Table 3-1, the values expressed in percentage refers to the binding rate and the values in nM refers to Ki.

As can be seen from Table 3-1, the compounds of the invention exhibit comparable or stronger affinity for the three opioid receptors than tramadol.

Example 3-28

Analgesia by Intracorporeal Hot Plate Method

Female mice weighing about 20 g were placed on a hot plate apparatus preheated to 55° C., and the latency of the hindfoot response of the mice was used as the pain threshold indicator. Animals were screened before the experiment, and those with response latency less than 5 s or greater than 30 s were excluded. To prevent foot scalding, the maximum observation time was set at 60 s. The basal pain threshold was the average of two measurements, with a 5-min interval between measurements. Pain thresholds were measured at 15 min, 30 min, 60 min and 120 min after intraperitoneal administration in each group of mice. The percentage of analgesic effectiveness (% MPE) was calculated according to the following formula.

$$MPE = \frac{\text{Incubation period after administration} - \text{Incubation period before administration}}{60 - \text{Incubation period after administration}} \times 100\%$$

$ED_{50}$ values were calculated based on the effective percentage of analgesia using Graphpad Prism 5.0.

TABLE 3-2

| Maximum percentage effective analgesic or $ED_{50}$ values of compound at 10 mg/kg dose by hot plate method | | |
|---|---|---|
| Compound | Structure | % MPE or ED50 @ 10 mg/kg |
| Tramadol | 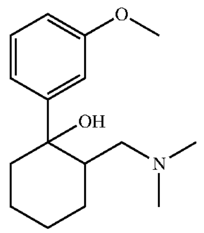 [SMILES: COc1cccc(C2(O)CCCCC2CN(C)C)c1] | 64.5% (@50 mg/kg, no effective @10 mg/kg) |

TABLE 3-2-continued

| Maximum percentage effective analgesic or $ED_{50}$ values of compound at 10 mg/kg dose by hot plate method | | |
|---|---|---|
| Compound | Structure | % MPE or ED50 @ 10 mg/kg |
| 3-((Dimethylamino)methyl)-4-hydroxy-4-(3-methoxyphenyl)-N-phenylpiperidine-1-carboxamide hydrochloride (FWBF1) | 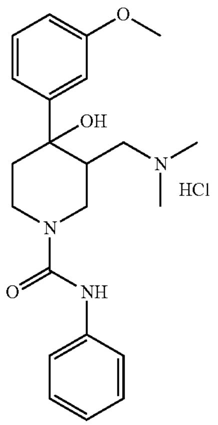 [SMILES: COc1cccc(C2(O)CCN(C(=O)Nc3ccccc3)CC2CN(C)C)c1 ; Cl] | 2.75 mg/kg |
| N-(3-Chlorophenyl)-3-((dimethylamino)methyl)-4-hydroxy-4-(3-methoxyphenyl)piperidine-1-carboxamide hydrochloride (FWBF2) | 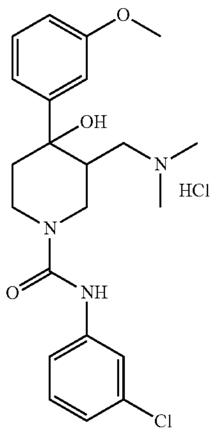 [SMILES: COc1cccc(C2(O)CCN(C(=O)Nc3cccc(Cl)c3)CC2CN(C)C)c1 ; Cl] | 21.27% |
| N-(3-Chlorophenyl)-3-((dimethylamino)methyl)-4-hydroxy-4-(3-methoxyphenyl)-N-methylpiperidine-1-carboxamide hydrochloride (FWBF3) | 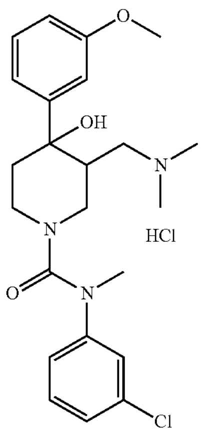 [SMILES: COc1cccc(C2(O)CCN(C(=O)N(C)c3cccc(Cl)c3)CC2CN(C)C)c1 ; Cl] | 3.36% |

TABLE 3-2-continued

| Compound | Structure | % MPE or ED50 @ 10 mg/kg |
|---|---|---|
| Maximum percentage effective analgesic or $ED_{50}$ values of compound at 10 mg/kg dose by hot plate method | | |
| N-(4-Chlorophenyl)-3-((dimethylamino)methyl)-4-hydroxy-4-(3-methoxyphenyl)piperidine-1-carboxamide hydrochloride (FWBF4) | 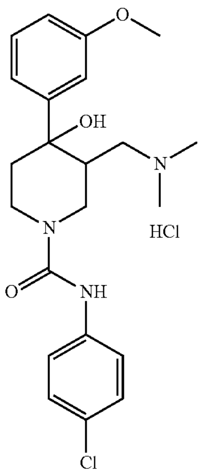 [SMILES: COc1cccc(C2(O)CCN(C(=O)Nc3ccc(Cl)cc3)CC2CN(C)C)c1 ; Cl] | 68.95% |
| N-(3,4-Dichlorophenyl)-3-((dimethylamino)methyl)-4-hydroxy-4-(3-methoxyphenyl)piperidine-1-carboxamide hydrochloride (FWBF5) | 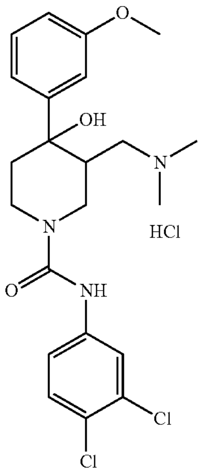 [SMILES: COc1cccc(C2(O)CCN(C(=O)Nc3ccc(Cl)c(Cl)c3)CC2CN(C)C)c1 ; Cl] | 25.42% |
| 3-((Dimethylamino)methyl)-4-hydroxy-4-(3-methoxyphenyl)-N-(3,4,5-trichlorophenyl)piperidine-1-carboxamide hydrochloride (FWBF6) | 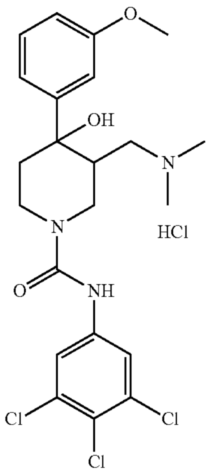 [SMILES: COc1cccc(C2(O)CCN(C(=O)Nc3cc(Cl)c(Cl)c(Cl)c3)CC2CN(C)C)c1 ; Cl] | 4.54% |

TABLE 3-2-continued

| Maximum percentage effective analgesic or $ED_{50}$ values of compound at 10 mg/kg dose by hot plate method | | |
|---|---|---|
| Compound | Structure | % MPE or ED50 @ 10 mg/kg |
| 3-((Dimethylamino)methyl)-N-(3-fluorophenyl)-4-hydroxy-4-(3-methoxyphenyl)piperidine-1-carboxamide hydrochloride (FWBF7) | 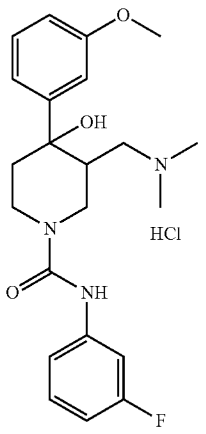 [SMILES: COc1cccc(C2(O)CCN(C(=O)Nc3cccc(F)c3)CC2CN(C)C)c1 ; Cl] | 4.12 mg/kg |
| N-(3,4-difluoropheny])-3-((dimethylamino)methyl)-4-hydroxy-4-(3-methoxyphenyl)piperidine-1-carboxamide hydrochloride (FWBF8) | 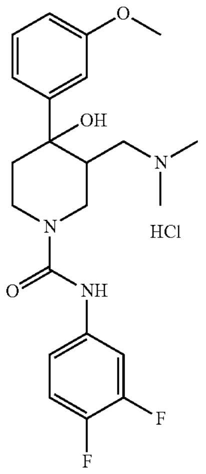 [SMILES: COc1cccc(C2(O)CCN(C(=O)Nc3ccc(F)c(F)c3)CC2CN(C)C)c1 ; Cl] | 21.76% |
| N-(3-chloro-4-fluorophenyl)-3-((dimethylamino)methyl)-4-hydroxy-4-(3-methoxyphenyl)piperidine-1-carboxamide hydrochloride (FWBF9) | 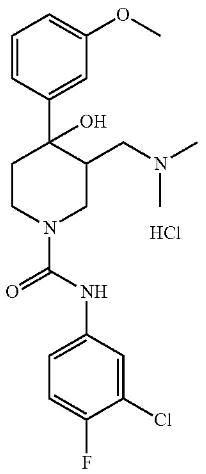 [SMILES: COc1cccc(C2(O)CCN(C(=O)Nc3ccc(F)c(Cl)c3)CC2CN(C)C)c1 ; Cl] | 18.15% |

TABLE 3-2-continued

| Maximum percentage effective analgesic or $ED_{50}$ values of compound at 10 mg/kg dose by hot plate method | | |
|---|---|---|
| Compound | Structure | % MPE or ED50 @ 10 mg/kg |
| N-(3,5-Bis(trifluoromethyl)phenyl)-3-((dimethylamino)methyl)-4-hydroxy-4-(3-methoxyphenyl)piperidine-1-carboxamide hydrochloride (FWBF10) | 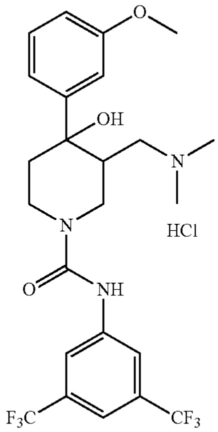 [SMILES: COc1cccc(C2(O)CCN(C(=O)Nc3cc(C(F)(F)F)cc(C(F)(F)F)c3)CC2CN(C)C)c1 ; Cl] | 7.74% |
| 3-((Dimethylamino)methyl)-4-hydroxy-4-(3-methoxyphenyl)-N-(naphthalen-2-yl)piperidine-1-carboxamide hydrochloride (FWBF11) | 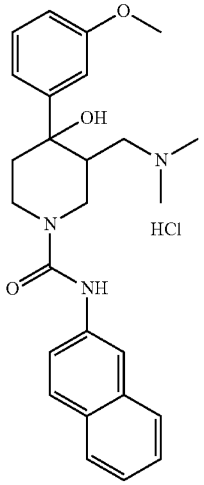 [SMILES: COc1cccc(C2(O)CCN(C(=O)Nc3ccc4ccccc4c3)CC2CN(C)C)c1 ; Cl] | 4.41% |
| N-Benzyl-3-((dimethylamino)methyl)-4-hydroxy-4-(3-methoxyphenyl)piperidine-1-carboxamide hydrochloride (FWBF12) | 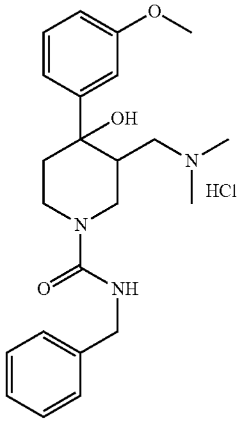 [SMILES: COc1cccc(C2(O)CCN(C(=O)NCc3ccccc3)CC2CN(C)C)c1 ; Cl] | 15.07% |

TABLE 3-2-continued

| Maximum percentage effective analgesic or $ED_{50}$ values of compound at 10 mg/kg dose by hot plate method | | |
|---|---|---|
| Compound | Structure | % MPE or ED50 @ 10 mg/kg |
| 3-((Dimethylamino)methyl)-4-hydroxy-4-(3-methoxyphenyl)-N-((S)-1-phenylethyl)piperidine-1-carboxamide hydrochloride (FWBF13) | 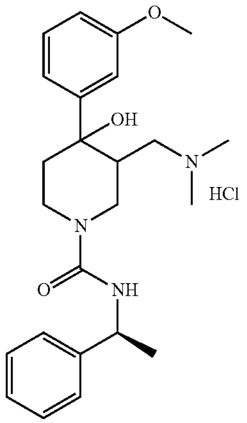 [SMILES: COc1cccc(C2(O)CCN(C(=O)N[C@@H](C)c3ccccc3)CC2CN(C)C)c1 ; Cl] | 5.77% |
| N-((3s,5s,7s)-adamantan-1-yl)-3-((dimethylamino)methyl)-4-hydroxy-4-(3-methoxyphenyl)piperidine-1-carboxamide hydrochloride (FWBF14) | 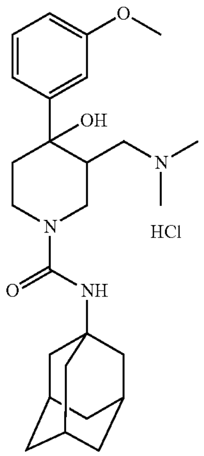 [SMILES: COc1cccc(C2(O)CCN(C(=O)NC34CC5CC(CC(C5)C3)C4)CC2CN(C)C)c1 ; Cl] | 24.15% |
| N-(1-((3r,5r,7r)-adamantan-1-yl)ethyl)-3-((dimethylamino)methyl)-4-hydroxy-4-(3-methoxyphenyl)piperidine-1-carboxamide hydrochloride (FWBF15) | 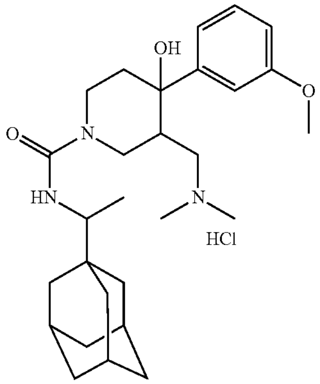 [SMILES: COc1cccc(C2(O)CCN(C(=O)NC(C)C34CC5CC(CC(C5)C3)C4)CC2CN(C)C)c1 ; Cl] | 22.07% |

TABLE 3-2-continued

| Maximum percentage effective analgesic or $ED_{50}$ values of compound at 10 mg/kg dose by hot plate method | | |
|---|---|---|
| Compound | Structure | % MPE or ED50 @ 10 mg/kg |
| 3-((Dimethylamino)methyl)-4-hydroxy-N-(1r,3s,5R,7S)-3-hydroxyadamantan-1-yl)-4-(3-methoxyphenyl)piperidine-1-carboxamide hydrochloride (FWBF16) | 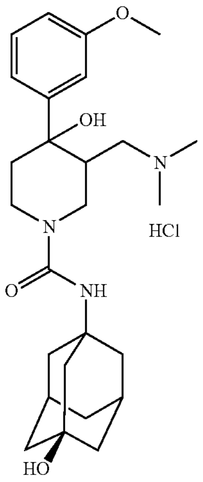 | 16.07% |
| Methyl 3-(3-((dimethylamino)methyl)-4-hydroxy-4-(3-methoxyphenyl)piperidine-1-carboxamide)thiophene-2-carboxylate hydrochloride (FWBF17) | 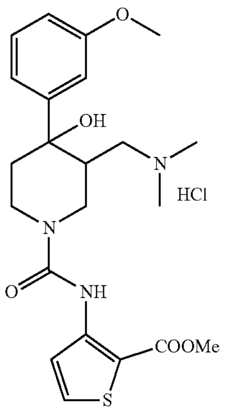 [SMILES: COC(=O)c1sccc1NC(=O)N1CCC(O)(c2cccc(OC)c2)C(CN(C)C)C1 ; Cl] | 19.34% |
| Methyl 2-(3-((dimethylamino)methyl)-4-hydroxy-4-(3-methoxyphenyl)piperidine-1-carboxamide)thiophene-3-carboxylate hydrochloride (FWBF18) | 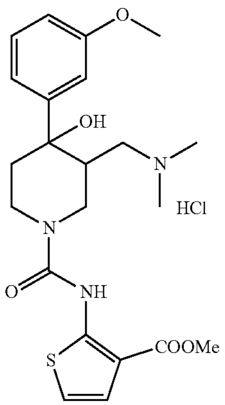 [SMILES: COC(=O)c1ccsc1NC(=O)N1CCC(O)(c2cccc(OC)c2)C(CN(C)C)C1 ; Cl] | 22.76% |

TABLE 3-2-continued

| Maximum percentage effective analgesic or $ED_{50}$ values of compound at 10 mg/kg dose by hot plate method | | |
|---|---|---|
| Compound | Structure | % MPE or ED50 @ 10 mg/kg |
| 3-((Dimethylamino)methyl)-4-hydroxy-4-(3-methoxyphenyl)-N-(thiophen-2-yl)piperidine-1-carboxamide hydrochloride (FWBF19) | 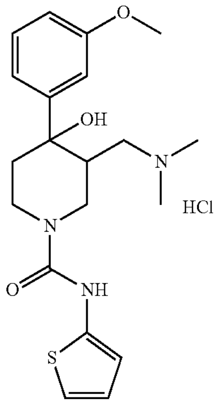 [SMILES: COc1cccc(C2(O)CCN(C(=O)Nc3cccs3)CC2CN(C)C)c1 ; Cl] | 20.07% |

In the column "Binding rate (%) or Ki (nM)" of Table 3-1, the values expressed in percentage refers to the binding rate and the values in nM refers to Ki.

As can be seen from Table 3-1, the compounds of the invention exhibit comparable or stronger affinity for the three opioid receptors than tramadol.

EXAMPLE 4

Example 4-1

Preparation of N-methyl-N-methylenemethanaminium chloride (Intermediate 2)

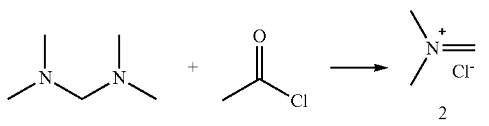

A 1 L three-necked flask with a nitrogen balloon, thermometer and constant pressure dropping funnel was charged with N,N,N',N'-tetramethylmethane diamine (60 g, 587.2 mmol, 1 eq.) and methyl tert-butyl ether (500 mL) and cooled to 0° C. Acetyl chloride (46.1 g, 587.2 mmol, 1 eq.) was added dropwise at 30° C. After dropwise addition, stirred for 30 min, extracted and filtered, the filter cake was added with acetonitrile (100 mL) and MTBE (25 mL) and stirred for 10 min, extracted and filtered, and the filter cake was evaporated under reduced pressure (55° C.) to yield 46 g of off-white solid in 83.7% yield.

Example 4-2

Preparation of tert-butyl 3-((dimethylamino) methyl)-4-oxopiperidine-1-carboxylate (Intermediate 3)

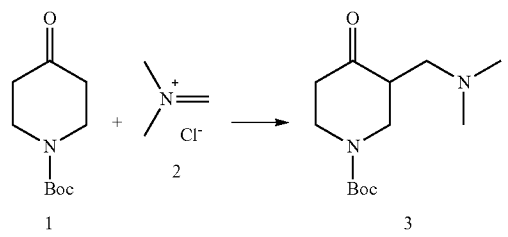

A 250 mL single-necked flask was added with Boc-piperidone (10 g, 50.2 mmol, 1 eq.), acetonitrile (100 mL), N-methyl-N-methylenemethonium chloride (5.64 g, 60.24 mmol, 1.2 eq.), acetyl chloride (0.20 g, 2.51 mmol, 0.05 eq.) under stirring. Stirring at room temperature (25-30° C.) for 2 h, TLC (DCM and DCM:MeOH=10:1, color development of ninhydrin) showed complete reaction of the raw materials. The acetonitrile was evaporated under reduced pressure (30° C.), and DCM (80 mL) and saturated sodium bicarbonate (80 mL) were added, mixed, left to stand, stratified and partitioned. Aqueous phase DCM (80+40 mL) was extracted. The organic phase was combined, washed with water (50 mL), dried with anhydrous magnesium sulfate, filtered, and the filtrate was evaporated under reduced pressure to yield 11.75 g of brownish yellow viscous liquid in 91.3% yield.

Example 4-3

Preparation of tert-butyl 3-((dimethylamino) methyl)-4-hydroxy-4-(3-methoxyphenyl)piperidine-1-carboxylate (Intermediate 5)

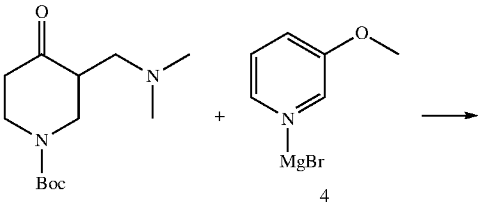

3 4

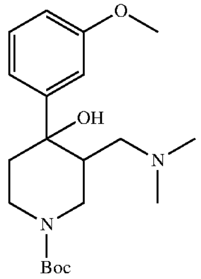

5

A 500 mL four-necked flask with a nitrogen bulb, constant pressure dropping funnel, condenser tube and thermometer was charged with magnesium flakes (2.75 g, 114.6 mmol, 2.5 eq.), THF (80 mL), 1 iodine grain, and a small amount of THF (30 mL) solution of m-bromomethyl ether (21.4 g, 114.6 mmol, 2.5 eq.), refluxed at elevated temperature and stopped heating. The THF solution of m-bromoanisole was added slowly dropwise (about 20 min). After dropwise addition, a solution of THF (50 mL) of Boc-dimethylaminomethylpiperidone (11.75 g, 45.84 mmol, 1 eq.) was added dropwise at 0° C. After the dropwise addition, keep warm and stir. The reaction solution was poured into an aqueous solution of saturated ammonium chloride (100 mL) and THF was evaporated under reduced pressure (30-40° C.). Extract with ethyl acetate (100+50 mL). The organic phases were combined, washed with water (30 mL), saturated sodium chloride (30 mL), dried with anhydrous magnesium sulfate, extracted and filtered, and the filtrate was evaporated under reduced pressure to yield 19.9 g of yellow liquid.

Example 4-4

Preparation of tert-butyl (3R,4S)-3-((dimethylamino)methyl)-4-hydroxy-4-(3-methoxyphenyl) piperidine-1-carboxylate

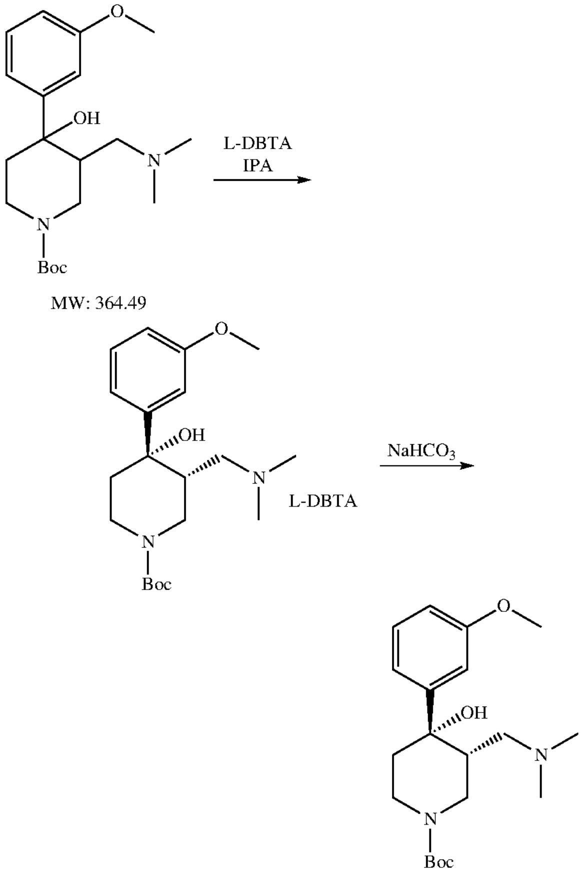

Example 4-3 The yellow oil obtained was added with IPA (isopropyl alcohol) (100 mL), L-DBTA (L-(−)-dibenzoyl-tartaric acid) (13.14 g, 36.67 mmol, 0.8 eq.) was added under stirring and dissolved at reflux at elevated temperature. The mixture was stirred to room temperature to add crystalline seeds (20 mg). The mixture was stirred overnight (12 h), precipitate solid, ice salt bath stirring (−10~0° C.) for 1.5 h. Filter, filter cake cold IPA (10 mL) dripping, evaporate dry under reduced pressure (60° C.), to obtain 8.1 g of off-white solid. After 2 h of filtration, the filter cake was washed with room temperature IPA (10 mL) and evaporated under reduced pressure to obtain 6.06 g of white solid. 5.96 g was dissolved by adding IPA (60 mL) at reflux at elevated temperature, stirred at lower temperature, and then stirred for 1 h at room temperature. The obtained solid was freed with saturated sodium bicarbonate solution and ethyl acetate to obtain the target conformational isomers. LC-MS-ESI$^+$: $[M+H]^+$ 365.3.

$$[\alpha]_D^{24.4} = 30.6°$$

(c=1, $CHCl_3$). $^1H$ NMR (400 MHz, $CD_3OD$), δ 7.252 (t, J=8 Hz, 1H), 7.043 (t, J=2 Hz, 1H), 6.980 (d, J=7.6 Hz, 1H), 6.792 (dd, J1=8 Hz, J2=2.4 Hz, 1H), 4.193~4.203 (m, 1H), 3.953~3.992 (m, 1H), 3.791 (s, 3H), 3.344 (s, 1H), 3.193 (s, 1H), 2.995~3.085 (t, 1H), 2.313~2.370 (q, 1H), 2.045~2.106 (m, 1H), 2.045 (s, 6H), 1.932~2.012 (m, 1H), 1.808 (d, J=12.8 Hz, 1H), 1.595 (d, J=14 Hz, 1H), 1.494 (s, 9H).

Examples 4-5

Preparation of tert-butyl (3S,4R)-3-((dimethylamino)methyl)-4-hydroxy-4-(3-methoxyphenyl) piperidine-1-carboxylate

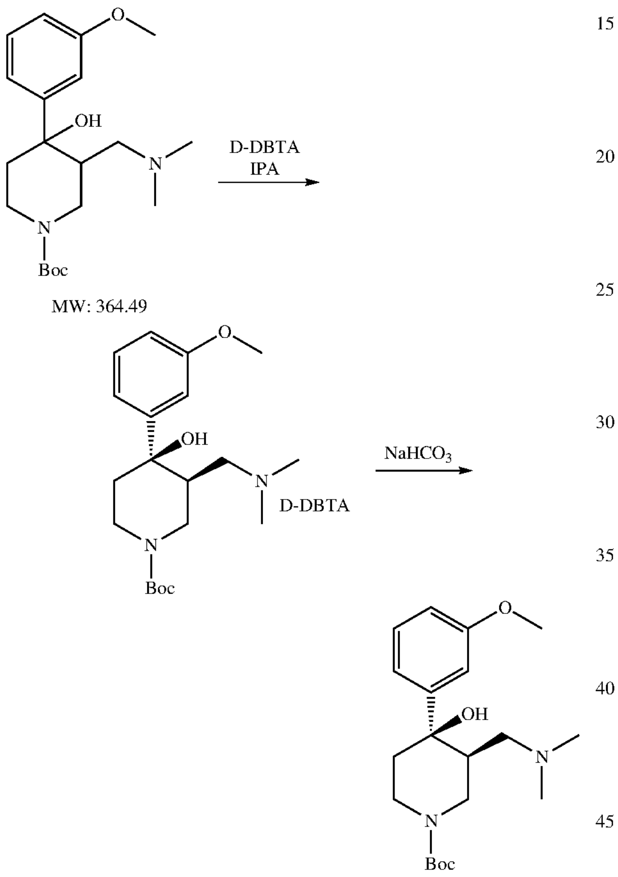

The crude product (13.44 g) and IPA (120 mL) were obtained by adding D-DBTA (D-(+)-dibenzoyltartaric acid, 13.14 g, 36.67 mmol, 0.8 eq.) in a 500 mL single-necked flask after salt formation in Example 4 and dissolving at reflux at elevated temperature. Cooled to room temperature with crystalline seeds (20 mg), stirred overnight (12 h), precipitated a large amount of solid, cooled in an ice water bath for 1 h. Filtered, the filter cake was drenched with cold IPA (10 mL) and evaporated under reduced pressure to yield 7.7 g of off-white solid. 7.6 g IPA (110 mL) was added and raised the temperature and dissolve at reflux, lower the temperature and stir. After stirring for 2 h at room temperature, the filter cake was filtered and evaporated under reduced pressure to yield 6.48 g of a white solid. 6.38 g of IPA (64 mL) was added and dissolved at reflux at elevated temperature, stirred at lower temperature. The filter cake was drenched with IPA (10 mL) and evaporated under reduced pressure (60° C.) to yield 5.88 g of a white solid. The obtained solid was freed with saturated sodium bicarbonate solution and ethyl acetate to obtain the target conformational isomers. LC-MS-ESI$^+$: $[M+H]^+$ 365.3.

$$[\alpha]_D^{30.5} = -32.4°$$

(c=1, $CHCl_3$). $^1H$ NMR (400 MHz, CD3OD), δ 7.251 (t, J=8 Hz, 1H), 7.043 (t, J=2 Hz, 1H), 6.979 (d, J=8 Hz, 1H), 6.791 (dd, J1=8 Hz, J2=2.4 Hz, 1H), 4.192~4.236 (m, 1H), 3.957~3.992 (m, 1H), 3.790 (s, 3H), 3.343 (s, 1H), 3.193 (s, 1H), 2.995~3.085 (t, 1H), 2.310~2.367 (q, 1H), 2.043~2.105 (m, 1H), 2.043 (s, 6H), 1.931~2.010 (m, 1H), 1.810 (d, J=12.8 Hz, 1H), 1.593 (d, J=14 Hz, 1H), 1.494 (s, 9H).

Examples 4-6

Preparation of (3R,4S)-3-((dimethylamino)methyl)-4-(3-methoxyphenyl)piperidin-4-ol hydrochloride

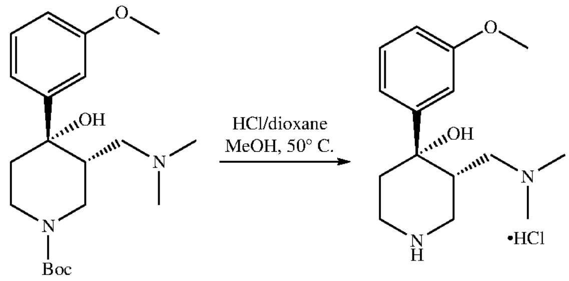 [SMILES: COc1cccc([C@]2(O)CCN(C(=O)OC(C)(C)C)C[C@H]2CN(C)C)c1 ; COc1cccc([C@]2(O)CCNC[C@H]2CN(C)C)c1 ; Cl]

A 100 mL single-port vial was added with (3R,4S)-3-((dimethylamino)methyl)-4-hydroxy-4-(3-methoxyphenyl) piperidine-1-carboxylic acid tert-butyl ester (2 g, 5.49 mmol, 1 eq.), methanol (10 mL), stirred to dissolve, and HCl/Dioxane (3.4 mL, 13.72 mmol, 2.5 eq.) was added and raised to 50° C. with stirring, stirred at ° C. 2 h later TLC (DCM:MeOH=10:1) showed complete reaction. The volatiles and solvent were evaporated under reduced pressure and used directly for condensation without purification.

Examples 4-7

Preparation of 1-((3R,4S)-3-((dimethylamino) methyl)-4-hydroxy-4-(3-methoxyphenyl)piperidin-1-yl)-2-(2,4,5-trifluorophenyl)ethyl-1-one

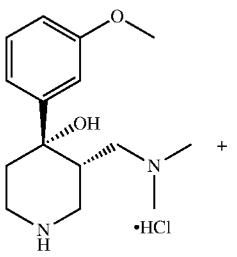

-continued

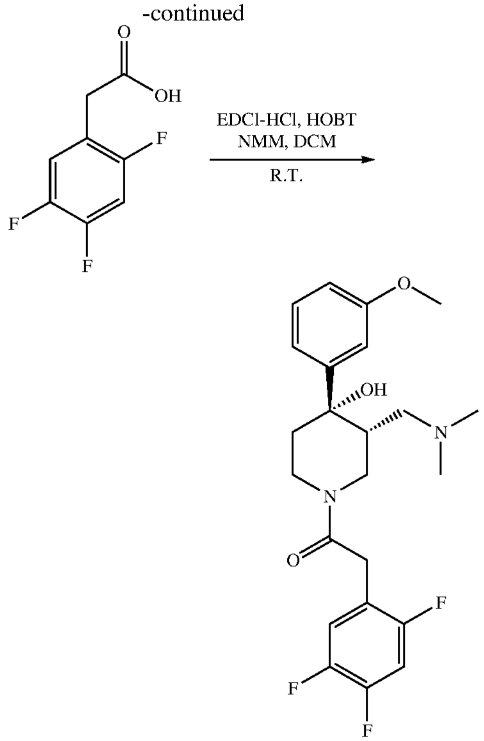

A 100 mL single-necked flask containing the hydrochloride obtained in Examples 4-6 was added with DCM (20 mL), 2,4,5-trifluorophenylacetic acid (1.15 g, 6.04 mmol, 1.1 eq.), HOBT (1.11 g, 8.24 mmol, 1.5 eq.), EDCI-HCl (1.6 g, 8.24 mmol, 1.5 eq.), NMM (2.22 g, 21.96 mmol, 4 eq.) and stirred at 25° C. TLC (DCM:MeOH=10:1) showed complete reaction after 5.5 h. Water (50 mL) was added, mixed, allowed to stand, stratified and partitioned. The aqueous phase was extracted with dichloromethane (50+25 mL). The organic phases were combined, washed three times with water (50+50+50 mL), dried over anhydrous magnesium sulfate, filtered, and the filtrate was evaporated under reduced pressure to yield 2.82 g of light yellow mucilage. Purified by silica gel column chromatography (DCM-DCM:MeOH=200:1 with 5‰ TEA), 2.2 g of colorless mucilage was obtained in 91.7% yield.

$$[\alpha]_D^{20.0} = 15.50$$

(c=1, $CHCl_3$). $^1H$ NMR (400 MHz, CD3OD), δ 7.24~7.29 (t, 2H), 7.14~7.21 (m, 1H), 7.06 (s, 1H), 6.98~7.02 (m, 1H), 6.81 (d, J=8 Hz, 1H), 4.92 (s, 2H), 4.59 (dd, J1=92 Hz, J2=16 Hz, 1H), 3.65~4.17 (m, 5H), 3.50 (m, J1=76 Hz, J2=12 Hz, 1H), 3.04 (m, J1=40 Hz, J2=12 Hz, 1H), 2.30~2.40 (m, 1H), 1.98~2.19 (m, 7H), 1.82 (t, J=12 Hz, 1H), 1.65~1.69 (m, 1H). $^{13}C$ NMR (150 MHz, $CD_3OD$) δ 170.03, 169.96, 161.28, 161.25, 151.24, 149.87, 149.83, 130.38, 130.35, 120.56, 120.43, 118.34, 118.30, 112.98, 112.94, 112.22, 106.48, 106.32, 106.15, 75.09, 74.85, 59.04, 58.93, 55.66, 47.49, 46.27, 46.23, 44.88, 44.15, 43.76, 43.58, 41.88, 41.00, 39.69, 33.67.

Examples 4-8

Preparation of 1-((3R,4S)-3-((dimethylamino)methyl)-4-hydroxy-4-(3-methoxyphenyl)piperidin-1-yl)-2-(2,4,5-trifluorophenyl)ethyl-1-one hydrochloride

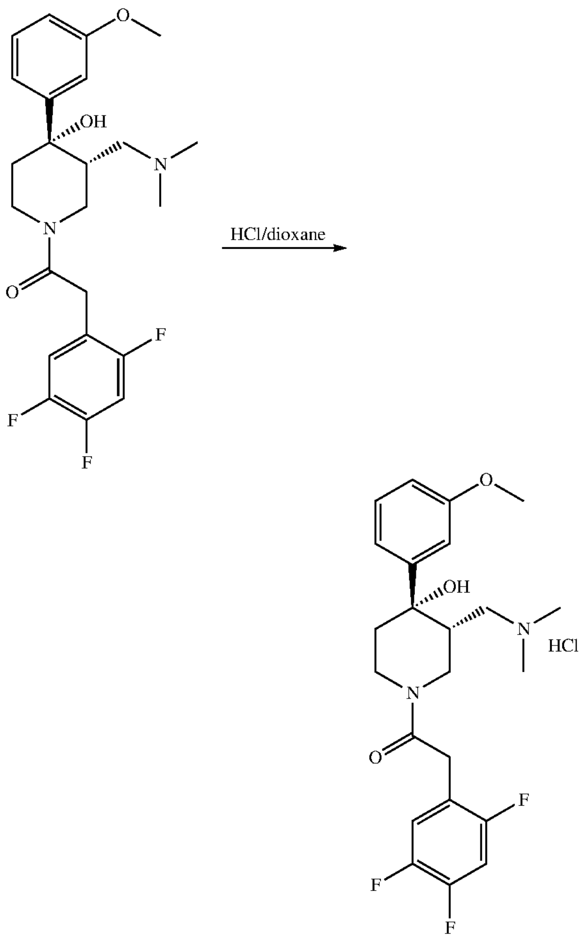

A 100 mL single-necked flask was added with 1-((3R,4S)-3-((dimethylamino)methyl)-4-hydroxy-4-(3-methoxyphenyl)piperidin-1-yl)-2-(2,4,5-trifluorophenyl)ethyl-1-one (0.83 g, 1.9 mmol, 1 eq.), methanol (1 mL), stirred to dissolve, and methyl tert-butyl ether (15 mL) was added. A solution of methyl tert-butyl ether (5 mL) with HCl/Dioxane was added dropwise (0.95 mL, 3.8 mmol, 2 eq.). And methyl tert-butyl ether (5 mL) was added and stirred. Gradually precipitate the solid. The filter cake was drenched with methyl tert-butyl ether and evaporated under reduced pressure to yield 0.85 g of off-white solid in 94.4% yield. m.p.: 217.4-220.4° C. $^1H$ NMR (400 MHz, $CD_3OD$), δ 7.26~7.36 (m, 2H), 7.07~7.22 (m, 3H), 6.88 (d, J=8 Hz, 1H), 4.36~4.64 (m, 1H), 4.01~4.08 (m, 1H), 3.89~3.92 (m, 2H), 3.51~3.61 (m, 1H), 3.03~3.16 (m, 2H), 2.53~2.82 (m, 7H), 2.26~2.32 (m, 1H), 2.13~2.24 (m, 1H), 1.72~1.81 (m, 1H). $^1C$ NMR (150 MHz, $CD_3OD$), δ 168.41, 167.14, 159.53, 146.58, 146.28, 145.04 (m), 128.91, 118.53~118.85 (m), 116.42, 116.27, 111.60, 111.51, 110.51, 110.48, 104.12~104.45 (m), 72.42, 72.23, 56.75, 56.34, 53.69, 44.78, 41.32, 40.83, 40.65, 40.32, 38.87, 37.86, 37.14, 31.98, 31.50. LC-MS:

$[M+H]^+$ 436.9. HRMS (ESI), calcd for $C_{23}H_{27}F_3N_2O_3$ [M+Na]+, 459.1866; found, 459.1847.

Examples 4-9

Preparation of 1-((3R,4S)-3-((dimethylamino)methyl)-4-hydroxy-4-(3-hydroxyphenyl)piperidin-1-yl)-2-(2,4,5-trifluorophenyl)ethyl-1-one

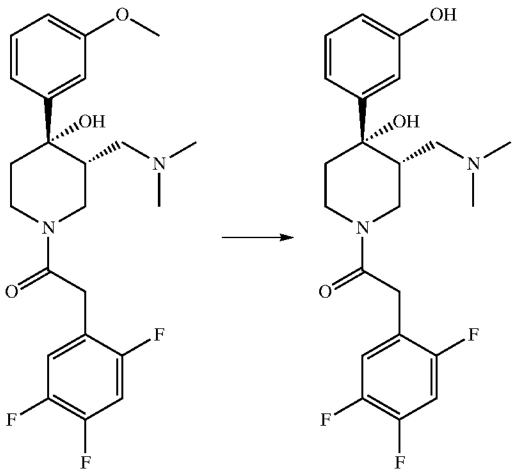 [SMILES: COc1cccc([C@]2(O)CCN(C(=O)Cc3cc(F)c(F)cc3F)C[C@H]2CN(C)C)c1 ; CN(C)C[C@@H]1CN(C(=O)Cc2cc(F)c(F)cc2F)CC[C@@]1(O)c1cccc(O)c1]

A 100 mL three-necked flask accompanied by a nitrogen balloon and thermometer was charged with 1-((3R,4S)-3-((dimethylamino)methyl)-4-hydroxy-4-(3-methoxyphenyl)piperidin-1-yl)-2-(2,4,5-trifluorophenyl)ethyl-1-one (1.3 g, 2.97 mmol, 1 eq.), DCM (50 mL), cooled and stirred in an ice water bath, and added dropwise BBr3 (1 mL, 2.65 g, 10.6 mmol, 3.6 eq.) in DCM (10 mL) solution was added dropwise. After dropwise addition, the ice water bath was withdrawn and stirred (about 10-15° C.), and TLC (DCM: MeOH=10:1) showed complete reaction after 22 h. Saturated sodium bicarbonate solution (100 mL) was added slowly at room temperature, stirred for 10 min, let stand, stratify and partition. The aqueous phase was extracted with DCM (50+25 mL). The organic phases were combined, washed with water (30 mL), dried with anhydrous magnesium sulfate, filtered, and the filtrate was evaporated under reduced pressure to yield 1.2 g of mucilage. After purification, 0.92 g of foamy substance was obtained in 70.8% yield.

$$[\alpha]_D^{20.1} = 10.2^0$$

(c=1, $CHCl_3$). $^1H$ NMR (400 MHz, CD3OD), δ 7.28~7.30 (m, 1H), 7.14~7.20 (m, 2H), 6.87~6.93 (m, 1H), 6.86 (d, J=8 Hz, 1H), 4.93 (s, 2H), 4.45~4.70 (m, 1H), 3.89~4.15 (m, 1H), 3.36~3.62 (m, 1H), 2.93~3.13 (m, 1H), 2.30~2.41 (m, 1H), 1.95~2.13 (m, 8H), 1.87 (d, J=12 Hz, 1H), 1.65~1.70 (m, 1H). $^{13}C$ NMR (150 MHz, $CD_3OD$) δ 170.03, 169.97, 158.58, 158.54, 149.81, 149.76, 130.35, 130.30, 120.59, 120.45, 117.21, 117.15, 114.60, 113.29, 113.25, 106.47, 106.32, 106.15, 75.01, 74.75, 59.02, 58.93, 47.51, 46.28, 46.22, 45.00, 44.17, 43.76, 43.60, 41.85, 40.92, 39.71, 33.67. LC-MS: $[M+H]^+$ 422.9.

Examples 4-10

1-((3R,4S)-3-((dimethylamino)methyl)-4-hydroxy-4-(3-hydroxyphenyl)piperidin-1-yl)-2-(2,4,5-trifluorophenyl)ethyl-1-one hydrochloride

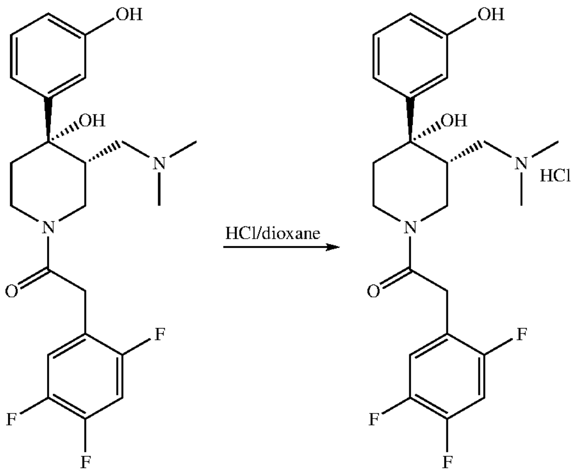 [SMILES: CN(C)C[C@@H]1CN(C(=O)Cc2cc(F)c(F)cc2F)CC[C@@]1(O)c1cccc(O)c1 ; CN(C)C[C@@H]1CN(C(=O)Cc2cc(F)c(F)cc2F)CC[C@@]1(O)c1cccc(O)c1 ; Cl]

A 100 mL single-necked flask was added with 1-((3R,4S)-3-((dimethylamino)methyl)-4-hydroxy-4-(3-hydroxyphenyl)piperidin-1-yl)-2-(2,4,5-trifluorophenyl)ethyl-1-one (0.18 g, 0.43 mmol, 1 eq.), methanol (1 mL), stirred to dissolve, and MTBE (7 mL) was added dropwise with HCl/Dioxane (0.21 mL, 0.86 mmol, 2 eq.) of MTBE (3 mL) solution was added dropwise. After dropwise addition, the solid was precipitated and MTBE (15 mL) was added and stirred. The filter cake was filtered, washed with MTBE and evaporated under reduced pressure to give 174 mg of a white solid in 88.2% yield. LC-MS: $[M+H]^+$ 422.9. $^1H$ NMR (400 MHz, $CD_3OD$), δ 7.13~7.33 (m, 3H), 6.95~7.02 (m, 2H), 6.73 (d, J=8 Hz, 1H), 4.33~4.64 (m, 1H), 4.01~4.08 (t, 1H), 3.84~3.94 (m, 2H), 3.50~3.65 (m, 1H), 3.21 (s, 1H), 3.01~3.16 (m, 2H), 2.71~2.76 (m, 4H), 2.53~2.60 (d, 3H), 2.10~2.27 (m, 2H), 1.77 (t, J=16 Hz, 1H), 1.19 (s, 3H). $^{13}C$ NMR (150 MHz, $CD_3OD$) δ 170.49, 170.20, 159.04, 148.62, 148.34, 130.92, 120.58~120.92 (m), 117.32, 117.17, 115.34, 113.58, 113.47, 106.19~106.51 (m), 74.37, 74.20, 68.17, 58.84, 58.44, 46.88, 45.96, 45.78, 43.41, 43.07, 42.76, 42.70, 42.50, 42.46, 40.86, 39.78, 39.23, 34.02, 33.57. HRMS (ESI), calcd for $C_{22}H_{25}F_3N_2O_3[M+Na]^+$, 445.1709; found, 445.1691.

Example 4-11

Preparation of (3S,4R)-3-((dimethylamino)methyl)-4-(3-methoxyphenyl)piperidin-4-ol hydrochloride

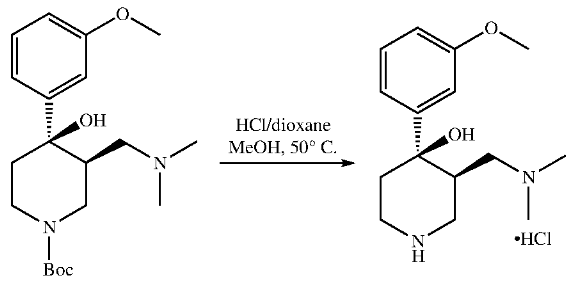 [SMILES: COc1cccc([C@@]2(O)CCN(C(=O)OC(C)(C)C)C[C@@H]2CN(C)C)c1 ; COc1cccc([C@@]2(O)CCNC[C@@H]2CN(C)C)c1 ; Cl]

A 100 mL single-mouth vial was added with (3S,4R)-3-((dimethylamino)methyl)-4-hydroxy-4-(3-methoxyphenyl) piperidine-1-carboxylic acid tert-butyl ester (2 g, 5.49 mmol, 1 eq.), methanol (10 mL), stirred to dissolve, and HCl/Dioxane (3.4 mL, 13.72 mmol, 2.5 eq.) was added at 25° C. with stirring. Stir. 1.5 h later TLC (DCM:MeOH=10:1) showed a small amount of raw material. Overnight (11.5 h), TLC showed complete reaction. The volatiles and solvent were evaporated under reduced pressure and used directly for condensation without purification.

Examples 4-12

Preparation of 1-((3S,4R)-3-((dimethylamino) methyl)-4-hydroxy-4-(3-methoxyphenyl)piperidin-1-yl)-2-(2,4,5-trifluorophenyl)ethyl-1-one

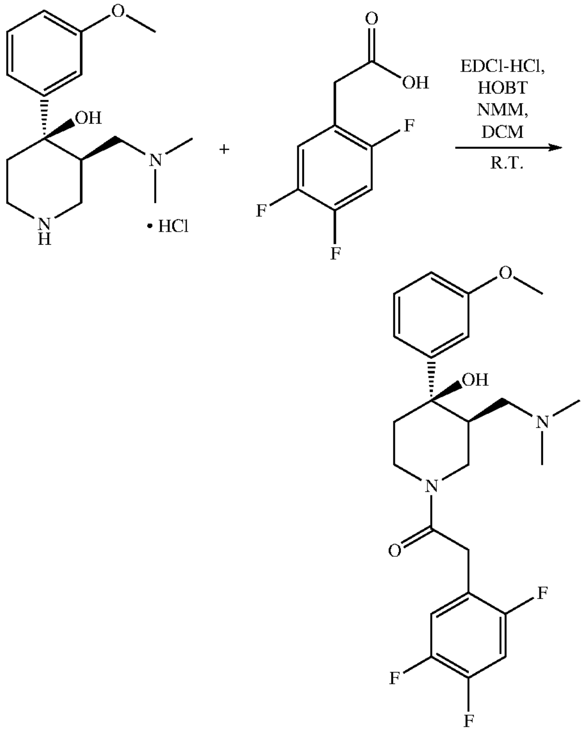

EMs: 436.20
MW: 436.48

A 100 mL single-necked flask containing (3S,4R)-3-((dimethylamino)methyl)-4-(3-methoxyphenyl)piperidin-4-ol hydrochloride was charged with DCM (20 mL), 2,4,5- trifluorophenylacetic acid (1.15 g, 6.04 mmol, 1.1 eq.), HOBT (1.11 g, 8.24 mmol, 1.5 eq.), EDCI-HCl (1.6 g, 8.24 mmol, 1.5 eq.), NMM (2.22 g, 21.96 mmol, 4 eq.), and stirred at room temperature. 11.5 h later TLC (DCM:MeOH=10:1) showed complete reaction. Water (50 mL) was added, mixed, allowed to stand, stratified and partitioned. The aqueous phase was extracted with dichloromethane (50+25 mL). The organic phases were combined, washed three times with water (50+50+50 mL), dried over anhydrous magnesium sulfate, filtered, and the filtrate was evaporated under reduced pressure to yield 2.82 g of light yellow mucilage. Purified by silica gel column chromatography (DCM-DCM:MeOH=200:1 with 5‰ TEA), 2.09 g of colorless mucilage was obtained in 87.1% yield.

$$[\alpha]_D^{20.1} = -14.6^0$$

(c=1, CHCl3). $^1$H NMR (400 MHz, $CD_3OD$), δ 7.24~7.31 (m, 2H), 7.14~7.20 (q, 1H), 7.06 (s, 1H), 7.00 (t, J=8 Hz, 1H), 6.81 (d, J=8 Hz, 1H), 4.92 (s, 2H), 4.59 (dd, J1=88 Hz, J2=16 Hz, 1H), 3.80~4.16 (m, 5H), 3.50 (m, J1=76 Hz, J2=12 Hz, 1H), 3.04 (m, J1=60 Hz, J2=12 Hz, 1H), 2.28~2.40 (m, 1H), 1.97~2.19 (m, 7H), 1.82 (t, J=12 Hz, 1H), 1.65~1.69 (m, 1H). $^{13}$C NMR (150 MHz, $CD_3OD$) δ 170.03, 169.97, 161.26, 158.52, 151.25, 149.87, 149.83, 149.61, 148.70, 147.10, 130.38, 130.35, 120.56, 120.43, 118.34, 118.30, 112.98, 112.94, 112.22, 106.49, 106.33, 106.15, 75.10, 74.85, 59.04, 58.93, 55.66, 54.84, 47.49, 46.27, 46.23, 44.88, 44.15, 43.76, 43.58, 41.88, 41.00, 39.69, 33.67. LC-MS: $[M+H]^+$ 436.8.

Examples 4-13

Preparation of 1-((3S,4R)-3-((dimethylamino) methyl)-4-hydroxy-4-(3-methoxyphenyl)piperidin-1-yl)-2-(2,4,5-trifluorophenyl)ethyl-1-one hydrochloride

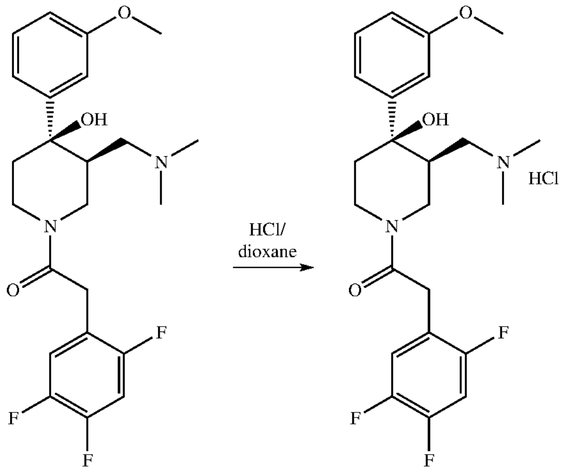 [SMILES: COc1cccc([C@@]2(O)CCN(C(=O)Cc3cc(F)c(F)cc3F)C[C@@H]2CN(C)C)c1 ; COc1cccc([C@@]2(O)CCN(C(=O)Cc3cc(F)c(F)cc3F)C[C@@H]2CN(C)C)c1 ; Cl]

A 100 mL single-necked flask was added with 1-((3S,4R)-3-((dimethylamino)methyl)-4-hydroxy-4-(3-methoxyphenyl)piperidin-1-yl)-2-(2,4,5-trifluorophenyl)ethyl-1-one (0.8 g, 1.83 mmol, 1 eq.), methanol (1 mL), stirred to dissolve, and methyl tert-butyl ether (15 mL) was added. A solution of methyl tert-butyl ether (5 mL) in HCl/Dioxane (0.92 mL, 3.67 mmol, 2 eq.) was added dropwise. The solid was separated and stirred with methyl tert-butyl ether (5 mL). The filter cake was drenched with methyl tert-butyl ether and evaporated under reduced pressure to yield 0.79 g of a white solid in 91.9% yield. LC-MS: $[M+H]^+$ 436.9. m.p.: 216.0-218.9° C. $^1H$ NMR (400 MHz, $CD_3OD$), δ 7.26~7.36 (m, 2H), 7.06~7.22 (m, 3H), 6.88 (m, J1=8 Hz, J2=4 Hz, 1H), 4.36~4.65 (m, 1H), 4.01~4.08 (m, 1H), 3.85~3.96 (m, 2H), 3.82 (m, 3H), 3.02~3.06 (m, 2H), 2.53~2.82 (m, 7H), 2.27~2.35 (m, 1H), 2.11~2.24 (m, 1H), 1.72~1.80 (m, 1H). $^{13}C$ NMR (150 MHz, $CD_3OD$) δ 170.48, 170.21, 161.60, 148.67, 148.36, 130.98, 130.95, 120.57~120.92, 118.49, 118.34, 113.67, 113.58, 112.58, 112.55, 106.19~106.52, 74.50, 74.31, 58.82, 58.41, 55.77, 46.86, 43.39, 42.92, 42.72, 42.40, 40.95, 39.94, 39.22, 34.06, 33.57. HRMS (ESI), calcd for $C_{23}H_{27}F_3N_2O_3[M+Na]^+$, 459.1866; found, 459.1850.

Examples 4-14

Preparation of 1-((3S,4R)-3-((dimethylamino)methyl)-4-hydroxy-4-(3-hydroxyphenyl)piperidin-1-yl)-2-(2,4,5-trifluorophenyl)ethyl-1-one

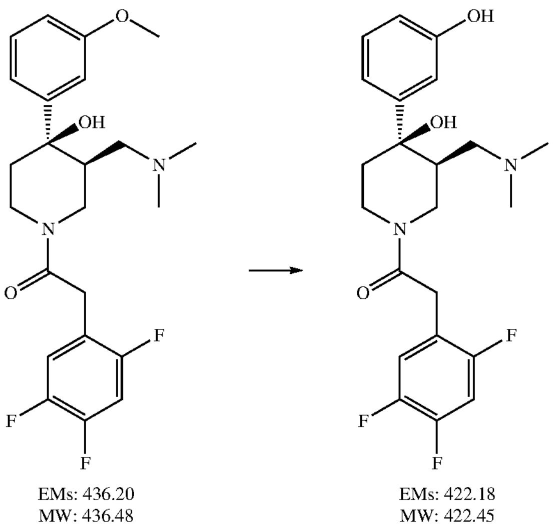 [SMILES: COc1cccc([C@@]2(O)CCN(C(=O)Cc3cc(F)c(F)cc3F)C[C@@H]2CN(C)C)c1 ; CN(C)C[C@H]1CN(C(=O)Cc2cc(F)c(F)cc2F)CC[C@]1(O)c1cccc(O)c1]

A 100 mL three-necked flask accompanied by a nitrogen balloon and thermometer was charged with 1-((3S,4R)-3-((dimethylamino)methyl)-4-hydroxy-4-(3-methoxyphenyl)piperidin-1-yl)-2-(2,4,5-trifluorophenyl)ethyl-1-one (1.33 g, 3.05 mmol, 1 eq.), DCM (50 mL), cooled and stirred in an ice water bath, and added dropwise BBr3 (1 mL, 2.65 g, 10.6 mmol, 3.5 eq.) in DCM (10 mL) solution was added dropwise. After dropwise addition, the ice water bath was withdrawn and stirred (about 10-15° C.), and TLC (DCM:MeOH=10:1) showed a small amount of raw material after 6.5 h. Increase to 25° C. and stir, TLC showed complete reaction after 39 h. Saturated sodium bicarbonate solution (100 mL) was slowly added at room temperature, stirred for 10 min, and allowed to stand, stratified and partitioned. The aqueous phase was extracted with DCM (50+50 mL). The organic phases were combined, washed with water (30 mL), dried with anhydrous magnesium sulfate, filtered, and the filtrate was evaporated under reduced pressure to yield 1.08 g of mucilage. Purified by silica gel column chromatography (DCM-DCM:MeOH=100:1), yielded 0.9 g of foamy material in 70% yield.

$$[\alpha]_D^{20.0} = -10.3^0$$

(c=1, CHC13). $^1H$ NMR (400 MHz, $CD_3OD$), δ 7.24~7.30 (q, 1H), 7.14~7.20 (m, 2H), 6.88~6.93 (m, 1H), 6.67 (dd, J1=8 Hz, J2=4 Hz, 1H), 4.93 (s, 2H), 4.44~4.69 (m, 1H), 3.89~4.16 (m, 1H), 3.36~3.62 (m, 1H), 2.93~3.14 (m, 1H), 2.31~2.45 (m, 1H), 1.85~2.14 (m, 9H), 1.68 (t, J1=12 Hz, 1H). $^{13}C$ NMR (150 MHz, $CD_3OD$) δ 170.02, 158.60, 158.55, 149.74, 147.18, 130.38, 130.31, 120.59, 120.46, 117.21, 117.15, 114.64, 114.61, 113.29, 113.26, 106.47, 106.32, 106.14, 74.97, 74.74, 59.02, 58.90, 47.71, 47.50, 46.25, 46.10, 44.98, 44.08, 43.70, 43.59, 41.80, 40.91, 39.70, 33.67. LC-MS: $[M+H]^+$ 422.9.

Examples 4-15

Preparation of 1-((3S,4R)-3-((dimethylamino)methyl)-4-hydroxy-4-(3-hydroxyphenyl)piperidin-1-yl)-2-(2,4,5-trifluorophenyl)ethyl-1-one hydrochloride

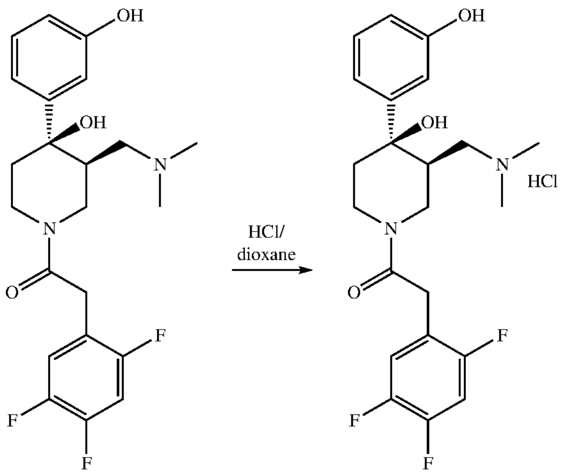 [SMILES: CN(C)C[C@H]1CN(C(=O)Cc2cc(F)c(F)cc2F)CC[C@]1(O)c1cccc(O)c1 ; CN(C)C[C@H]1CN(C(=O)Cc2cc(F)c(F)cc2F)CC[C@]1(O)c1cccc(O)c1 ; Cl]

A 100 mL single-necked flask was added with 1-((3S,4R)-3-((dimethylamino)methyl)-4-hydroxy-4-(3-hydroxyphenyl)piperidin-1-yl)-2-(2,4,5-trifluorophenyl)ethyl-1-one (0.24 g, 0.57 mmol, 1 eq.), methanol (1 mL), stirred to dissolve, and MTBE (7 mL) was added dropwise with HCl/Dioxane (0.3 mL, 1.14 mmol, 2 eq.) of MTBE (3 mL) solution was added dropwise. After dropwise addition, the solid was precipitated and MTBE (15 mL) was added and stirred. The filter cake was filtered, washed with MTBE and dried under reduced pressure to give 190 mg of a white solid in 73% yield. LC-MS: $[M+H]^+$ 422.9. $^1H$ NMR (400 MHz, $CD_3OD$), δ 7.16~7.33 (m, 3H), 6.95~7.02 (m, 2H), 6.73 (d, J=8 Hz, 1H), 4.32~4.62 (m, 1H), 4.00~4.07 (m, 1H), 3.84~3.94 (m, 2H), 3.50~3.66 (m, 1H), 3.22 (s, 1H), 3.02~3.13 (m, 2H), 2.71~2.76 (m, 4H), 2.53~2.60 (d, 3H), 2.10~2.27 (m, 2H), 1.77 (t, J=16 Hz, 1H), 1.19 (s, 2H). $^{13}C$ NMR (150 MHz, $CD_3OD$) δ 170.49, 170.19, 159.04, 148.34, 130.92, 120.59~120.91 (m), 117.32, 117.17, 115.34, 113.58, 113.46, 106.18~106.52 (m), 74.20, 68.17, 58.84, 58.45, 47.95, 46.86, 45.96, 45.78, 43.41, 43.07, 42.76, 42.50, 42.46, 40.86, 39.78, 39.24, 34.00, 33.57. HRMS (ESI), calcd for $C_{22}H_{25}F_3N_2O_3$[M+Na]+, 445.1709; found, 445.1689.

Examples 4-16

Preparation of tert-butyl (3R,4S)-4-(benzoyloxy)-3-((dimethylamino)methyl)-4-(3-methoxyphenyl) piperidin-1-ylcarboxylate

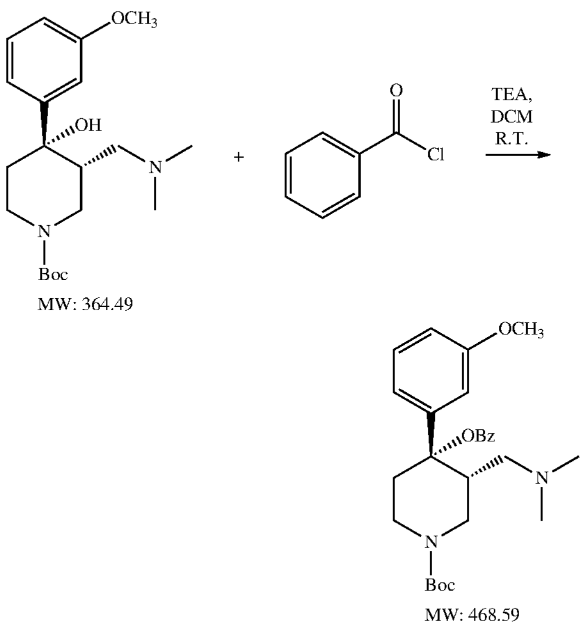

A 100 mL single-necked flask accompanied by a thermometer and a nitrogen bulb was charged with (3R,4S)-3-((dimethylamino)methyl)-4-hydroxy-4-(3-methoxyphenyl) piperidine-1-carboxylic acid tert-butyl ester (4.4 g, 12.07 mmol, 1 eq.), dichloromethane (44 mL), triethylamine (2.44 g, 24.14 mmol, 2 eq.) and cooled in an ice-water bath. Benzoyl chloride (2.55 g, 18.11 mmol, 1.5 eq.) was added dropwise at 20° C. After dropwise addition, the ice water bath was withdrawn and stirred. 8.5 h later TLC (DCM: MeOH=10:1) showed a small amount of free base of the raw material. Benzoyl chloride (0.85 g, 0.5 eq.) was added additionally. Overnight (15.5 h), TLC showed complete reaction. After water (50 mL) added, the mixture was stirred for 10 min, stood, partitioned, and fractionated. The aqueous phase was extracted with dichloromethane (50 mL). The organic phases were combined, washed with saturated sodium chloride (20 mL), dried with anhydrous magnesium sulfate, filtered, and the filtrate was evaporated under reduced pressure to yield 7.45 g of yellow liquid. Purified by silica gel column chromatography (DCM-DCM: MeOH=200:1, plus 0.5% c triethylamine), yielded 5.36 g colorless liquid, 93.8% yield. $^1$H NMR (400 MHz, $CD_3OD$), δ 8.086 (d, J=8 Hz, 2H), 7.675 (t, J=7.6 Hz, 1H), 7.554 (t, J=8 Hz, 2H), 7.261 (t, J=8 Hz, 1H), 6.813~6.864 (m, 2H), 6.766 (s, 1H), 4.392 (d, J=13.6 Hz, 1H), 4.075 (d, J=13.6 Hz, 1H), 3.739 (s, 3H), 3.121 (d, J=14.4 Hz, 2H), 2.889 (s, 1H), 2.537~2.594 (q, 1H), 2.346~2.425 (m, 1H), 1.989~2.061 (m, 8H), 1.484 (s, 9H).

$$[\alpha]_D^{22.3} = 29.2°$$

(c=1, MeOH).

Example 4-17

Preparation of (3S,4S)-3-((dimethylamino)methyl)-4-(3-methoxyphenyl)piperidin-4-ylbenzoic acid hydrochloride

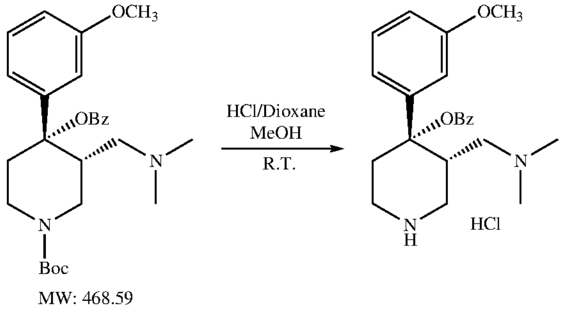

A 100 mL single-necked flask was spiked with (3R,4S)-4-(benzoyloxy)-3-((dimethylamino) methyl)-4-(3-methoxyphenyl)piperidin-1-ylcarboxylic acid tert-butyl ester (5.2 g, 11.1 mmol, 1 eq.), methanol (26 mL), HCl/Dioxane (8.33 mL, 33.3 mmol, 3 eq.) and stirred at room temperature. After 12 h TLC (DCM:MeOH=10:1) showed complete reaction. The solvent was evaporated under reduced pressure and DCM (20 mL) was added and evaporated under reduced pressure to give the mucilage. Without purification, it was directly used in the next step.

Examples 4-18

Preparation of (3R,4S)-1-(benzylsulfonyl)-3-((dimethylamino)methyl)-4-(3-methoxyphenyl) piperidin-4-yl benzoate

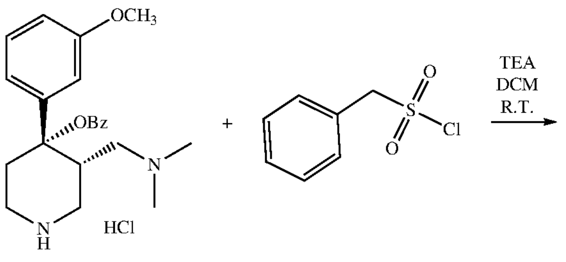

-continued

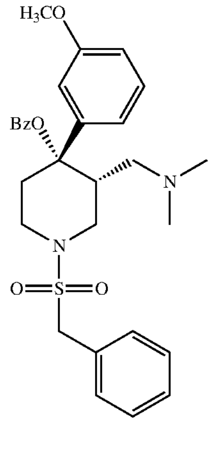

A 100 mL three-necked flask containing (3S,4S)-3-((dimethylamino)methyl)-4-(3-methoxyphenyl)piperidin-4-yl-benzoic acid hydrochloride was charged with dichloromethane (45 mL), benzylsulfonyl chloride (3.17 g, 16.7 mmol, 1.5 eq.), triethylamine (5.62 g, 55.5 mmol, 5 eq.), DMAP (68 mg, 0.56 mmmol, 0.05 eq.), and tetrabutylammonium bromide (358 mg, 1.11 mmol, 0.1 eq.) dropwise and stirred at room temperature. mg, 0.56 mmmol, 0.05 eq.), tetrabutylammonium bromide (358 mg, 1.11 mmol, 0.1 eq.) and stirred at room temperature. 24 h later the reaction was basically complete by TLC (DCM:MeOH=10:1). Water (50 mL) and dichloromethane (20 mL) was added, and the mixture was mixed, stood, partitioned and fractionated. Dichloromethane extraction of the aqueous phase (50+25 mL). The organic phases were combined, washed with water (25 mL), saturated sodium bicarbonate (25 mL), saturated sodium chloride solution (25 mL), dried with anhydrous magnesium sulfate, filtered, and the filtrate was evaporated under reduced pressure to yield 7 g of yellow mucilage. Purified by silica gel column chromatography (DCM with 5% c triethylamine), 4.06 g of colorless mucilage was obtained, with a 2-step yield of 70%. $^1$H NMR (400 MHz, $CD_3OD$), δ 8.081~8.105 (m, 2H), 7.728~7.772 (m, 1H), 7.63 (t, J=7.6 Hz, 2H), 7.380 (d, J=8 Hz, 2H), 7.254 (t, J=8 Hz, 1H), 7.202 (t, J=7.6 Hz, 1H), 7.031 (t, J=8 Hz, 2H), 6.849 (dd, J1=8.4 Hz, J2=2.4 Hz, 1H), 6.764~6.789 (m, 1H), 6.711~6.712 (m, 1H), 4.419 (q, J=21.2 Hz, 2H), 3.993 (dd, J1=12.8 Hz, J2=4.4 Hz, 1H), 3.735 (s, 3H), 3.538 (d, J=12.4 Hz, 1H), 3.038~3.106 (m, 2H), 2.490~2.557 (m, 2H), 2.297~2.374 (m, 1H), 1.925~2.087 (m, 8H). LC-MS-ESI$^+$: $[M+H]^+$ 523.2.

$$[\alpha]_D^{16.2} = -70.8°$$

(c=1, EtOH).

Example 4-19

Preparation of (3R,4S)-1-(benzylsulfonyl)-3-((dimethylamino)methyl)-4-(3-methoxyphenyl) piperidin-4-ol

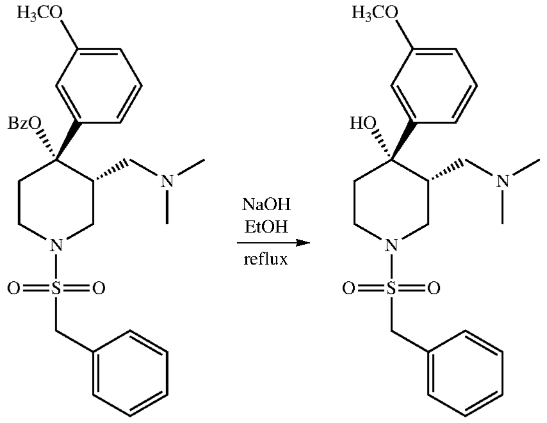

A 250 mL single-necked flask was spiked with (3R,4S)-1-(benzylsulfonyl)-3-((dimethylamino)methyl)-4-(3-methoxyphenyl)piperidin-4-yl benzoate (4.12 g, 7.9 mmol, 1 eq.), ethanol (40 mL), and sodium hydroxide (0.63 g, 15.8 mmol, 2 eq.) and refluxed at elevated temperature. 2 h later TLC (DCM:MeOH=50:1) showed complete reaction. The ethanol was evaporated under reduced pressure and water (80 mL) was added. Ethyl acetate was extracted (50+50 mL). The organic phases were combined, washed with saturated sodium bicarbonate solution (30 mL), water (30 mL), saturated sodium chloride solution (30 mL), dried with anhydrous magnesium sulfate, filtered, and the filtrate was evaporated under reduced pressure to yield 3.82 g of yellow viscous material. Purified by silica gel column chromatography (DCM, 0.5‰ TEA), 3.1 g of colorless mucilage was obtained in 93.7% yield.

$$[\alpha]_D^{18.7} = -48.2°$$

(c=1, MeOH). $^1$H NMR (400 MHz, $CD_3OD$), δ 7.469~7.499 (m, 2H), 7.353~7.429 (m, 3H), 7.854 (t, J=8 Hz, 1H), 7.012 (t, J=2.4 Hz, 1H), 6.962 (d, J=8 Hz, 8H), 6.779~6.808 (m, 1H), 4.399 (s, 2H), 3.790 (s, 3H), 3.758~3.804 (m, 1H), 3.491~3.534 (m, 1H), 3.121 (m, J1=12.4 Hz, J2=2.4 Hz, 1H), 3.001 (t, J=12 Hz, 1H), 2.282 (q, J=12.8 Hz, 1H), 2.074~2.127 (m, 1H), 1.960~2.039 (m, 7H), 1.739 (dd, J1=12.8 Hz, J2=2.4 Hz, 1H), 1.579 (m, J1=14 Hz, J2=2.4 Hz, 1H). LC-MS-ESI$^+$: $[M+H]^+$ 419.3.

Example 4~20

(3R,4S)-1-(benzylsulfonyl)-3-((dimethylamino) methyl)-4-(3-methoxyphenyl)piperidinv-4-ol hydrochloride

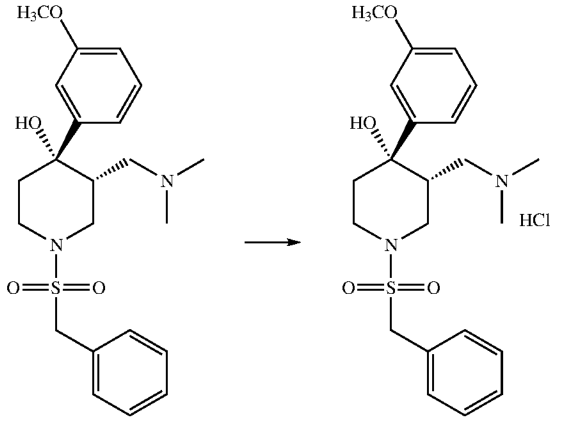 [SMILES: COc1cccc([C@]2(O)CCN(S(=O)(=O)Cc3ccccc3)C[C@H]2CN(C)C)c1 ; COc1cccc([C@]2(O)CCN(S(=O)(=O)Cc3ccccc3)C[C@H]2CN(C)C)c1 ; Cl]

A 250 mL single-necked flask 1 was added with (3R,4S)-1-(benzylsulfonyl)-3-((dimethylamino)methyl)-4-(3-methoxyphenyl)piperidin-4-ol (1 g, 2.9 mmol, 1 eq.), dichloromethane (10 mL), MeOH (0.5 mL), stirred to dissolve, and HCl/Dioxane (0.72 mL, 2.87 mmol, 1.2 eq.). MTBE (44 mL) was added and stirred at room temperature overnight (12 h), filtered and the filter cake was drenched with MTBE and evaporated under reduced pressure (60° C.) to give 1.07 g of off-white solid in 98% yield. $^1$H NMR (400 MHz, $CD_3OD$), δ 7.484~7.505 (m, 2H), 7.388~7.422 (m, 3H), 7.332 (t, J=8 Hz, 1H), 7.077 (s, 1H), 7.039 (d, J=7.6 Hz, 1H), 6.868 (d, J=8.4 Hz, 1H), 4.448 (s, 2H), 3.795~3.814 (m, 1H), 3.555 (d, J=12.8 Hz, 1H), 3.129~3.211 (m, 2H), 3.295~3.010 (t, 1H), 2.665~2.693 (m, 4H), 2.516 (s, 3H), 2.319 (s, 1H), 2.188 (t, J=12.8 Hz, 1H), 1.682 (d, J=14 Hz, 1H). $^{13}$C NMR (150 MHz, $CD_3OD$) δ 161.59, 148.39, 132.16, 131.00, 130.83, 129.78, 118.35, 113.56, 112.58, 73.81, 68.17, 58.33, 57.40, 55.76, 46.43, 45.73, 43.29, 42.95, 42.53, 40.47, 27.24. LC-MS-ESI$^+$: [M+H]$^+$ 419.1.

Example 4~21

Preparation of (3R,4S)-1-(benzylsulfonyl)-3-((dimethylamino)methyl)-4-(3-hydroxyphenyl) piperidin-4-ol

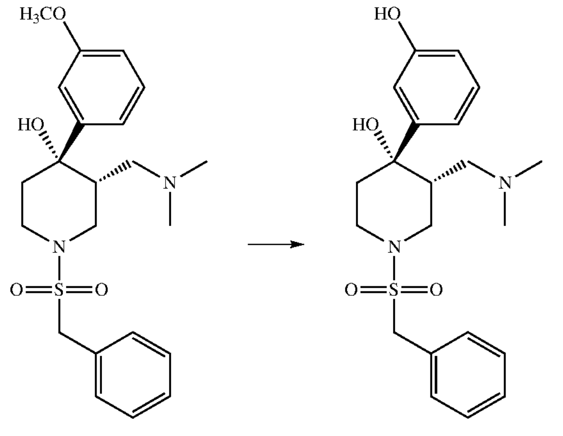 [SMILES: COc1cccc([C@]2(O)CCN(S(=O)(=O)Cc3ccccc3)C[C@H]2CN(C)C)c1 ; CN(C)C[C@@H]1CN(S(=O)(=O)Cc2ccccc2)CC[C@@]1(O)c1cccc(O)c1]

A 100 mL three-necked flask accompanied by a nitrogen bulb and thermometer was charged with (3R,4S)-1-(benzylsulfonyl)-3-((dimethylamino)methyl)-4-(3-methoxyphenyl)piperidin-4-ol (1.5 g, 3.6 mmol, 1 eq.), dichloromethane (40 mL). Cooled to −15° C., solution of BBr3 (1.98 g, 7.92 mmol, 2.2 eq.) was added dropwise at −5° C. a in dichloromethane (10 mL). After the drop, the reaction was kept warm and stirred. 1.5 h TLC (DCM:MeOH=10:1) showed complete reaction. The reaction solution was slowly poured into saturated sodium bicarbonate solution (80 mL), stirred for 10 min, allowed to stand, stratified and partitioned. The aqueous phase was extracted with dichloromethane (50 mL). The organic phase was combined, washed with water (30 mL), dried with anhydrous magnesium sulfate, filtered, and the filtrate was evaporated under reduced pressure to yield 1.5 g of foam. Purified by silica gel column chromatography (DCM-DCM:MeOH=100:1) to give 0.96 g of mucilage. Methanol (5 mL) was crystallized to give 0.35 g of off-white solid. The mother liquor was evaporated under reduced pressure and purified by preparative plate (DCM: MeOH=10:1) to give 0.27 g of off-white solid with a combined yield of 42.5%. $^1$H NMR (400 MHz, $CD_3OD$), δ 7.47~7.49 (m, 2H), 7.37~7.43 (m, 3H), 7.15 (t, J=8 Hz, 1H), 6.865 (d, J=12 Hz, 2H), 6.65 (d, J=8 Hz, 1H), 4.39 (s, 2H), 7.35~7.38 (m, 1H), 3.505 (d, J=12 Hz, 1H), 3.11 (t, J=12 Hz, 1H), 2.99 (t, J=12 Hz, 1H), 2.28 (t, J=12 Hz, 1H), 1.91~2.09 (m, 8H), 1.77 (d, J=16 Hz, 1H), 1.58 (d, J=16 Hz, 1H). LC-MS-ESI$^+$: [M+H]$^+$ 405.0.

$$[\alpha]_D^{12.4} = -24.2°$$

[c=0.5, CHC13/MeOH (v/v, 1:1)].

Example 4-22

(3R,4S)-1-(benzylsulfonyl)-3-((dimethylamino) methyl)-4-(3-hydroxyphenyl)piperidin-4-ol hydrochloride

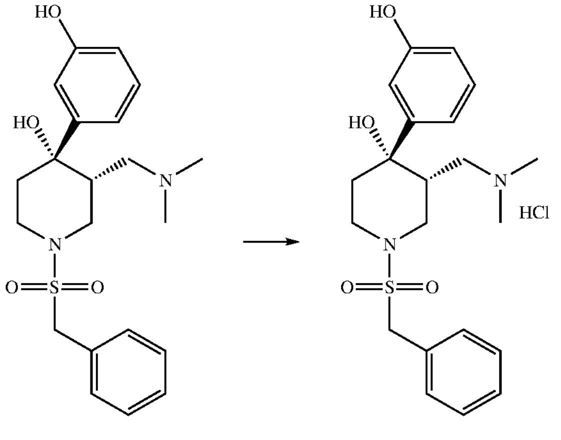 [SMILES: CN(C)C[C@@H]1CN(S(=O)(=O)Cc2ccccc2)CC[C@@]1(O)c1cccc(O)c1 ; CN(C)C[C@@H]1CN(S(=O)(=O)Cc2ccccc2)CC[C@@]1(O)c1cccc(O)c1 ; Cl]

A 50 mL single-necked flask was added with (3R,4S)-1-(benzylsulfonyl)-3-((dimethylamino)methyl)-4-(3-hydroxyphenyl)piperidin-4-ol (0.12 g, 0.3 mmol, 1 eq.), dichloromethane (3 mL), methanol (0.5 mL) and stirred to dissolve. 1,4,-dioxane solution of hydrogen chloride (0.113 mL, 0.45 mmol, 1.5 eq.) was added. Then the mixture was stirred at room temperature and added methyl tert-butyl ether (10.5 mL). Then the solid was precipitated slowly. The filter cake was evaporated under reduced pressure to give 83 mg of a white solid in 63% yield. $^1$H NMR (400 MHz, $CD_3OD$), δ 7.48~7.50 (m, 2H), 7.39~7.44 (m, 3H), 7.22 (t, J=8 Hz, 1H), 6.92~6.94 (d, 2H), 6.71 (d, J=8 Hz, 1H), 4.44 (s, 2H), 3.74~3.77 (m, 1H), 7.545 (d, J=6 Hz, 1H), 3.11~3.17 (m, 2H), 2.94~2.99 (m, 1H), 2.69~2.73 (m, 4H), 2.51 (s, 3H), 2.13~2.26 (m, 2H), 1.685 (d, J=12 Hz, 1H). $^{13}$C NMR (150 MHz, $CD_3OD$) δ 159.04, 148.38, 132.17, 130.94, 130.83, 129.78, 129.76, 117.19, 115.38, 113.43, 73.71, 68.17, 58.36, 57.44, 46.46, 45.71, 43.31, 43.06, 42.56, 40.35, 27.24. LC-MS-ESI$^+$: $[M+H]^+$ 405.0.

Example 4-23

Preparation of tert-butyl (3S,4R)-4-(benzoyloxy)-3-((dimethylamino)methyl)-4-(3-methoxyphenyl) piperidin-1-ylcarboxylate

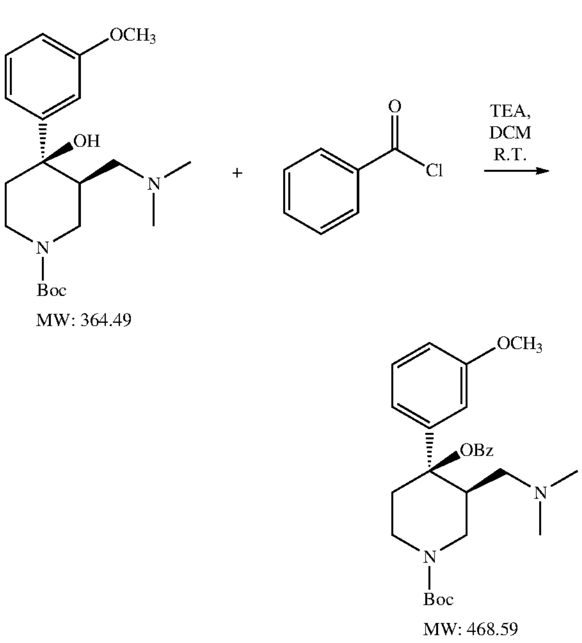

A 100 mL single-necked flask accompanied by a thermometer and a nitrogen bulb was charged with (3S,4R)-3-((dimethylamino)methyl)-4-hydroxy-4-(3-methoxyphenyl) piperidine-1-carboxylic acid tert-butyl ester (4.7 g, 12.9 mmol, 1 eq.), dichloromethane (45 mL), triethylamine (2.61 g, 25.8 mmol, 2 eq.) and cooled in an ice-water bath. Benzoyl chloride (2.72 g, 19.35 mmol, 1.5 eq.) was added dropwise at 20° C. After dropwise addition, the ice water bath was withdrawn and stirred. 1 h later TLC (DCM: MeOH=10:1) showed complete reaction. After dropwise addition of water (50 mL), the mixture was mixed, stood, stratified and partitioned. The aqueous phase was extracted with dichloromethane (50 mL). The organic phases were combined, washed with saturated sodium chloride (20 mL), dried over anhydrous magnesium sulfate, filtered, and the filtrate was evaporated under reduced pressure to yield 7.3 g of yellow liquid. Purified by silica gel column chromatography (DCM-DCM:MeOH=200:1, plus 0.5% c triethylamine), yielded 5.66 g colorless liquid, 93.6% yield.

$$[\alpha]_D^{24.9} = -32.5^0$$

(c=1, MeOH). $^1$H NMR (400 MHz, $CD_3OD$), δ 8.09 (d, J=8 Hz, 2H), 7.68 (t, J=8 Hz 1H), 7.56 (t, J=7.6 Hz, 2H), 7.261 (t, J=8 Hz, 1H), 6.811~6.864 (m, 2H), 6.758~6.769 (m, 1H), 4.394 (d, J=13.6 Hz, 1H), 4.078 (d, J=13.6 Hz, 1H), 3.738 (s, 3H), 3.122 (d, J=14.4 Hz, 1H), 2.884 (s, 1H), 2.543~2.600 (m, 1H), 2.347~2.425 (m, 1H), 1.984~2.025 (m, 8H), 1.484 (s, 9H).

Example 4-24

Preparation of (3R,4R)-3-((dimethylamino)methyl)-4-(3-methoxyphenyl)piperidin-4-ylbenzoic acid hydrochloride

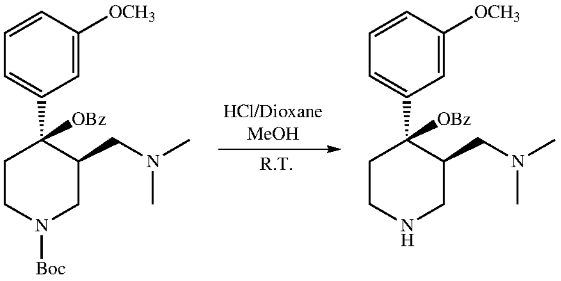

A 100 mL single-necked flask was spiked with (3S,4R)-4-(benzoyloxy)-3-((dimethylamino)methyl)-4-(3-methoxyphenyl)piperidin-1-ylcarboxylic acid tert-butyl ester (3.2 g, 6.83 mmol, 1 eq.), methanol (15 mL), HCl/Dioxane (5.1 mL, 20.5 mmol, 3 eq.) and stirred at 25° C. After 3 h TLC (DCM:MeOH=10:1) showed complete reaction. The mucilage was obtained by evaporation under reduced pressure. It was used directly in the next step without purification.

Example 4-25

Preparation of (3S,4R)-1-(benzylsulfonyl)-3-((dimethylamino)methyl)-4-(3-methoxyphenyl) piperidin-4-yl benzoate

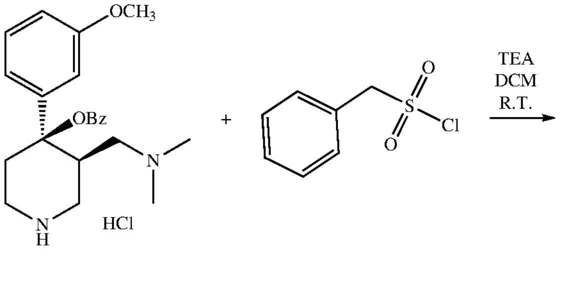

-continued

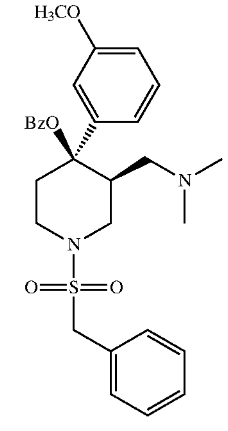

A 100 mL single-necked flask containing (3R,4R)-3-((dimethylamino)methyl)-4-(3-methoxyphenyl)piperidin-4-ylbenzoic acid hydrochloride was added with DCM (20 mL), benzylsulfonyl chloride (1.95 g, 10.25 mmol, 1.5 eq.), water (20 mL), potassium carbonate (3.8 g, 27.32 mmol, 4 eq.), at room temperature Stir. Allow TLC to show complete reaction. After dropwise addition of water (30 mL) and DCM (30 mL), the mixture was mixed, stood, stratified and partitioned. Aqueous phase DCM extraction (30 mL). The organic phases were combined, washed with saturated sodium bicarbonate solution (20 mL), dried with anhydrous magnesium sulfate, filtered, and the filtrate was evaporated under reduced pressure to yield 4.5 g of mucilage. Purified by silica gel column chromatography (DCM-DCM: MeOH=500:1, plus 0.5% c), 1.65 g of off-white solid was obtained in 46% yield.

$$[\alpha]_D^{17.6} = 72.3^0$$

(c=1, EtOH). $^1$H NMR (400 MHz, $CD_3OD$), δ 8.098 (d, J=7.2 Hz, 2H), 7.755 (t, J=7.2 Hz, 1H), 7.634 (t, J=7.2 Hz, 2H), 7.379 (d, J=7.6 Hz, 2H), 7.253 (t, J=8.4 Hz, 1H), 7.196 (t, J=7.6 Hz, 1H), 7.017 (t, J=7.6 Hz, 2H), 6.849 (t, J=4.2 Hz, 1H), 6.774 (t, J=7.2 Hz, 1H), 6.713 (s, 1H), 4.422 (q, J1=22 Hz, J2=14 Hz, 2H), 3.980~4.017 (m, 1H), 3.734 (s, 3H), 3.534 (d, J=12.8 Hz, 1H), 3.039~3.109 (m, 2H), 2.476~2.544 (m, 2H), 2.297~2.374 (m, 1H), 1.906~2.051 (m, 2H), 1.986 (s, 6H).

Example 4-26

Preparation of (3S,4R)-1-(benzylsulfonyl)-3-((dimethylamino)methyl)-4-(3-methoxyphenyl) piperidin-4-ol

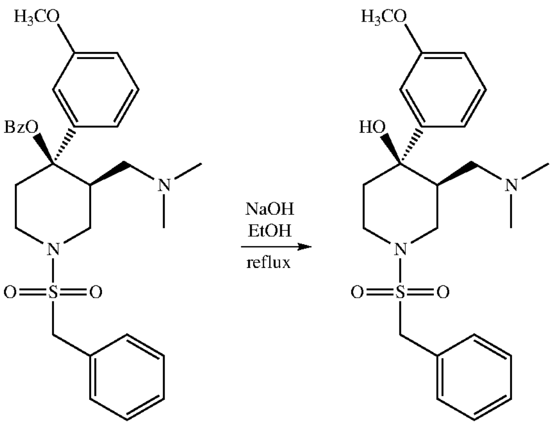

MW 522.66

MW: 418.55

A 250 mL single-necked flask was spiked with (3S,4R)-1-(benzylsulfonyl)-3-((dimethylamino)methyl)-4-(3-methoxyphenyl)piperidin-4-yl benzoate (3.7 g, 7.1 mmol, 1 eq.), ethanol (40 mL), sodium hydroxide (0.57 g, 14.2 mmol, 2 eq.) and refluxed at elevated temperature. 2 h later TLC (DCM MeOH=25:1) showed complete reaction. The ethanol was evaporated under reduced pressure and water (80 mL) was added. Ethyl acetate was extracted (50+50 mL). The organic phases were combined, washed with saturated sodium bicarbonate solution (30 mL), water (30 mL), saturated sodium chloride solution (30 mL), dried with anhydrous magnesium sulfate, filtered, and the filtrate was evaporated under reduced pressure to yield 3 g of yellow mucilage. Purified by silica gel column chromatography (DCM, 0.5‰ TEA), 2.83 g of colorless liquid was obtained in 95.3% yield.

$$[\alpha]_D^{18.1} = 49.1°$$

(c=1, MeOH). $^1$H NMR (400 MHz, $CD_3OD$), δ 7.48~7.50 (m, 2H), 7.35~7.43 (m, 3H), 7.25 (t, J=8 Hz, 1H), 7.01 (s, 1H), 6.96 (d, J=8 Hz, 1H), 6.795 (dd, J1=8 Hz, J2=4 Hz, 1H), 4.40 (s, 2H), 3.76~3.80 (m, 4H), 3.49~3.53 (m, 1H), 3.115 (m, J1=12 Hz, J2=4 Hz, 1H), 3.00 (t, J=12 Hz, 1H), 2.25~2.31 (m, 1H), 2.07~2.13 (m, 1H), 1.98~2.04 (m, 7H), 1.725 (d, J=12 Hz, 1H), 1.575 (d, J=12 Hz, 1H). LC-MS-ESI$^+$: $[M+H]^+$ 419.1.

Example 4-27

Preparation of (3S,4R)-1-(benzylsulfonyl)-3-((dimethylamino)methyl)-4-(3-methoxyphenyl) piperidin-4-ol hydrochloride

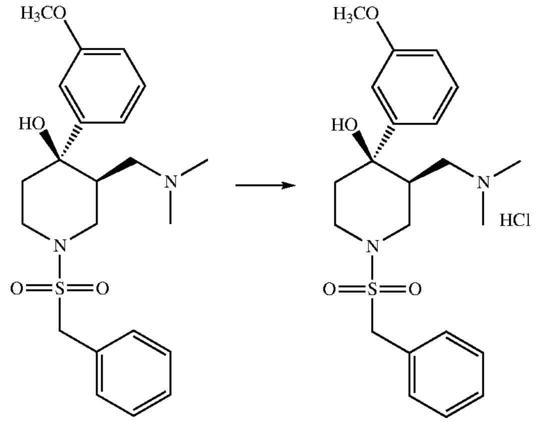 [SMILES: COc1cccc([C@@]2(O)CCN(S(=O)(=O)Cc3ccccc3)C[C@@H]2CN(C)C)c1 ; COc1cccc([C@@]2(O)CCN(S(=O)(=O)Cc3ccccc3)C[C@@H]2CN(C)C)c1 ; Cl]

A 250 mL single-necked flask was added with (3R,4S)-1-(benzylsulfonyl)-3-((dimethylamino)methyl)-4-(3-methoxyphenyl)piperidin-4-ol (1 g, 2.9 mmol, 1 eq.), dichloromethane (10 mL), MeOH (0.5 mL), stirred to dissolve, and HCl/Dioxane (0.72 mL, 2.87 mmol, 1.2 eq.), no solid was precipitated. MTBE (50 mL) was added and the solid was precipitated, filtered and the filter cake was drenched with MTBE and evaporated under reduced pressure (60° C.) to give 1.03 g of off-white solid in 94.5% yield. $^1$H NMR (400 MHz, $CD_3OD$), δ 7.489~7.505 (m, 2H), 7.396~7.440 (m, 3H), 7.310~7.351 (m, 1H), 7.075 (s, 1H), 7.037 (d, J=7.6 Hz, 1H), 6.865 (d, J=4.2 Hz, 1H), 4.451 (s, 2H), 3.779~3.815 (m, 4H), 3.551 (d, J=12.8 Hz, 1H), 3.131~3.232 (m, 3H), 3.982 (t, J=12 Hz, 1H), 2.663~2.700 (m, 4H), 2.515 (s, 3H), 2.322 (s, 1H), 2.180 (t, J=13.6 Hz, 1H), 1.678 (d, J=14.4 Hz, 1H). $^{13}C$ NMR (150 MHz, $CD_3OD$) δ 161.58, 148.40, 132.17, 131.00, 130.83, 129.77, 118.35, 113.57, 112.57, 73.80, 68.17, 58.32, 57.40, 55.76, 46.45, 45.74, 43.28, 42.93, 42.52, 40.48, 27.24. LC-MS-ESI$^+$: $[M+H]^+$ 419.1.

Example 4-28

Preparation of (3S,4R)-1-(benzylsulfonyl)-3-((dimethylamino)methyl)-4-(3-hydroxyphenyl) piperidin-4-ol

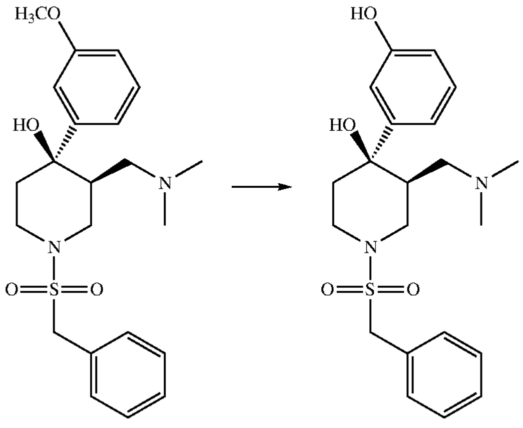

MW 418.55 MW 404.53

A 50 mL three-necked flask accompanied by a nitrogen balloon and thermometer was added with (3R,4S)-1-(benzylsulfonyl)-3-((dimethylamino)methyl)-4-(3-methoxyphenyl)piperidin-4-ol (0.6 g, 1.434 mmol, 1 eq.), DCM (15 mL), cooled to −15° C., and a solution of boron tribromide (0.79 g, 3.154 mmol, 2.2 eq.) was added dropwise at −5° C. mmol, 2.2 eq.) in dichloromethane (2 mL) solution at −5° C. After addition, keep warm and stir, TLC (DCM:MeOH=10:1) showed complete reaction after 1.5 h. Saturated sodium bicarbonate solution (50 mL), DCM (50 mL) was added. The mixture was mixed, left, stratified and partitioned. Aqueous phase DCM extraction (30 mL). The organic phases were combined, washed with water (15 mL), dried with anhydrous magnesium sulfate, filtered, and the filtrate was evaporated under reduced pressure to yield 0.58 g of foamy material. The preparation plate was purified (EA: MeOH=80:1) to give 0.22 g of off-white solid in 38% yield.

$$[\alpha]_D^{12.3} = 24.8°$$

[c=0.5, CHCl3/MeOH (v/v, 1:1)]. LC-MS-ESI$^+$: $[M+H]^+$ 405.1. $^1H$ NMR (400 MHz, $CD_3OD$), δ 7.47~7.49 (m, 2H), 7.37~7.43 (m, 3H), 7.15 (d, J=8 Hz, 1H), 6.85~6.88 (m, 2H), 6.65 (d, J=8 Hz, 1H), 4.40 (s, 2H), 3.75~3.78 (m, 1H), 3.49~3.52 (m, 1H), 3.08~3.14 (m, 1H), 2.99 (t, J=12 Hz, 1H), 2.27~2.33 (m, 1H), 1.94~2.07 (m, 8H), 1.795 (d, J=12 Hz, 1H), 1.585 (d, J=12 Hz, 1H).

Example 4-29

(3S,4R)-1-(Benzylsulfonyl)-3-((dimethylamino)methyl)-4-(3-hydroxyphenyl)piperidin-4-ol hydrochloride

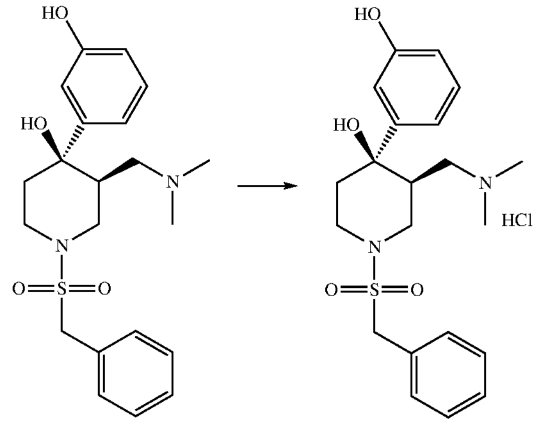 [SMILES: CN(C)C[C@H]1CN(S(=O)(=O)Cc2ccccc2)CC[C@]1(O)c1cccc(O)c1 ; CN(C)C[C@H]1CN(S(=O)(=O)Cc2ccccc2)CC[C@]1(O)c1cccc(O)c1 ; Cl]

(3S,4R)-1-(benzylsulfonyl)-3-((dimethylamino) methyl)-4-(3-hydroxyphenyl) piperidin-4-ol (0.1 g, 0.25 mmol, 1 eq.), dichloromethane (3 mL), methanol (0.5 mL) was added to a 50 mL single-necked flask and stirred to dissolve. 1,4,-dioxane solution of hydrogen chloride (0.1 mL, 0.375 mmol, 1.5 eq.) was added. The mixture was stirred at room temperature, added methyl tert-butyl ether (7 mL) and precipitated the solid slowly. The filter cake was evaporated under reduced pressure to give 50 mg of a white solid in 45% yield. $^1H$ NMR (400 MHz, CD3OD), δ 7.48~7.50 (m, 2H), 7.39~7.45 (m, 3H), 7.22 (t, J=8 Hz, 1H), 6.92~6.94 (m, 1H), 6.715 (d, J-4 Hz, 1H), 4.44 (s, 2H), 3.74~3.77 (m, 1H), 3.545 (d, J=12 Hz, 1H), 3.12~3.17 (m, 1H), 2.94~3.00 (m, 1H), 2.69~2.74 (m, 4H), 2.51 (s, 3H), 2.13~2.26 (m, 2H), 1.685 (d, J=12 Hz, 1H). 13C NMR (150 MHz, CD3OD) δ 159.04, 148.38, 132.17, 130.93, 130.84, 129.78, 129.76, 117.19, 115.38, 113.43, 73.71, 58.36, 57.44, 46.47, 45.71, 43.31, 43.06, 42.56, 40.35. LC-MS-ESI$^+$: $[M+H]^+$ 405.1.

Example 4-30

Structural analysis of (3R,4S)-1-(benzylsulfonyl)-3-((dimethylamino) methyl)-4-(3-hydroxyphenyl) piperidin-4-ol 1. Instrument model: Bruker SMART APEX-II single crystal X-ray diffractometer
2. Test conditions: CuKα radiation, graphite monochromator, single tube diameter $=0.50 mm, crystal and CCD detector distance d=60.3 mm, tube voltage 40 kV, tube current 30 mA, scan mode: φ/ω scan.
3. Using the direct method (Shelxs97) to resolve the crystal structure, the HHM9-18A crystal is a monoclinic crystal system with the space group P21, cell parameters: a=6.1179 (12), b=19.316 (3), c=8.7594 (18) Å, α=γ=90.00°, β=96.18 (3)°, cell volume V=1029.1 (4) The structure parameters and the discriminant atomic species were corrected by the least squares method, and all the hydrogen atom positions were obtained by the geometric calculation and the difference Fourier method. The final reliability factors were R1=0.0327, wR2=0.0849 (w=1/σ|F|2), and S=1.139. The final stoichiometric formula was determined as C21H28N2O4S, with a calculated molecular weight of 404.51 and a calculated crystal density of

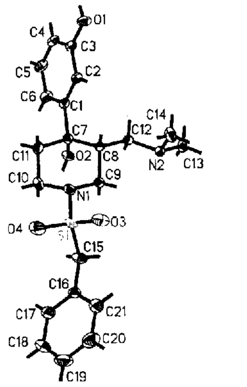

1.305 g/cm3.

FIG. 2 Ellipsoidal diagram of the molecular stereo structure

TABLE 1

| Crystal data and structure refinement | | |
|---|---|---|
| Identification code | S1113 | |
| Empirical formula | $C_{21}H_{28}N_2O_4S$ | |
| Formula weight | 404.51 | |
| Temperature | 293(2) K | |
| Wavelength | 1.54178 A | |
| Crystal system, space group | Monoclinic, P2(1) | |
| Unit cell dimensions | a = 6.1179(12) A | alpha = 90 deg. |
| | b = 19.316(4) A | beta = 96.18(3) deg. |
| | c = 8.7594(18) A | gamma = 90 deg. |
| Volume | 1029.1(4) A^3 | |
| Z, Calculated density | 2, 1.305 Mg/m^3 | |
| Absorption coefficient | 1.640 mm^-1 | |
| F(000) | 432 | |
| Crystal size | 0.160 × 0.120 × 0.110 mm | |
| Theta range for data collection | 4.578 to 68.113 deg. | |
| Limiting indices | −6 <= h <= 7, −23 <= k <= 23, −10 <= l <= 9 | |
| Reflections collected/unique | 5070/2849 [R(int) = 0.0211] | |
| Completeness to theta = 67.679 | 96.5% | |
| Absorption correction | Semi-empirical from equivalents | |
| Max. and min. transmission | 0.7530 and 0.6227 | |
| Refinement method | Full-matrix least-squares on F^2 | |
| Data/restraints/parameters | 2849/1/261 | |
| Goodness-of-fit on F^2 | 1.139 | |
| Final R indices [I > 2sigma(I)] | R1 = 0.0327, wR2 = 0.0848 | |
| R indices (all data) | R1 = 0.0328, wR2 = 0.0849 | |
| Absolute structure parameter | 0.113(9) | |
| Extinction coefficient | n/a | |
| Largest diff. peak and hole | 0.205 and −0.264 e.A^-3 | |

TABLE 2

Atomic coordinates (×10^4) and equivalent isotropic displacement parameters (A^2 × 10^3)

| | x | y | z | U(eq) |
|---|---|---|---|---|
| S (1) | 3900 (1) | 3289 (1) | 4522 (1) | 37 (1) |
| O (1) | 2701 (3) | 5587 (1) | 12527 (2) | 48 (1) |
| O (2) | −2268 (3) | 4505 (1) | 6824 (2) | 40 (1) |
| O (3) | 5821 (3) | 3681 (2) | 4304 (3) | 55 (1) |
| O (4) | 4146 (4) | 2590 (1) | 5031 (3) | 60 (1) |
| N (1) | 2607 (4) | 3702 (1) | 5786 (3) | 36 (1) |
| N (2) | 2232 (3) | 5942 (1) | 5485 (3) | 32 (1) |
| C (1) | −461 (4) | 4751 (1) | 9298 (3) | 32 (1) |
| C (2) | 1242 (4) | 5062 (2) | 10219 (3) | 33 (1) |
| C (3) | 961 (4) | 5292 (1) | 11692 (3) | 34 (1) |
| C (4) | −1072 (4) | 5211 (2) | 12241 (3) | 38 (1) |
| C (5) | −2759 (4) | 4893 (2) | 11340 (3) | 46 (1) |

TABLE 2-continued

Atomic coordinates (×10^4) and equivalent isotropic displacement parameters (A^2 × 10^3)

| | x | y | z | U(eq) |
|---|---|---|---|---|
| C (6) | −2481 (4) | 4665 (2) | 9875 (3) | 43 (1) |
| C (7) | −173 (4) | 4446 (1) | 7711 (3) | 31 (1) |
| C (8) | 1590 (4) | 4819 (1) | 6865 (3) | 29 (1) |
| C (9) | 1974 (4) | 4424 (1) | 5409 (3) | 32 (1) |
| C (10) | 914 (4) | 3312 (2) | 6494 (3) | 42 (1) |
| C (11) | 491 (5) | 3684 (2) | 7962 (3) | 40 (1) |
| C (12) | 870 (4) | 5567 (1) | 6500 (3) | 34 (1) |
| C (13) | 1275 (6) | 6626 (2) | 5137 (4) | 48 (1) |
| C (14) | 4508 (5) | 6019 (2) | 6177 (4) | 52 (1) |
| C (15) | 2161 (4) | 3304 (2) | 2740 (3) | 45 (1) |
| C (16) | 2953 (5) | 2815 (2) | 1572 (3) | 39 (1) |
| C (17) | 1734 (6) | 2239 (2) | 1137 (4) | 56 (1) |
| C (18) | 2408 (8) | 1785 (2) | 54 (5) | 71 (1) |
| C (19) | 4281 (8) | 1902 (3) | −599 (5) | 74 (1) |
| C (20) | 5503 (7) | 2472 (3) | −165 (5) | 72 (1) |
| C (21) | 4873 (6) | 2933 (2) | 920 (4) | 56 (1) |
| H (1A) | 2500 (70) | 5680 (30) | 13390 (50) | 62 (12) |

TABLE 2-continued

Atomic coordinates (×10^4) and equivalent isotropic displacement parameters (A^2 × 10^3)

| | x | y | z | U(eq) |
|---|---|---|---|---|
| H (2A) | −2340 (60) | 4200 (20) | 6180 (50) | 50 (10) |
| H (2B) | 2599 | 5117 | 9847 | 40 |
| H (4B) | −1290 | 5372 | 13214 | 46 |
| H (5A) | −4107 | 4831 | 11721 | 56 |
| H (6A) | −3642 | 4454 | 9277 | 51 |
| H (8A) | 2971 | 4829 | 7545 | 34 |
| H (9A) | 642 | 4429 | 4700 | 39 |
| H (9B) | 3129 | 4648 | 4915 | 39 |
| H (10A) | 1414 | 2844 | 6725 | 50 |
| H (10B) | −429 | 3290 | 5797 | 50 |
| H (11A) | 1811 | 3663 | 8681 | 48 |
| H (11B) | −667 | 3444 | 8421 | 48 |

TABLE 2-continued

| Atomic coordinates (x10^4) and equivalent isotropic displacement parameters (A^2 × 10^3) | | | | |
|---|---|---|---|---|
| | x | y | z | U(eq) |
| H (12A) | −636 | 5561 | 6023 | 40 |
| H (12B) | 891 | 5820 | 7458 | 40 |
| H (13A) | −216 | 6574 | 4684 | 71 |
| H (13B) | 1299 | 6890 | 6067 | 71 |
| H (13C) | 2113 | 6862 | 4431 | 71 |
| H (14A) | 5132 | 5569 | 6404 | 78 |
| H (14B) | 5349 | 6254 | 5472 | 78 |
| H (14C) | 4536 | 6282 | 7108 | 78 |
| H (15A) | 678 | 3177 | 2924 | 55 |
| H (15B) | 2116 | 3771 | 2330 | 55 |
| H (17A) | 442 | 2151 | 1574 | 67 |
| H (18A) | 1563 | 1396 | −228 | 85 |
| H (19A) | 4725 | 1598 | −1329 | 89 |
| H (20A) | 6793 | 2555 | −608 | 87 |
| H (21A) | 5736 | 3317 | 1205 | 67 |

TABLE 3

| Bond lengths [A] | |
|---|---|
| Bond | Bond lengths [A] |
| S(1)—O(4) | 1.424 (3) |
| S(1)—O(3) | 1.429 (3) |
| S(1)—N(1) | 1.636 (2) |
| S(1)—C(15) | 1.792 (3) |
| O(1)—C(3) | 1.351 (4) |
| O(1)—H(1A) | 0.80 (5) |
| O(2)—C(7) | 1.430 (3) |
| O(2)—H(2A) | 0.81 (4) |
| N(1)—C(10) | 1.470 (4) |
| N(1)—C(9) | 1.475 (3) |
| N(2)—C(13) | 1.463 (4) |
| N(2)—C(14) | 1.465 (4) |
| N(2)—C(12) | 1.473 (3) |
| C(1)—C(2) | 1.384 (4) |
| C(1)—C(6) | 1.395 (4) |
| C(1)—C(7) | 1.537 (3) |
| C(2)—C(3) | 1.393 (4) |
| C(2)—H(2B) | 0.9300 |
| C(3)—C(4) | 1.390 (4) |
| C(4)—C(5) | 1.374 (4) |
| C(4)—H(4B) | 0.9300 |
| C(5)—C(6) | 1.385 (4) |
| C(5)—H(5A) | 0.9300 |
| C(6)—H(6A) | 0.9300 |
| C(7)—C(11) | 1.536 (4) |
| C(7)—C(8) | 1.550 (3) |
| C(8)—H(8A) | 0.9800 |
| C(8)—C(9) | 1.526 (3) |
| C(8)—C(12) | 1.534 (4) |
| C(9)—H(9A) | 0.9700 |
| C(9)—H(9B) | 0.9700 |
| C(10)—C(11) | 1.519 (4) |
| C(10)—H(10A) | 0.9700 |
| C(10)—H(10B) | 0.9700 |
| C(11)—H(11A) | 0.9700 |
| C(11)—H(11B) | 0.9700 |
| C(12)—H(12A) | 0.9700 |
| C(12)—H(12B) | 0.9700 |
| C(13)—H(13A) | 0.9600 |
| C(13)—H(13B) | 0.9600 |
| C(13)—H(13C) | 0.9600 |
| C(14)—H(14A) | 0.9600 |
| C(14)—H(14B) | 0.9600 |
| C(14)—H(14C) | 0.9600 |
| C(15)—C(16) | 1.510 (4) |
| C(15)—H(15A) | 0.9700 |
| C(15)—H(15B) | 0.9700 |
| C(16)—C(17) | 1.371 (5) |
| C(16)—C(21) | 1.379 (4) |
| C(17)—C(18) | 1.387 (5) |

TABLE 3-continued

| Bond lengths [A] | |
|---|---|
| Bond | Bond lengths [A] |
| C(17)—H(17A) | 0.9300 |
| C(18)—C(19) | 1.353 (7) |
| C(18)—H(18A) | 0.9300 |
| C(19)—C(20) | 1.363 (7) |
| C(19)—H(19A) | 0.9300 |
| C(20)—C(21) | 1.386 (6) |
| C(20)—H(20A) | 0.9300 |
| C(21)—H(21A) | 0.9300 |

TABLE 5

| Bond angles [deg] | |
|---|---|
| | angles [deg] |
| O(4)—S(1)—O(3) | 118.93 (16) |
| O(4)—S(1)—N(1) | 107.04 (14) |
| O(3)—S(1)—N(1) | 107.23 (13) |
| O(4)—S(1)—C(15) | 108.75 (17) |
| O(3)—S(1)—C(15) | 107.12 (16) |
| N(1)—S(1)—C(15) | 107.25 (12) |
| C(3)—O(1)—H(1A) | 115 (3) |
| C(7)—O(2)—H(2A) | 107 (3) |
| C(10)—N(1)—C(9) | 113.5 (2) |
| C(10)—N(1)—S(1) | 116.75 (18) |
| C(9)—N(1)—S(1) | 116.37 (18) |
| C(13)—N(2)—C(14) | 109.7 (2) |
| C(13)—N(2)—C(12) | 109.3 (2) |
| C(14)—N(2)—C(12) | 112.0 (2) |
| C(2)—C(1)—C(6) | 118.8 (2) |
| C(2)—C(1)—C(7) | 122.7 (2) |
| C(6)—C(1)—C(7) | 118.3 (2) |
| C(1)—C(2)—C(3) | 121.2 (2) |
| C(1)—C(2)—H(2B) | 119.4 |
| C(3)—C(2)—H(2B) | 119.4 |
| O(1)—C(3)—C(4) | 122.8 (2) |
| O(1)—C(3)—C(2) | 117.9 (2) |
| C(4)—C(3)—C(2) | 119.3 (3) |
| C(5)—C(4)—C(3) | 119.7 (2) |
| C(5)—C(4)—H(4B) | 120.1 |
| C(3)—C(4)—H(4B) | 120.1 |
| C(4)—C(5)—C(6) | 121.0 (2) |
| C(4)—C(5)—H(5A) | 119.5 |
| C(6)—C(5)—H(5A) | 119.5 |
| C(5)—C(6)—C(1) | 120.0 (3) |
| C(5)—C(6)—H(6A) | 120.0 |
| C(1)—C(6)—H(6A) | 120.0 |
| O(2)—C(7)—C(11) | 111.2 (2) |
| O(2)—C(7)—C(1) | 106.1 (2) |
| C(11)—C(7)—C(1) | 107.0 (2) |
| O(2)—C(7)—C(8) | 109.4 (2) |
| C(11)—C(7)—C(8) | 109.0 (2) |
| C(1)—C(7)—C(8) | 114.1 (2) |
| C(9)—C(8)—C(12) | 111.30 (19) |
| C(9)—C(8)—C(7) | 110.2 (2) |
| C(12)—C(8)—C(7) | 109.7 (2) |
| C(9)—C(8)—H(8A) | 108.5 |
| C(12)—C(8)—H(8A) | 108.5 |
| C(7)—C(8)—H(8A) | 108.5 |
| N(1)—C(9)—C(8) | 110.3 (2) |
| N(1)—C(9)—H(9A) | 109.6 |
| C(8)—C(9)—H(9A) | 109.6 |
| N(1)—C(9)—H(9B) | 109.6 |
| C(8)—C(9)—H(9B) | 109.6 |
| C(19)—C(20)—C(21) | 121.7 (4) |
| C(19)—C(20)—H(20A) | 119.2 |
| C(21)—C(20)—H(20A) | 119.2 |
| C(11)—C(10)—H(10A) | 110.1 |
| N(1)—C(10)—H(10B) | 110.1 |
| C(11)—C(10)—H(10B) | 110.1 |
| H(10A)—C(10)—H(10B) | 108.4 |
| C(10)—C(11)—C(7) | 113.5 (2) |
| C(10)—C(11)—H(11A) | 108.9 |

TABLE 5-continued

| | |
|---|---|
| C(7)—C(11)—H(11A) | 108.9 |
| C(10)—C(11)—H(11B) | 108.9 |
| C(7)—C(11)—H(11B) | 108.9 |
| H(11A)—C(11)—H(11B) | 107.7 |
| N(2)—C(12)—C(8) | 114.9 (2) |
| N(2)—C(12)—H(12A) | 108.5 |
| C(8)—C(12)—H(12A) | 108.5 |
| N(2)—C(12)—H(12B) | 108.5 |
| C(8)—C(12)—H(12B) | 108.5 |
| H(12A)—C(12)—H(12B) | 107.5 |
| N(2)—C(13)—H(13A) | 109.5 |
| N(2)—C(13)—H(13B) | 109.5 |
| H(13A)—C(13)—H(13B) | 109.5 |
| N(2)—C(13)—H(13C) | 109.5 |
| H(13A)—C(13)—H(13C) | 109.5 |
| H(13B)—C(13)—H(13C) | 109.5 |
| N(2)—C(14)—H(14A) | 109.5 |
| N(2)—C(14)—H(14B) | 109.5 |
| H(14A)—C(14)—H(14B) | 109.5 |
| N(2)—C(14)—H(14C) | 109.5 |
| H(14A)—C(14)—H(14C) | 109.5 |
| H(14B)—C(14)—H(14C) | 109.5 |
| C(16)—C(15)—S(1) | 112.1 (2) |
| C(16)—C(15)—H(15A) | 109.2 |
| S(1)—C(15)—H(15A) | 109.2 |
| C(16)—C(15)—H(15B) | 109.2 |
| S(1)—C(15)—H(15B) | 109.2 |
| H(9A)—C(9)—H(9B) | 108.1 |
| N(1)—C(10)—C(11) | 107.9 (2) |
| N(1)—C(10)—H(10A) | 110.1 |
| H(15A)—C(15)—H(15B) | 107.9 |
| C(17)—C(16)—C(21) | 118.7 (3) |
| C(17)—C(16)—C(15) | 119.4 (3) |
| C(21)—C(16)—C(15) | 121.8 (3) |
| C(16)—C(17)—C(18) | 120.7 (3) |
| C(16)—C(17)—H(17A) | 119.7 |
| C(18)—C(17)—H(17A) | 119.7 |
| C(19)—C(18)—C(17) | 120.8 (4) |
| C(19)—C(18)—H(18A) | 119.6 |
| C(17)—C(18)—H(18A) | 119.6 |
| C(18)—C(19)—C(20) | 118.8 (4) |
| C(18)—C(19)—H(19A) | 120.6 |
| C(20)—C(19)—H(19A) | 120.6 |
| C(16)—C(21)—C(20) | 119.4 (3) |
| C(16)—C(21)—H(21A) | 120.3 |
| C(20)—C(21)—H(21A) | 120.3 |

Torsion angles [deg]

| | Torsion angles [deg] |
|---|---|
| O(4)—S(1)—N(1)—C(10) | −35.8 (2) |
| O(3)—S(1)—N(1)—C(10) | −164.4 (2) |
| C(15)—S(1)—N(1)—C(10) | 80.8 (2) |
| O(4)—S(1)—N(1)—C(9) | −174.1 (2) |
| O(3)—S(l)—N(1)—C(9) | 57.2 (2) |
| C(15)—S(l)—N(1)—C(9) | −57.6 (2) |
| C(6)—C(l)—C(2)—C(3) | −0.6 (4) |
| C(7)—C(l)—C(2)—C(3) | −175.8 (3) |
| C(1)—C(2)—C(3)—O(l) | 179.7 (3) |
| C(1)—C(2)—C(3)—C(4) | −0.3 (4) |
| O(1)—C(3)—C(4)—C(5) | −178.7 (3) |
| C(2)—C(3)—C(4)—C(5) | 1.4 (4) |
| C(3)—C(4)—C(5)—C(6) | −1.4 (5) |
| C(4)—C(5)—C(6)—C(1) | 0.5 (5) |
| C(2)—C(1)—C(6)—C(5) | 0.5 (5) |
| C(7)—C(1)—C(6)—C(5) | 175.9 (3) |
| C(2)—C(1)—C(7)—O(2) | −151.0 (2) |
| C(6)—C(1)—C(7)—O(2) | 33.8 (3) |
| C(2)—C(1)—C(7)—C(11) | 90.2 (3) |
| C(6)—C(1)—C(7)—C(11) | −85.0 (3) |
| C(2)—C(1)—C(7)—C(8) | −30.4 (3) |
| C(6)—C(1)—C(7)—C(8) | 154.4 (2) |
| O(2)—C(7)—C(8)—C(9) | −68.8 (2) |
| C(11)—C(7)—C(8)—C(9) | 53.0 (3) |
| C(1)—C(7)—C(8)—C(9) | 172.5 (2) |
| O(2)—C(7)—C(8)—C(12) | 54.1 (3) |
| C(11)—C(7)—C(8)—C(12) | 175.9 (2) |
| C(1)—C(7)—C(8)—C(12) | −64.6 (3) |
| C(10)—N(1)—C(9)—C(8) | 61.3 (3) |
| S(1)—N(1)—C(9)—C(8) | −159.04 (17) |
| C(12)—C(8)—C(9)—N(1) | −178.5 (2) |
| C(7)—C(8)—C(9)—N(1) | −56.5 (3) |
| C(9)—N(1)—C(10)—C(11) | −59.4 (3) |
| S(1)—N(1)—C(10)—C(11) | 161.09 (18) |
| N(1)—C(10)—C(11)—C(7) | 56.2 (3) |
| O(2)—C(7)—C(11)—C(10) | 66.4 (3) |
| C(1)—C(7)—C(11)—C(10) | −178.1 (2) |
| C(8)—C(7)—C(11)—C(10) | −54.3 (3) |
| C(13)—N(2)—C(12)—C(8) | 175.7 (2) |
| C(14)—N(2)—C(12)—C(8) | −62.6 (3) |
| C(9)—C(8)—C(12)—N(2) | −48.6 (3) |
| C(7)—C(8)—C(12)—N(2) | −170.8 (2) |
| O(4)—S(1)—C(15)—C(16) | −52.7 (3) |
| O(3)—S(1)—C(15)—C(16) | 77.1 (3) |
| N(1)—S(1)—C(15)—C(16) | −168.1 (2) |
| S(1)—C(15)—C(16)—C(17) | 111.6 (3) |
| S(1)—C(15)—C(16)—C(21) | −68.6 (4) |
| C(21)—C(16)—C(17)—C(18) | −0.5 (6) |
| C(15)—C(16)—C(17)—C(18) | 179.2 (4) |
| C(16)—C(17)—C(18)—C(19) | 0.0 (7) |
| C(17)—C(18)—C(19)—C(20) | 0.4 (7) |
| C(18)—C(19)—C(20)—C(21) | −0.1 (8) |
| C(17)—C(16)—C(21)—C(20) | 0.8 (5) |
| C(15)—C(16)—C(21)—C(20) | −179.0 (4) |
| C(19)—C(20)—C(21)—C(16) | −0.5 (7) |

TABLE 6

Hydrogen bonds [A and deg.]

| D-H . . . A | d(D-H) | d(H . . . A) | d(D . . . A) | <(DHA) |
|---|---|---|---|---|
| O(2)—H(2A) . . . O(3)#1 | 0.81(4) | 2.14(4) | 2.866(3) | 149(4) |
| O(1)—H(1A) . . . N(2)#2 | 0.80(5) | 1.93(5) | 2.725(3) | 176(5) |

Symmetry transformations used to generate equivalent atoms:
#1 x − 1, y, z
#2 x, y, z + 1

Example 4-31

Preparation of Membrane Receptors

CHO cells expressing μ opioid receptor, δ opioid receptor or κ opioid receptor were cultured in 10 cm2 culture dishes (F-12 medium+10% neonatal bovine serum) for several days, and the cells were grown to the bottom of the dishes and the culture solution was aspirated; 3 mL of PBS/EDTA solution (0.1 M NaCl, 0.01 M $NaH_2PO_4$, 0.04% EDTA) was added for 3-5 min of digestion, The cells were collected in a 40 mL centrifuge tube and centrifuged at 5000 rpm for 5 min, and the supernatant was removed; ice-cold homogenate (50 mM HEPES PH 7.4, 3 mM MgCl, 1 mM EGTA) was added to the centrifuge tube, and the solution and precipitate were transferred to a homogenizer for homogenization; then the homogenate was transferred to a centrifuge tube and centrifuged at 18000 rpm. Centrifuge for 15 min, 2 times; the obtained precipitate was homogenized with appropriate amount of 50 mM Tris-HCl, pH 7.4 buffer and divided into centrifuge tubes and stored at −70° C. in the refrigerator until use.

Competition Binding Assay

Total binding tubes were spiked with 20-30 μg of expressed membrane receptor protein and [3H]-labeled ligand (1-2 nM), corresponding non-specific binding tubes were spiked with 1 μM of the corresponding ligand, and sample tubes were spiked with various screened opioid ligands in a final volume of 100 μl, incubated at 30° C. for 30 min, and the reaction was terminated in ice water. The reaction was terminated by incubation in ice-cold water for 30 min at 30° C. The samples were filtered under negative pressure through GF/C (whatman) glass fiber filter paper on a Millipore sample collector. The reaction was rinsed three times with 4 mL of 50 mM Tris-HCl (pH 7.4), the filter paper was dried and placed in 0.5 mL Eppendorf tubes with 0.5 mL of lipophilic scintillation solution, and the radioactivity was measured by PERKIN ELMER PRI-CARB 2910 liquid scintillation counter to calculate the inhibition rate.

Inhibition rate (or binding rate)=(total binding rate dpm−sample tube dpm)/(total binding tube dpm−non-specific binding tube dpm)×100%

$IC_{50}$ was calculated using Graphpad Prism 5.0 software. Ki values were calculated according to the following formula, Ki=$IC_{50}$/(1+[L]/Kd), [L] is the concentration of the added labeled ligand, and Kd is the equilibrium dissociation parameter of the labeled ligand Table 4-1 shows the Ki values of affinity constants of representative compounds for opioid receptors, expressed as the mean±standard deviation of three independent measurements.

TABLE 4-1

Opioid receptor binding rate or Ki at 1 μM concentration of compound.

| Name | Structure | Binding rate (%) or Ki(nM) μOR | δOR | κOR |
|---|---|---|---|---|
| Tramadol | 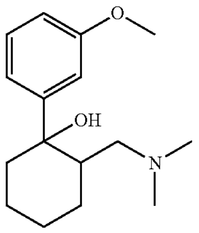 [SMILES: COc1cccc(C2(O)CCCCC2CN(C)C)c1] | 6.0 ± 0.4% | 0% | 0% |
| 1-((3R,4S)-3-((dimethylamino)methyl)-4-hydroxy-4-(3-methoxyphenyl)piperidin-1-yl)-2-(2,4,5-trifluorophenyl)ethyl-1-one hydrochloride | 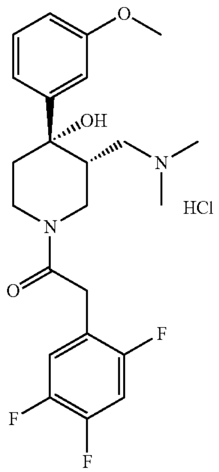 [SMILES: COc1cccc([C@]2(O)CCN(C(=O)Cc3cc(F)c(F)cc3F)C[C@H]2CN(C)C)c1 ; Cl] | 164.8 ± 22.3 | 26.6 ± 3.9% | 33.0 ± 4.1% |
| 1-((3R,4S)-3-((dimethylamino)methyl)-4-hydroxy-4-(3-hydroxyphenyl)piperidin-1-yl)-2-(2,4,5-trifluorophenyl)ethyl-1-one hydrochloride | 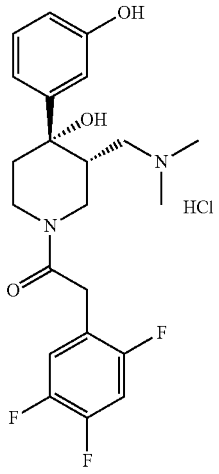 [SMILES: CN(C)C[C@@H]1CN(C(=O)Cc2cc(F)c(F)cc2F)CC[C@@]1(O)c1cccc(O)c1 ; Cl] | 1.77 ± 0.18 | 178.3 ± 17.9 nM | 126.9 ± 1.6 nM |

TABLE 4-1-continued

| Opioid receptor binding rate or Ki at 1 μM concentration of compound. | | | | |
|---|---|---|---|---|
| | | Binding rate (%) or Ki(nM) | | |
| Name | Structure | μOR | δOR | κOR |
| 1-((3S,4R)-3-((dimethylamino)methyl)-4-hydroxy-4-(3-methoxyphenyl)piperidin-1-yl)-2-(2,4,5-trifluorophenyl)ethyl-1-one hydrochloride | 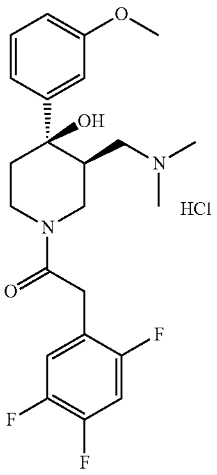 [SMILES: COc1cccc([C@@]2(O)CCN(C(=O)Cc3cc(F)c(F)cc3F)C[C@@H]2CN(C)C)c1 ; Cl] | 2312.0 ± 234.0 | 0% | 23.4 ± 3.9% |
| 1-((3S,4R)-3-((dimethylamino)methyl)-4-hydroxy-4-(3-hydroxyphenyl)piperidin-1-yl)-2-(2,4,5-trifluorophenyl)ethyl-1-one hydrochloride | 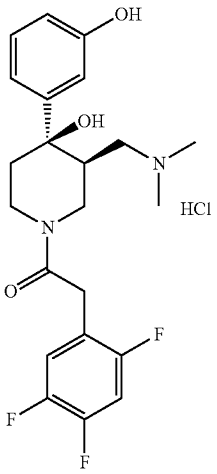 [SMILES: CN(C)C[C@H]1CN(C(=O)Cc2cc(F)c(F)cc2F)CC[C@]1(O)c1cccc(O)c1 ; Cl] | 53.5 ± 0.09 | 3564.5 ± 96.5 nM | 42.3 ± 0.6 nM |
| (3R,4S)-1-(Benzylsulfonyl)-3-((dimethylamino)methyl)-4-(3-methoxyphenyl)piperidin-4-ol hydrochloride salt | 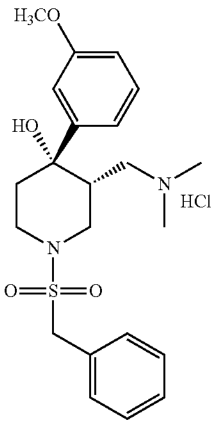 [SMILES: COc1cccc([C@]2(O)CCN(S(=O)(=O)Cc3ccccc3)C[C@H]2CN(C)C)c1 ; Cl] | 27.52 ± 1.54% [a] | 10.5 ± 3.7% [a] | 15.25 ± 1.56% [a] |

TABLE 4-1-continued

Opioid receptor binding rate or Ki at 1 μM concentration of compound.

| Name | Structure | Binding rate (%) or Ki(nM) μOR | δOR | κOR |
|---|---|---|---|---|
| (3R,4S)-1-(Benzylsulfonyl)-3-((dimethylamino)methyl)-4-(3-hydroxyphenyl)piperidin-4-ol hydrochloride | 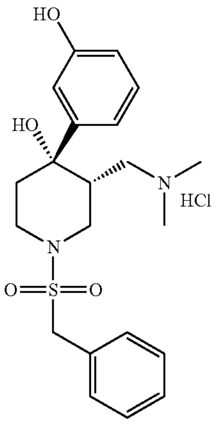 [SMILES: CN(C)C[C@@H]1CN(S(=O)(=O)Cc2ccccc2)CC[C@@]1(O)c1cccc(O)c1 ; Cl] | 0.17 ± 0.01 | 1105 ± 42 nM | 33.66 ± 3.26 |
| (3S,4R)-1-(Benzylsulfonyl)-3-((dimethylamino)methyl)-4-(3-methoxyphenyl)piperidin-4-ol hydrochloride | 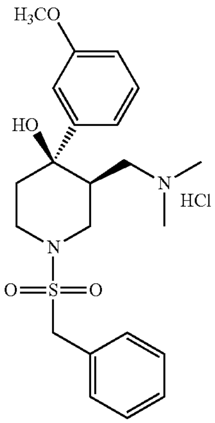 [SMILES: COc1cccc([C@@]2(O)CCN(S(=O)(=O)Cc3ccccc3)C[C@@H]2CN(C)C)c1 ; Cl] | 24.47 ± 0.64% [a] | 7.3 ± 4.5% [a] | 20.75 ± 0.13% [a] |
| (3S,4R)-1-(Benzylsulfonyl)-3-((dimethylamino)methyl)-4-(3-hydroxyphenyl)piperidin-4-ol hydrochloride | 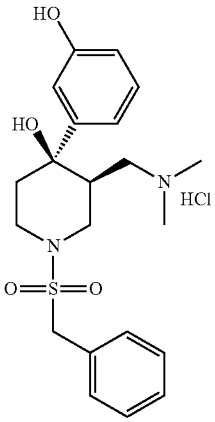 [SMILES: CN(C)C[C@H]1CN(S(=O)(=O)Cc2ccccc2)CC[C@]1(O)c1cccc(O)c1 ; Cl] | 38.27 ± 1.18 nM | 1089 ± 9 nM | 230.7 ± 13.10 nM |

[a] Inhibition rate of 0.1 μM

In the column of "Binding rate (%) or Ki (nM)" in Table 4-1, the values expressed as percentages refer to the binding rate, and the values in nM refer to Ki. As seen in Table 4-1, all compounds had stronger affinity for μ opioid receptors than tramadol, and stronger affinity for δ opioid receptors and κ opioid receptors than tramadol or comparable to tramadol.

Example 4-32

In Vivo Hot Plate Method Analgesia Test

Female mice weighing about 20 g were placed on a hot plate apparatus preheated to 55° C., and the latency of the hindfoot response of the mice was used as the pain threshold indicator. Animals were screened before the experiment, and those with response latency less than 5 s or more than 30 s were excluded. To prevent foot scalding, the maximum observation time was set at 60 s. The basal pain threshold was the average of two measurements, with a 5-min interval between measurements. pain thresholds were measured at 15 min, 30 min, 60 min and 120 min after intraperitoneal administration in each group of mice. The analgesic effective percentage (% MPE) was calculated according to the following formula: analgesic effective percentage (% MPE)=(latency after drug administration−latency before drug administration)/(60−latency before drug administration)×100%. $ED_{50}$ values were calculated based on the effective percentage of analgesia using the software Graphpad prism 5.0.

TABLE 4-2

Maximum percentage effective analgesic or $ED_{50}$ values of compound hot plate at 10 mg/kg dose

| Name | Structure | % MPE/$ED_{50}$ |
|---|---|---|
| Tramadol | 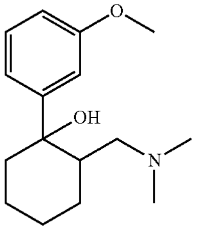 [SMILES: COc1cccc(C2(O)CCCCC2CN(C)C)c1] | 64.5% (50 mg/kg dose, no analgesic effect at 10 mg/kg dose) |
| 1-((3R,4S)-3-((dimethylamino)methyl)-4-hydroxy-4-(3-methoxyphenyl)piperidin-1-yl)-2-(2,4,5-trifluorophenyl)ethyl-1-one hydrochloride | 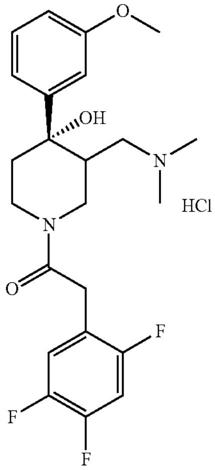 [SMILES: COc1cccc([C@]2(O)CCN(C(=O)Cc3cc(F)c(F)cc3F)CC2CN(C)C)c1 ; Cl] | 0.54 mg/kg |
| 1-((3R,4S)-3-((dimethylamino)methyl)-4-hydroxy-4-(3-hydroxyphenyl)piperidin-1-yl)-2-(2,4,5-trifluorophenyl)ethyl-1-one hydrochloride | 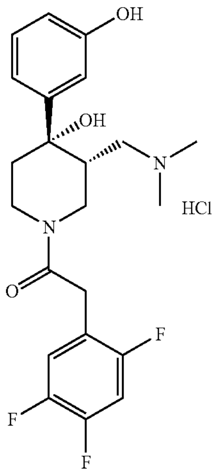 [SMILES: CN(C)C[C@@H]1CN(C(=O)Cc2cc(F)c(F)cc2F)CC[C@@]1(O)c1cccc(O)c1 ; Cl] | 29.7% |

TABLE 4-2-continued

Maximum percentage effective analgesic or $ED_{50}$ values of compound hot plate at 10 mg/kg dose

| Name | Structure | % MPE/$ED_{50}$ |
|---|---|---|
| 1-((3S,4R)-3-((dimethylamino)methyl)-4-hydroxy-4-(3-methoxyphenyl)piperidin-1-yl)-2-(2,4,5-trifluorophenyl)ethyl-1-one hydrochloride | 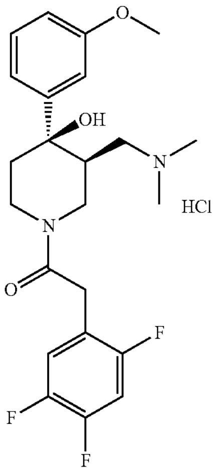 [SMILES: COc1cccc([C@@]2(O)CCN(C(=O)Cc3cc(F)c(F)cc3F)C[C@@H]2CN(C)C)c1 ; Cl] | 10.5% |
| 1-((3S,4R)-3-((dimethylamino)methyl)-4-hydroxy-4-(3-hydroxyphenyl)piperidin-1-yl)-2-(2,4,5-trifluorophenyl)ethyl-1-one hydrochloride | 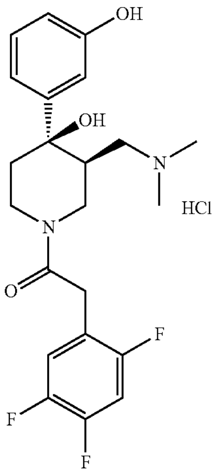 [SMILES: CN(C)C[C@H]1CN(C(=O)Cc2cc(F)c(F)cc2F)CC[C@]1(O)c1cccc(O)c1 ; Cl] | — |
| (3R,4S)-1-(Benzylsulfonyl)-3-((dimethylamino)methyl)-4-(3-methoxyphenyl)piperidin-4-ol hydrochloride | 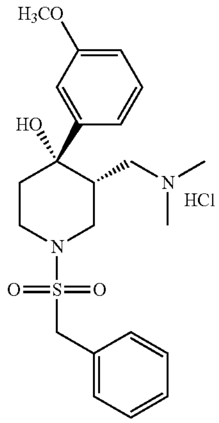 [SMILES: COc1cccc([C@]2(O)CCN(S(=O)(=O)Cc3ccccc3)C[C@H]2CN(C)C)c1 ; Cl] | 0.49 mg/kg |

TABLE 4-2-continued

| Maximum percentage effective analgesic or $ED_{50}$ values of compound hot plate at 10 mg/kg dose | | |
| --- | --- | --- |
| Name | Structure | % MPE/$ED_{50}$ |
| (3R,4S)-1-(Benzylsulfonyl)-3-((dimethylamino)methyl)-4-(3-hydroxyphenyl)piperidin-4-ol hydrochloride | 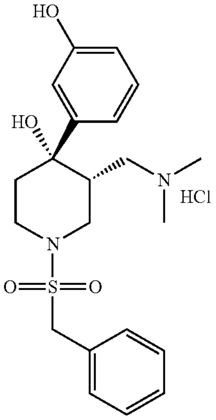 [SMILES: CN(C)C[C@@H]1CN(S(=O)(=O)Cc2ccccc2)CC[C@@]1(O)c1cccc(O)c1 ; Cl] | — |
| (3S,4R)-1-(Benzylsulfonyl)-3-((dimethylamino)methyl)-4-(3-methoxyphenyl)piperidin-4-ol hydrochloride | 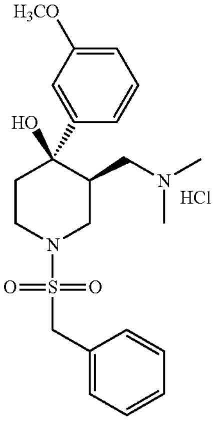 [SMILES: COc1cccc([C@@]2(O)CCN(S(=O)(=O)Cc3ccccc3)C[C@@H]2CN(C)C)c1 ; Cl] | 13.4% |
| (3S,4R)-1-(Benzylsulfonyl)-3-((dimethylamino)methyl)-4-(3-hydroxyphenyl)piperidin-4-ol hydrochloride | 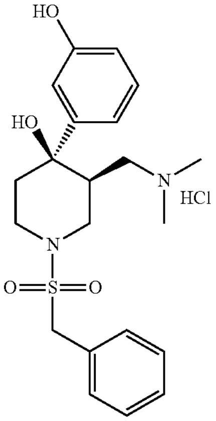 [SMILES: CN(C)C[C@H]1CN(S(=O)(=O)Cc2ccccc2)CC[C@]1(O)c1cccc(O)c1 ; Cl] | — |

In the column "% MPE or $ED_{50}$", the values expressed in percentages refer to % MPE and the values in mg/kg refer to $ED_{50}$.

As can be seen from Table 4-2, the analgesic effect of the compounds of the present invention is stronger than that of tramadol.

EXAMPLE 5

The invention is illustrated by the following examples, which are for illustrative purposes only and are not limited to the scope of the invention. Compounds of formula (FWBE) can be prepared as described in the generic synthetic routes and examples below.

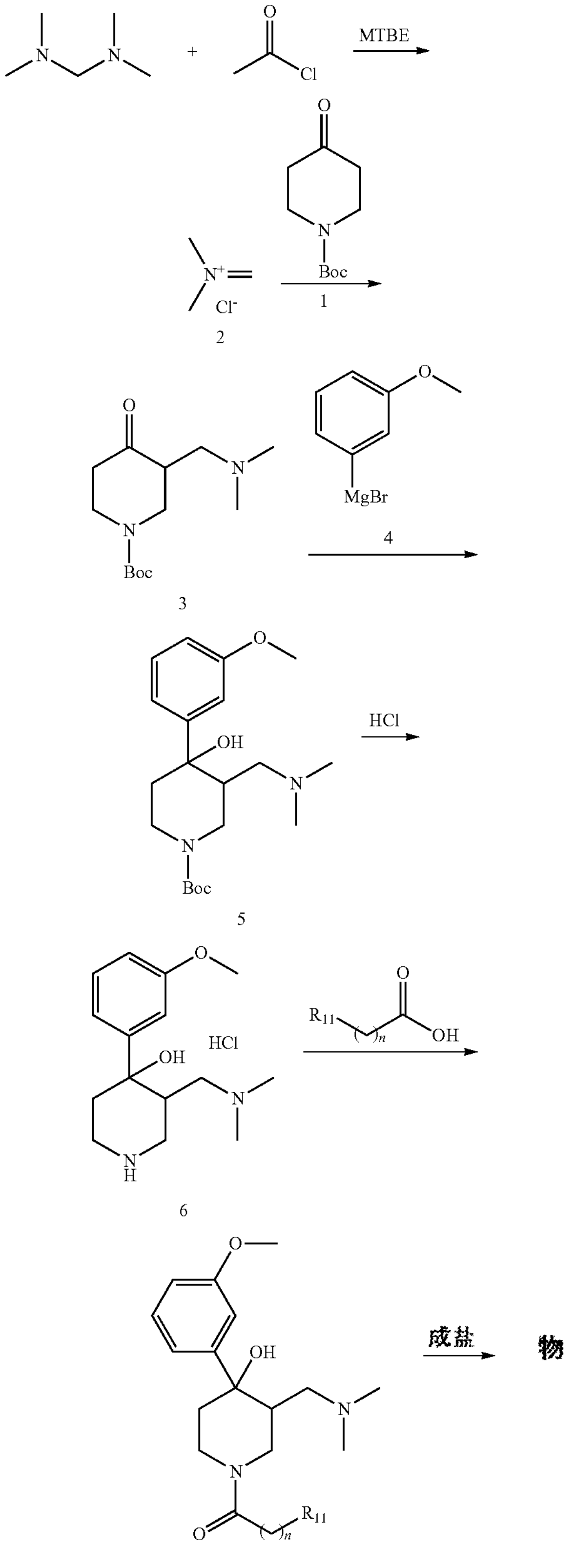

Example 5-1

Preparation of Intermediate 2:

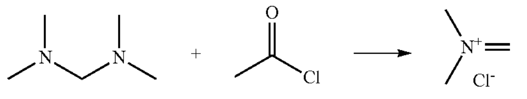

2

A 1 L flask with a nitrogen balloon, thermometer and constant pressure dropping funnel was charged with N,N,N',N'-tetramethylmethane diamine (60 g, 587.2 mmol, 1 eq.), methyl tert-butyl ether (500 mL), cooled to 0° C. and acetyl chloride (46.1 g, 587.2 mmol, 1 eq., approx. 20 min) was added dropwise at 30° C. The filter cake was stirred with acetonitrile (100 mL) and MTBE (25 mL) for 10 min, filtered and evaporated under reduced pressure (55° C.) to give 46 g of off-white solid (very hygroscopic) in 83.7% yield.

Example 5-2

Preparation of Intermediate 3:

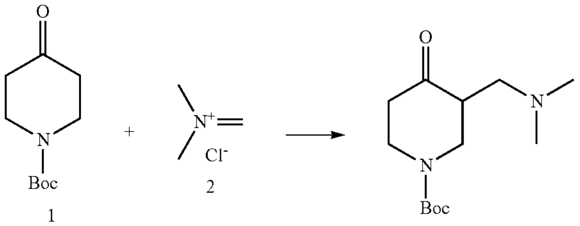

1 2 3

A 1 L flask with a thermometer and a nitrogen bulb was charged with Boc-piperidone (35 g, 175.66 mmol, 1 eq.), acetonitrile (350 mL), stirred and dissolved, and Intermediate 2 (19.72 g, 210.8 mmol, 1.2 eq.) was added. The reaction was carried out at an internal temperature of 30-35° C. for 24 h. TLC showed that the reaction was essentially complete after 24 h. The acetonitrile was evaporated under reduced pressure, DCM (300 mL) was added and saturated sodium bicarbonate (250 mL) was added, mixed, left to stand, layered and partitioned. The aqueous phase was extracted with DCM (200+100 mL). The organic phases were combined, washed with water (50 mL), dried over anhydrous magnesium sulphate, filtered and the filtrate evaporated under reduced pressure to give 43.3 g of a reddish brown viscous liquid in 93.5% yield.

Example 5-3

Preparation of Intermediates 5:

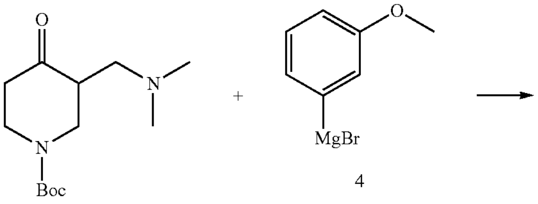

3 4

-continued

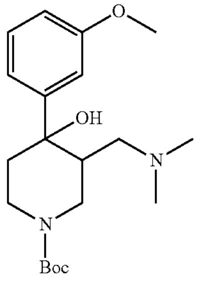

5

A 1 L four-necked flask with a nitrogen bulb, constant pressure dropping funnel, condenser tube and thermometer was refluxed with magnesium flakes (11 g, 451.68 mmol, 3 eq.), THF (300 mL), 3 iodine grains and a small amount of m-bromomethyl ether (84.5 g, 451.68 mmol, 3 eq.) in a solution of THF (70 mL) and heated to reflux. Allow the yellow colour to fade and stop heating. Slowly added the THF solution of m-bromoanisole dropwise (approx. 1 h) until the dropwise addition was complete. After 30 min, add a solution of Intermediate 3 (37.76 g, 1 eq.) in THF (100 mL) dropwise at 25° C. After the dropwise addition, the ice water bath was withdrawn and stirred and left at room temperature overnight (18 h). The reaction solution was poured into a mixture of aqueous ammonium chloride (200 mL) and ice (approx. 100 g), stirred for 5 min and the THF is evaporated under reduced pressure (30° C.). Added ethyl acetate (300 mL), stirred, left to stand, stratify and partition. The aqueous phase was extracted with ethyl acetate (300 mL). The organic phases were combined, washed with water (100 mL), dried over anhydrous magnesium sulphate, filtered and the filtrate was evaporated under reduced pressure to give 76.5 g of yellow liquid, which was purified by column chromatography to give 21.4 g of a light yellow viscous liquid in 38.9% yield (two steps, as boc-piperidone). $^1H$ NMR (400 MHz, $CD_3OD$), δ 7.26 (t, J=8 Hz, 1H), 7.04~7.05 (m, 1H), 6.98 (d, J=8 Hz, 1H), 6.81 (dd, J=8 Hz, J=4 Hz, 1H), 4.20~4.25 (m, 1H), 3.96~4.00 (m, 1H), 3.79 (s, 3H), 3.35 (s, 1H), 3.03~3.22 (m, 2H), 2.31~2.37 (m, 1H), 2.07~2.11 (m, 1H), 2.04 (s, 6H), 1.94~2.01 (m, 1H), 1.78~1.81 (m, 1H), 1.58~1.62 (m, 1H), 1.50 (s, 9H).

Example 5-4

Preparation of Intermediate 6:

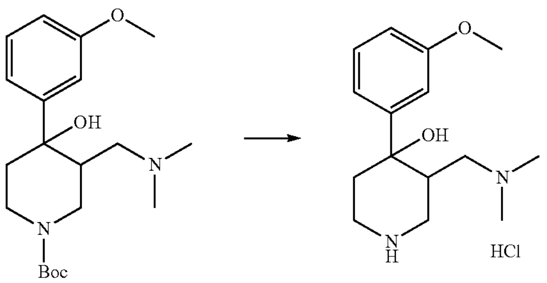

5 6

A 250 mL single-topped vial was added with 5 (9.5 g, 26.06 mmol, 1 eq.)), methanol (76 mL), stirred, and HCl/1,4-dioxane solution (16.3 mL, 65.15 mmol, 2.5 eq.) was added dropwise and the internal temperature was raised to approximately 36° C. After stirring for 2 hours, TLC showed a significant amount of raw material. Increase the temperature to 50° C. and stir, after 2 hours TLC shows an essentially complete reaction. Added MTBE (150 mL) and stirred, gradually precipitate solid, stir overnight (24 h). The filter cake was filtered with MTBE (20 mL) and spun dry under reduced pressure to give 8.63 g of a white solid in 98.3% yield. $^1H$ NMR (400 MHz, $CD_3OD$), δ 7.38 (t, J=8 Hz, 1H), 7.15~7.16 (m, 1H), 7.12 (d, J=8 Hz, 1H), 6.92 (dd, $J_1$=8 Hz, $J_2$=4 Hz, 1H), 3.83 (s, 3H), 3.75 (dd, $J_1$=12 Hz, $J_2$=4 Hz, 1H), 3.41~3.43 (m, 3H), 3.09~3.15 (m, 1H), 2.85~2.92 (m, 1H), 2.75 (s, 3H), 2.75~2.78 (m, 1H), 2.57 (s, 3H), 2.54~2.62 (m, 1H), 1.89~1.94 (m, 1H).

Example 5-5

General Method of Condensation:

100 mL single-topped vial with Intermediate 6 (1 eq.), carboxylic acid (1 eq.), EDCI-HCl (1.5 eq.), HOBT (1.5 eq.), DMF (6 mL), NMM (4 eq.), stirred at room temperature until TLC showed a complete reaction. Water and sodium bicarbonate solution were added and DCM extracted. The organic phases were combined, washed with water, dried over anhydrous magnesium sulphate, filtered and the filtrate was evaporated under reduced pressure to give the residue. The resulting residue was purified by column chromatography with aluminium trioxide to give the target product.

Example 5-6

General Method of Salt Formation:

A 100 mL monolithic bottle of free base (1 eq.) was added with dichloromethane, stirred to dissolve and clarify, and methyl tert-butyl ether is added; a 1,4-dioxane solution of HCl (1.2 eq.) was added slowly dropwise to precipitate a solid. Stirring, filtration, drenching of the filter cake with methyl tert-butyl ether (2 mL) and pumping dried to give the target product.

Example 5-7

1-(3-((Dimethylamino)methyl)-4-hydroxy-4-(3-methoxyphenyl)piperidin-1-yl)-2-(thiophen-3-yl)ethyl-1-one

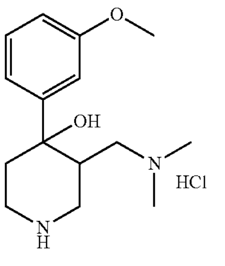

+

MW: 300.82

-continued

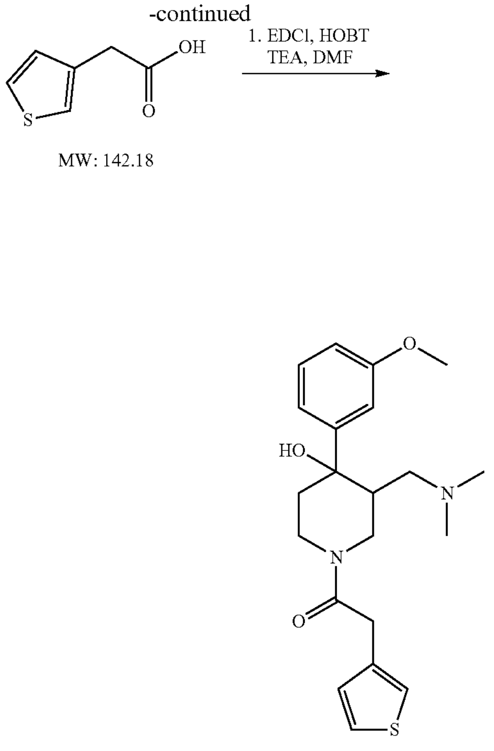

MW: 142.18

MW: 424.98

The target product was obtained from 2-(thiophen-3-yl) acetic acid. Yield: 34%. $^1H$ NMR (400 MHz, $CD_3OD$), δ 7.40~7.43 (m, 1H), 7.20~7.26 (m, 2H), 7.06~7.09 (m, 1H), 6.93~6.97 (m, 1H), 6.87~6.91 (m, 1H), 6.76~6.79 (m, 1H), 4.48~4.72 (m, 1H), 3.75~4.12 (m, 4H), 3.78 (s, 3H), 3.28~3.51 (m, 1H), 3.04~3.01, 2.90~2.96 (m, 1H), 2.98 (s, 1H), 2.85 (s, 1H), 2.24~2.40 (m, 1H), 2.07 (s, 3H), 1.84~2.02 (m, 3H), 1.91 (m, 1H), 1.47~1.51, 1.70~1.73 (m, 1H), 1.62~1.66 (m, 1H). LC-MS-ESI$^+$: [M+H]$^+$ 389.

Example 5-8

1-(3-((Dimethylamino)methyl)-4-hydroxy-4-(3-methoxyphenyl)piperidin-1-yl)-2-(thiophen-3-yl)ethyl-1-one hydrochloride (FWBE2)

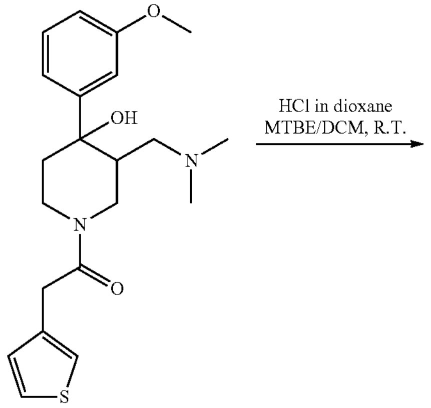

-continued

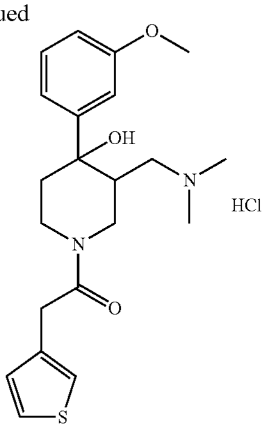

The target product was obtained as 1-(3-((dimethylamino)methyl)-4-hydroxy-4-(3-methoxyphenyl)piperidin-1-yl)-2-(thiophen-3-yl)ethyl-1-one. Yield: 59.6%. $^1$H NMR (400 MHz, $CD_3OD$), δ 7.42~7.45 (m, 1H), 7.28~7.37 (m, 2H), 7.08~7.14 (m, 1H), 6.94~7.07 (m, 2H), 6.83~6.87 (m, 1H), 4.53~4.66 (m, 1H), 3.92~4.01 m, 1H), 3.79 (s, 3H), 3.78~3.86 (m, 1H), 3.40~3.59 (m, 1H), 3.95~3.14 (m, 1H), 2.60~2.73 (q, 6H), 2.29 (s, 1H), 2.16~2.23 (m, 1H), 2.08~2.16, 1.75~1.86 (m, 1H), 1.59~1.75 (m, 1H). LS-MS-ESI$^+$: [M+H]$^+$ 389.

Example 5-9

2-(3,5-Bis(trifluoromethyl)phenyl)-1-(3-((dimethylamino)methyl)-4-hydroxy-4-(3-methoxyphenyl)piperidin-1-yl)ethyl-1-one hydrochloride (FWBE1)

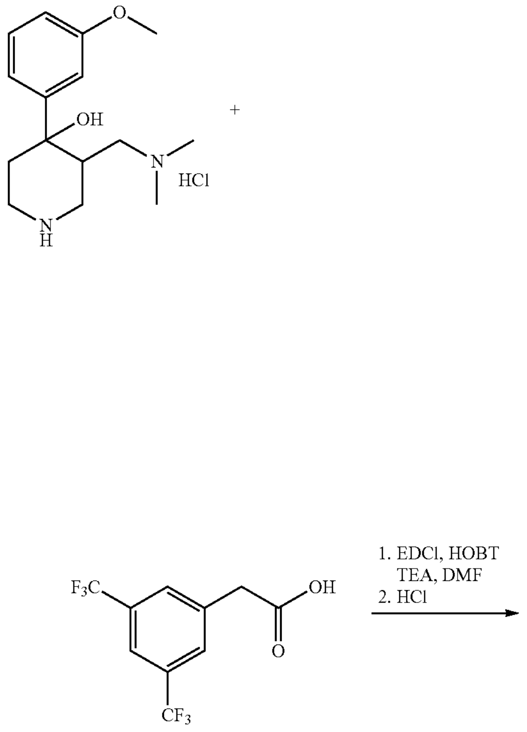

-continued

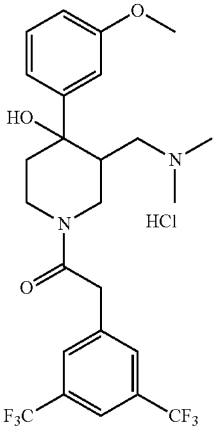

3,5-Bis(trifluoromethyl)phenylacetic acid was used as raw material to obtain the target product. Yield: 34%. $^1$H NMR (400 MHz, $CD_3OD$), δ 7.91~7.93 (d, 2H), 7.87 (s, 1H), 7.24 (t, J=8 Hz, 1H), 7.04 (t, J=4 Hz, 1H), 6.94~6.98 (m, 1H), 6.80 (dd, $J_1$=8 Hz, $J_2$=4 Hz, 1H), 4.48~4.73 (m, 1H), 3.93~4.15 (m, 3H), 3.79 (s, 3H), 3.33~3.61 (m, 1H), 2.93~3.13 (m, 1H), 2.27~2.39 (m, 1H), 1.93~2.11 (m, 2H), 2.04 (s, 3H), 1.96 (s, 3H), 1.74~1.87 (m, 1H), 1.63~1.69 (m, 1H). LC-MS-ESI$^+$: [M+H]$^+$ 519.0.

The salt was formed from 2-(3,5-bis(trifluoromethyl)phenyl)-1-(3-((dimethylamino)methyl)-4-hydroxy-4-(3-methoxyphenyl)piperidin-1-yl)ethyl-1-one to give the target product. Yield: 95.3%. $^1$H NMR (400 MHz, $CD_3OD$), δ 7.92~7.95 (d, 2H), 7.86~7.88 (d, 1H), 7.31~7.35 (m, 1H), 7.05~7.16 (m, 2H), 6.87 (dd, $J_1$=8 Hz, $J_2$=4 Hz, 1H), 4.44~4.86 (m, 2H), 4.16~4.31 (q, 1H), 4.10 (s, 1H), 4.00~4.07 (m, 1H), 3.81~3.82 (d, 3H), 3.48~3.54, 3.71~3.79 (m, 1H), 3.59~3.66 (m, 1H), 3.01~3.30 (m, 3H), 2.63~2.81 (m, 3H), 2.45~2.60 (m, 3H), 2.29~2.45 (m, 1H). 2.12~2.34 (m, 1H), 1.75 (t, J=8 Hz, 1H). LC-MS-ESI$^+$: [M+H]$^+$ 519.0.

Example 5-10

1-(3-((Dimethylamino)methyl)-4-hydroxy-4-(3-methoxyphenyl)piperidin-1-yl)-2-phenylethyl-1-one

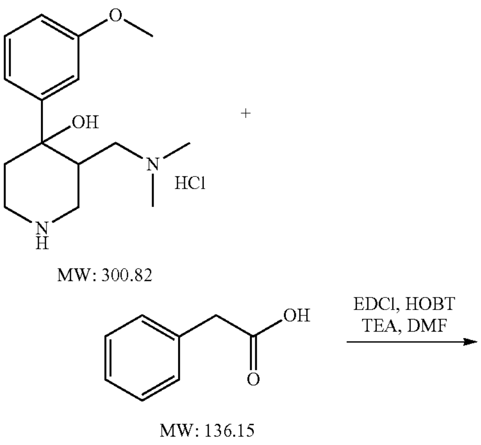

-continued

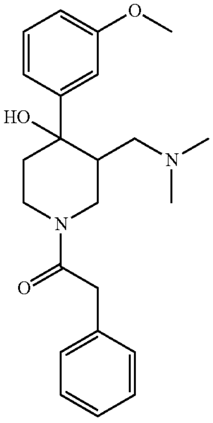

MW: 382.50

Phenylacetic acid was used as raw material to obtain the target product. Yield: 38.2%. $^{1}$H NMR (400 MHz, $CD_3OD$), δ 7.30~7.37 (m, 4H), 7.19~7.27 (m, 2H), 6.84~6.95 (m, 2H), 6.75~6.79 (m, 1H), 4.50~4.73 (m, 1H), 3.88~3.94 (m, 1H), 3.72~3.86 (m, 2H), 3.77 (s, 3H), 3.26~3.49 (m, 1H), 2.89~3.11 (m, 1H), 2.21~2.37 (m, 1H), 2.04 (s, 3H), 1.80~2.01 (m, 3H), 1.85 (s, 3H), 1.65~1.69 (m, 1H), 1.42~1.63 (m, 1H). LC-MS-ESI$^{+}$: $[M+H]^{+}$ 383.

Example 5-11

1-(3-((Dimethylamino)methyl)-4-hydroxy-4-(3-methoxyphenyl)piperidin-1-yl)-2-phenylethyl-1-one hydrochloride (FWBE3)

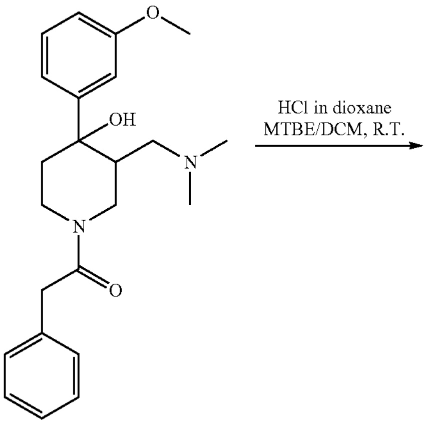

-continued

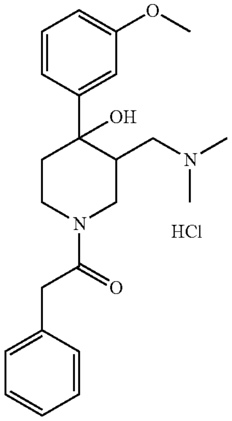

The target product was obtained as 1-(3-((dimethylamino) methyl)-4-hydroxy-4-(3-methoxyphenyl)piperidin-1-yl)-2-phenylethyl-1-one. Yield: 99%. $^{1}$H NMR (400 MHz, $CD_3OD$), δ 7.25~7.40 (m, 7H), 6.92~7.06 (m, 2H), 6.83~6.87 (m, 1H), 4.27~4.32, 4.63~4.67 (m, 1H), 3.94~4.07, 4.54~4.58 (m, 2H), 3.80 (s, 3H), 3.39~3.54 (m, 1H), 2.94~3.14 (m, 2H), 2.59~2.73 (m, 7H), 2.08~2.24 (m, 1H), 1.56~1.85 (m, 2H). LC-MS-ESI$^{+}$: $[M+H]^{+}$ 383.

Example 5-12

1-(3-((Dimethylamino)methyl)-4-hydroxy-4-(3-methoxyphenyl)piperidin-1-yl)-2-(3-(trifluoromethyl)phenyl)ethyl-1-one

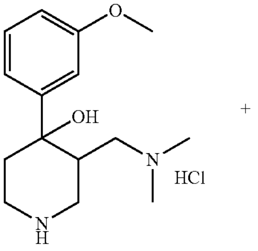

MW: 300.83

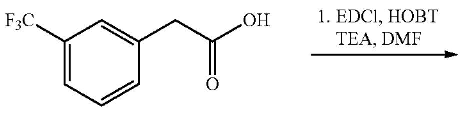

MW: 204.15

-continued

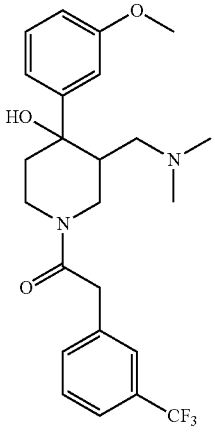

MW: 450.50

2-(3-(Trifluoromethyl)phenyl)acetic acid was used as the raw material to obtain the target product. Yield: 58%. $^1$H NMR (400 MHz, CD3OD), δ 7.47 (s, 1H), 7.35~7.43 (m, 3H), 7.03~7.08 (m, 1H), 6.81~6.83 (m, 1H), 6.73 (dd, $J_1$=16 Hz, $J_2$=8 Hz, 1H), 6.62 (dd, $J_1$=8 Hz, $J_2$=4 Hz, 1H), 4.33~4.57 (m, 1H), 3.71~3.95 (m, 3H), 3.61 (s, 3H), 2.89~2.96, 3.34~3.38 (m, 1H), 2.68~2.81 (q, 3H), 2.07~2.20 (m, 2H), 1.86 (s, 3H), 1.72~1.84 (m, 2H), 1.72 (s, 3H), 1.36~1.40, 1.54~1.58 (m, 1H), 1.47~1.53 (m, 1H).

Example 5-13

1-(3-((Dimethylamino)methyl)-4-hydroxy-4-(3-methoxyphenyl)piperidin-1-yl)-2-(3-(trifluoromethyl)phenyl)ethyl-1-one hydrochloride (FWBE4)

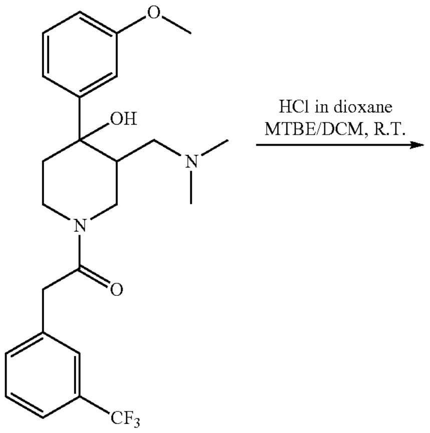

-continued

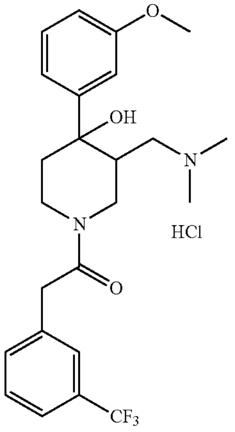

1-(3-((Dimethylamino)methyl)-4-hydroxy-4-(3-methoxyphenyl)piperidin-1-yl)-2-(3-(trifluoromethyl)phenyl)ethyl-1-one as raw material. Yield: 97.6%. $^1$H NMR (400 MHz, CD$_3$OD), δ 7.55~7.66 (m, 4H), 7.29~7.34 (q, 1H), 6.97~7.13 (m, 2H), 6.84~6.88 (m, 1H), 4.52~4.67 (m, 1H), 4.03~4.41 (m, 1H), 3.99~4.03 (m, 2H), 3.80~3.81 (d, 3H), 3.44~3.60 (m, 1H), 3.04~3.12 (m, 2H), 2.86~3.02 (m, 1H), 2.41~2.73 (q, 6H), 1.98~2.18 (m, 1H), 1.67~1.76 (m, 1H). LC-MS-ESI$^+$: [M+H]$^+$ 451.1.

Example 5-14

(3-((Dimethylamino)methyl)-4-hydroxy-4-(3-methoxyphenyl)piperidin-1-yl)(2,4,5-trifluorophenyl)methanone

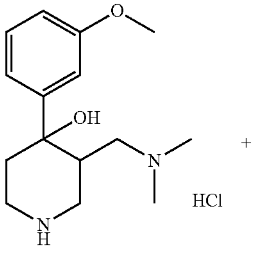

MW: 300.83

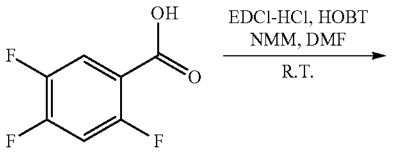

MW: 176.09

-continued

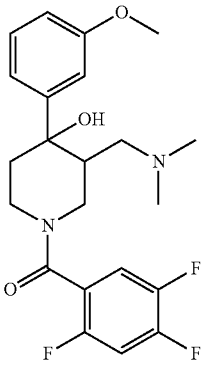

MW: 422.45

2,4,5-Trifluorobenzoic acid was used as raw material to obtain the target product. Yield: 47%. $^1$H NMR (400 MHz, $CD_3OD$), δ 7.30~7.37 (m, 1H), 7.24~7.28 (m, 1H), 7.12~7.22 (m, 1H), 7.00~7.10 (m, 2H), 6.81 (dd, $J_1$=8 Hz, $J_2$=4 Hz H), 4.55~4.87 (m, 1H), 3.79 (s, 3H), 3.57~3.69 (m, 1H), 3.34~3.44 (m, 1H), 3.09~3.30 (m, 1H), 2.23~2.27, 2.39~2.45 (m, 1H), 1.99~2.04, 2.11~2.22 (m, 2H), 2.08 (s, 3H), 1.88 (s, 3H), 1.58~1.86 (m, 3H). LC-MS-ESI$^+$: [M+H]$^+$ 423.

Example 5-15

(3-((Dimethylamino)methyl)-4-hydroxy-4-(3-methoxyphenyl)piperidin-1-yl)(2,4,5-trifluorophenyl)methanone hydrochloride (FWBE5)

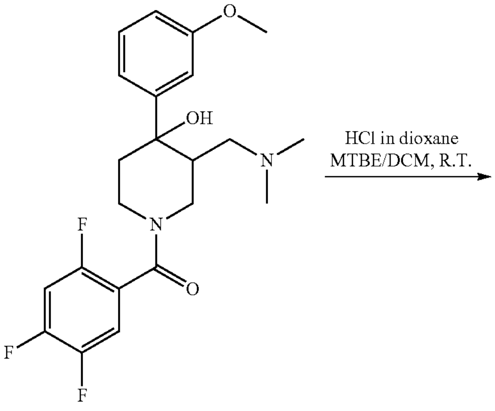

MW: 422.45

-continued

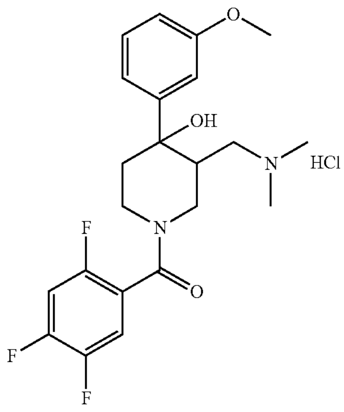

MW: 458.91

The target product was obtained as (3-((dimethylamino)methyl)-4-hydroxy-4-(3-methoxyphenyl)piperidin-1-yl)(2,4,5-trifluorophenyl)methanone. Yield: 86%. $^1$H NMR (400 MHz, $CD_3OD$), δ 7.55 (s, 1H), 7.32~7.39 (m, 2H), 7.08~7.13 (m, 2H), 6.87 (dd, J=8 Hz, 1H), 4.60~4.80 (m, 1H), 3.81 (s, 3H), 3.58~3.78 (m, 2H), 3.48~3.53 (m, 1H), 3.26~3.34 (m, 1H), 3.12~3.20 (m, 1H), 2.73~2.77 (m, 3H), 3.61~3.68 (d, 3H), 2.41~2.48 (m, 2H), 2.13~2.21 (m, 1H), 1.67~1.84 (m, 1H).

Example 5-16

1-(3-((Dimethylamino)methyl)-4-hydroxy-4-(3-methoxyphenyl)piperidin-1-yl)-2-(3-(trifluoromethoxy)phenyl)ethyl-1-one

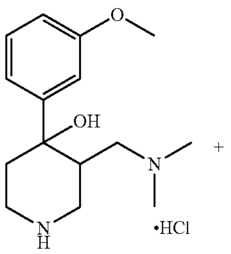

MW: 300.82

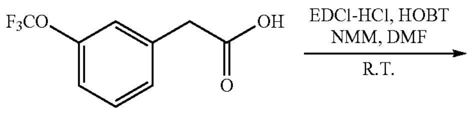

MW: 220.15

-continued

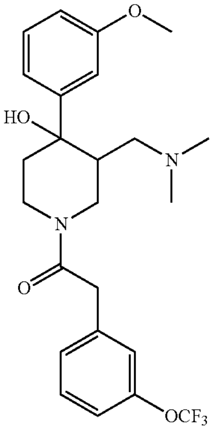

MW: 466.49

2-(3-(Trifluoromethoxy)phenyl)acetic acid was used as the raw material to obtain the target product. Yield: 77%. $^1$H NMR (400 MHz, $CD_3OD$), δ 7.42~7.47 (m, 1H), 7.31~7.34 (m, 1H), 7.08~7.26 (m, 3H), 6.96~7.02 (m, 1H), 6.86~6.92 (m, H), 6.76~6.80 (m, 1H), 4.49~4.87 (m, 1H), 3.88~4.11 (m, 3H), 3.78 (s, 3H), 3.28~3.53 (m, 1H), 2.91~3.12 (m, 1H), 3.23~3.38 (m, 1H), 2.00~2.04 (d, 3H), 1.92~1.98 (m, 1H), 1.90 (m, 3H), 1.51~1.85 (m, 2H). LC-MS-ESI$^+$: [M+H]$^+$ 467.0.

Example 5-17

1-(3-((Dimethylamino)methyl)-4-hydroxy-4-(3-methoxyphenyl)piperidin-1-yl)-2-(3-(trifluoromethoxy)phenyl)ethyl-1-one hydrochloride (FWBE6)

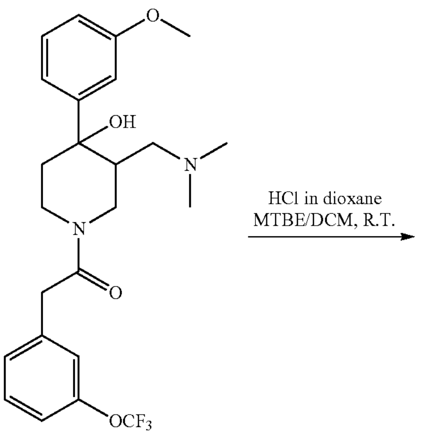

-continued

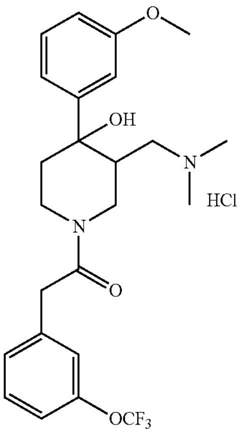

The target product was obtained as 1-(3-((dimethylamino)methyl)-4-hydroxy-4-(3-methoxyphenyl)piperidin-1-yl)-2-(3-(trifluoromethoxy)phenyl)ethyl-1-one. Yield: 94.2%. $^1$H NMR (400 MHz, $CD_3OD$), δ 7.42~7.48 (m, 1H), 7.26~7.38 (m, 3H), 7.17~7.21 (m, 1H), 6.96~7.07 (m, 2H), 6.84~6.88 (m, 1H), 4.34~4.66 (m, 1H), 4.00~4.14 (m, 1H), 3.94~3.97 (m, 2H), 3.80~3.81(3H), 3.42~3.59 (m, 1H), 2.97~3.41 (m, 2H), 2.39~2.77 (m, 7H), 2.21~2.39 (m, 2H), 1.94~218 (m, 1H), 1.66~1.76 (m, 1H). LC-MS-ESI$^+$: [M+H]$^+$ 467.0.

Example 5-18

1-(3-((Dimethylamino)methyl)-4-hydroxy-4-(3-methoxyphenyl)piperidin-1-yl)-2-(1H-tetrazol-1-yl)ethyl-1-one

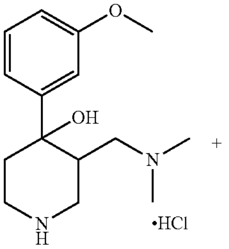

MW: 300.82

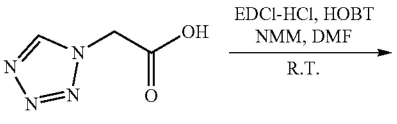

MW: 128.09

-continued

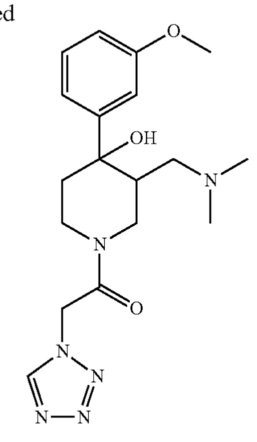

MW: 374.44

2-(1H-tetrazol-1-yl)acetic acid was used as the raw material to obtain the target product. Yield: 56%. $^1$H NMR (400 MHz, $CD_3OD$), δ 9.17 (s, 1H), 7.25~7.29 (m, 1H), 7.03~7.05 (m, 1H), 7.08~7.09 (m, 1H), 6.82 (dd, $J_1$=8 Hz, $J_2$=4 Hz, 1H), 5.61~5.79 (m, 2H), 4.38~4.66 (m, 1H), 3.82~4.04 (m, 1H), 3.80 (s, 3H), 3.43~3.69 (m, 1H), 3.01~3.20 (m, 1H), 2.22~2.40 (m, 2H), 2.14~2.21 (m, 1H), 2.00~2.09 (m, 7H), 1.83~1.87 (m, 1H), 1.65~1.76 (m, 1H). LC-MS-ESI$^+$: $[M+H]^+$ 375.1.

Example 5-19

1-(3-((Dimethylamino)methyl)-4-hydroxy-4-(3-methoxyphenyl)piperidin-1-yl)-2-(1H-tetrazol-1-yl)ethyl-1-one hydrochloride (FWBE7)

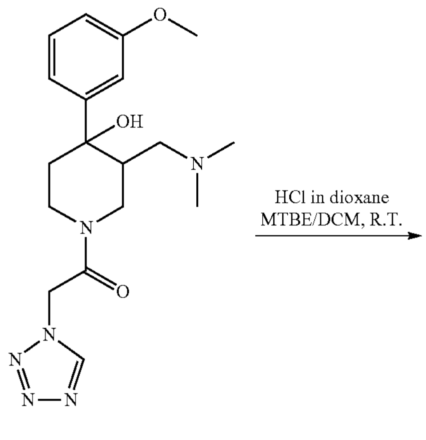

-continued

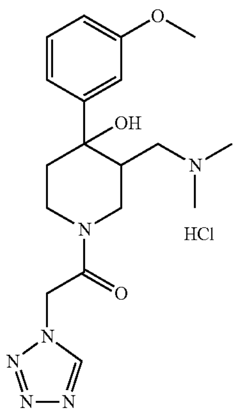

The target product was obtained as 1-(3-((dimethylamino)methyl)-4-hydroxy-4-(3-methoxyphenyl)piperidin-1-yl)-2-(1H-tetrazol-1-yl)ethyl-1-one. Yield: 99%. $^1$H NMR (400 MHz, $CD_3OD$), δ 9.21 (s, 1H), 9.34 (t, J=8 Hz, 1H), 7.11~7.17 (m, 2H), 6.88 (dd, $J_1$=8 Hz, $J_2$=4 Hz, 1H), 5.63~6.08 (m, 2H), 4.32~4.37, 4.57~4.62 (m, 1H), 3.90~3.94, 4.42~4.46 (m, 1H), 3.82 (s, 3H), 3.54~3.60, 3.66~3.73 (m, 1H), 2.99~3.21 (m, 2H), 2.65~2.86 (m, 5H), 2.51~2.59 (d, 2H), 2.15~2.44 (m, 1H), 1.72~1.91 (m, 1H). LC-MS-ESI$^+$: $[M+H]^+$ 375.1.

Example 5-20

1-(3-((Dimethylamino)methyl)-4-hydroxy-4-(3-methoxyphenyl)piperidin-1-yl)-2-(thiophen-2-yl)ethyl-1-one

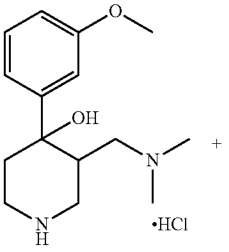

MW: 300.82

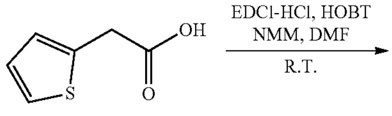

MW: 128.09

-continued

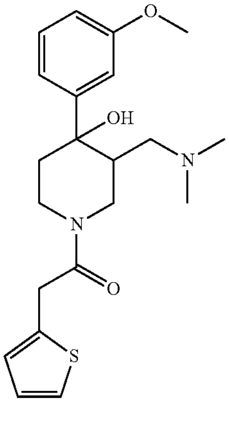

MW: 388.52

2-(Thiophen-1-yl)acetic acid was used as raw material to obtain the target product. Yield: 76%. $^1$H NMR (400 MHz, $CD_3OD$), δ 7.30~7.32 (m, 1H), 7.21~7.26 (m, 1H), 6.95~7.01 (m, 3H), 6.88~6.93 (m, 1H), 6.77~6.80 (m, 1H), 5.49 (s, 1H), 4.47~4.71 (m, 1H), 3.92~4.17 (m, 2H), 3.78 (s, 3H), 3.29~3.59 (m, 1H), 2.91~3.12 (m, 1H), 2.25~2.39 (m, 1H), 2.05 (s, 3H), 1.83~1.96 (m, 5H), 1.71~1.76 (m, 1H), 1.51~1.69 (m, 1H). LC-MS-ESI$^+$: [M+H]$^+$ 389.

Example 5-21

1-(3-((Dimethylamino)methyl)-4-hydroxy-4-(3-methoxyphenyl)piperidin-1-yl)-2-(thiophen-2-yl) ethyl-1-one hydrochloride (FWBE8)

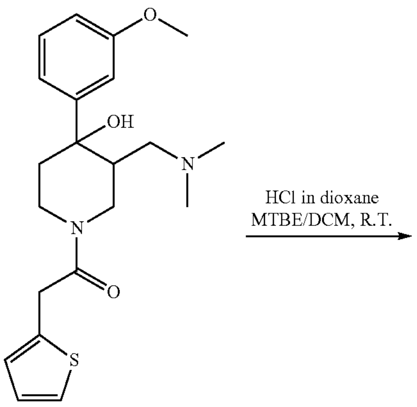

-continued

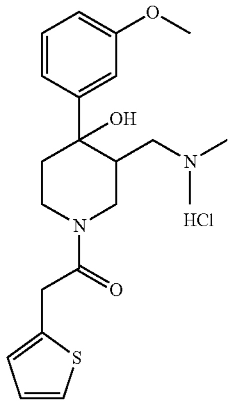

The target product was obtained as 1-(3-((dimethylamino) methyl)-4-hydroxy-4-(3-methoxyphenyl)piperidin-1-yl)-2-(thiophen-2-yl)ethyl-1-one. Yield: 84.5%. $^1$H NMR (400 MHz, CD3OD), δ 7.28~7.34 (m, 2H), 6.95~7.07 (m, 4H), 6.84~6.87 (m, 1H), 4.51~4.63 (m, 1H), 4.16~4.32 (m, 1H), 4.01~4.12 (m, 1H), 3.79 (s, 3H), 3.45~3.60 (m, 1H), 2.97~3.14 (m, 2H), 2.37~2.74 (m, 8H), 2.19~2.25 (m, 1H), 1.87~2.16 (m, 1H), 1.62~1.75 (m, 1H). LC-MS-ESI$^+$: [M+H]$^+$ 389.

Example 5-22

2-(3-Chlorophenyl)-1-(3-((dimethylamino)methyl)-4-hydroxy-4-(3-methoxyphenyl)piperidin-1-yl)ethyl-1-one

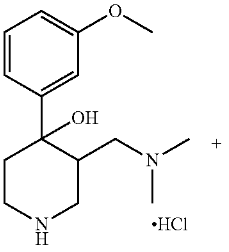

MW: 300.82

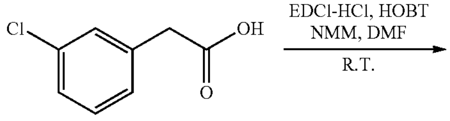

MW: 170.59

-continued

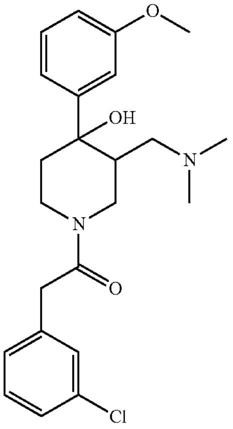

MW: 416.94

The target product was obtained using m-chlorophenylacetic acid as raw material. Yield: 58%. $^1$H NMR (400 MHz, $CD_3OD$), δ 7.23~7.37 (m, 5H), 6.98~6.99 (m, 1H), 6.89~6.92 (m, 1H), 6.77~6.80 (m, 1H), 4.49~4.71 (m, 1H), 3.88~4.11 (m, 2H), 3.78 (s, 3H), 3.74~3.86 (m, 2H), 3.28~3.53 (m, 1H), 2.93~3.12 (m, 1H), 2.25~2.47 (m, 1H), 2.13 (m, 3H), 1.91 (s, 3H), 1.85~2.08 (m, 2H), 1.70~1.78 (m, 1H), 1.51~1.68 (m, 1H), 1.21~1.30 (m, 1H). LC-MS-ESI$^+$: $[M+H]^+$ 417.0, 419.0.

Example 5-23

2-(3-Chlorophenyl)-1-(3-((dimethylamino)methyl)-4-hydroxy-4-(3-methoxyphenyl)piperidin-1-yl)ethyl-1-one hydrochloride (FWBE9)

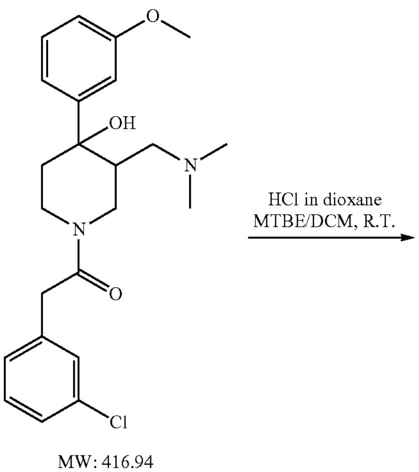

MW: 416.94

-continued

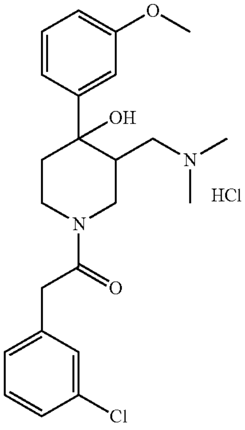

MW: 453.40

2-(3-Chlorophenyl)-1-(3-((dimethylamino)methyl)-4-hydroxy-4-(3-methoxyphenyl)piperidin-1-yl)ethyl-1-one was used as the raw material to obtain the target product. Yield: 84.7%. $^1$H NMR (400 MHz, $CD_3OD$), δ 7.25~7.41 (m, 5H), 6.97~7.11 (m, 2H), 6.84~6.87 (m, 1H), 3.34~3.38, 4.62~4.66 (m, 1H), 3.95~3.97, 4.51~4.55 (m, 1H), 3.96~4.09 (m, 1H), 3.89 (s, 1H), 3.81 (s, 3H), 3.41~3.59 (m, 1H), 2.97~3.14 (m, 2H), 2.34~2.73 (m, 7H), 2.22~2.28 (m, 1H), 1.92~2.17 (m, 1H), 1.64~1.75 (m, 1H). LC-MS-ESI$^+$: $[M+H]^+$ 417.0, 419.0.

Example 5-24

1-(3-((Dimethylamino)methyl)-4-hydroxy-4-(3-methoxyphenyl)piperidin-1-yl)-3-(3-(trifluoromethyl)phenyl)propyl-1-one hydrochloride (FWBE10)

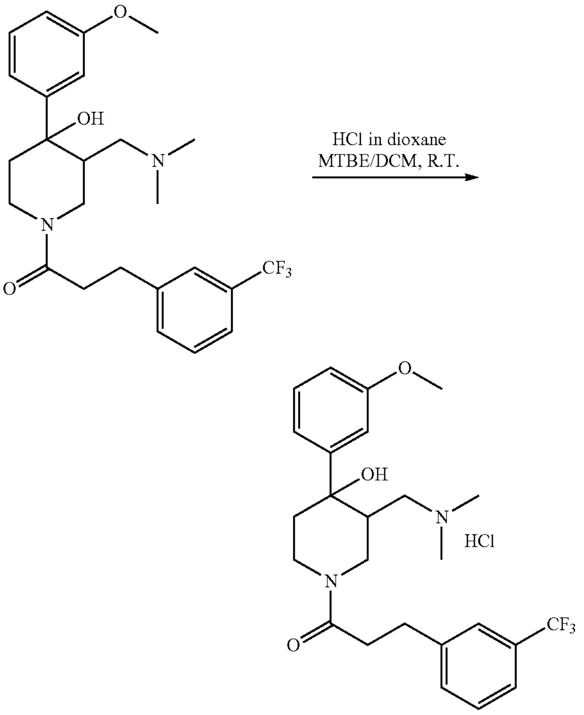

The target product was obtained as 1-(3-((dimethylamino)methyl)-4-hydroxy-4-(3-methoxyphenyl)piperidin-1-yl)-3-(3-(trifluoromethyl)phenyl)propyl-1-one. Yield: 84.2%. $^{1}$H NMR (400 MHz, CD3OD), δ 7.56~7.63 (m, 2H), 7.46~7.54 (m, 2H), 7.31 (t, J=8 Hz 1H), 7.05~7.09 (m, 1H), 6.94~7.03 (m, 1H), 6.86 (dd, $J_1$=8 Hz, $J_2$=4 Hz H), 4.25~4.28, 4.58~4.62 (m, 1H), 3.86~3.90, 4.48~4.52 (m, 1H), 3.80 (s, 3H), 3.33~3.51 (m, 1H), 3.05~3.08 (m, 3H), 2.73~3.02 (m, 4H), 2.70, 2.73 (d, 3H), 2.44, 2.60 (d, 3H), 2.13~2.32 (m, 1H), 1.92~2.09 (m, 1H), 1.66~1.72 (m, 1H). LC-MS-ESI$^+$: $[M+H]^+$ 465.

Example 5-25

1-(3-((Dimethylamino)methyl)-4-hydroxy-4-(3-methoxyphenyl)piperidin-1-yl)-2-(3-fluorophenyl)ethyl-1-one hydrochloride (FWBE12)

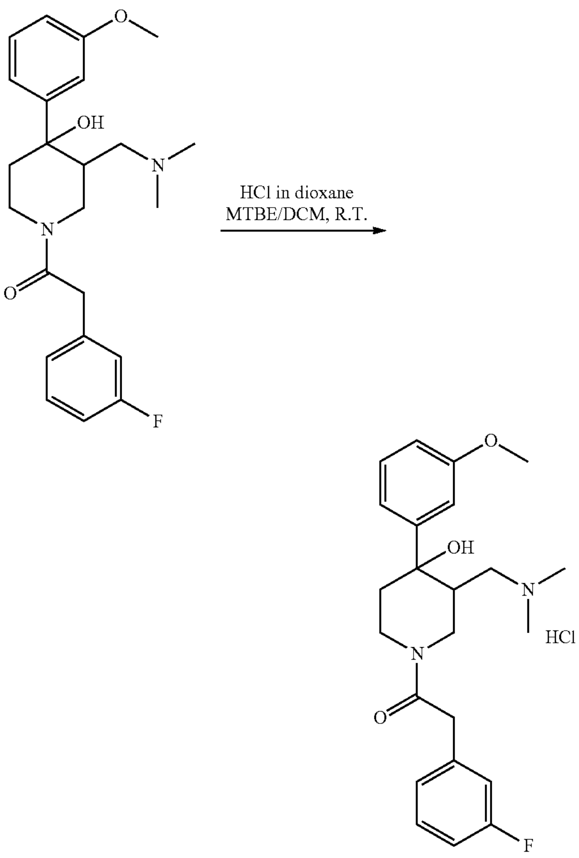

1-(3-((Dimethylamino)methyl)-4-hydroxy-4-(3-methoxyphenyl)piperidin-1-yl)-2-(3-fluorophenyl)ethyl-1-one was used as the raw material to obtain the target product. Yield: 92%. $^{1}$H NMR (400 MHz, CD3OD), δ 7.34~7.40 (m, 1H), 7.29~7.33 (m, 1H), 7.02~7.19 (m, 4H), 6.97~7.00 (m, 1H), 6.84~6.86 (m, 1H), 4.30~4.35, 4.62~4.66 (m, 1H), 3.90~4.10, 4.52~4.56 (m, 3H), 3.80 (s, 3H), 3.41~3.56 (m, 1H), 2.97~3.13 (m, 2H), 2.36~2.73 (m, 7H), 2.23~2.33 (m, 1H), 1.90~2.17 (m, 1H), 1.63~1.75 (m, 1H). LC-MS-ESI$^+$: $[M+H]^+$ 401.3

Example 5-26

2-(3-Bromophenyl)-1-(3-((dimethylamino)methyl)-4-hydroxy-4-(3-methoxyphenyl)piperidin-1-yl)ethyl-1-one

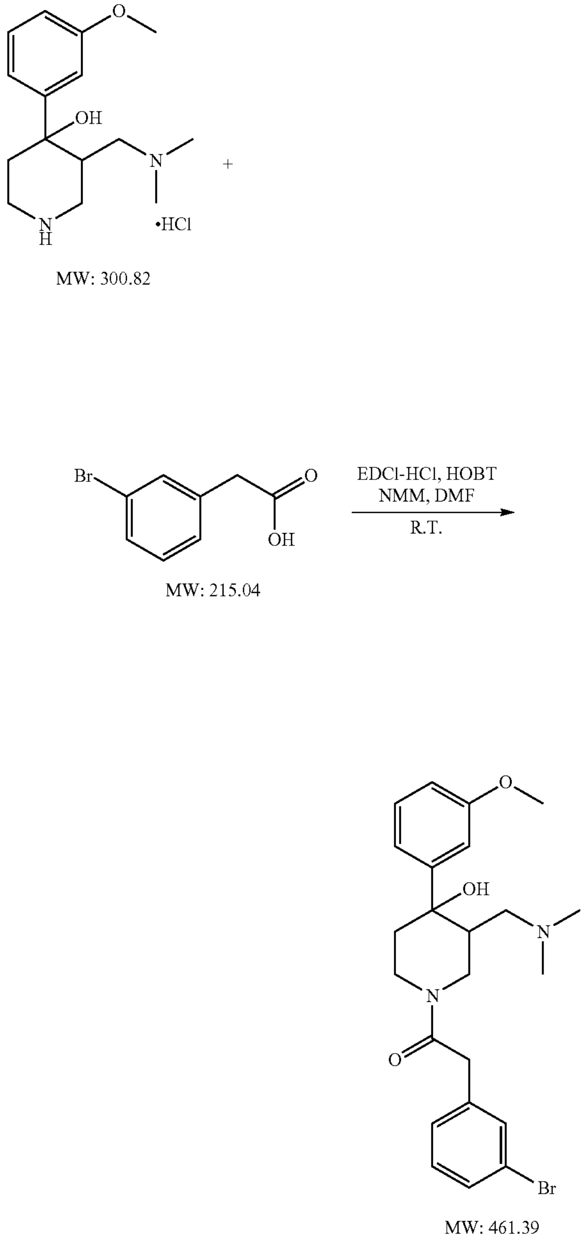

The target product was obtained by using m-bromophenylacetic acid as raw material. Yield: 78.43%. $^{1}$H NMR (400 MHz, $CD_3OD$), δ 7.50~7.52 (m, 1H), 7.41~7.44 (m, 1H), 7.21~7.32 (m, 3H), 6.97~6.99 (m, 1H), 6.87~6.92 (m, 1H), 6.78 (dd, $J_1$=8 Hz, $J_2$=4 Hz, 1H), 4.49~4.73 (m, 1H), 3.79~4.10 (m, 3H), 3.77 (s, 3H), 3.26~3.33, 3.44~3.52 (m, 1H), 2.90~2.96, 3.04~3.12 (m, 1H), 2.23~2.37 (m, 1H), 1.80~2.03 (m, 3H), 2.03 (s, 3H), 1.88 (s, 3H), 1.49~1.73 (m, 2H). LC-MS-ESI$^+$: $[M+H]^+$ 463.2.

Example 5-27

2-(3-Bromophenyl)-1-(3-((dimethylamino)methyl)-4-hydroxy-4-(3-methoxyphenyl)piperidin-1-yl)ethyl-1-one hydrochloride (FWBE11)

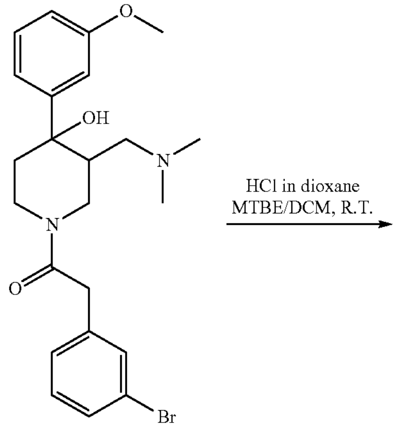

MW: 461.39

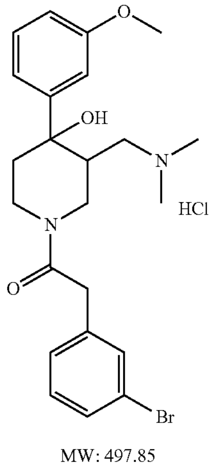

MW: 497.85

2-(3-Bromophenyl)-1-(3-((dimethylamino)methyl)-4-hydroxy-4-(3-methoxyphenyl)piperidin-1-yl)ethyl-1-one was used as the raw material to obtain the target product. Yield: 94%. $^1$H NMR (400 MHz, $CD_3OD$), δ 7.51~7.55 (m, 1H), 7.42~7.46 (m, 1H), 7.26~7.36 (m, 3H), 6.97~7.10 (m, 2H), 6.84~6.88 (m, 1H), 4.29~4.33, 4.61~4.65 (m, 1H), 3.88~4.06, 4.52~4.56 (m, 3H), 3.81 (s, 3H), 3.42~3.59 (m, 1H), 2.98~3.14 (m, 2H), 2.35~2.73 (m, 7H), 2.22~2.31 (m, 1H), 1.91~2.17 (m, 1H), 1.63~1.75 (m, 1H). LC-MS-ESI$^+$: $[M+H]^+$ 463.

Example 5-28

1-(3-((Dimethylamino)methyl)-4-hydroxy-4-(3-methoxyphenyl)piperidin-1-yl)-2-(1H-indol-3-yl)ethyl-1-one (FWBE13)

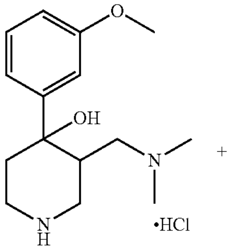

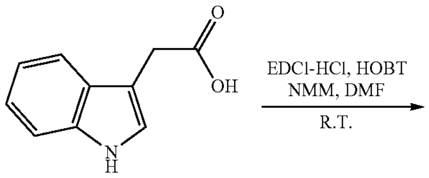

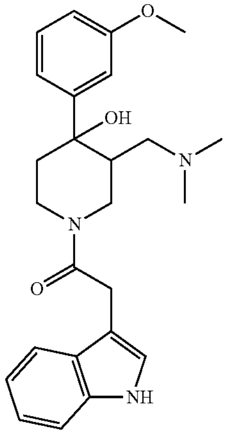

2-(1H-indol-3-yl)acetic acid was used as the raw material to obtain the target product. Yield: 54.8%. $^1$H NMR (400 MHz, $CD_3OD$), δ 7.65~7.71 (m, 1H), 7.34~7.40 (m, 1H), 7.03~7.21 (m, 4H), 6.08~6.80 (m, 3H), 4.53~4.67 (m, 1H), 4.05~4.13 (m, 2H), 3.81~3.95 (m, 2H), 3.70 (s, 3H), 3.03~3.09, 3.37~3.43 (m, 1H), 2.58~2.97 (m, 1H), 2.30 (s, 3H), 1.71~2.12 (m, 1H), 1.83 (s, 1H), 1.54~1.61 (m, 1H), 1.05~1.26 (m, 3H). LC-MS-ESI$^+$: $[M+H]^+$ 422.3.

Example 5-29

1-(3-((Dimethylamino)methyl)-4-hydroxy-4-(3-methoxyphenyl)piperidin-1-yl)-2-(1H-indol-1-yl) ethyl-1-one hydrochloride (FWBE14)

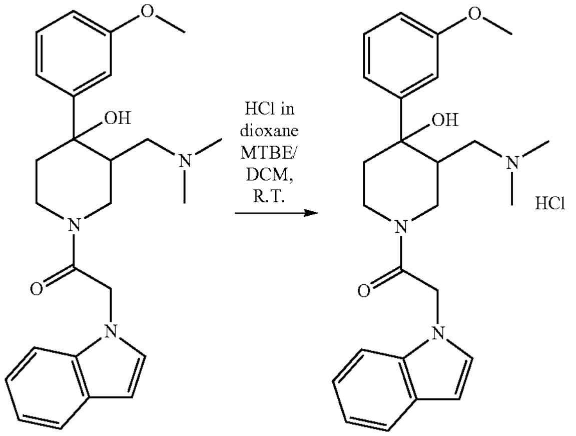

MW: 421.53 MW: 457.99

The target product was obtained as 1-(3-((dimethylamino) methyl)-4-hydroxy-4-(3-methoxyphenyl)piperidin-1-yl)-2-(1H-indol-1-yl)ethyl-1-one. Yield: 98%. $^1$H NMR (400 MHz, $CD_3OD$), δ 7.55~7.59 (t, 1H), 7.35~7.43 (t, 1H), 7.23~7.35 (m, 2H), 7.17 (t, J=8 Hz H), 6.77~7.11 (m, 4H), 6.50~6.52 (m, 1H), 5.16~5.52 (m, 2H), 4.29~4.33, 4.57~4.61 (m, 1H), 4.94~4.98, 4.43~4.46 (m, 1H), 3.81 (s, 3H), 3.47~3.65 (m, 1H), 2.92~3.13 (m, 2H), 2.57~2.74 (m, 6H), 1.88~2.14 (m, 2H), 1.62~1.74 (m, 1H). LC-MS-ESI$^+$: $[M+H]^+$ 422.3.

Example 5-30

1-(3-((Dimethylamino)methyl)-4-hydroxy-4-(3-methoxyphenyl)piperidin-1-yl)-2-(naphthalen-2-yl) ethyl-1-one

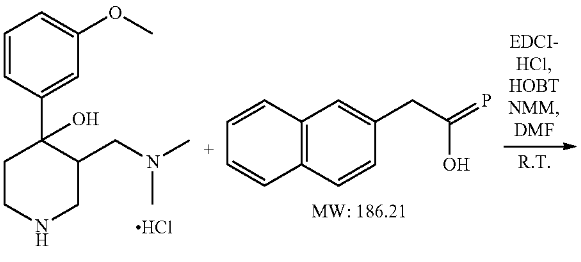

MW: 300.82 MW: 186.21

-continued

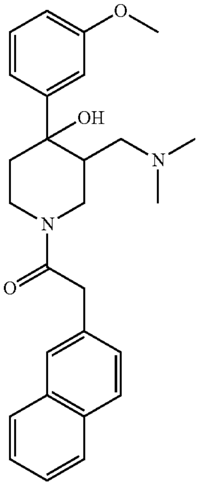

MW: 432.55

2-(Naphthalen-2-yl)acetic acid was used as the raw material to obtain the target product. Yield: 42%. $^1$H NMR (400 MHz, $CD_3OD$), δ 7.78~7.87 (m, 4H), 7.42~7.50 (m, 3H), 7.11~7.19 (m, 1H), 6.82~6.86 (m, 1H), 6.71~6.76, 6.89~6.90 (m, 2H), 4.55~4.75 (m, 1H), 3.91~4.41 (m, 3H), 3.71 (s, 3H), 3.27~3.50 (m, 1H), 2.91~3.13 (m, 1H), 2.16~2.39 (m, 1H), 1.73~2.06 (m, 5H), 1.51~1.68 (m, 5H), 1.27~1.43 (m, 2H).

Example 5-31

1-(3-((Dimethylamino)methyl)-4-hydroxy-4-(3-methoxyphenyl)piperidin-1-yl)-2-(naphthalen-2-yl) ethyl-1-one hydrochloride (FWBE15)

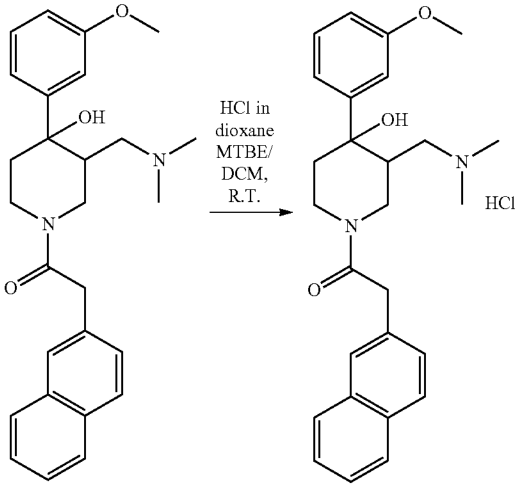 [SMILES: COc1cccc(C2(O)CCN(C(=O)Cc3ccc4ccccc4c3)CC2CN(C)C)c1 ; COc1cccc(C2(O)CCN(C(=O)Cc3ccc4ccccc4c3)CC2CN(C)C)c1 ; Cl]

The target product was obtained as 1-(3-((dimethylamino) methyl)-4-hydroxy-4-(3-methoxyphenyl)piperidin-1-yl)-2-(naphthalen-2-yl)ethyl-1-one. Yield: 88%. $^1$H NMR (400 MHz, $CD_3OD$), δ 7.81~7.90 (m, 4H), 7.44~7.52 (m, 3H), 7.20~7.29 (m, 1H), 6.94~6.95 (m, 1H), 6.79~6.85, 7.02~7.03 (m, 2H), 4.58~4.69 (m, 1H), 4.01~4.32 (m, 3H), 3.76 (d, 3H), 3.42~3.59 (m, 1H), 2.90~3.17 (m, 2H), 2.56~2.72 (m, 6H), 2.18~2.23 (m, 1H), 1.78~2.16 (m, 2H), 1.54~1.76 (m, 1H). LC-MS-ESI$^+$: $[M+H]^+$ 433.3.

Example 5-32

1-(3-((Dimethylamino)methyl)-4-hydroxy-4-(3-methoxyphenyl)piperidin-1-yl)-2-(naphthalen-1-yl)ethyl-1-one hydrochloride (FWBE16)

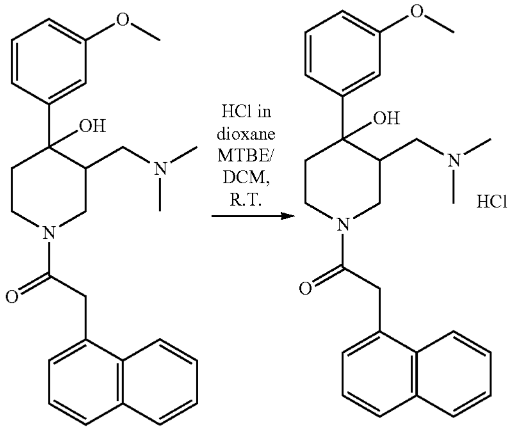 [SMILES: COc1cccc(C2(O)CCN(C(=O)Cc3cccc4ccccc34)CC2CN(C)C)c1 ; COc1cccc(C2(O)CCN(C(=O)Cc3cccc4ccccc34)CC2CN(C)C)c1 ; Cl]

The target product was obtained as 1-(3-((dimethylamino)methyl)-4-hydroxy-4-(3-methoxyphenyl)piperidin-1-yl)-2-(naphthalen-1-yl)ethyl-1-one. Yield: 99%. $^1$H NMR (400 MHz, $CD_3OD$), δ 8.03~8.09 (m, 1H), 7.89~7.93 (m, 1H), 7.83 (d, J=8 Hz, 1H), 7.46~7.59 (m, 3H), 7.41~7.45 (m, 1H), 7.28~7.36 (m, 1H), 7.02~7.06 (m, 1H), 6.83~6.88, 7.10~7.11 (m, 2H), 4.58~4.69 (m, 1H), 4.34~4.48 (m, 2H), 3.98~4.27 (m, 1H), 3.81 (s, 3H), 3.49~3.54 (m, 1H), 2.92~3.20 (m, 2H), 2.54~2.69 (m, 6H), 1.87~2.32 (m, 3H), 1.56~1.78 (m, 1H). LC-MS-ESI$^+$: [M+H]+ 433.3.

Example 5-33

2-(3,4-Dichlorophenyl)-1-(3-((dimethylamino)methyl)-4-hydroxy-4-(3-methoxyphenyl)piperidin-1-yl)ethyl-1-one hydrochloride (FWBE17)

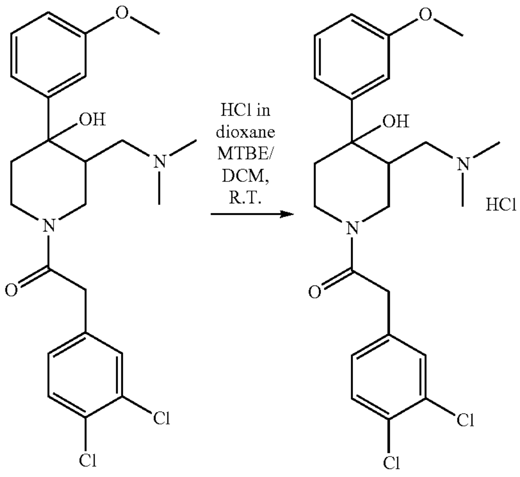 [SMILES: COc1cccc(C2(O)CCN(C(=O)Cc3ccc(Cl)c(Cl)c3)CC2CN(C)C)c1 ; COc1cccc(C2(O)CCN(C(=O)Cc3ccc(Cl)c(Cl)c3)CC2CN(C)C)c1 ; Cl]

2-(3,4-Dichlorophenyl)-1-(3-((dimethylamino)methyl)-4-hydroxy-4-(3-methoxyphenyl)piperidin-1-yl)ethyl-1-one was used as the target product. Yield: 88%. $^1$H NMR (400 MHz, $CD_3OD$), δ 7.48~7.54 (m, 2H), 7.23~7.35 (m, 2H), 7.00~7.13 (m, 2H), 6.84~6.88 (m, 1H), 4.31~4.35, 4.60~4.65 (m, 1H), 3.94~4.06, 4.50~4.54 (m, 2H), 3.88 (s, 1H), 3.81 (s, 3H), 3.43~3.60 (m, 1H), 2.98~3.13 (m, 2H), 2.65~2.69 (m, 6H), 2.24~2.45 (m, 2H), 1.68~2.18 (m, 2H). LC-MS-ESI$^+$: [M+H]+ 451.2.

Example 5-34

1-(3-((Dimethylamino)methyl)-4-hydroxy-4-(3-methoxyphenyl)piperidin-1-yl)-2-(2,4,5-trifluorophenyl)ethyl-1-one hydrochloride (FWBE18)

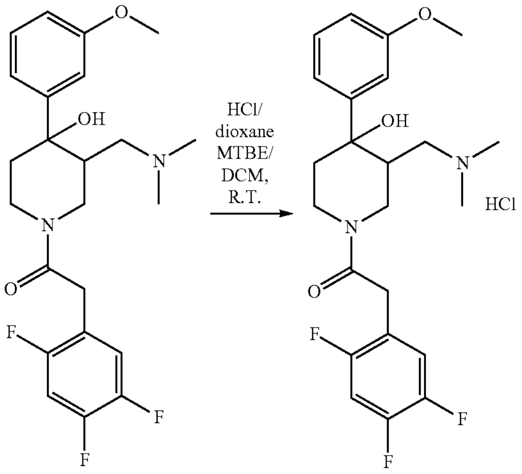 [SMILES: COc1cccc(C2(O)CCN(C(=O)Cc3cc(F)c(F)cc3F)CC2CN(C)C)c1 ; COc1cccc(C2(O)CCN(C(=O)Cc3cc(F)c(F)cc3F)CC2CN(C)C)c1 ; Cl]

The target product was obtained as 1-(3-((dimethylamino)methyl)-4-hydroxy-4-(3-methoxyphenyl)piperidin-1-yl)-2-(2,4,5-trifluorophenyl)ethyl-1-one. Yield: 94.6%. $^1$H NMR (400 MHz, $CD_3OD$), δ 7.26~7.36 (m, 2H), 7.06~7.22 (m, 3H), 6.87 (d, J=8 Hz, 1H), 4.47~4.65 (m, 1H), 3.84~4.43 (m, 3H), 3.81 (s, 3H), 3.50~3.67 (m, 1H), 3.02~3.15 (m, 2H), 2.67~2.82 (m, 6H), 2.29~2.57 (m, 2H), 2.11~2.27 (m, 1H), 1.71~1.81 (m, 1H).

LC-MS-ESI$^+$: $[M+H]^+$ 437.2.

Example 5-35

2-(4-Chlorophenyl)-1-(3-((dimethylamino)methyl)-4-hydroxy-4-(3-methoxyphenyl)piperidin-1-yl)ethyl-1-one hydrochloride (FWBE19)

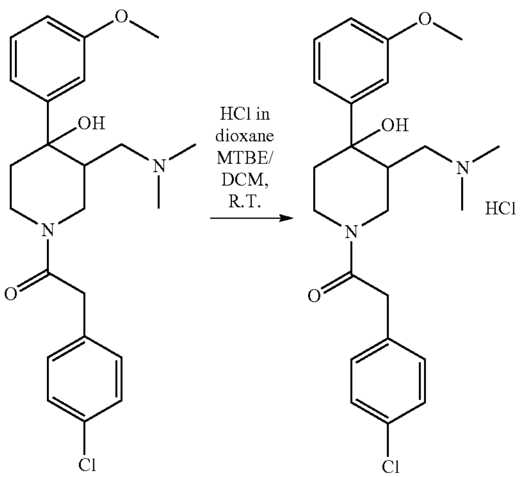 [SMILES: COc1cccc(C2(O)CCN(C(=O)Cc3ccc(Cl)cc3)CC2CN(C)C)c1 ; COc1cccc(C2(O)CCN(C(=O)Cc3ccc(Cl)cc3)CC2CN(C)C)c1 ; Cl]

2-(4-Chlorophenyl)-1-(3-((dimethylamino)methyl)-4-hydroxy-4-(3-methoxyphenyl)piperidin-1-yl)ethyl-1-one was used as the raw material to obtain the target product. Yield: 97.7%. $^{1}$H NMR (400 MHz, $CD_3OD$), δ 7.29~7.38 (m, 5H), 6.97~7.10 (m, 2H), 6.83~6.87 (m, 1H), 4.51~4.66 (m, 1H), 3.87~4.38 (m, 3H), 3.81 (s, 3H), 3.40~3.57 (m, 1H), 3.96~3.13 (m, 2H), 2.60~2.73 (m, 6H), 2.22~2.42 (m, 1H), 1.90~2.18 (m, 1H), 1.63~1.75 (m, 1H). LC-MS-ESI$^{+}$: $[M+H]^{+}$ 417.2, 419.2.

Example 5-36

2-(2-Chlorophenyl)-1-(3-((dimethylamino)methyl)-4-hydroxy-4-(3-methoxyphenyl)piperidin-1-yl)ethyl-1-one hydrochloride (FWBE20)

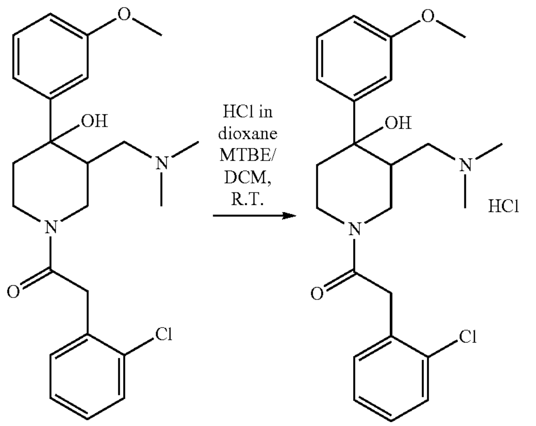 [SMILES: COc1cccc(C2(O)CCN(C(=O)Cc3ccccc3Cl)CC2CN(C)C)c1 ; COc1cccc(C2(O)CCN(C(=O)Cc3ccccc3Cl)CC2CN(C)C)c1 ; Cl]

2-(2-Chlorophenyl)-1-(3-((dimethylamino)methyl)-4-hydroxy-4-(3-methoxyphenyl)piperidin-1-yl)ethyl-1-one was used as the raw material to obtain the target product. Yield: 84%. $^{1}$H NMR (400 MHz, $CD_3OD$), δ 7.41~7.44 (m, 1H), 7.25~7.38 (m, 4H), 7.02~7.13 (m, 2H), 6.85~6.89 (m, 1H), 4.31~4.35, 4.61~4.63 (m, 1H), 3.94~4.41, 4.51~4.54 (m, 3H), 3.81 (s, 3H), 3.52~3.65 (m, 1H), 3.02~3.20 (m, 2H), 2.60~2.80 (m, 6H), 2.25~2.48 (m, 2H), 2.11~2.20 (m, 1H), 1.71~1.77 (m, 1H). LC-MS-ESI$^{+}$: $[M+H]^{+}$ 417; 419.

Example 5-37

1-(3-((Dimethylamino)methyl)-4-hydroxy-4-(3-methoxyphenyl)piperidin-1-yl)-2-(3-nitrophenyl) ethyl-1-one hydrochloride (FWBE22)

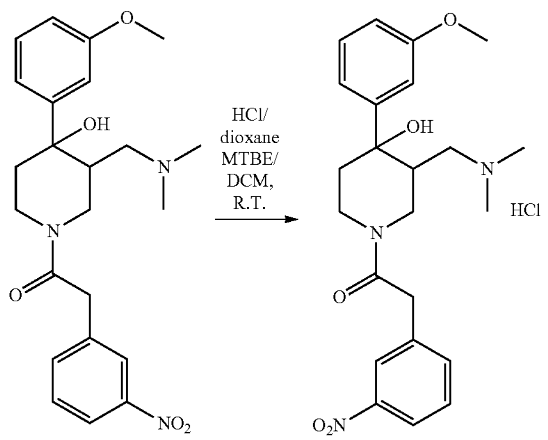 [SMILES: COc1cccc(C2(O)CCN(C(=O)Cc3cccc([N+](=O)[O-])c3)CC2CN(C)C)c1 ; COc1cccc(C2(O)CCN(C(=O)Cc3cccc([N+](=O)[O-])c3)CC2CN(C)C)c1 ; Cl]

1-(3-((Dimethylamino)methyl)-4-hydroxy-4-(3-methoxyphenyl)piperidin-1-yl)-2-(3-nitrophenyl)ethyl-1-one was used as the raw material to obtain the target product. Yield: 96.8%. $^{1}$H NMR (400 MHz, $CD_3OD$), δ 8.13~8.25 (m, 2H), 7.71~7.77 (m, 1H), 7.57~7.63 (m, 1H), 7.29~7.35 (m, 1H), 7.02~7.14 (m, 2H), 6.84~6.88 (m, 1H), 4.39~4.44, 4.63~4.67 (m, 1H), 4.00~4.17, 4.51~4.55 (m, 3H), 3.81 (s, 3H), 3.47~3.65 (m, 1H), 3.01~3.15 (m, 2H), 2.46~2.79 (m, 7H), 2.28~2.33, 2.50~2.55 (m, 1H), 2.08~2.20 (m, 1H), 1.71~1.76 (m, 1H). LC-MS-ESI$^{+}$: $[M+H]^{+}$ 428.3.

Example 5-38

3-(2-(3-((Dimethylamino)methyl)-4-hydroxy-4-(3-methoxyphenyl)piperidin-1-yl)-2-oxoethyl) benzonitrile hydrochloride (FWBE21)

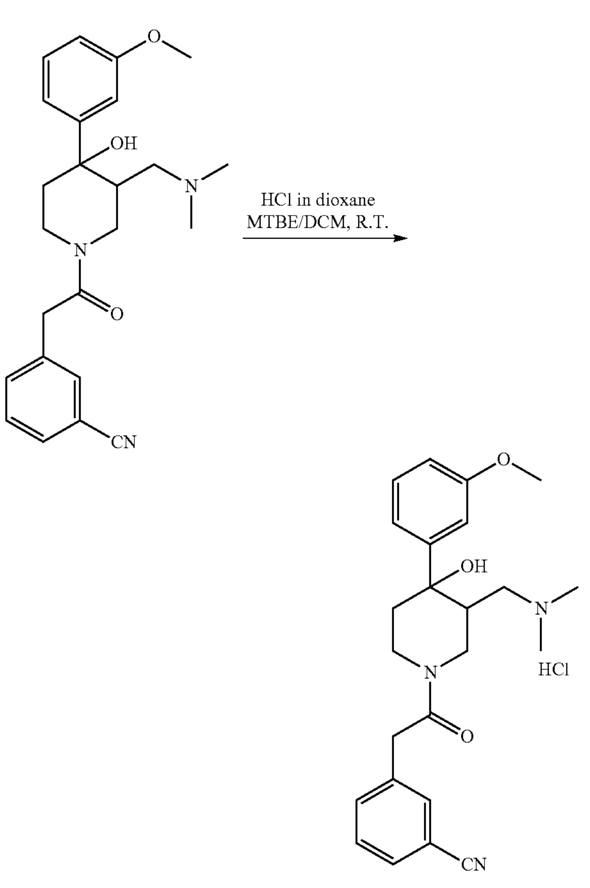

3-(2-(3-((Dimethylamino)methyl)-4-hydroxy-4-(3-methoxyphenyl)piperidin-1-yl)-2-oxoethyl)benzonitrile was used as the raw material to obtain the target product. Yield: 89.5%. $^{1}$H NMR (400 MHz, $CD_3OD$), δ 7.62~7.73 (m, 2H), 7.50~7.56 (m, 1H), 7.30~7.35 (m, 1H), 7.02~7.14 (m, 2H), 6.85~6.88 (m, 1H), 4.38~4.42, 4.61~4.66 (m, 1H), 3.96~4.15, 4.50~4.54 (m, 3H), 3.81 (m, 3H), 2.99~3.13 (m, 2H), 2.44~2.78 (m, 7H), 2.27~2.33, 2.47~2.49 (m, 1H), 2.05~2.19 (m, 1H), 1.70~1.75 (m, 1H). LC-MS-ESI$^{+}$: $[M+H]^{+}$ 408.3.

Example 5-39

(3-((Dimethylamino)methyl)-4-hydroxy-4-(3-methoxyphenyl)piperidin-1-yl)(1-phenylcyclopropyl)methanone hydrochloride (FWBE24)

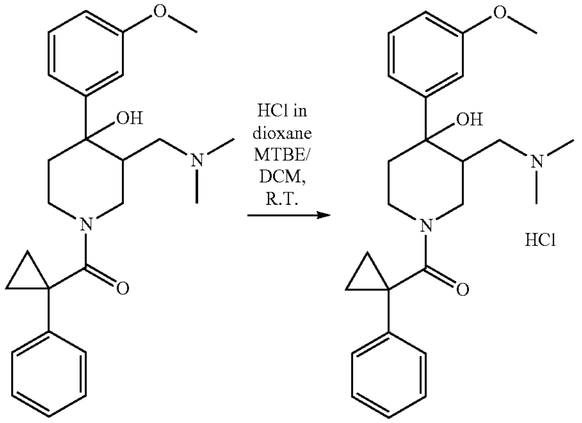 [SMILES: COc1cccc(C2(O)CCN(C(=O)C3(c4ccccc4)CC3)CC2CN(C)C)c1 ; COc1cccc(C2(O)CCN(C(=O)C3(c4ccccc4)CC3)CC2CN(C)C)c1 ; Cl]

The target product was obtained as (3-((dimethylamino)methyl)-4-hydroxy-4-(3-methoxyphenyl)piperidin-1-yl)(1-phenylcyclopropyl)methanone. Yield: 80%. $^1$H NMR (400 MHz, $CD_3OD$), δ 7.24~7.41 (m, 6H), 6.83~6.98 (m, 3H), 4.64~4.67 (m, 1H), 4.10~4.25 (m, 1H), 3.81 (s, 3H), 3.30~3.33 (m, 1H), 2.95~3.23 (m, 1H), 2.46~2.77 (m, 6H), 2.24~2.28 (m, 1H), 1.65~1.86 (m, 3H), 1.00~1.46 (m, 4H). LC-MS-ESI$^+$: [M+H]$^+$ 409.3.

Example 5-40

1-(3-((Dimethylamino)methyl)-4-hydroxy-4-(3-methoxyphenyl)piperidin-1-yl)-2-methyl-2-phenylpropan-1-one hydrochloride (FWBE23)

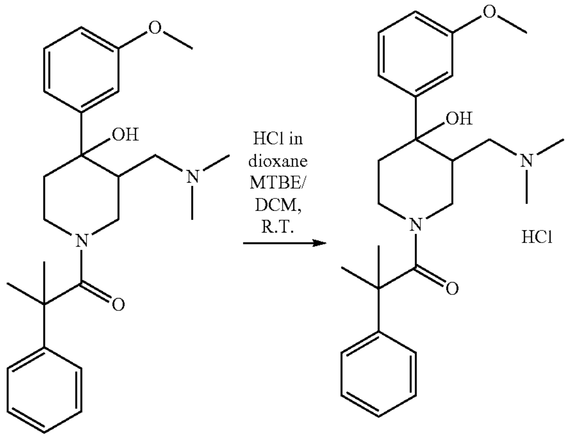 [SMILES: COc1cccc(C2(O)CCN(C(=O)C(C)(C)c3ccccc3)CC2CN(C)C)c1 ; COc1cccc(C2(O)CCN(C(=O)C(C)(C)c3ccccc3)CC2CN(C)C)c1 ; Cl]

The target product was obtained as 1-(3-((dimethylamino)methyl)-4-hydroxy-4-(3-methoxyphenyl)piperidin-1-yl)-2-methyl-2-phenylpropan-1-one. Yield: 85.7%. $^1$H NMR (400 MHz, $CD_3OD$), δ 7.36~7.45 (m, 4H), 7.25~7.33 (m, 2H), 6.97 (s, 1H), 6.91 (d, J=8 Hz, 1H), 6.84 (d, J=1 Hz, 1H), 4.69 (d, J=8 Hz, 1H), 3.80 (s, 3H), 3.47 (s, 1H), 3.01~3.13 (m, 3H), 2.71 (s, 6H), 2.20 (s, 1H), 1.64 (s, 3H), 1.56 (s, 3H), 1.12~1.41 (m, 2H). LC-MS-ESI$^+$: [M+H]$^+$ 411.3.

Example 5-41

(3-((Dimethylamino)methyl)-4-hydroxy-4-(3-methoxyphenyl)piperidin-1-yl)(1-phenylcyclopentyl)methanone hydrochloride (FWBE26)

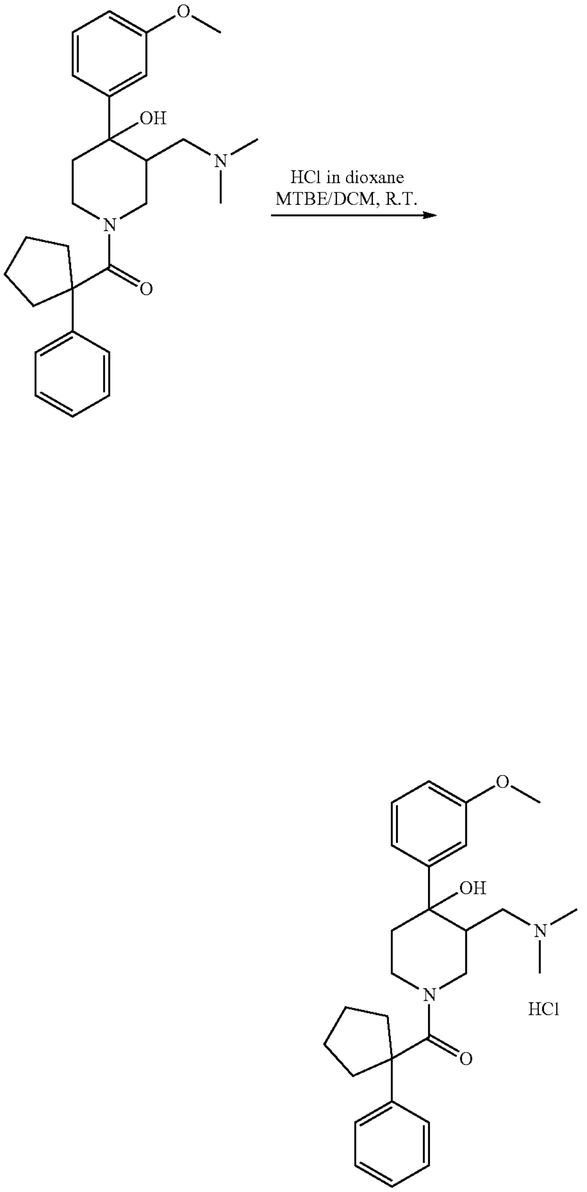

The target product was obtained as (3-((dimethylamino)methyl)-4-hydroxy-4-(3-methoxyphenyl)piperidin-1-yl)(1-phenylcyclopentyl)methanone. Yield: 72.4%. $^1$H NMR (400 MHz, $CD_3OD$), δ 7.35~7.42 (m, 4H), 7.24~7.31 (m, 2H), 6.82~6.91 (m, 3H), 4.63~4.66 (m, 1H), 3.79 (s, 3H), 3.61~3.66 (m, 1H), 2.99~3.21 (m, 3H), 2.75 (s, 3H), 2.65 (s, 3H), 2.62~2.69 (m, 1H), 2.13~2.34 (m, 3H), 1.70~1.88 (m, 6H), 1.10~1.22 (m, 1H). LC-MS-ESI$^+$: [M+H]$^+$ 437.3.

Example 5-42

(3-((Dimethylamino)methyl)-4-hydroxy-4-(3-methoxyphenyl)piperidin-1-yl)(1-phenylcyclohexyl) methanone hydrochloride (FWBE27)

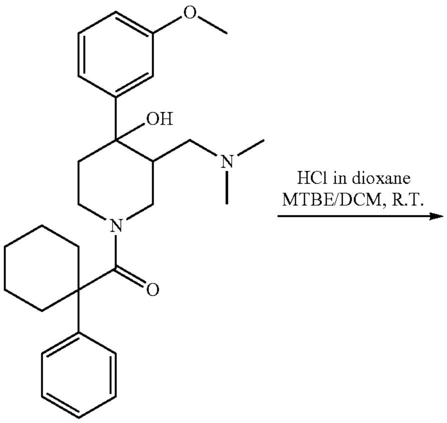

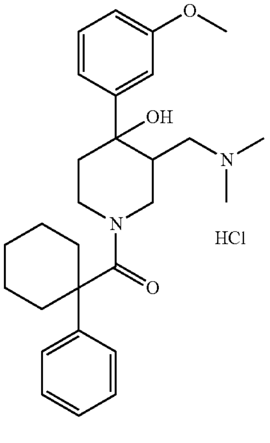

The target product was obtained as (3-((dimethylamino) methyl)-4-hydroxy-4-(3-methoxyphenyl)piperidin-1-yl)(1-phenylcyclohexyl)methanone. Yield: 55.8%. H NMR (400 MHz, $CD_3OD$), δ 7.43 (d, J=4 Hz, 4H), 7.23~7.31 (m, 2H), 6.89 (s, 1H), 6.83 (dd, $J_1$=8 Hz, $J_2$=4 Hz, 2H), 4.55 (s, 1H), 3.79 (s, 3H), 3.59~3.65 (m, 1H), 3.02~3.20 (m, 3H), 2.74 (s, 3H), 2.69 (s, 3H), 2.40~2.74 (m, 3H), 1.81~2.06 (m, 4H), 1.31~1.40 (m, 1H), 1.03 (m, 1H). LC-MS-ESI$^+$: $[M+H]^+$ 451.3.

Example 5-43

(3-((Dimethylamino)methyl)-4-hydroxy-4-(3-methoxyphenyl)piperidin-1-yl)(1-phenylcyclobutyl) methanone hydrochloride (FWBE25)

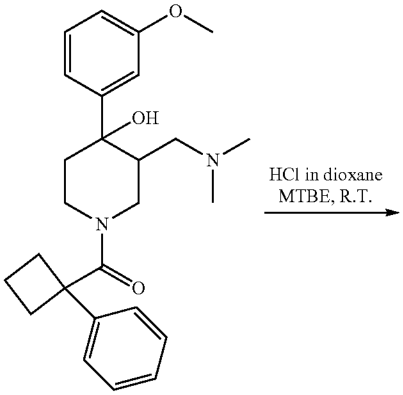

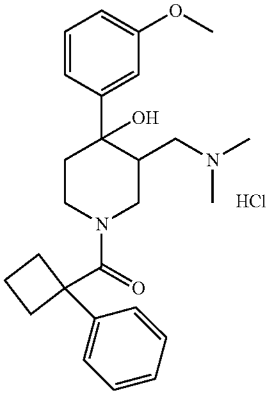

The target product was obtained as (3-((dimethylamino) methyl)-4-hydroxy-4-(3-methoxyphenyl) piperidin-1-yl)(1-phenylcyclobutyl)methanone. Yield: 84.9%. $^{1}$H NMR (400 MHz, $CD_3OD$), δ 7.43~7.58 (m, 4H), 7.24~7.32 (m, 2H), 6.77~6.91 (m, 3H), 4.60 (d, $J_1$=8 Hz, $J_2$=4 Hz, H), 3.78 (s, 3H), 3.39~3.42 (m, 1H), 2.99~3.22 (m, 4H), 2.61~2.75 (m, 8H), 2.23~2.29 (m, 1H), 1.92~2.09 (m, 4H), 1.08~1.23 (m, 2H). LC-MS-ESI$^+$: $[M+H]^+$ 423.3.

Example 5-44

Preparation of Membrane Receptors

CHO cells expressing p opioid receptor, δ opioid receptor and κ opioid receptor were cultured in 10 $cm^2$ culture dishes (F-12 medium+10% neonatal bovine serum) for several days, the cells grew to the bottom of the dishes and the culture fluid was aspirated; 3 mL of PBS/EDTA solution (0.1 M NaCl, 0.01 M $NaH_2PO_4$, 0.04% EDTA) was added and digested for 3-5 min, The cells were collected in a 40 mL centrifuge tube and centrifuged at 5000 rpm for 5 min, the supernatant was removed; ice-cold homogenate (50 mM HEPES pH 7.4, 3 mM MgCl, 1 mM EGTA) was added to the centrifuge tube and the solution and sediment were transferred to a homogenizer for homogenization; the homogenate was then transferred to a centrifuge tube and centrifuged at 18000 rpm. Centrifuge for 15 min, 2 times; add 50 mM Tris-HCl, pH 7.4 buffer to the precipitate and homogenise it in centrifuge tubes, store in the refrigerator at −70° C. until use.

Competition Binding Test

The total binding tube was spiked with 20-30 μg of expressed membrane receptor protein and [3H]-labelled ligand (1-2 nM), the corresponding non-specific binding tube was spiked with 1 μM of the corresponding ligand, and the sample tubes were spiked with various screened opioid ligands in a final volume of 100 μl and incubated for 30 min at 30° C. and terminated in ice water. The reaction was terminated by incubation at 30° C. for 30 min in ice-cold water. The sample was filtered under negative pressure through GF/C (whatman) glass fibre filter paper on a Millipore sample collector. The samples were rinsed three times with 4 mL of 50 mM Tris-HCl (pH 7.4), the filter paper was dried and placed in 0.5 mL Eppendorf tubes with 0.5 mL of lipophilic scintillation solution and the radioactivity was measured on a PERKIN ELMER PRI-CARB 2910 liquid scintillation counter to calculate the inhibition rate, and the experiment was repeated more than three times with three replicate tubes per group.

Inhibition rate (or binding rate)=(total binding dpm−sample tube dpm)/(total binding tube dpm−non-specific binding tube dpm)×100%

Calculate the $IC_{50}$ using Graphpad Prism 5.0 software. calculate the Ki value as follows, Ki=IC50/(1+[L]/Kd), [L] is the concentration of the labeled ligand added and Kd is the equilibrium dissociation parameter of the labeled ligand Table 5-1 shows the Ki values of the affinity constants for opioid receptors for representative compounds, expressed as the mean±standard deviation of three independent measurements.

TABLE 5-1

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| Tramadol | 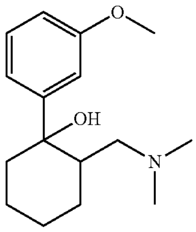 [SMILES: COc1cccc(C2(O)CCCCC2CN(C)C)c1] | 6.0 ± 0.4% | 0% | 0% |
| 2-(3,5-Bis(trifluoromethyl)phenyl)-1-(3-((dimethylamino)methyl)-4-hydroxy-4-(3-methoxyphenyl)piperidin-1-yl)ethyl-1-one hydrochloride (FWBE1) | 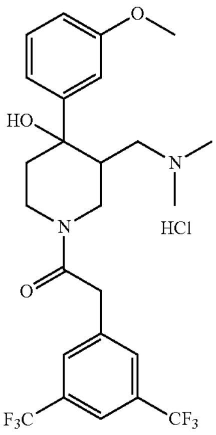 [SMILES: COc1cccc(C2(O)CCN(C(=O)Cc3cc(C(F)(F)F)cc(C(F)(F)F)c3)CC2CN(C)C)c1 ; Cl] | 25.3 ± 4.9 nM | 4392 ± 351.1 nM | 4424 ± 181.5 nM |
| 1-(3-((Dimethylamino)methyl)-4-hydroxy-4-(3-methoxyphenyl)piperidin-1-yl)-2-(thiophen-3-yl)ethyl-1-one hydrochloride (FWBE2) | 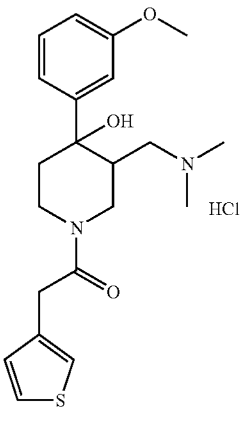 [SMILES: COc1cccc(C2(O)CCN(C(=O)Cc3ccsc3)CC2CN(C)C)c1 ; Cl] | 40.6 ± 0.9% | 14.7 ± 0.9% | 20.8 ± 1.9% |

TABLE 5-1-continued

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| 1-(3-((Dimethylamino)methyl)-4-hydroxy-4-(3-methoxyphenyl)piperidin-1-yl)-2-phenylethyl-1-one hydrochloride (FWBE3) | 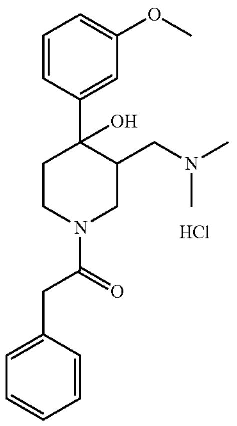 [SMILES: COc1cccc(C2(O)CCN(C(=O)Cc3ccccc3)CC2CN(C)C)c1 ; Cl] | 41.1 ± 2.3% | 11.7 ± 0.9% | 23.4 ± 5.7% |
| 1-(3-((Dimethylamino)methyl)-4-hydroxy-4-(3-methoxyphenyl)piperidin-1-yl)-2-(3-(trifluoromethyl)phenyl)ethyl-1-one hydrochloride (FWBE4) | 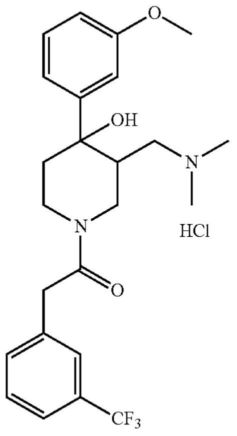 [SMILES: COc1cccc(C2(O)CCN(C(=O)Cc3cccc(C(F)(F)F)c3)CC2CN(C)C)c1 ; Cl] | 37.8 ± 2.9% | >10000 | 3031 ± 150.5 nm |
| (3-((Dimethylamino)methyl)-4-hydroxy-4-(3-methoxyphenyl)piperidin-1-yl)(2,4,5-trifluorophenyl)methanone hydrochloride (FWBE5) | 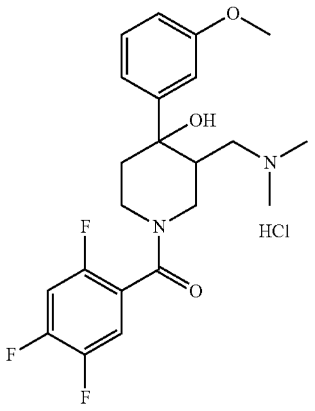 [SMILES: COc1cccc(C2(O)CCN(C(=O)c3cc(F)c(F)cc3F)CC2CN(C)C)c1 ; Cl] | 13.0 ± 0.2% | 7.0 ± 6.3% | 23.0 ± 5.9% |

TABLE 5-1-continued

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| 1-(3-((Dimethylamino)methyl)-4-hydroxy-4-(3-methoxyphenyl)piperidin-1-yl)-2-(3-(trifluoromethoxy)phenyl)ethyl-1-one hydrochloride (FWBE6) | 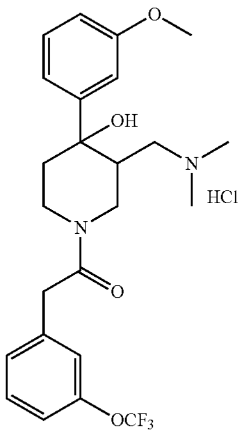 [SMILES: COc1cccc(C2(O)CCN(C(=O)Cc3cccc(OC(F)(F)F)c3)CC2CN(C)C)c1 ; Cl] | 21.5 ± 0.1% | 13.2 ± 1.0% | 13.5 ± 0.6% |
| 1-(3-((Dimethylamino)methyl)-4-hydroxy-4-(3-methoxyphenyl)piperidin-1-yl)-2-(1H-tetrazol-1-yl)ethyl-1-one hydrochloride (FWBE7) | 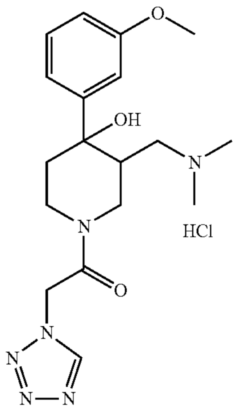 [SMILES: COc1cccc(C2(O)CCN(C(=O)Cn3cnnn3)CC2CN(C)C)c1 ; Cl] | 0% | 8.9 ± 2.4% | 22.9 ± 0.6% |
| 1-(3-((Dimethylamino)methyl)-4-hydroxy-4-(3-methoxyphenyl)piperidin-1-yl)-2-(thiophen-2-yl)ethyl-1-one hydrochloride (FWBE8) | 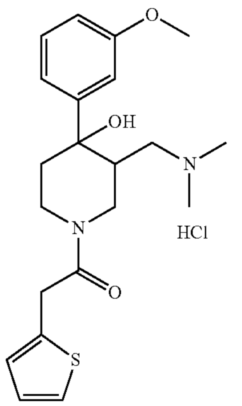 [SMILES: COc1cccc(C2(O)CCN(C(=O)Cc3cccs3)CC2CN(C)C)c1 ; Cl] | 34.8 ± 1.1 nM | 18.7 ± 1.9% | 32.5 ± 4.4% |

TABLE 5-1-continued

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| 2-(3-Chlorophenyl)-1-(3-((dimethylamino)methyl)-4-hydroxy-4-(3-methoxyphenyl)piperidin-1-yl)ethyl-1-one hydrochloride (FWBE9) | 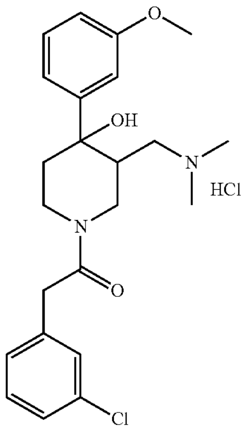 [SMILES: COc1cccc(C2(O)CCN(C(=O)Cc3cccc(Cl)c3)CC2CN(C)C)c1 ; Cl] | 24.2 ± 0.0 nM | 1635 ± 148.5 | 1009 ± 60.1 |
| 1-(3-((Dimethylamino)methyl)-4-hydroxy-4-(3-methoxyphenyl)piperidin-1-yl)-3-(3-(trifluoromethyl)phenyl)propyl-1-one hydrochloride (FWBE10) | 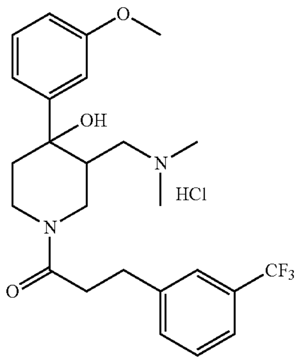 [SMILES: COc1cccc(C2(O)CCN(C(=O)CCc3cccc(C(F)(F)F)c3)CC2CN(C)C)c1 ; Cl] | 218.8 ± 9.8 nM | >10000 nM | >5000 nM |
| 2-(3-Bromophenyl)-1-(3-((dimethylamino)methyl)-4-hydroxy-4-(3-methoxyphenyl)piperidin-1-yl)ethyl-1-one hydrochloride (FWBE11) | 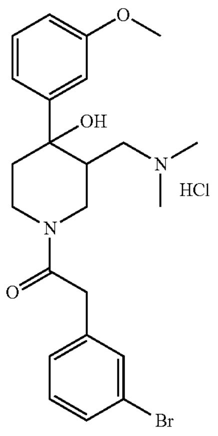 [SMILES: COc1cccc(C2(O)CCN(C(=O)Cc3cccc(Br)c3)CC2CN(C)C)c1 ; Cl] | 57.6 ± 0.1 nM | >10000 nM | >5000 nM |

TABLE 5-1-continued

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| 1-(3-((Dimethylamino)methyl)-4-hydroxy-4-(3-methoxyphenyl)piperidin-1-yl)-2-(3-fluorophenyl)ethyl-1-one hydrochloride (FWBE12) | 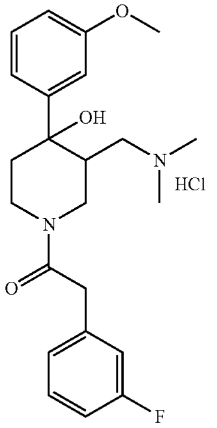 [SMILES: COc1cccc(C2(O)CCN(C(=O)Cc3cccc(F)c3)CC2CN(C)C)c1 ; Cl] | 82.3 ± 3.8 nM | 2388 ± 46.0 nM | 2357 ± 95.5 nM |
| 1-(3-((Dimethylamino)methyl)-4-hydroxy-4-(3-methoxyphenyl)piperidin-1-yl)-2-(1H-indol-3-yl)ethyl-1-one (FWBE13) | 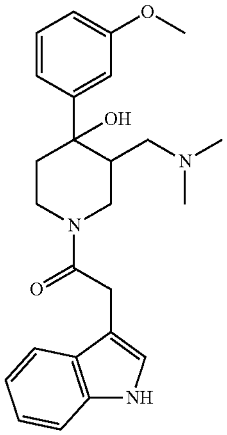 [SMILES: COc1cccc(C2(O)CCN(C(=O)Cc3c[nH]c4ccccc34)CC2CN(C)C)c1] | 115.4 ± 4.1 nM | >5000 nM | 3098 ± 79.5 nM |
| 1-(3-((Dimethylamino)methyl)-4-hydroxy-4-(3-methoxyphenyl)piperidin-1-yl)-2-(1H-indol-1-yl)ethyl-1-one hydrochloride (FWBE14) | 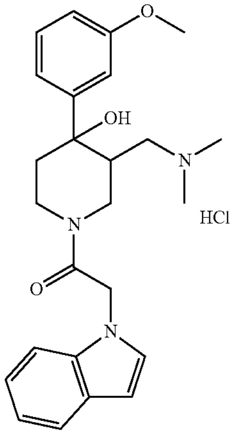 [SMILES: COc1cccc(C2(O)CCN(C(=O)Cn3ccc4ccccc43)CC2CN(C)C)c1 ; Cl] | 72.9 ± 0.1 nM | 1176 ± 219.5 nM | 4055 ± 382.1 nM |

TABLE 5-1-continued

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| 1-(3-((Dimethylamino)methyl)-4-hydroxy-4-(3-methoxyphenyl)piperidin-1-yl)-2-(naphthalen-2-yl)ethyl-1-one hydrochloride (FWBE15) | 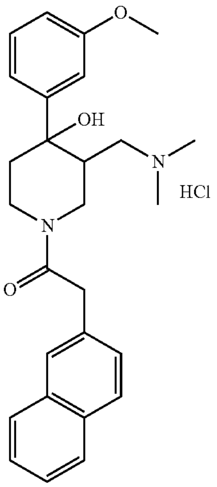 [SMILES: COc1cccc(C2(O)CCN(C(=O)Cc3ccc4ccccc4c3)CC2CN(C)C)c1 ; Cl] | 81.6 ± 1.0 nM | >10000 nM | 2651 ± 3.5 nM |
| 1-(3-((Dimethylamino)methyl)-4-hydroxy-4-(3-methoxyphenyl)piperidin-1-yl)-2-(naphthalen-1-yl)ethyl-1-one hydrochloride (FWBE16) | 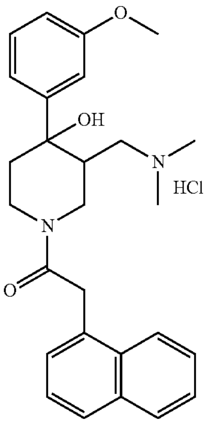 [SMILES: COc1cccc(C2(O)CCN(C(=O)Cc3cccc4ccccc34)CC2CN(C)C)c1 ; Cl] | 353.0 ± 4.5 nM | 2155 ± 72.0 nM | 1701 ± 378.6 nM |
| 2-(3,4-Dichlorophenyl)-1-(3-((dimethylamino)methyl)-4-hydroxy-4-(3-methoxyphenyl)piperidin-1-yl)ethyl-1-one hydrochloride (FWBE17) | 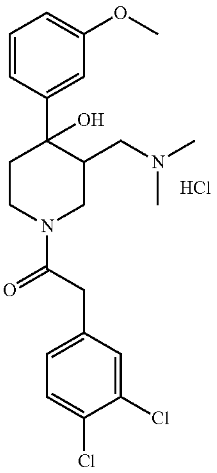 [SMILES: COc1cccc(C2(O)CCN(C(=O)Cc3ccc(Cl)c(Cl)c3)CC2CN(C)C)c1 ; Cl] | 69.2 ± 0.4 nM | 805.3 ± 173.4 nM | 287.6 ± 12.8 nM |

TABLE 5-1-continued

Opioid receptor binding rate at 1 μM concentration of compound or Ki

| Name | Structure | Combination rate (%) or Ki (nM) | | |
|---|---|---|---|---|
| | | μOR | δOR | κOR |
| 1-(3-((Dimethylamino)methyl)-4-hydroxy-4-(3-methoxyphenyl)piperidin-1-yl)-2-(2,4,5-trifluorophenyl)ethyl-1-one hydrochloride (FWBE18) | 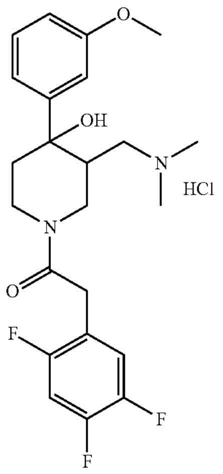 [SMILES: COc1cccc(C2(O)CCN(C(=O)Cc3cc(F)c(F)cc3F)CC2CN(C)C)c1 ; Cl] | 29.7 ± 1.9% | 0% | 61.6 ± 0.7% |
| 2-(4-Chlorophenyl)-1-(3-((dimethylamino)methyl)-4-hydroxy-4-(3-methoxyphenyl)piperidin-1-yl)ethyl-1-one hydrochloride (FWBE19) | 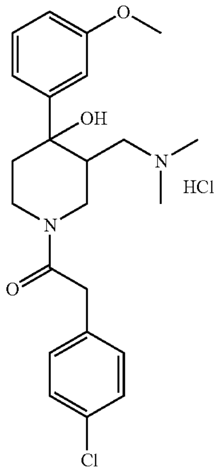 [SMILES: COc1cccc(C2(O)CCN(C(=O)Cc3ccc(Cl)cc3)CC2CN(C)C)c1 ; Cl] | 25.2 ± 5.2% | 0% | 39.4 ± 4.5% |
| 2-(2-Chlorophenyl)-1-(3-((dimethylamino)methyl)-4-hydroxy-4-(3-methoxyphenyl)piperidin-1-yl)ethyl-1-one hydrochloride (FWBE20) | 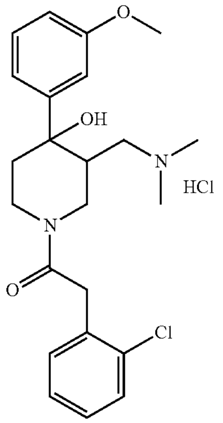 [SMILES: COc1cccc(C2(O)CCN(C(=O)Cc3ccccc3Cl)CC2CN(C)C)c1 ; Cl] | 28.3 ± 7.2% | 0% | 34.8 ± 0.7% |

TABLE 5-1-continued

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| 3-(2-(3-((Dimethylamino)methyl)-4-hydroxy-4-(3-methoxyphenyl)piperidin-1-yl)-2-oxoethyl)benzonitrile hydrochloride (FWBE21) | 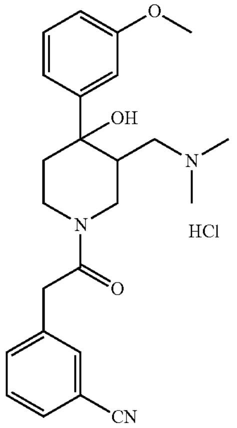 [SMILES: COc1cccc(C2(O)CCN(C(=O)Cc3cccc(C#N)c3)CC2CN(C)C)c1 ; Cl] | 28.9 ± 17.0% | 25.4 ± 4.4% | 42.3 ± 3.3% |
| 1-(3-((Dimethylamino)methyl)-4-hydroxy-4-(3-methoxyphenyl)piperidin-1-yl)-2-(3-nitrophenyl)ethyl-1-one hydrochloride (FWBE22) | 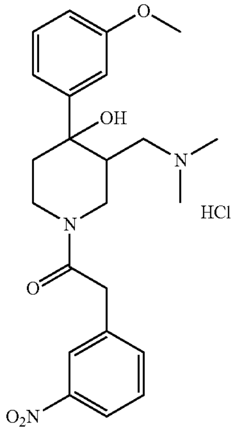 [SMILES: COc1cccc(C2(O)CCN(C(=O)Cc3cccc([N+](=O)[O-])c3)CC2CN(C)C)c1 ; Cl] | 85.6 ± 15.4 nM | >10000 nM | 1987 ± 145.5 nM |
| 1-(3-((Dimethylamino)methyl)-4-hydroxy-4-(3-methoxyphenyl)piperidin-1-yl)-2-methyl-2-phenylpropan-1-one hydrochloride (FWBE23) | 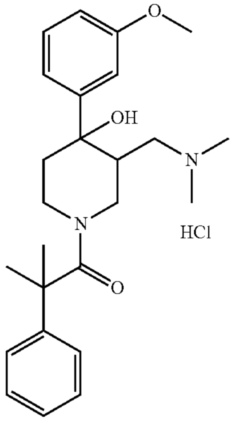 [SMILES: COc1cccc(C2(O)CCN(C(=O)C(C)(C)c3ccccc3)CC2CN(C)C)c1 ; Cl] | 52.62 ± 3.83 nM | 687.7 ± 540.4 nM | 44.42 ± 0.96 nM |

TABLE 5-1-continued

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| (3-((Dimethylamino)methyl)-4-hydroxy-4-(3-methoxyphenyl)piperidin-1-yl)(1-phenylcyclopropyl)methanone hydrochloride (FWBE24) | 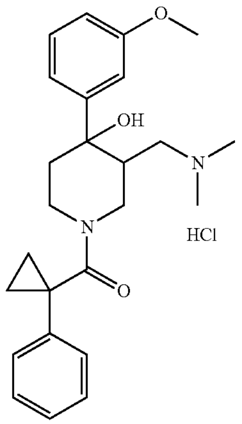 [SMILES: COc1cccc(C2(O)CCN(C(=O)C3(c4ccccc4)CC3)CC2CN(C)C)c1 ; Cl] | 67.15 ± 0.08 nM | 847.6 ± 529.4 nM | 33.86 ± 0.92 nM |
| (3-((Dimethylamino)methyl)-4-hydroxy-4-(3-methoxyphenyl)piperidin-1-yl)(1-phenylcyclobutyl)methanone hydrochloride (FWBE25) | 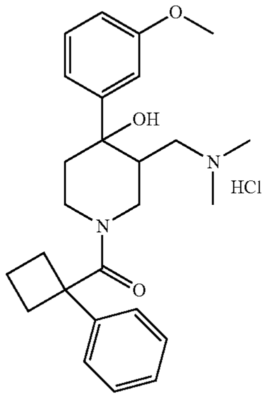 [SMILES: COc1cccc(C2(O)CCN(C(=O)C3(c4ccccc4)CCC3)CC2CN(C)C)c1 ; Cl] | 80.89 ± 5.67 nM | 717.1 ± 253.2 nM | 205.0 ± 40.9 nM |

TABLE 5-1-continued

| Opioid receptor binding rate at 1 μM concentration of compound or Ki | | | | |
|---|---|---|---|---|
| | | Combination rate (%) or Ki (nM) | | |
| Name | Structure | μOR | δOR | κOR |
| (3-((Dimethylamino)methyl)-4-hydroxy-4-(3-methoxyphenyl)piperidin-1-yl)(1-phenylcyclopentyl)methanone hydrochloride (FWBE26) | 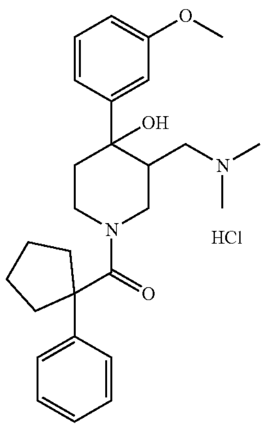 [SMILES: COc1cccc(C2(O)CCN(C(=O)C3(c4ccccc4)CCCC3)CC2CN(C)C)c1 ; Cl] | 73.72 ± 0.32 nM | 1641.6 ± 1161.5 nM | 32.63 ± 4.35 nM |
| (3-((Dimethylamino)methyl)-4-hydroxy-4-(3-methoxyphenyl)piperidin-1-yl)(1-phenylcyclohexyl)methanone hydrochloride (FWBE27) | 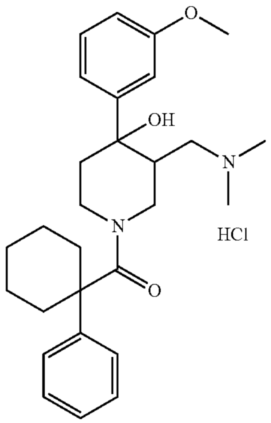 [SMILES: COc1cccc(C2(O)CCN(C(=O)C3(c4ccccc4)CCCCC3)CC2CN(C)C)c1 ; Cl] | 51.57 ± 2.24 nM | 93.63 ± 1.08% | 30.70 ± 0.96 nM |

In the column "Binding ate (%) or Ki (nM)" in Table 5-1, the values expressed as a percentage refer to the binding rate and the values in nM refer to Ki.

As can be seen from Table 5-1, the compounds have a higher affinity for the three opioid receptors than tramadol and can exhibit a stronger analgesic effect in vivo.

Example 5-45

In Vivo Hot Plate Analgesia Test

Female mice weighing about 20 g were placed on a hot plate apparatus preheated to 55° C. and the latency of the hindfoot response was used as an indicator of pain threshold. Animals were screened before the experiment and those with a response latency of less than 5 s or greater than 30 s were excluded. To prevent foot scalding, the maximum observation time was set at 60 s. The basal pain threshold was the average of two measurements taken 5 min apart, and the pain thresholds were measured 15 min, 30 min, 60 min and 120 min after intraperitoneal injection in each group. The percentage analgesic effectiveness (% MPE) was calculated according to the following formula: percentage analgesic effectiveness (% MPE)=(post-administration latency−pre-administration latency)/(60−pre-administration latency)×100%. ED50 values were calculated from the percentage effective analgesia using Graphpad Prism 5.0 software.

TABLE 5-2

| Maximum percentage effective analgesia (% MPE) or $ED_{50}$ values for compound hot plate at 10 mg/kg dose | | |
|---|---|---|
| Name | Structure | % MPE or $ED_{50}$ |
| Tramadol | 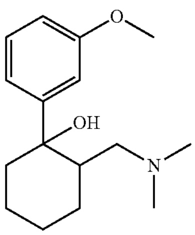 [SMILES: COc1cccc(C2(O)CCCCC2CN(C)C)c1] | 64.5% (50 mg/kg dose, no analgesic effect at 10 mg/kg dose) |

TABLE 5-2-continued

Maximum percentage effective analgesia (% MPE) or $ED_{50}$ values for compound hot plate at 10 mg/kg dose

| Name | Structure | % MPE or $ED_{50}$ |
|---|---|---|
| 2-(3,5-Bis(trifluoro-methyl)phenyl)-1-(3-((dimethylamino) methyl)-4-hydroxy-4-(3-methoxyphenyl) piperidin-1-yl)ethyl-1-one hydrochloride (FWBE1) | 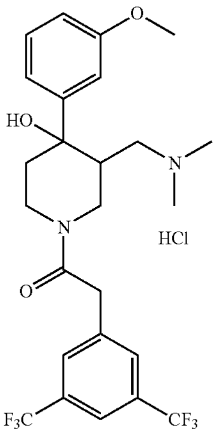 [SMILES: COc1cccc(C2(O)CCN(C(=O)Cc3cc(C(F)(F)F)cc(C(F)(F)F)c3)CC2CN(C)C)c1 ; Cl] | 17.8% |
| 1-(3-((Dimethylamino) methyl)-4-hydroxy-4-(3-methoxyphenyl)piperi-din-1-yl)-2-(thiophen-3-yl)ethyl-1-one hydrochloride (FWBE2) | 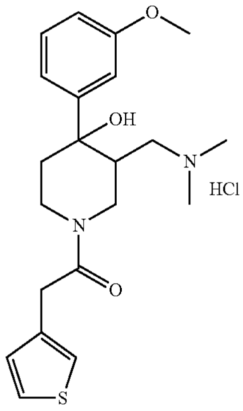 [SMILES: COc1cccc(C2(O)CCN(C(=O)Cc3ccsc3)CC2CN(C)C)c1 ; Cl] | 42% |
| 1-(3-((Dimethylamino) methyl)-4-hydroxy-4-(3-methoxyphenyl)piperi-din-1-yl)-2-phenylethyl-1-one hydrochloride (FWBE3) | 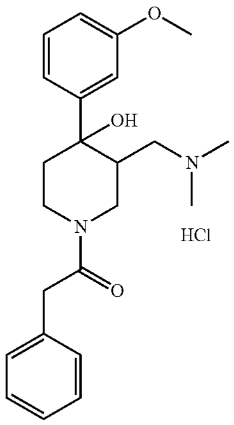 [SMILES: COc1cccc(C2(O)CCN(C(=O)Cc3ccccc3)CC2CN(C)C)c1 ; Cl] | 63.5% |

TABLE 5-2-continued

Maximum percentage effective analgesia (% MPE) or $ED_{50}$ values for compound hot plate at 10 mg/kg dose

| Name | Structure | % MPE or $ED_{50}$ |
|---|---|---|
| 1-(3-((Dimethylamino) methyl)-4-hydroxy-4-(3-methoxyphenyl)piperi-din-1-yl)-2-(3-(trifluorometh-yl)phenyl)ethyl-1-one hydrochloride (FWBE4) | 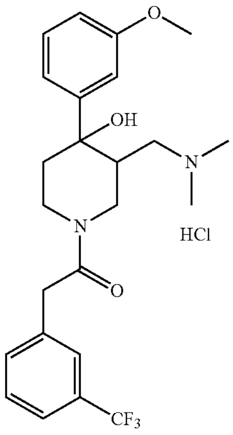 [SMILES: COc1cccc(C2(O)CCN(C(=O)Cc3cccc(C(F)(F)F)c3)CC2CN(C)C)c1 ; Cl] | 69% |
| (3-((Dimethylamino) methyl)-4-hydroxy-4-(3-methoxyphenyl)piperi-din-1-yl)(2,4,5-trifluorophenyl) methanone hydrochloride (FWBE5) | 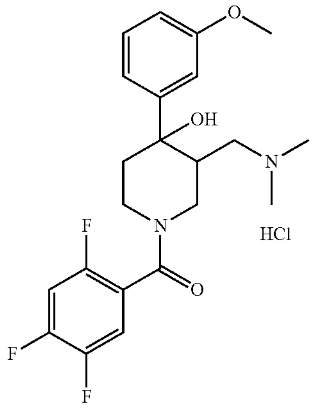 [SMILES: COc1cccc(C2(O)CCN(C(=O)c3cc(F)c(F)cc3F)CC2CN(C)C)c1 ; Cl] | 3% |
| 1-(3-((Dimethylamino) methyl)-4-hydroxy-4-(3-methoxyphenyl)piper-idin-1-yl)-2-(3-(trifluorometh-oxy)phenyl)ethyl-1-one hydrochloride (FWBE6) | 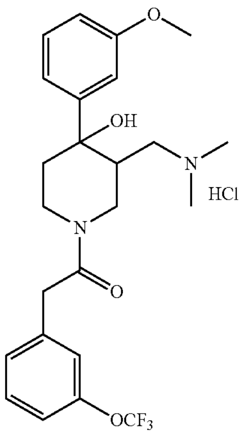 [SMILES: COc1cccc(C2(O)CCN(C(=O)Cc3cccc(OC(F)(F)F)c3)CC2CN(C)C)c1 ; Cl] | 47% |

TABLE 5-2-continued

Maximum percentage effective analgesia (% MPE) or $ED_{50}$ values for compound hot plate at 10 mg/kg dose

| Name | Structure | % MPE or $ED_{50}$ |
|---|---|---|
| 1-(3-((Dimethylamino)methyl)-4-hydroxy-4-(3-methoxyphenyl)piperidin-1-yl)-2-(1H-tetrazol-1-yl)ethyl-1-one hydrochloride (FWBE7) | 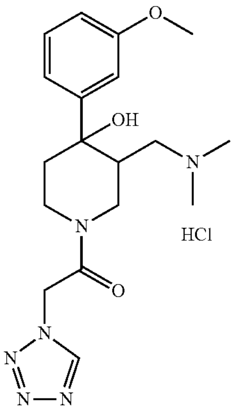 [SMILES: COc1cccc(C2(O)CCN(C(=O)Cn3cnnn3)CC2CN(C)C)c1 ; Cl] | 12.0% |
| 1-(3-((Dimethylamino)methyl)-4-hydroxy-4-(3-methoxyphenyl)piperidin-1-yl)-2-(thiophen-2-yl)ethyl-1-one hydrochloride (FWBE8) | 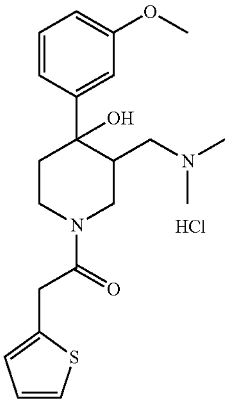 [SMILES: COc1cccc(C2(O)CCN(C(=O)Cc3cccs3)CC2CN(C)C)c1 ; Cl] | 93.0% |
| 2-(3-Chlorophenyl)-1-(3-((dimethylamino)methyl)-4-hydroxy-4-(3-methoxyphenyl)piperidin-1-yl)ethyl-1-one hydrochloride (FWBE9) | 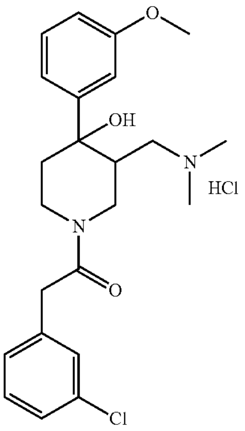 [SMILES: COc1cccc(C2(O)CCN(C(=O)Cc3cccc(Cl)c3)CC2CN(C)C)c1 ; Cl] | 86.38% |

TABLE 5-2-continued

Maximum percentage effective analgesia (% MPE) or $ED_{50}$ values for compound hot plate at 10 mg/kg dose

| Name | Structure | % MPE or $ED_{50}$ |
|---|---|---|
| 1-(3-((Dimethylamino)methyl)-4-hydroxy-4-(3-methoxyphenyl)piperidin-1-yl)-3-(3-(trifluoromethyl)phenyl)propyl-1-one hydrochloride (FWBE10) | 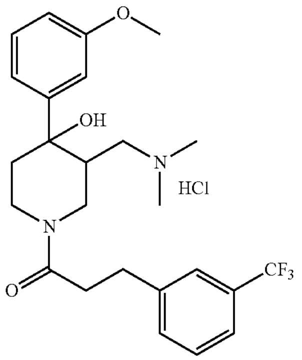 [SMILES: COc1cccc(C2(O)CCN(C(=O)CCc3cccc(C(F)(F)F)c3)CC2CN(C)C)c1 ; Cl] | 17.33% |
| 2-(3-Bromophenyl)-1-(3-((dimethylamino)methyl)-4-hydroxy-4-(3-methoxyphenyl)piperidin-1-yl)ethyl-1-one hydrochloride (FWBE11) | 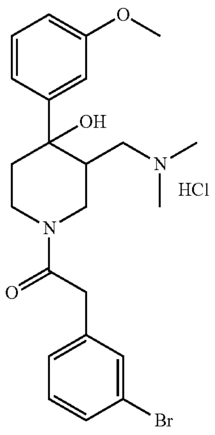 [SMILES: COc1cccc(C2(O)CCN(C(=O)Cc3cccc(Br)c3)CC2CN(C)C)c1 ; Cl] | 98.31% |
| 1-(3-((Dimethylamino)methyl)-4-hydroxy-4-(3-methoxyphenyl)piperidin-1-yl)-2-(3-fluorophenyl)ethyl-1-one hydrochloride (FWBE12) | 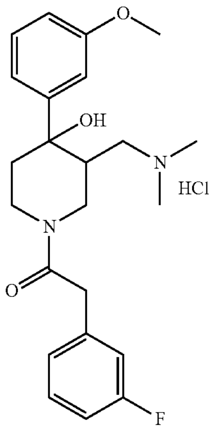 | 88.38% |

TABLE 5-2-continued

Maximum percentage effective analgesia (% MPE) or $ED_{50}$ values for compound hot plate at 10 mg/kg dose

| Name | Structure | % MPE or $ED_{50}$ |
|---|---|---|
| 1-(3-((Dimethylamino)methyl)-4-hydroxy-4-(3-methoxyphenyl)piperidin-1-yl)-2-(1H-indol-3-yl)ethyl-1-one (FWBE13) | 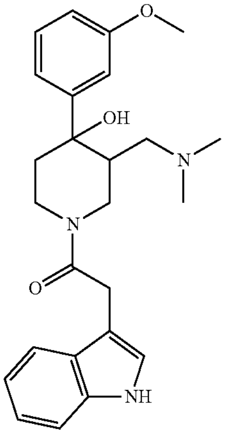 [SMILES: COc1cccc(C2(O)CCN(C(=O)Cc3c[nH]c4ccccc34)CC2CN(C)C)c1] | 66.95% |
| 1-(3-((Dimethylamino)methyl)-4-hydroxy-4-(3-methoxyphenyl)piperidin-1-yl)-2-(1H-indol-1-yl)ethyl-1-one hydrochloride (FWBE14) | 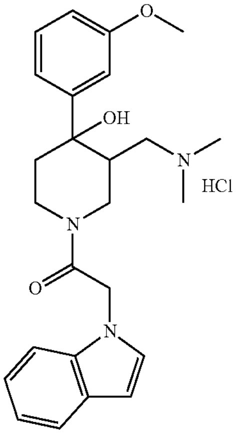 [SMILES: COc1cccc(C2(O)CCN(C(=O)Cn3ccc4ccccc43)CC2CN(C)C)c1 ; Cl] | 54.23% |
| 1-(3-((Dimethylamino)methyl)-4-hydroxy-4-(3-methoxyphenyl)piperidin-1-yl)-2-(naphthalen-2-yl)ethyl-1-one hydrochloride (FWBE15) | 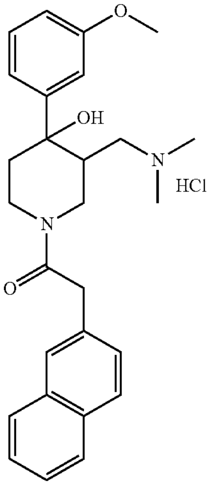 [SMILES: COc1cccc(C2(O)CCN(C(=O)Cc3ccc4ccccc4c3)CC2CN(C)C)c1 ; Cl] | 0% |

TABLE 5-2-continued

Maximum percentage effective analgesia (% MPE) or $ED_{50}$ values for compound hot plate at 10 mg/kg dose

| Name | Structure | % MPE or $ED_{50}$ |
|---|---|---|
| 1-(3-((Dimethylamino)methyl)-4-hydroxy-4-(3-methoxyphenyl)piperidin-1-yl)-2-(naphthalen-1-yl)ethyl-1-one hydrochloride (FWBE16) | 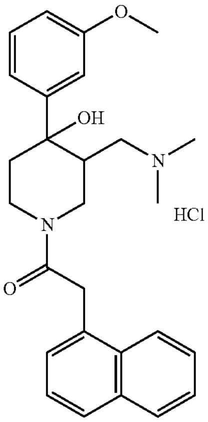 [SMILES: COc1cccc(C2(O)CCN(C(=O)Cc3cccc4ccccc34)CC2CN(C)C)c1 ; Cl] | 78.72% |
| 2-(3,4-Dichlorophenyl)-1-(3-((dimethylamino)methyl)-4-hydroxy-4-(3-methoxyphenyl)piperidin-1-yl)ethyl-1-one hydrochloride (FWBE17) | 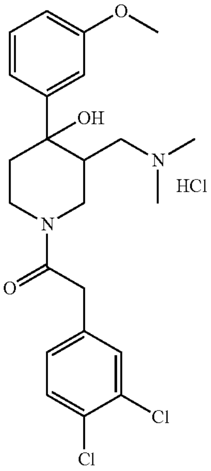 [SMILES: COc1cccc(C2(O)CCN(C(=O)Cc3ccc(Cl)c(Cl)c3)CC2CN(C)C)c1 ; Cl] | 70.66% |
| 1-(3-((Dimethylamino)methyl)-4-hydroxy-4-(3-methoxyphenyl)piperidin-1-yl)-2-(2,4,5-trifluorophenyl)ethyl-1-one hydrochloride (FWBE18) | 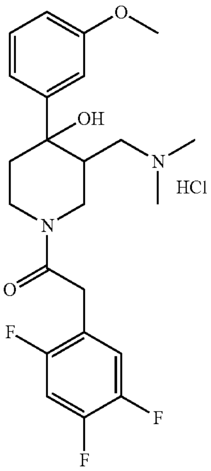 [SMILES: COc1cccc(C2(O)CCN(C(=O)Cc3cc(F)c(F)cc3F)CC2CN(C)C)c1 ; Cl] | 1.11 mg/kg |

TABLE 5-2-continued

Maximum percentage effective analgesia (% MPE) or $ED_{50}$ values for compound hot plate at 10 mg/kg dose

| Name | Structure | % MPE or $ED_{50}$ |
|---|---|---|
| 2-(4-Chlorophenyl)-1-(3-((dimethylamino) methyl)-4-hydroxy-4-(3-methoxyphenyl) piperidin-1-yl)ethyl-1-one hydrochloride (FWBE19) | 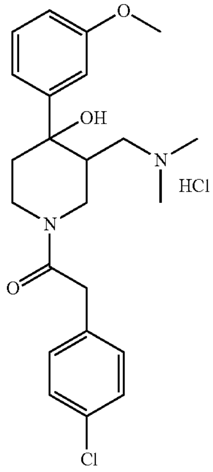 [SMILES: COc1cccc(C2(O)CCN(C(=O)Cc3ccc(Cl)cc3)CC2CN(C)C)c1 ; Cl] | 73.98% |
| 2-(2-Chlorophenyl)-1-(3-((dimethylamino) methyl)-4-hydroxy-4-(3-methoxyphenyl) piperidin-1-yl)ethyl-1-one hydrochloride (FWBE20) | 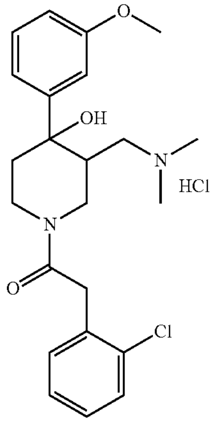 [SMILES: COc1cccc(C2(O)CCN(C(=O)Cc3ccccc3Cl)CC2CN(C)C)c1 ; Cl] | — |
| 3-(2-(3-((Dimethylamino) methyl)-4-hydroxy-4-(3-methoxyphenyl) piperidin-1-yl)-2-oxoethyl)benzonitrile hydrochloride (FWBE21) | 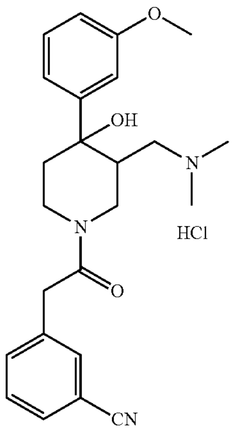 [SMILES: COc1cccc(C2(O)CCN(C(=O)Cc3cccc(C#N)c3)CC2CN(C)C)c1 ; Cl] | 67.09% |
| 1-(3-((Dimethylamino) methyl)-4-hydroxy-4-(3-methoxyphenyl) piperidin-1-yl)-2-(3-nitrophenyl)ethyl-1-one hydrochloride (FWBE22) | 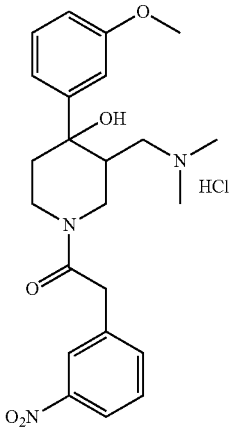 [SMILES: COc1cccc(C2(O)CCN(C(=O)Cc3cccc([N+](=O)[O-])c3)CC2CN(C)C)c1 ; Cl] | 72.88% |
| 1-(3-((Dimethylamino) methyl)-4-hydroxy-4-(3-methoxyphenyl) piperidin-1-yl)-2-methyl-2-phenylpropan-1-one hydrochloride (FWBE23) | 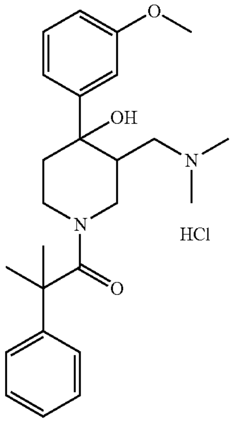 [SMILES: COc1cccc(C2(O)CCN(C(=O)C(C)(C)c3ccccc3)CC2CN(C)C)c1 ; Cl] | 33.72% |
| (3-((Dimethylamino) methyl)-4-hydroxy-4-(3-methoxyphenyl) piperidin-1-yl)(1-phenylcyclo-propyl)methanone hydrochloride (FWBE24) | 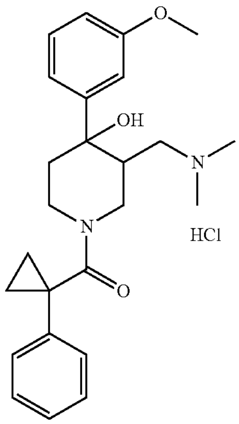 [SMILES: COc1cccc(C2(O)CCN(C(=O)C3(c4ccccc4)CC3)CC2CN(C)C)c1 ; Cl] | 29.85% |

TABLE 5-2-continued

| Maximum percentage effective analgesia (% MPE) or $ED_{50}$ values for compound hot plate at 10 mg/kg dose | | |
|---|---|---|
| Name | Structure | % MPE or $ED_{50}$ |
| (3-((Dimethylamino) methyl)-4-hydroxy-4-(3-methoxyphenyl) piperidin-1-yl)(1-phenylcyclobutyl) methanone hydrochloride (FWBE25) | 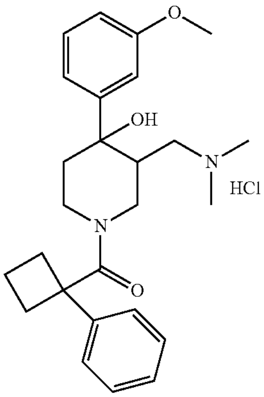 [SMILES: COc1cccc(C2(O)CCN(C(=O)C3(c4ccccc4)CCC3)CC2CN(C)C)c1 ; Cl] | 5.03% |
| (3-((Dimethylamino) methyl)-4-hydroxy-4-(3-methoxyphenyl) piperidin-1-yl)(1-phenylcyclopent-yl)methanone hydrochloride (FWBE26) | 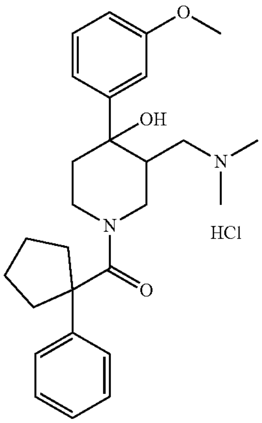 [SMILES: COc1cccc(C2(O)CCN(C(=O)C3(c4ccccc4)CCCC3)CC2CN(C)C)c1 ; Cl] | 52.96% |
| (3-((Dimethylamino) methyl)-4-hydroxy-4-(3-methoxyphenyl) piperidin-1-yl)(1-phenylcyclohex-yl)methanone hydrochloride (FWBE27) | 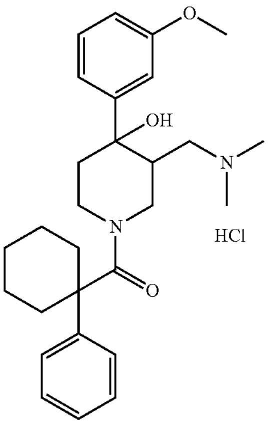 [SMILES: COc1cccc(C2(O)CCN(C(=O)C3(c4ccccc4)CCCCC3)CC2CN(C)C)c1 ; Cl] | 61.21% |

In the column "% MPE or $ED_{50}$" in Table 5-2, values expressed as a percentage refer to % MPE and values in mg/kg refer to $ED_{50}$.

As can be seen from Table 5-2, the compounds obtained from the present invention all have a stronger analgesic effect compared to tramadol.

The above-mentioned embodiments are preferred embodiments of the present invention, but the embodiments of the present invention are not limited by the above-mentioned embodiments. Any other changes, modifications, substitutions, combinations, simplifications made without departing from the spirit and principles of the present invention shall be equivalent substitutions and are included in the scope of protection of the present invention.

What is claimed is:

1. A compound or pharmaceutically acceptable salt thereof selected from:

2-((dimethylamino) methyl)-1-(3-methoxyphenyl)-4-(phenylsulfonyl)cyclohexyl benzoate;

N-(3-((dimethylamino) methyl)-4-hydroxy-4-(3-methoxyphenyl) cyclohexyl) benzenesulfonamide;

4-((3-chlorophenyl) sulfonamido)-2-((dimethylamino) methyl)-1-(3-methoxyphenyl) cyclohexyl benzoate;

3-chloro-N-(3-((dimethylamino) methyl)-4-hydroxy-4-(3-methoxyphenyl) cyclohexyl) benzenesulfonamide;

2-((dimethylamino) methyl)-1-(3-methoxyphenyl)-4-(thiophene-2-sulfonamido) cyclohexyl benzoate;

N-(3-((dimethylamino) methyl)-4-hydroxy-4-(3-methoxyphenyl) cyclohexyl) thiophene-2-sulfonamide;

N-(3-((dimethylamino) methyl)-4-hydroxy-4-(3-methoxyphenyl) cyclohexyl) thiophene-2-sulfonamide;

2-((dimethylamino) methyl)-1-(3-methoxyphenyl)-4-((phenylmethyl) sulfonamido) cyclohexyl benzoate;

N-(3-((dimethylamino) methyl)-4-hydroxy-4-(3-methoxyphenyl) cyclohexyl)-1-benzenesulfonamide hydrochloride;

4-(((3-chlorophenyl)methyl) sulfonamido)-2-((dimethylamino) methyl)-1-(3-methoxyphenyl) cyclohexyl benzoate;

1-(3-chlorophenyl)-N-(3-((dimethylamino) methyl)-4-hydroxy-4-(3-methoxyphenyl) cyclohexyl) methanesulfonamide;

2-((dimethylamino) methyl)-1-(3-methoxyphenyl)-4-(N-methylbenzenesulfonamido) cyclohexyl benzoate;

N-(3-((dimethylamino) methyl)-4-hydroxy-4-(3-methoxyphenyl) cyclohexyl)-N-methylbenzenesulfonamide;

4-((3-chloro-N-methylphenyl) sulfonamido)-2-((dimethylamino) methyl)-1-(3-methoxyphenyl) cyclohexyl benzoate;

3-chloro-N-(3-((dimethylamino) methyl)-4-hydroxy-4-(methoxyphenyl) cyclohexyl)-N-methylbenzenesulfonamide;

2-((dimethylamino) methyl)-1-(3-methoxyphenyl)-4-(N-methylthiophene-2-sulfonamido) cyclohexyl benzoate;

N-(3-((dimethylamino) methyl)-4-hydroxy-4-(3-methoxyphenyl) cyclohexyl)-N-methylthiophene-2-sulfonamide;

2-((dimethylamino) methyl)-1-(3-methoxyphenyl)-4-((N-methyl-1-benzyl) sulfonamido) cyclohexyl benzoate;

N-(3-((dimethylamino) methyl)-4-hydroxy-4-(3-methoxyphenyl) cyclohexyl)-N-methyl-1-phenylmethanesulfonamide;

4-((1-(3-chlorophenyl)-N-methyl) sulfonamido)-2-((dimethylamino) methyl)-1-(3-methoxyphenyl) cyclohexyl benzoate;

N-benzyl-N-(3-((dimethylamino) methyl)-4-hydroxy-4-(3-methoxyphenyl) cyclohexyl) benzenesulfonamide;

N-benzyl-3-chloro-N-(3-((dimethylamino) methyl)-4-hydroxy-4-(3-methoxyphenyl) cyclohexyl) benzenesulfonamide;

N-benzyl-N-(3-((dimethylamino) methyl)-4-hydroxy-4-(3-methoxyphenyl) cyclohexyl) thiophene-2-sulfonamide;

4-(benzylsulfonyl)-2-((dimethylamino) methyl)-1-(3-methoxyphenyl) cyclohexan-1-ol; and 2-((dimethylamino) methyl)-1-(3-methoxyphenyl)-4-((phenylsulfonyl) methyl) cyclohex-1-ol.

2. A pharmaceutical composition, comprising: the compound or pharmaceutically acceptable salt according to claim 1, or a solvate or hydrate thereof; and a pharmaceutically acceptable carrier.

3. A method of treating an opioid receptor-related indication, the method comprising administering a pharmaceutical composition to a subject in need of treating the opioid receptor-related indication, wherein the pharmaceutical composition is a pharmaceutical composition according to claim 2.

4. The method of claim 3, wherein the opioid receptor-related indication is selected from the group consisting of pain, irritable bowel syndrome, pruritus, addiction, depression.

5. The method of claim 4, wherein the opioid receptor-related indication is pain, and the pain is selected from the group consisting of pain during surgery, chronic pain, neuropathic pain, and cancer pain.

* * * * *